US009861774B2

(12) United States Patent
Fu et al.

(10) Patent No.: US 9,861,774 B2
(45) Date of Patent: Jan. 9, 2018

(54) SINGLE STAGE, AXIAL SYMMETRIC BLOWER AND PORTABLE VENTILATOR

(75) Inventors: Timothy Tsun-Fai Fu, Pyrmont (AU); Dion Charles Chewe Martin, Concord (AU); Philippe Auguste Chalvignac, Les Arcs sur Argens (FR); Quangang Yang, Kellyville (AU); David Creusot, Castle Hill (AU)

(73) Assignee: ResMed Motor Technologies Inc., Chatsworth, CA (US)

( * ) Notice: Subject to any disclaimer, the term of this patent is extended or adjusted under 35 U.S.C. 154(b) by 577 days.

(21) Appl. No.: 13/384,971

(22) PCT Filed: Aug. 11, 2010

(86) PCT No.: PCT/AU2010/001031
§ 371 (c)(1),
(2), (4) Date: Jan. 19, 2012

(87) PCT Pub. No.: WO2011/017763
PCT Pub. Date: Feb. 17, 2011

(65) Prior Publication Data
US 2012/0138058 A1   Jun. 7, 2012

Related U.S. Application Data

(60) Provisional application No. 61/272,043, filed on Aug. 11, 2009, provisional application No. 61/272,188, (Continued)

(51) Int. Cl.
*A61M 16/00* (2006.01)
*A61M 16/06* (2006.01)
(Continued)

(52) U.S. Cl.
CPC .... *A61M 16/0066* (2013.01); *A61M 16/0069* (2014.02); *A61M 16/0605* (2014.02); (Continued)

(58) Field of Classification Search
CPC .......... A61M 16/0066; A61M 16/0666; A61M 16/0683; A61M 2205/42; A61M 16/0488;
(Continued)

(56) References Cited

U.S. PATENT DOCUMENTS 1,408,715 A   3/1922   Seelig et al.
2,325,842 A   8/1943   Findley
(Continued)

FOREIGN PATENT DOCUMENTS

CN   1826151 A   8/2006
CN   1905917 A   1/2007
(Continued)

OTHER PUBLICATIONS

Patent Examination Report issued in a corresponding Australian Application No. 2010282228 (dated Aug. 14, 2012).
(Continued)

*Primary Examiner* — Kathryn E Ditmer
(74) *Attorney, Agent, or Firm* — Nixon & Vanderhye P.C.

(57) ABSTRACT

A blower (10) includes a housing (20) including a proximal opening (23) and a distal opening (25) that are co-axially aligned, a stator component (30) provided to the housing, an impeller (60) positioned between the proximal opening of the housing and the stator component, and a motor (40) adapted to drive the impeller. The impeller includes a plurality of impeller blades. The stator component includes a plurality of air directing grooves (35) along its exterior surface. The leading edge of the air directing grooves extend tangentially outwards from the outer tips of the impeller blades and are configured to collect the air exiting the impeller blades and direct it from a generally tangential direction to a generally radial direction by dividing the air
(Continued)

from the impeller and directing the air along a curved path towards the distal opening so that airflow becomes substantially laminar.

64 Claims, 125 Drawing Sheets

Related U.S. Application Data filed on Aug. 28, 2009, provisional application No. 61/261,527, filed on Nov. 16, 2009, provisional application No. 61/272,919, filed on Nov. 19, 2009.

(51) Int. Cl.

| | | |
|---|---|---|
| *A61M 16/10* | (2006.01) | |
| *F04D 17/08* | (2006.01) | |
| *F04D 25/08* | (2006.01) | |
| *F04D 29/44* | (2006.01) | |
| *F04D 25/06* | (2006.01) | |
| *A61M 16/04* | (2006.01) | |
| *A61M 16/08* | (2006.01) | |

(52) U.S. Cl.
CPC .... *A61M 16/0633* (2014.02); *A61M 16/0666* (2013.01); *A61M 16/0683* (2013.01); *A61M 16/0858* (2014.02); *A61M 16/1045* (2013.01); *F04D 25/0606* (2013.01); *F04D 25/084* (2013.01); *F04D 29/444* (2013.01); *A61M 16/0465* (2013.01); *A61M 16/0488* (2013.01); *A61M 16/0875* (2013.01); *A61M 16/107* (2014.02); *A61M 16/1055* (2013.01); *A61M 16/1065* (2014.02); *A61M 2016/0027* (2013.01); *A61M 2016/0039* (2013.01); *A61M 2205/0227* (2013.01); *A61M 2205/42* (2013.01); *A61M 2205/8206* (2013.01); *A61M 2209/086* (2013.01); *A61M 2209/088* (2013.01); *A61M 2230/202* (2013.01); *A61M 2230/432* (2013.01); *A61M 2230/435* (2013.01); *A61M 2230/63* (2013.01); *F05D 2250/52* (2013.01)

(58) Field of Classification Search
CPC .... A61M 2209/086; A61M 2016/0027; A61M 2205/8206; A61M 2209/088; A61M 2230/63; A61M 16/0875; A61M 16/0057; F04D 25/084; F04D 25/0606; F04D 17/08; F04D 17/165; F04D 25/0666; F04D 25/08; F04D 25/082; F04D 29/4253; F04D 29/44
USPC ............ 128/204.18, 201.25, 200.24, 204.21, 128/206.17, 205.12, 205.27, 205.29
See application file for complete search history.

(56) References Cited

U.S. PATENT DOCUMENTS

| | | | | |
|---|---|---|---|---|
| 2,609,141 | A * | 9/1952 | Aue | F04D 17/165 |
| | | | | 415/208.2 |
| 3,195,807 | A * | 7/1965 | Sheets | F01D 5/141 |
| | | | | 415/199.4 |
| 3,243,102 | A * | 3/1966 | McMahan | F04D 17/165 |
| | | | | 415/182.1 |
| 4,679,990 | A * | 7/1987 | Yamaura | F04D 29/661 |
| | | | | 415/119 |
| 4,767,285 | A * | 8/1988 | Jyoraku | F04D 25/06 |
| | | | | 415/119 |
| 4,798,518 | A | 1/1989 | Holzberger et al. | |
| 5,046,480 | A * | 9/1991 | Harris | F04D 17/165 |
| | | | | 126/247 |
| 5,211,171 | A | 5/1993 | Choromokos | |
| 5,391,064 | A * | 2/1995 | Lopez | 417/423.14 |
| 5,494,418 | A * | 2/1996 | Moriya | F04D 29/167 |
| | | | | 403/338 |
| 5,511,942 | A * | 4/1996 | Meier | F04D 29/544 |
| | | | | 415/211.2 |
| 5,701,883 | A | 12/1997 | Hete et al. | |
| 5,878,743 | A | 3/1999 | Zdrojkowski et al. | |
| 6,230,708 | B1 | 5/2001 | Radko | |
| 6,382,023 | B1 | 5/2002 | Yonezawa et al. | |
| 6,526,974 | B1 | 3/2003 | Brydon et al. | |
| 6,595,746 | B1 | 7/2003 | Goto et al. | |
| 6,659,737 | B2 * | 12/2003 | Bader | F04D 29/588 |
| | | | | 415/206 |
| 7,318,437 | B2 | 1/2008 | Gunaratnam et al. | |
| 2004/0184914 | A1 * | 9/2004 | Doege | F04D 29/30 |
| | | | | 415/220 |
| 2004/0265136 | A1 * | 12/2004 | Martling | F23D 17/002 |
| | | | | 417/53 |
| 2005/0036887 | A1 | 2/2005 | Nadjafizadeh et al. | |
| 2005/0051174 | A1 | 3/2005 | Emerson | |
| 2005/0103339 | A1 * | 5/2005 | Daly | A61M 16/0057 |
| | | | | 128/204.18 |
| 2006/0213511 | A1 * | 9/2006 | Hansen | 128/200.24 |
| 2007/0176121 | A1 * | 8/2007 | Lyons | G01B 13/12 |
| | | | | 250/492.1 |
| 2007/0199566 | A1 | 8/2007 | Be'eri | |
| 2008/0178879 | A1 * | 7/2008 | Roberts | A61M 16/0066 |
| | | | | 128/204.18 |
| 2008/0304986 | A1 * | 12/2008 | Kenyon | A61M 16/0066 |
| | | | | 417/423.12 |
| 2009/0044808 | A1 | 2/2009 | Guney et al. | |
| 2009/0269196 | A1 | 10/2009 | Hsu et al. | |
| 2010/0170513 | A1 * | 7/2010 | Bowditch | A61M 16/00 |
| | | | | 128/204.23 |
| 2010/0228754 | A1 | 9/2010 | Shimakura | |
| 2011/0164995 | A1 | 7/2011 | Genster | |

FOREIGN PATENT DOCUMENTS

| | | | |
|---|---|---|---|
| DE | 19605742 A1 * | 8/1997 | ............... A47L 5/22 |
| DE | 20 2005 010185 U1 | 4/2006 | |
| GB | 604 121 A | 6/1948 | |
| GB | 2048382 | 12/1980 | |
| JP | 59041700 A * | 3/1984 | ........... F04D 17/165 |
| JP | 60-159399 | 8/1985 | |
| JP | S63-92358 | 4/1988 | |
| JP | H11-502440 | 3/1999 | |
| JP | 2000-54987 | 2/2000 | |
| JP | 2000-511093 A | 8/2000 | |
| JP | 2001-91322 A | 4/2001 | |
| JP | 2002-513117 | 5/2002 | |
| JP | 2002-206498 | 7/2002 | |
| JP | 2003-530907 A | 10/2003 | |
| JP | 2006-130320 | 5/2006 | |
| JP | 2007-529681 | 10/2007 | |
| JP | 2009-515084 | 4/2009 | |
| WO | WO 97/19629 A1 | 6/1997 | |
| WO | WO 9719629 A1 * | 6/1997 | ............... A47L 5/22 |
| WO | WO 99/56022 A1 | 11/1999 | |
| WO | 00/43060 A1 | 7/2000 | |
| WO | 03/002176 A2 | 1/2003 | |
| WO | WO 2007/048206 | 3/2007 | |
| WO | WO 2007/134405 A1 | 11/2007 | |
| WO | WO 2008/092235 | 8/2008 | |
| WO | WO 2008/092235 A1 | 8/2008 | |
| WO | WO 2009/052560 | 4/2009 | |
| WO | WO 2009/108995 | 9/2009 | |
| WO | WO 2010/139014 | 12/2010 | |
| WO | WO 2010/141983 | 12/2010 | |

(56) References Cited

FOREIGN PATENT DOCUMENTS

| WO | WO 2011/017763 | 2/2011 |
|----|----------------|--------|
| WO | WO 2011/022779 | 3/2011 |

OTHER PUBLICATIONS

Office Action issued in corresponding Japanese Appln. No. 2012-524056 dated May 26, 2014, with English language translation thereof.
Extended European Search Report in corresponding European Appln. No. 10 80 7801.5, dated Jul. 10, 2014.
Notification of First Office Action and English translation in CN 201080045834.4 dated Jun. 4, 2014.
Chinese Office Action issued in corresponding Application No. 201080045834.4 dated Dec. 29, 2014, with English language translation thereof.
Decision of Rejection issued in corresponding Japanese Appln. No. 2012-524056 dated Feb. 9, 2015, with English translation thereof.
Third Office Action issued in corresponding Chinese Application No. 201080045834.4 dated Jul. 2, 2015, with English translation thereof.
First Office Action issued in corresponding Japanese Patent Application No. 2015-113129 dated Jun. 6, 2016, with English language translation thereof.
Further Examination Report issued in corresponding New Zealand Patent Application No. 705165 dated Jun. 14, 2016.
Office Action issued in corresponding Japanese Patent Application No. 2012-524056 dated Jul. 11, 2016 with English language translation thereof.
Notice of Opposition to Grant of Patent (Section 21) filed Jan. 25, 2017 by Fisher & Paykel Healthcare Limited in New Zealand Application No. 705165 (3 pages).
First Examination Report dated Sep. 29, 2016 issued in New Zealand Application No. 724043 (3 pages).
Communication dated Apr. 10, 2017 issued in New Zealand Application No. 705165 (2 pages).
Amended Notice of Opposition to Grant of Patent (Section 21), with no markups, dated Mar. 30, 2017 filed by Fisher & Paykel Healthcare Limited in New Zealand Application No. 705165 (2 pages).
Amended Notice of Opposition to Grant of Patent (Section 21), with markups, dated Mar. 30, 2017 filed by Fisher & Paykel Healthcare Limited in New Zealand Application No. 705165 (2 pages).
Statement of Case dated Mar. 30, 2017 filed by Fisher & Paykel Healthcare Limited in New Zealand Application No. 705165 (14 pages).
Office Action dated Aug. 1, 2017 issued in Chinese Application No. 201610081091.5 with English translation (10 pages).
International Search Report issued in PCT/AU2010/001031 (dated Nov. 4, 2010).
Extended European Search Report dated Oct. 26, 2017 issued in European Application No. 17178004.2 (7 pages).

* cited by examiner

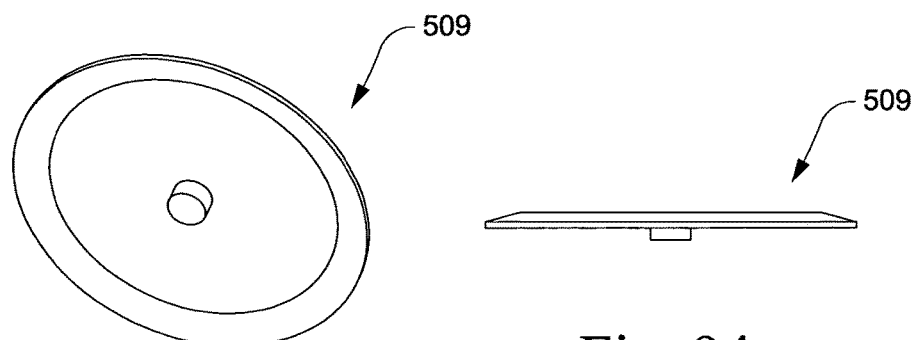
Fig. 93
Fig. 94
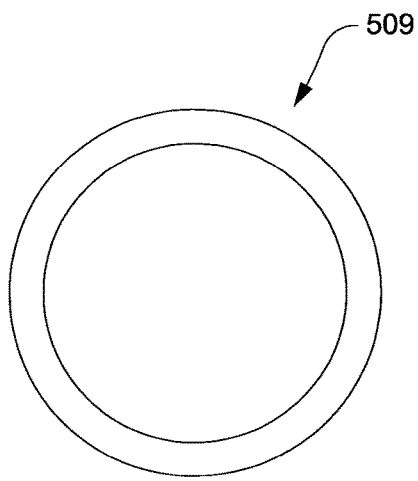
Fig. 95
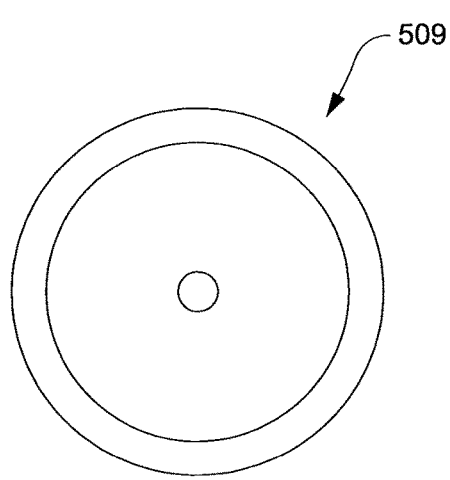
Fig. 96

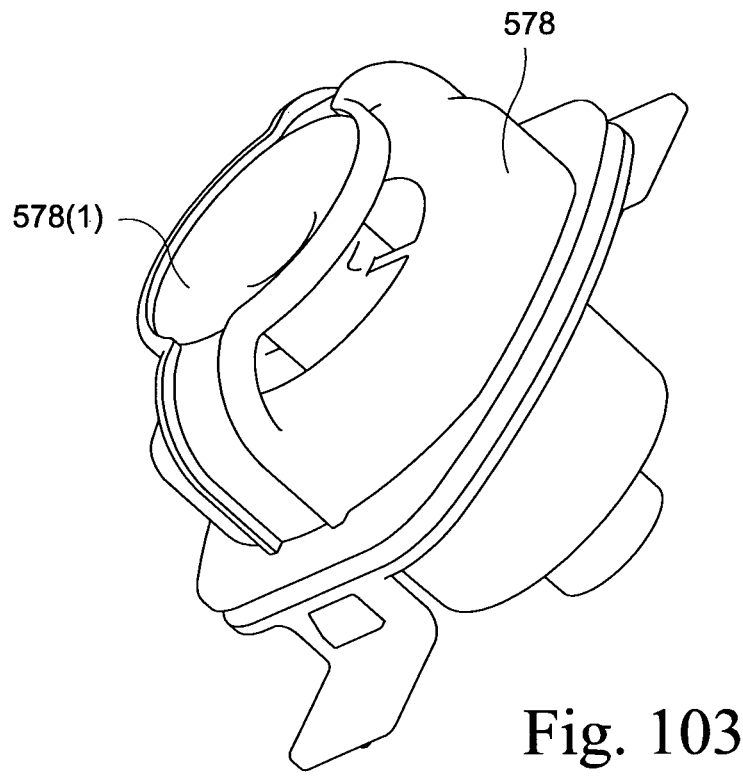
Fig. 103
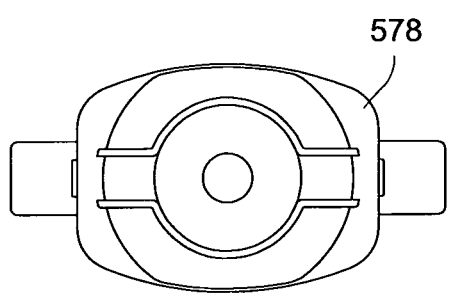
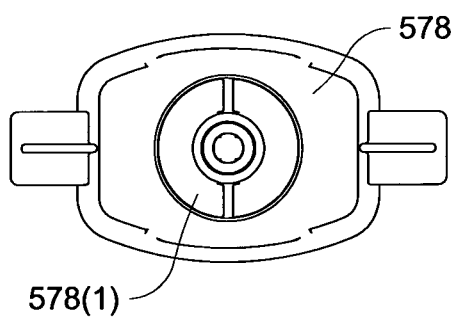
Fig. 104     Fig. 105

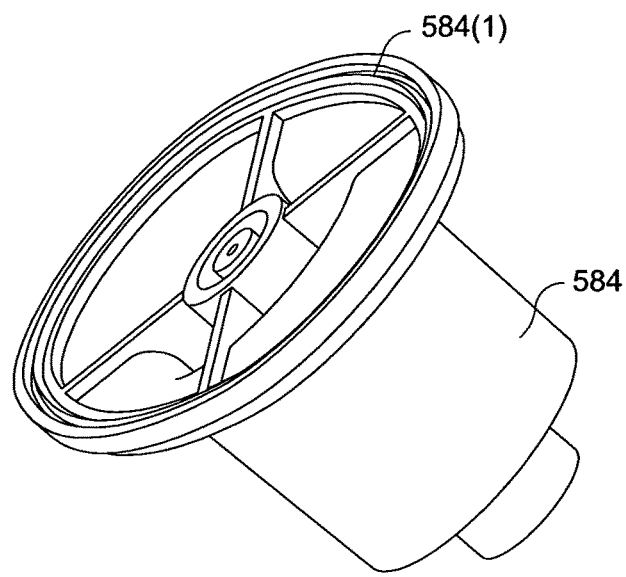
Fig. 121
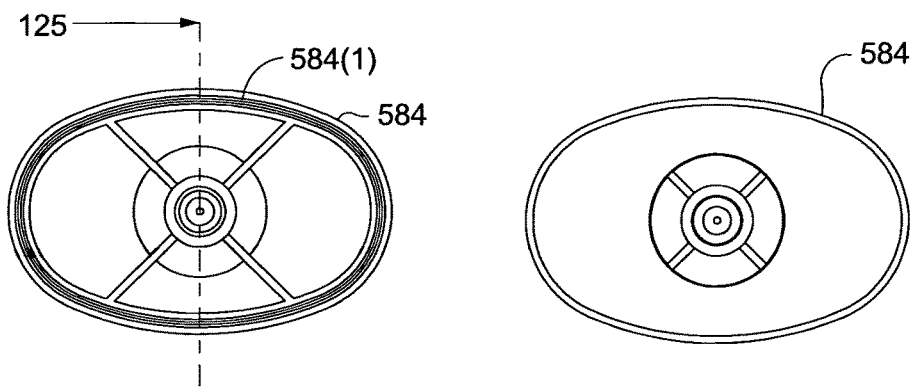
Fig. 122
Fig. 123
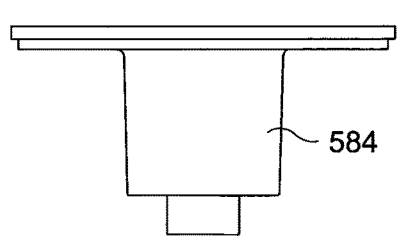
Fig. 124
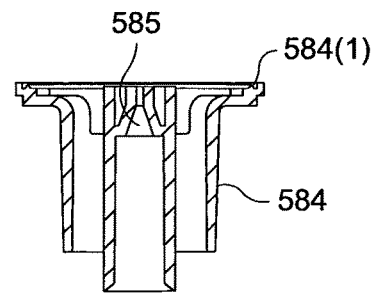
Fig. 125

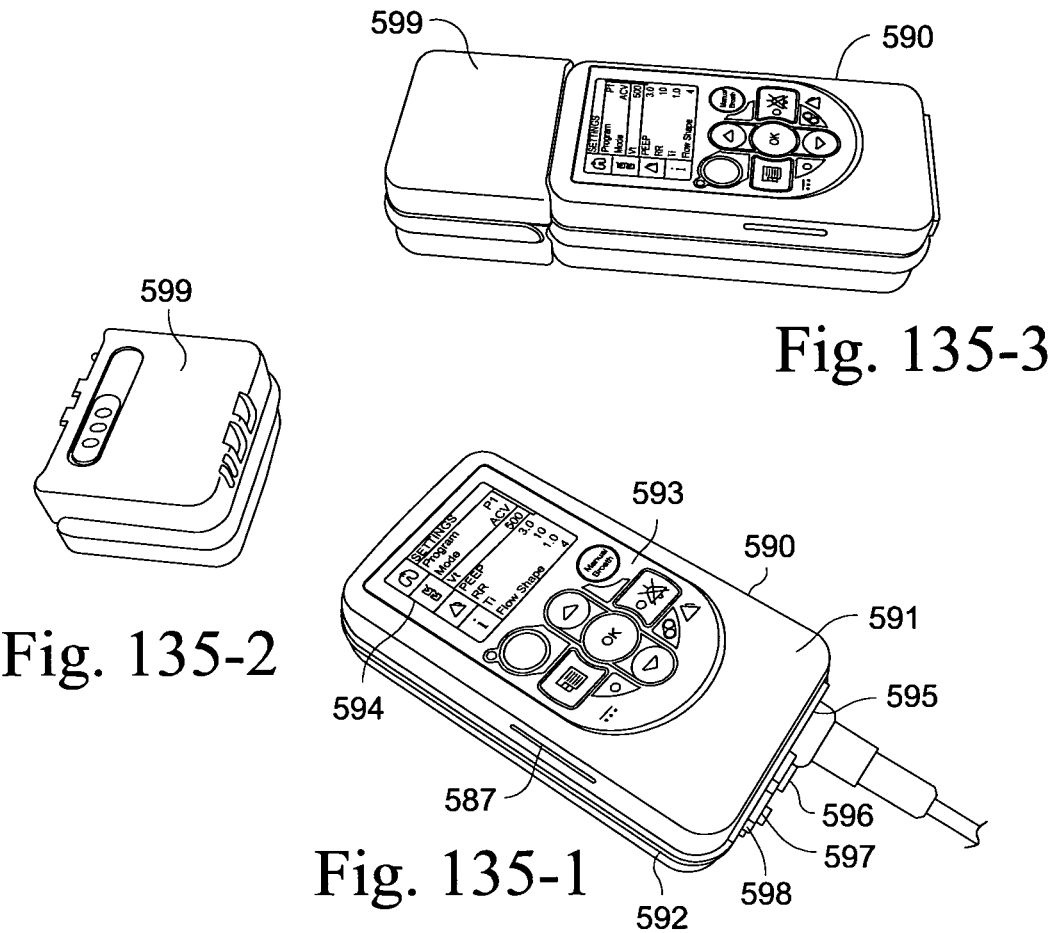
Fig. 135-3
Fig. 135-2
Fig. 135-1
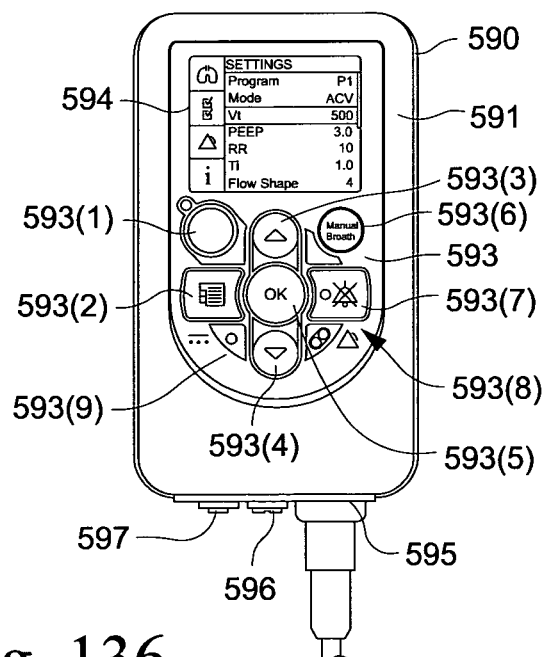
Fig. 136

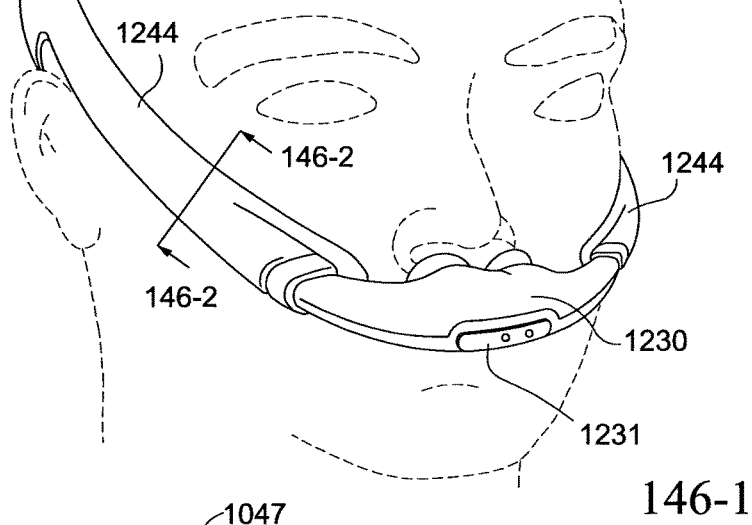
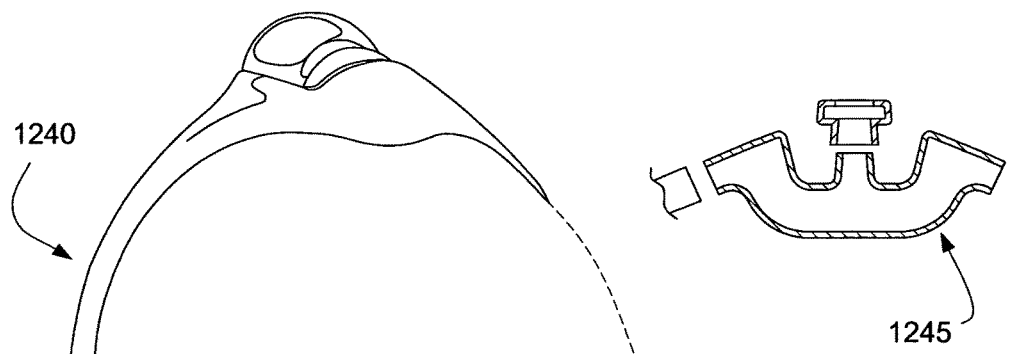
FIG. 146-4
146-1
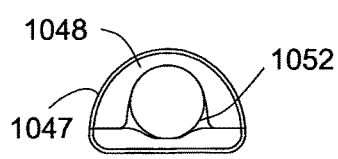
FIG. 146-2-1
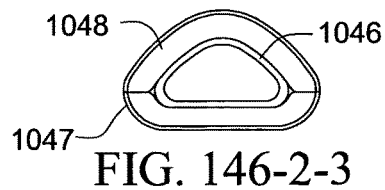
FIG. 146-2-2
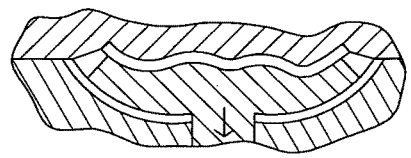
FIG. 146-3
FIG. 146-2-3

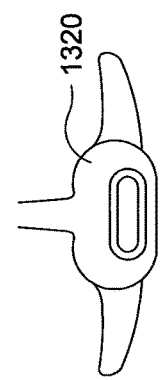
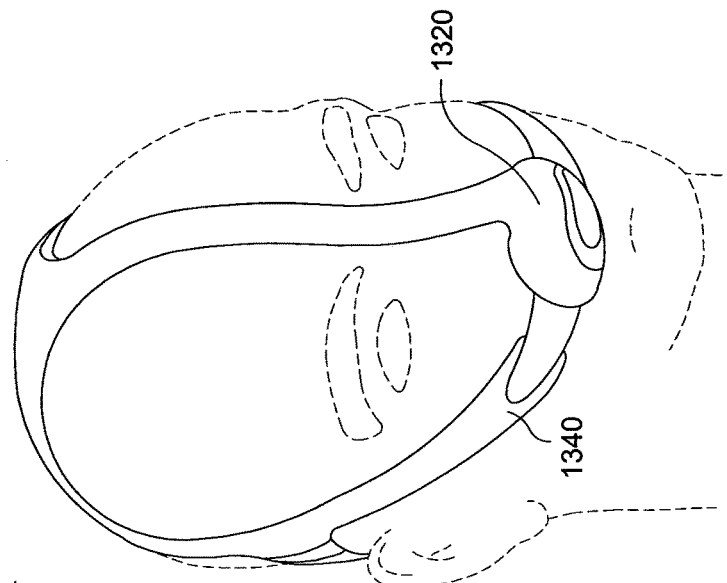
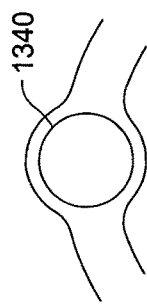
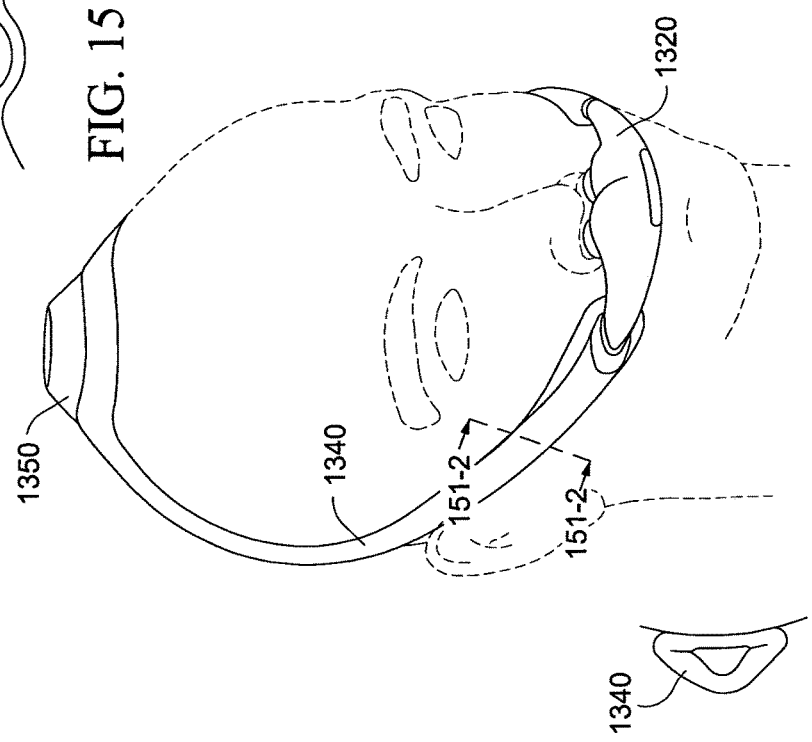
FIG. 152-2
FIG. 152-1
FIG. 151-3
FIG. 151-1
FIG. 151-2

SINGLE STAGE, AXIAL SYMMETRIC BLOWER AND PORTABLE VENTILATOR

CROSS-REFERENCE TO APPLICATION

This application is the U.S. national phase of International Application No. PCT/AU2010/001031 filed 11 Aug. 2010 which designated the U.S. and claims priority to U.S. Provisional Application Nos. 61/272,043 filed 11 Aug. 2009, 61/272,188 filed 28 Aug. 2009, 61/261,527 filed 16 Nov. 2009 and 61/272,919 filed 19 Nov. 2009, the entire contents of each of which are hereby incorporated by reference.

FIELD OF THE INVENTION

The present invention relates to a blower for generating a pressure differential (e.g., air at positive or negative (vacuum) pressure). In an embodiment, the blower may be used in a ventilator system. In an embodiment, the blower may be used in a positive airway pressure (PAP) device used for the delivery of respiratory therapy to a patient. Examples of such therapies are Assist/Control Ventilation, Intermittent Mandatory Ventilation, Pressure Support Ventilation, Continuous Positive Airway Pressure (CPAP) treatment. These may be delivered via a non-invasive patient interface or invasive patient interface. The therapy is used for treatment of various respiratory conditions including respiratory failure, respiratory insufficiency, or Sleep Disordered Breathing (SDB). However, the blower may be used in other applications (e.g., vacuum applications (medical or otherwise)).

BACKGROUND OF THE INVENTION

A need has developed in the art for blower designs that are quieter, more compact and less expensive. The present invention provides alternative arrangements of blowers that consider this need.

An example of prior art in this field is described in U.S. Patent Application Publication No. US 2005/0036887 (Nadjafizadeh et al.).

SUMMARY OF THE INVENTION

An aspect of the invention relates to a small, portable ventilator system located proximal to the patient, and thus allows inspiration and expiration through the system.

Another aspect of the invention relates to a ventilator including an efficient powerful miniature motor combined with an efficient low-inertia impeller and small blower.

Another aspect of the invention relates to a ventilator located proximal to the patient. The proximal location of the ventilator allows the use of a short breathing circuit which provides minimal circuit resistance to enhance compliance, requires low deadspace within the ventilator, allows the use of a separate battery and user interface from the ventilator, and allows more accurate flow and volume sensing as sensors are closer to the patient.

Another aspect of the invention relates to a blower structured to efficiently manage heat produced by the motor. For example, the blower may include a non-electrically conductive sleeve close to a central segment of the motor. This arrangement avoids electrically conductive material close to the central segment of the motor to reduce eddy current induced inductive losses, a consequence of a high-performance miniature motor embodiment. In another example, heat conductive elements (e.g., aluminum stator, aluminum flow sensor) coupled to the motor are maximized to act as heat sinks.

Another aspect of the invention relates to a ventilator including a valve arrangement at the proximal or patient side opening of the blower structured to control the dual direction of air flow through the ventilator, and thus minimize rebreathed volumes.

Another aspect of the invention relates to a ventilator including a single flow element and single flow sensor that measures flow in both directions and acts as a heat sink for the motor. Proximal use of such a ventilator results in the flow sensor being exposed to moist exhalant from the patient, which increases the risk of potential errors for flow measurement. As the flow sensor according to an embodiment of the invention acts as heat sink for the motor, the motor will warm the flow sensor and prevent condensation. Thus, there is no requirement for a separate heater to heat the flow sensor.

Another aspect of the invention relates to a ventilator structured to stabilize pressure and flow around the flow sensor to enhance flow sensing. For example, the ventilator may include a plenum chamber around the impeller that provides a uniform pressure source for the stator to minimize offset and impulse noise in the flow sensing. Also, the ventilator may provide a downstream chamber to allow flow recirculation through the stator without affecting the flow sensing as flow is fully developed before flow hits the flow sensor.

Another aspect of the invention relates to a ventilator having low source impedance by maximizing the cross-sectional area of the flow path (e.g., stator angles, impeller vane geometry) while balancing this with minimal deadspace within the ventilator since the patient breathes entirely through the ventilator.

Another aspect of the invention relates to a ventilator including a battery pack arrangement where both the ventilator and the battery pack include a micro-controller or microprocessor to allow the transfer of ventilator settings and patient details between the modules to make it easy to transfer patients onto a new ventilator or replace the battery.

Another aspect of the invention relates to a modular system having separate modules for ventilator, handset (controller/user interface), oxygen enhancement, extension battery, heat moisture exchange filter (HMEF), mucous trap, and/or harness or vest.

Another aspect of the invention relates to a ventilator for a patient including a blower structured to provide a source of pressurized air. The blower includes a housing having a proximal opening or proximal end (e.g., patient side opening or opening proximal to the patient) and a distal opening or distal end (e.g., ambient side opening or opening distal from the patient), a stator component provided to the housing, an impeller positioned between the proximal opening of the housing and the stator component, and a motor adapted to drive the impeller.

The ventilator may include one or more of the following aspects. For example, the ventilator may include a valve assembly provided to the proximal opening of the blower and structured to allow air to flow through the blower along a flow path in both directions. The valve assembly is structured to allow air to flow into the blower via the proximal opening during an inhalation phase of the patient's breathing cycle and allow air to exit the blower via the proximal opening during an exhalation phase of the patient's breathing cycle. The stator component may include a plurality of air directing grooves along its exterior surface, the leading edge of the air directing grooves extending tangentially outwards from the outer tips of the impeller blades and configured to collect the air exiting the impeller blades and direct it from a generally tangential direction to a generally radial direction by dividing the air from the impeller and directing the air along a curved path towards the distal opening so that airflow becomes substantially laminar. The ventilator may include a flow element provided to the motor along the flow path structured to measure flow in both directions and conduct heat from the motor. The housing and stator component may cooperate to define a plenum chamber around the impeller. The ventilator may include a chamber downstream from the plenum chamber to allow flow recirculation through the stator component without passing through the flow element. The ventilator may include a non-electrically conductive sleeve surrounding the central segment of the motor along the flow path. The flow element and the stator component may be constructed of heat conductive material to conduct heat from the motor. The flow element and the stator component may be constructed of aluminum. The ventilator may include a mucous trap provided to the distal opening of the blower. The mucous trap provides a capture plate adapted to capture any particulate matter expired by the patient. The ventilator may include a heat moisture exchange filter provided to the distal opening of the blower. The heat moisture exchange filter includes a filter and/or pad to condition air inhaled by the patient and/or protect the ventilator from particulate matter expired by the patient. The cross-sectional area of the flow path may be maximized and balanced with minimal deadspace within the ventilator to provide low source impedance. The ventilator may include a battery powered control unit separate from the ventilator. The ventilator and control unit may both include a micro-controller configured to record patient data and allow transfer of ventilator settings and patient details. The ventilator may be adapted for use at a location proximal to the patient. The ventilator may be incorporated into a headworn system. The ventilator may be adapted to be mounted to a structure including a wall, bed, bed head, wheelchair, table or chair, and connected via tubing to a patient interface. The ventilator may be adapted to fit into a support structure incorporated into clothing. The clothing may be a shirt, T-shirt, or pajamas. The ventilator blower may be built into a patient interface unit. The ventilator may be supported by a shoulder-type harness. The ventilator may be supported by a pendant-type arrangement. The ventilator may be supported by a strap or band around a part of the user's body. The strap or band may be a chest band. The strap or band may be an arm band. The flow element may include an inner core and a plurality of vanes extending from the inner core. The flow element may include 40-60 vanes. The inner core of the flow element may include a split configuration structured to allow the flow element to be fit around the motor and to expand and contract with changes in heat from the motor.

Another aspect of the invention relates to a modular ventilator system including a ventilator module and one or more of the following individually replaceable modules: a control module to remotely control the ventilator module; an extension battery module for the control module; an oxygen enhancement module provided to the ventilator module; a mucous trap module provided to a distal opening of the ventilator module; a heat moisture exchange filter module provided to a distal opening of the ventilator module; and/or a strap module including one or more straps to stabilize the ventilator module and/or the control module. The control module may include an internal accelerometer and allow a pulse oximeter and/or a $CO_2$ monitor to be connected thereto.

One aspect of the invention relates to a blower including a housing including a proximal opening and a distal opening that are co-axially aligned, a stator component provided to the housing, an impeller positioned between the proximal opening of the housing and the stator component, and a motor adapted to drive the impeller. The impeller includes a plurality of impeller blades. The stator component includes a plurality of air directing grooves along its exterior surface. The leading edge of the air directing grooves extend tangentially outwards from the outer tips of the impeller blades and are configured to collect the air exiting the impeller blades and direct it from a generally tangential direction to a generally radial direction by dividing the air from the impeller and directing the air along a curved path towards the distal opening so that airflow becomes substantially laminar.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 93 is a perspective view of an air outlet membrane valve of the filter/valve assembly according to an embodiment of the invention;

FIG. 94-96 are side, top, and bottom views of the air outlet membrane valve of FIG. 93;

FIG. 103 is a perspective view of an inner case of the mucous trap according to an embodiment of the invention;

FIGS. 104-107 are top, bottom, front, and side views of inner case of FIG. 103;

FIG. 121 is a perspective view of an inner casing of the HMEF according to an embodiment of the invention;

FIGS. 122-124 are top, bottom, and side views of the inner casing of FIG. 121;

FIG. 125 is a cross-sectional view of the inner casing of FIG. 121;

FIG. 135-1 is a perspective view of a remote or handset for the ventilator system according to an embodiment of the invention;

FIG. 135-2 is a perspective view of an optional extension battery for the handset of FIG. 135-1;

FIG. 135-3 is a perspective view of the handset of FIG. 135-1 coupled to the extension battery of FIG. 135-2;

FIG. 136 is a top view of the handset of FIG. 135-1;

FIGS. 144-1 to 144-3 show a headworn ventilator system according to an embodiment of the invention;

FIGS. 146-1 to 146-4 show a headworn ventilator system according to an embodiment of the invention;

FIGS. 151-1 to 151-3 show a headworn ventilator system according to an embodiment of the invention;

FIGS. 152-1 and 152-2 show a headworn ventilator system according to an embodiment of the invention;

FIGS. 160-1 and 160-2 show a patient interface with a built-in blower according to an embodiment of the invention;

FIGS. 161-1 and 161-2 show a patient interface with a built-in blower according to an embodiment of the invention;

FIGS. 162-1 and 162-2 show a patient interface with a built-in blower according to an embodiment of the invention;

FIGS. 163-1 and 163-2 show a patient interface with a built-in blower according to an embodiment of the invention;

FIGS. 164-1 to 164-3 shows a patient interface with a built-in blower according to an embodiment of the invention;

FIG. 165 shows a patient interface with a built-in blower according to an embodiment of the invention;

FIG. 166 shows a patient interface with a built-in blower according to an embodiment of the invention;

FIG. 167 shows a patient interface with a built-in blower according to an embodiment of the invention;

FIGS. 168-1 and 168-2 show a patient interface with a built-in blower according to an embodiment of the invention;

FIG. 169 shows a patient interface with a built-in blower according to an embodiment of the invention;

FIG. 170 shows a patient interface with a built-in blower according to an embodiment of the invention;

FIG. 171 shows a patient interface with a built-in blower according to an embodiment of the invention;

FIG. 172 shows a patient interface with a built-in blower according to an embodiment of the invention;

FIG. 173 shows a patient interface with a built-in blower according to an embodiment of the invention;

FIG. 174 shows a patient interface with a built-in blower according to an embodiment of the invention;

FIG. 175 shows a patient interface with a built-in blower according to an embodiment of the invention;

Figure 1:
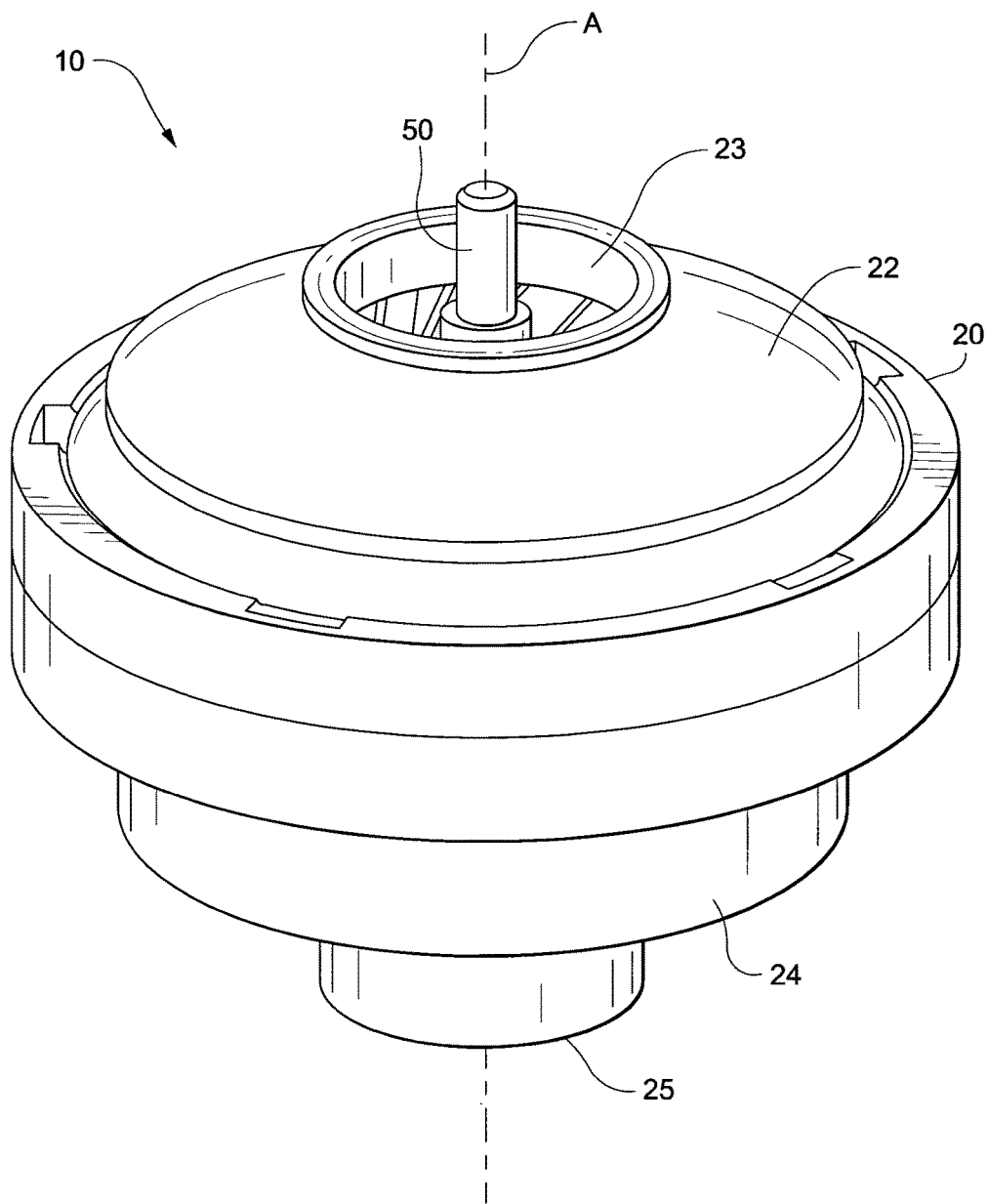
FIG. 1 is a perspective view of a blower according to an embodiment of the present invention.
Figure 2:
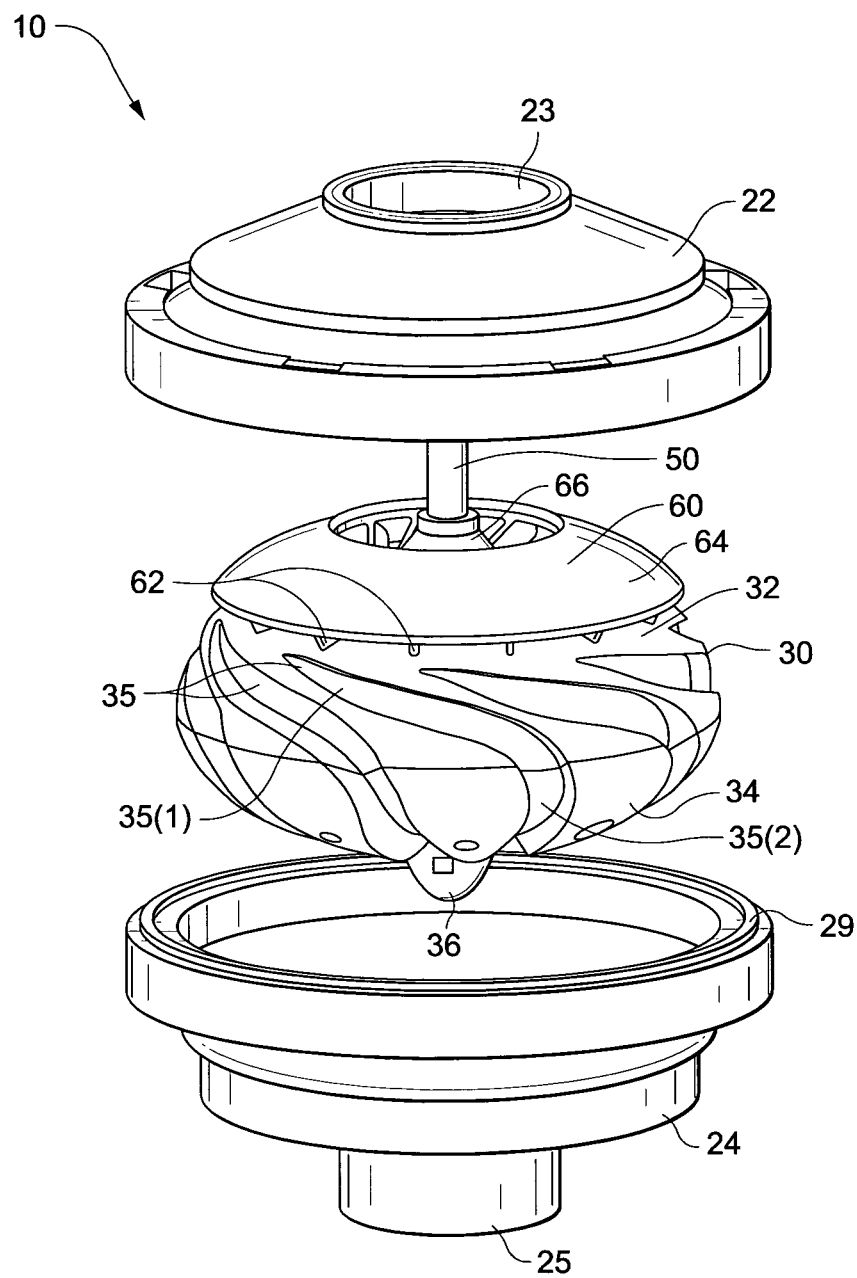
FIG. 2 is an exploded view of the blower of FIG. 1.
Figure 3:
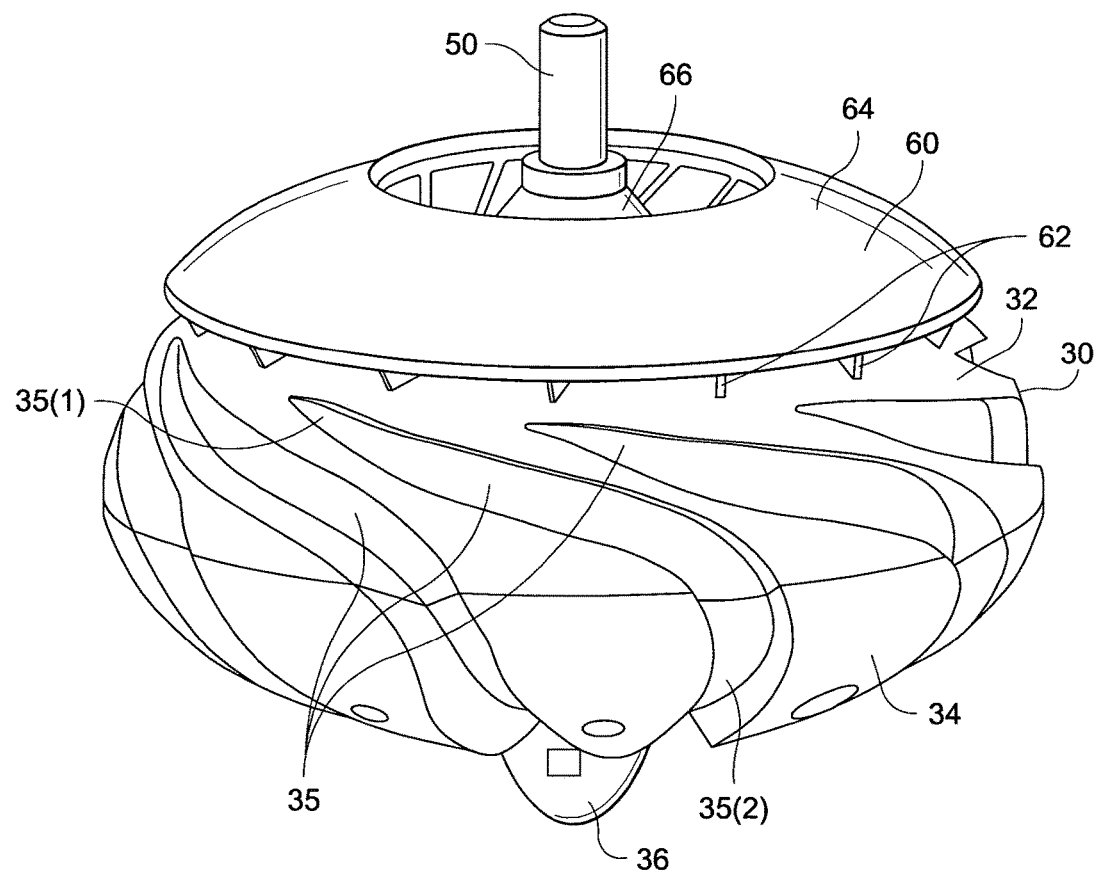
FIG. 3 is a perspective view of the stator component and impeller of the blower of FIG. 1.
Figure 4:
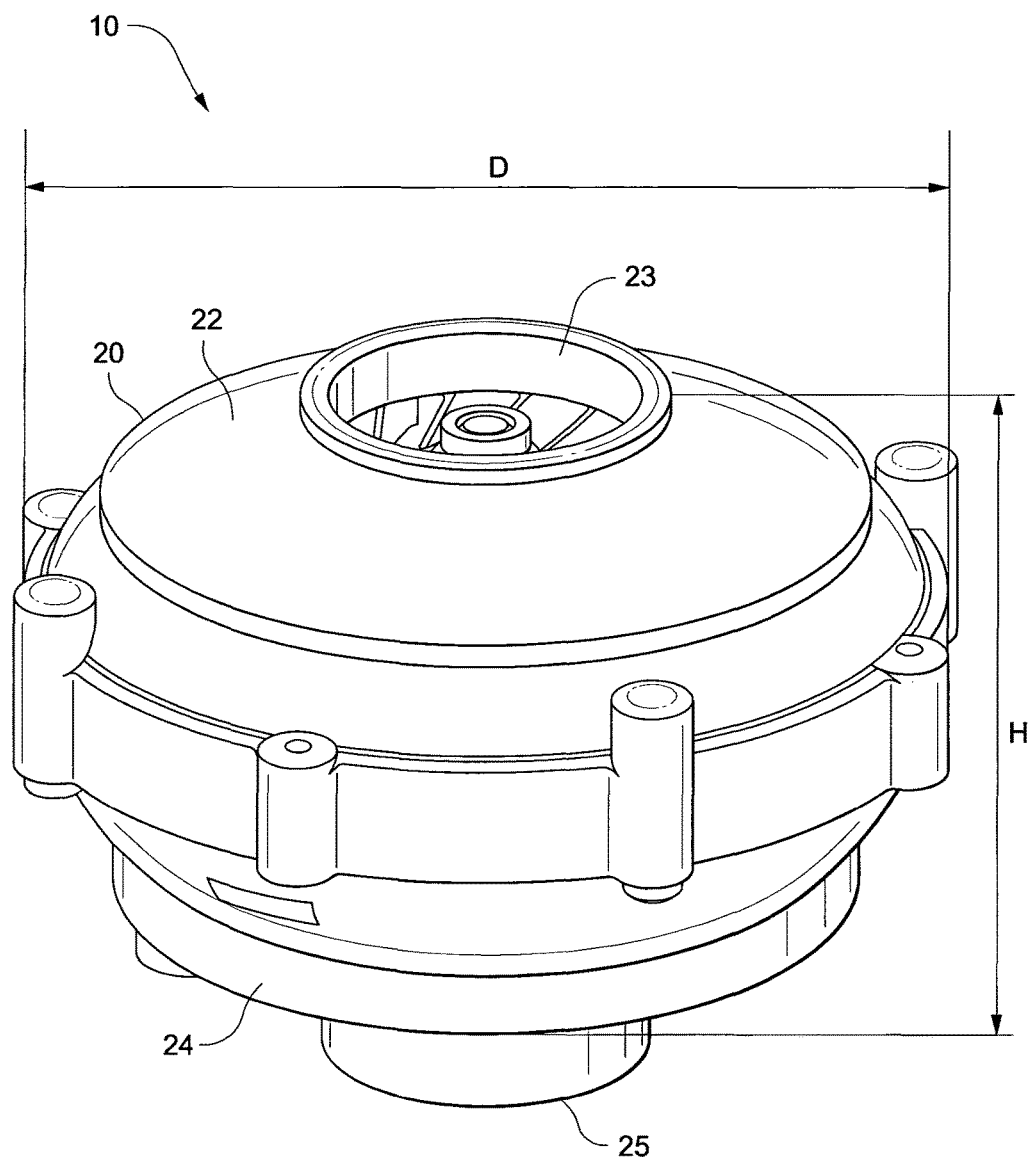
FIG. 4 is a perspective view of a blower according to another embodiment of the present invention.
Figure 176:
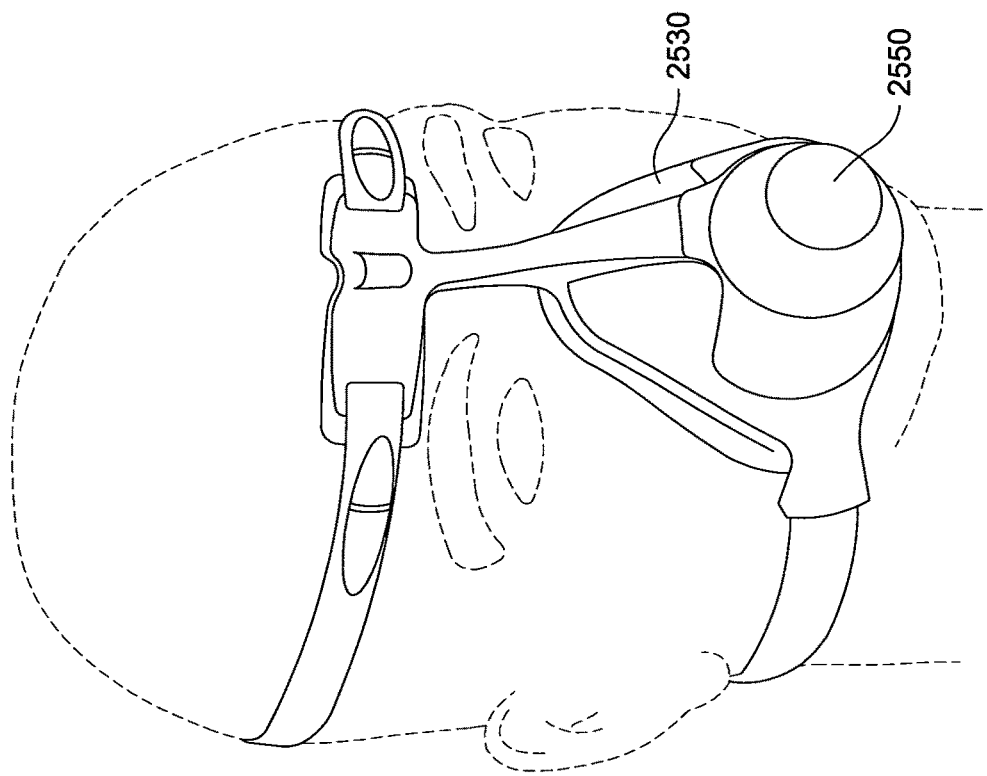
Figure 175:
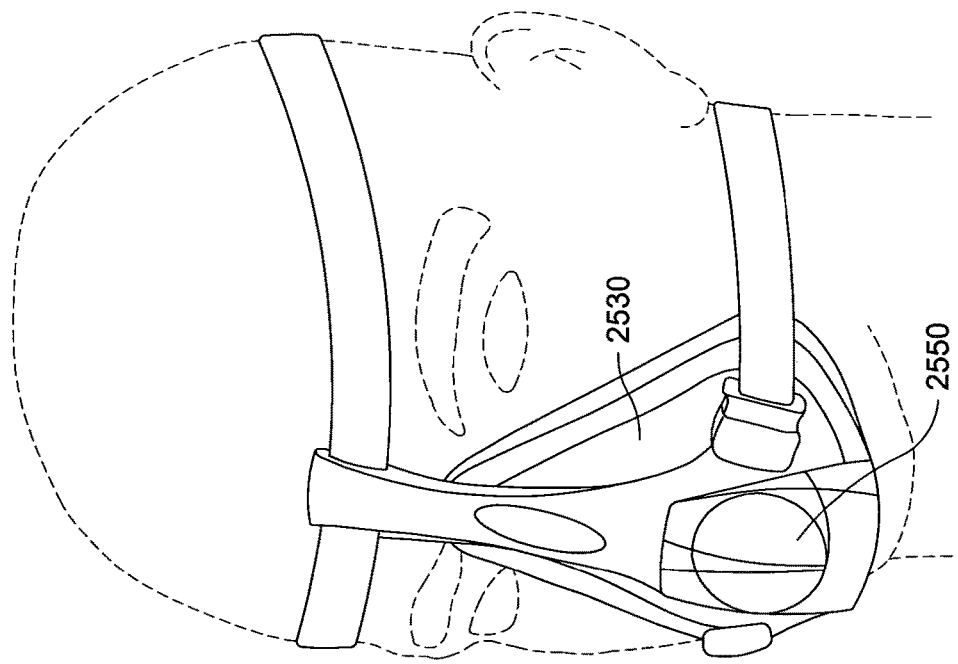
Figure 177:
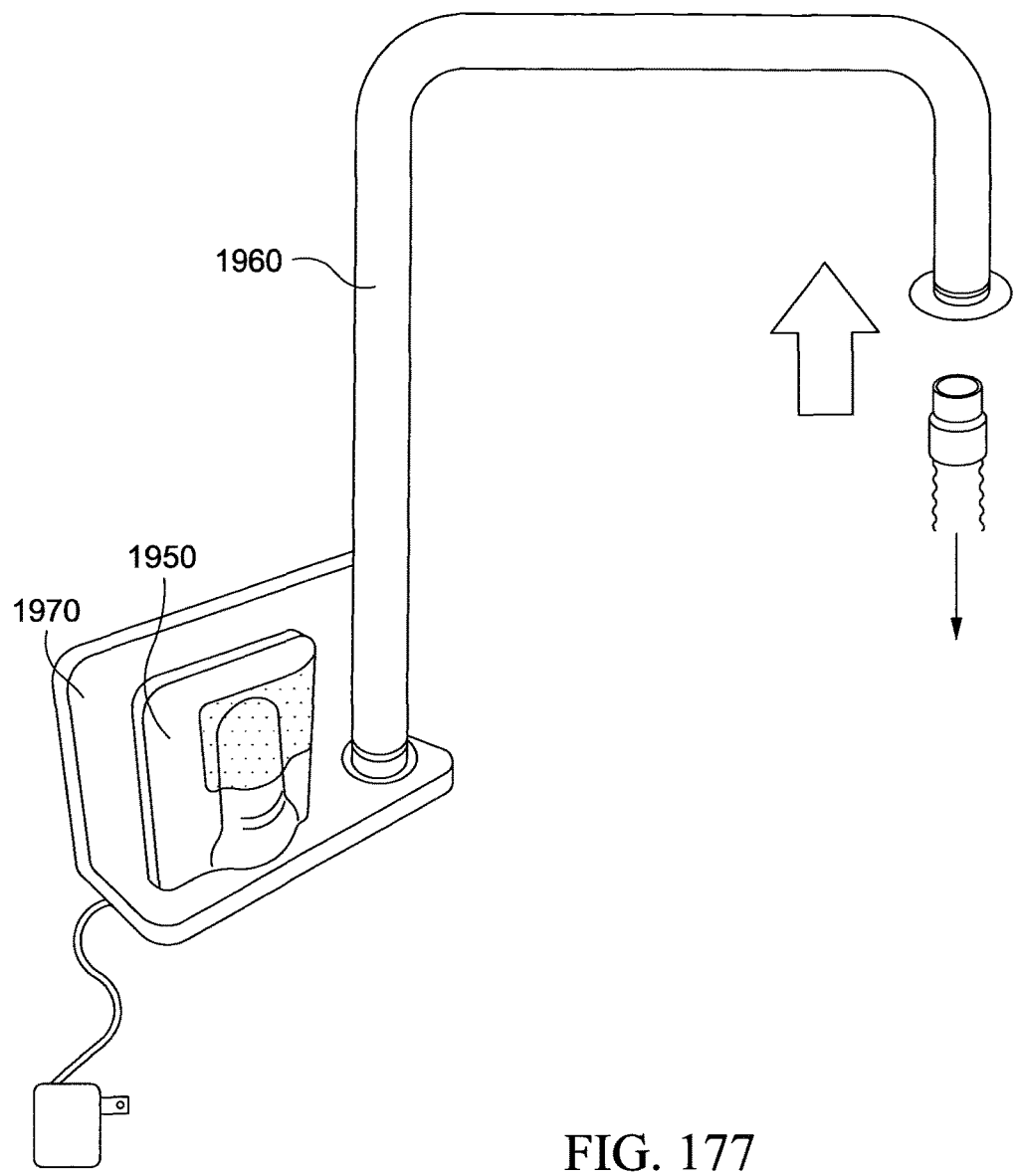
Figure 178:
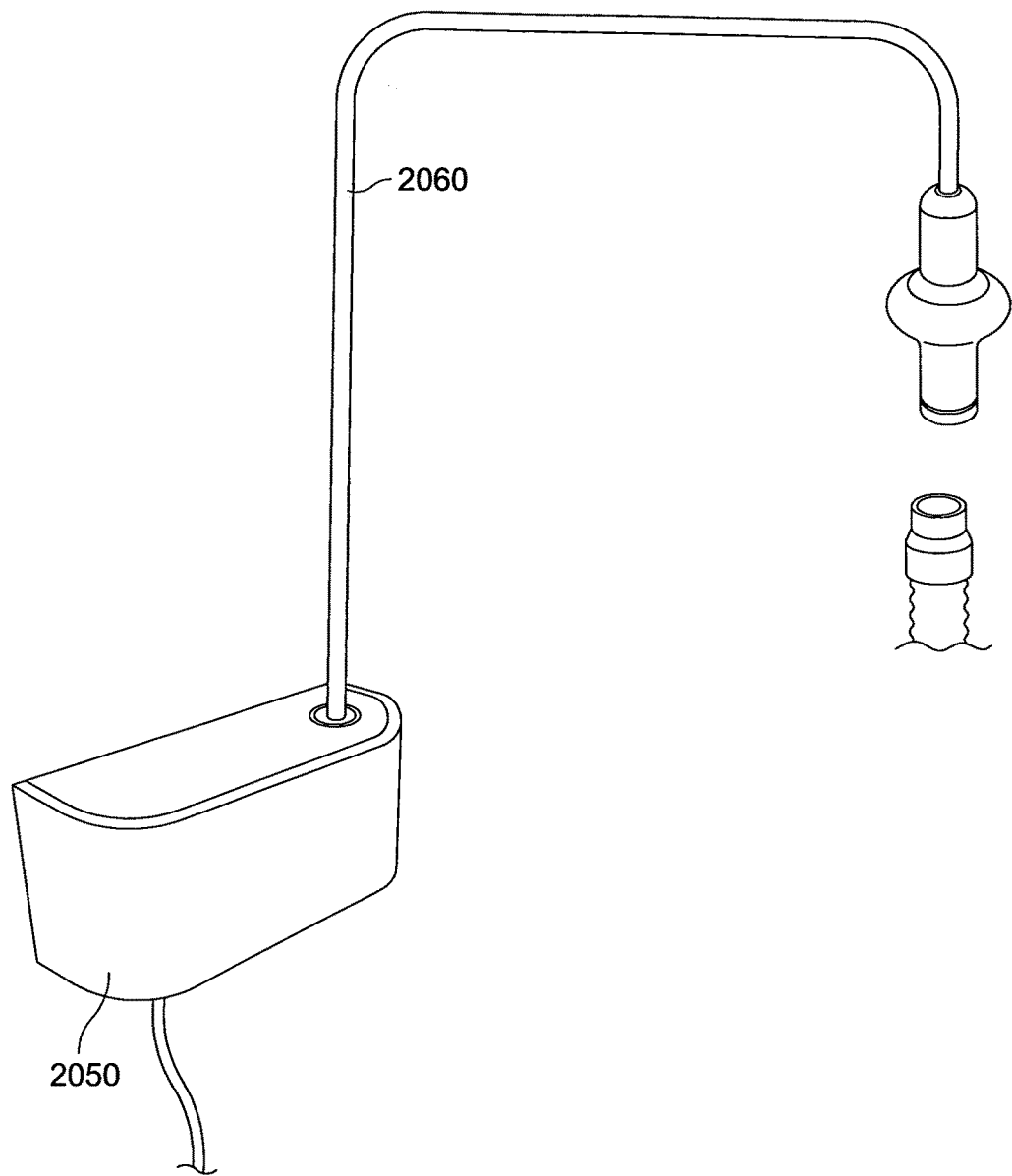
Figure 179:
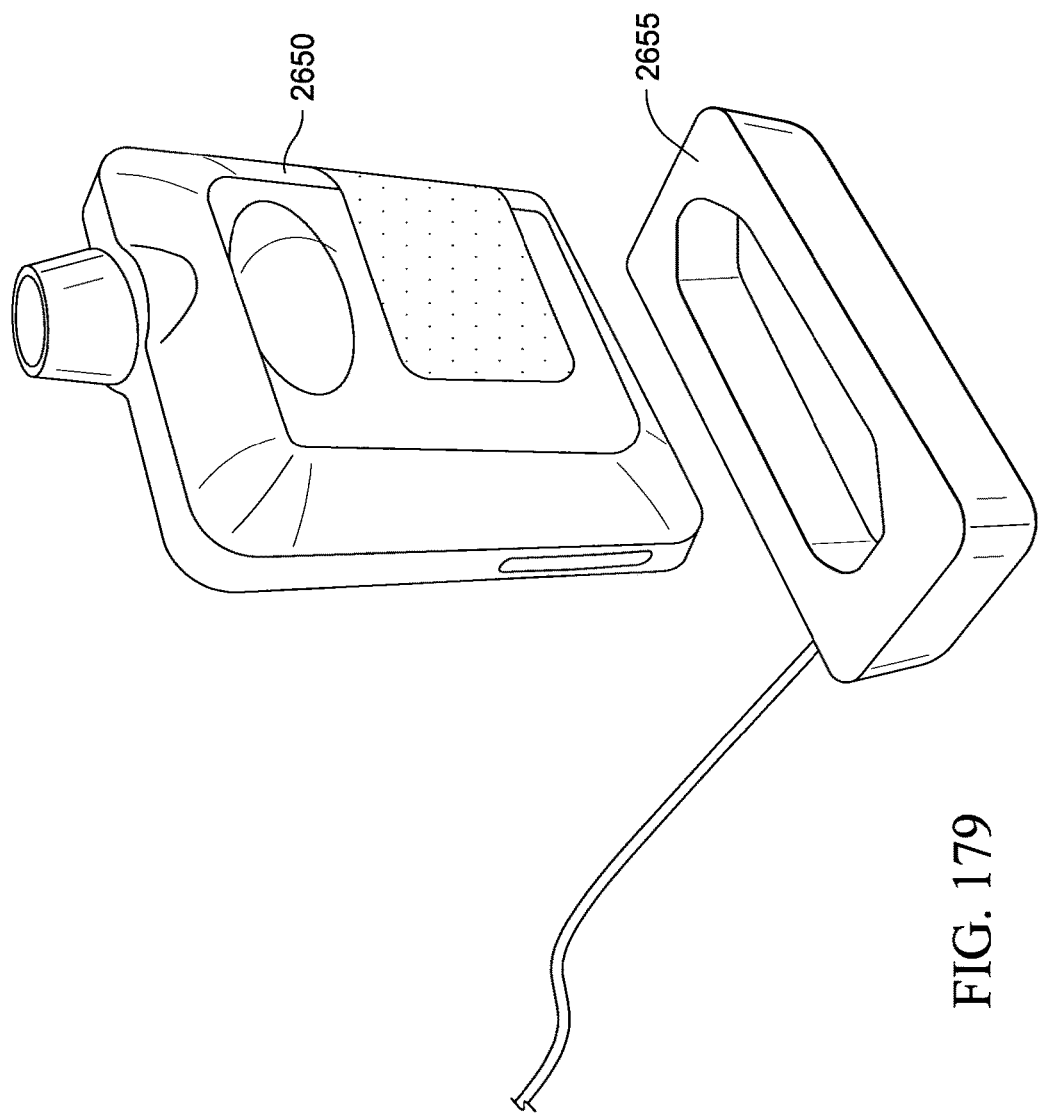
Figures 1, 180:
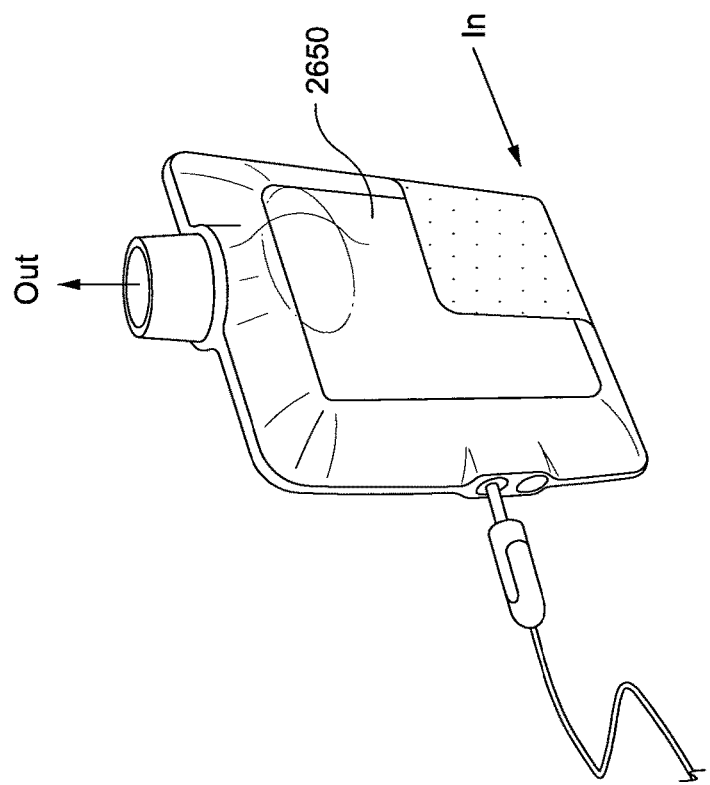
Figures 2, 180:
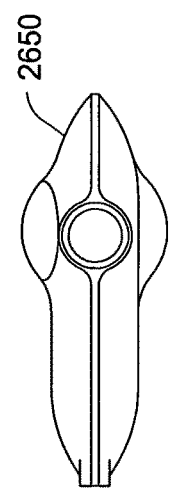
Figures 1, 181:
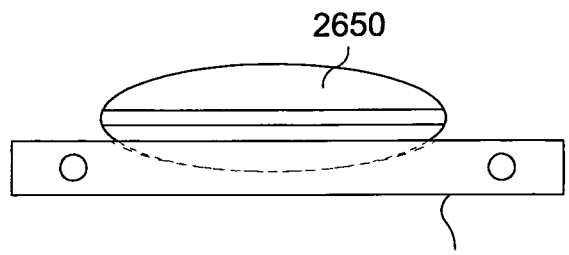
Figures 2, 181:
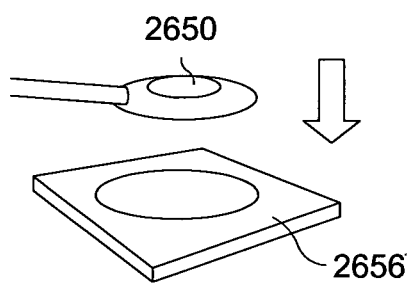
Figures 3, 181:
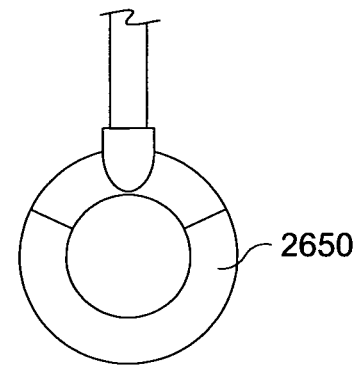
Figures 4, 181:
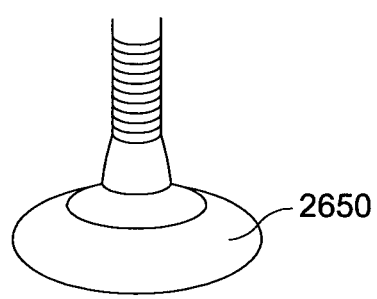
Figure 182:
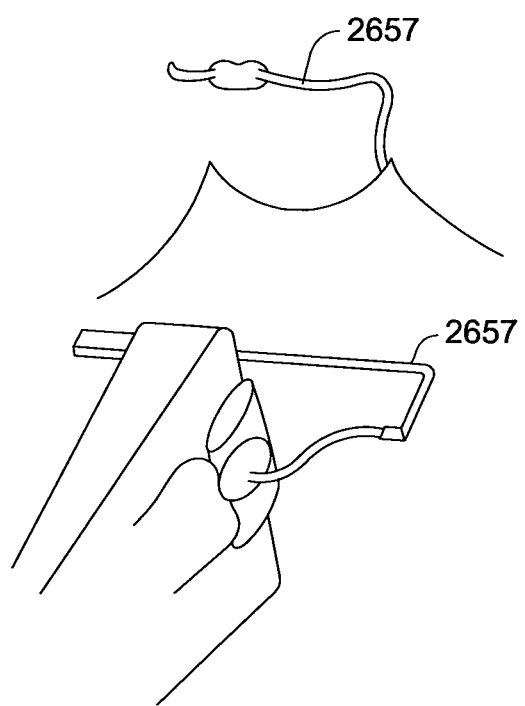
Figure 183:
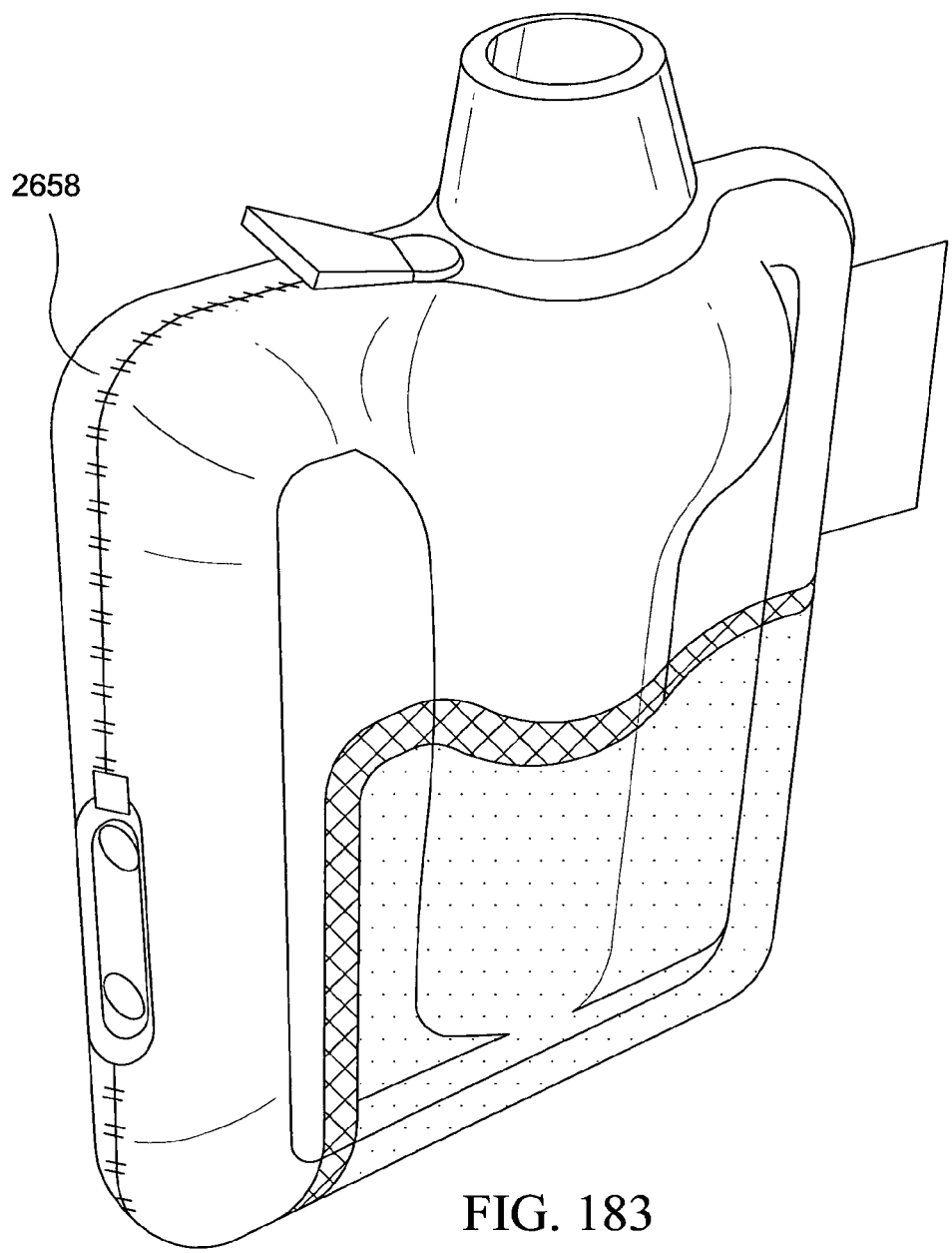
Figure 184:
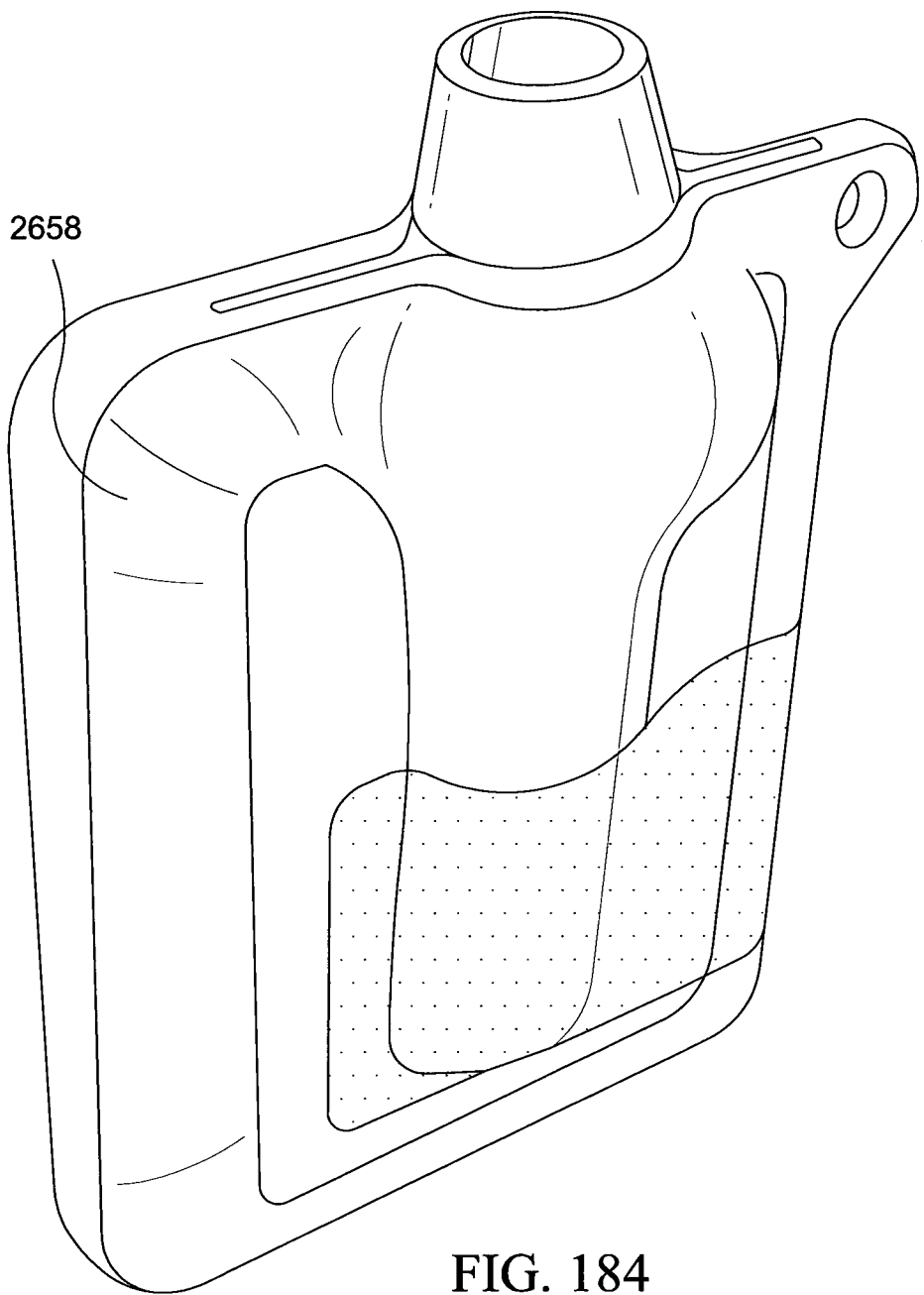
Figure 185:
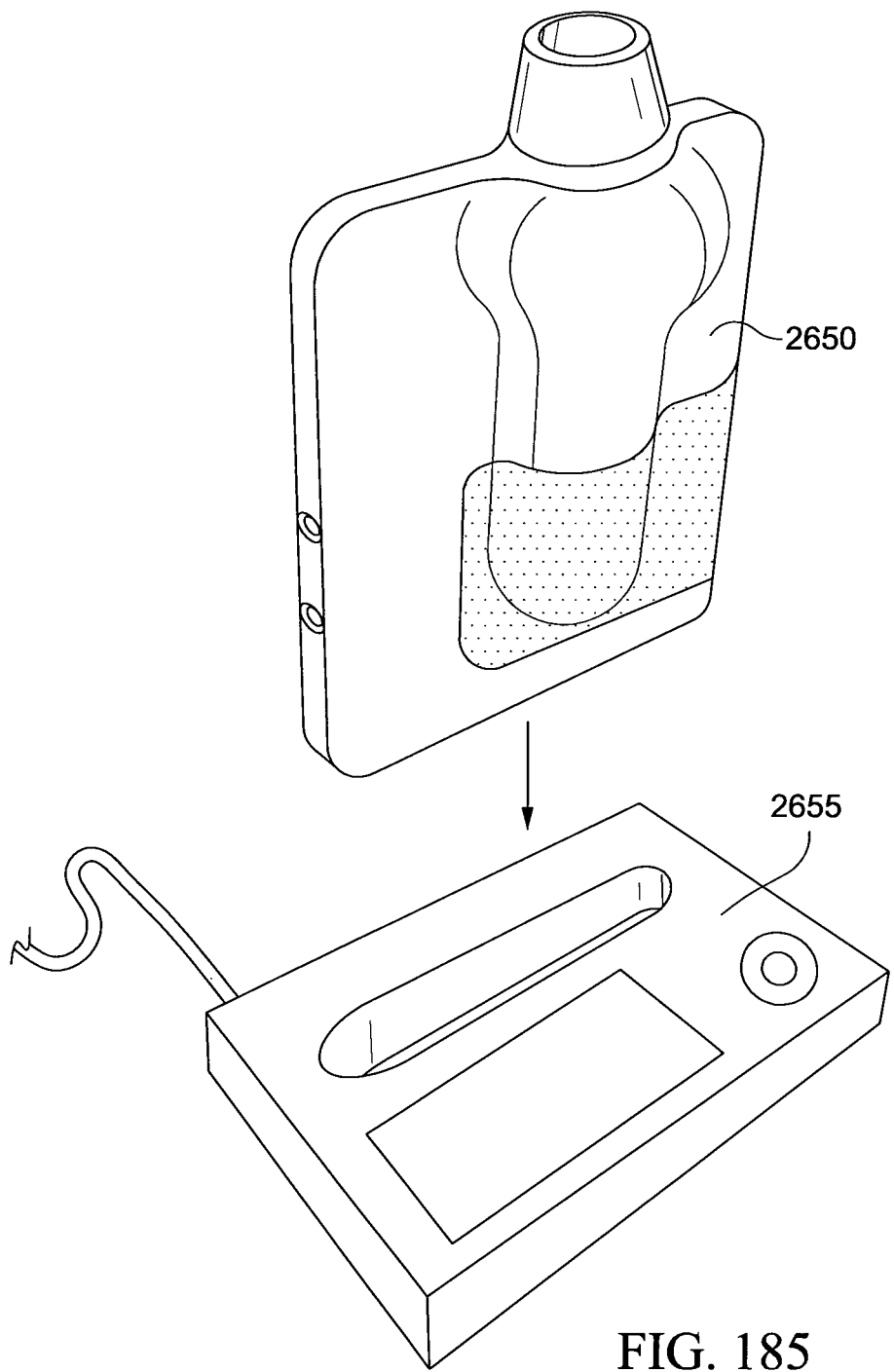
Figure 186:
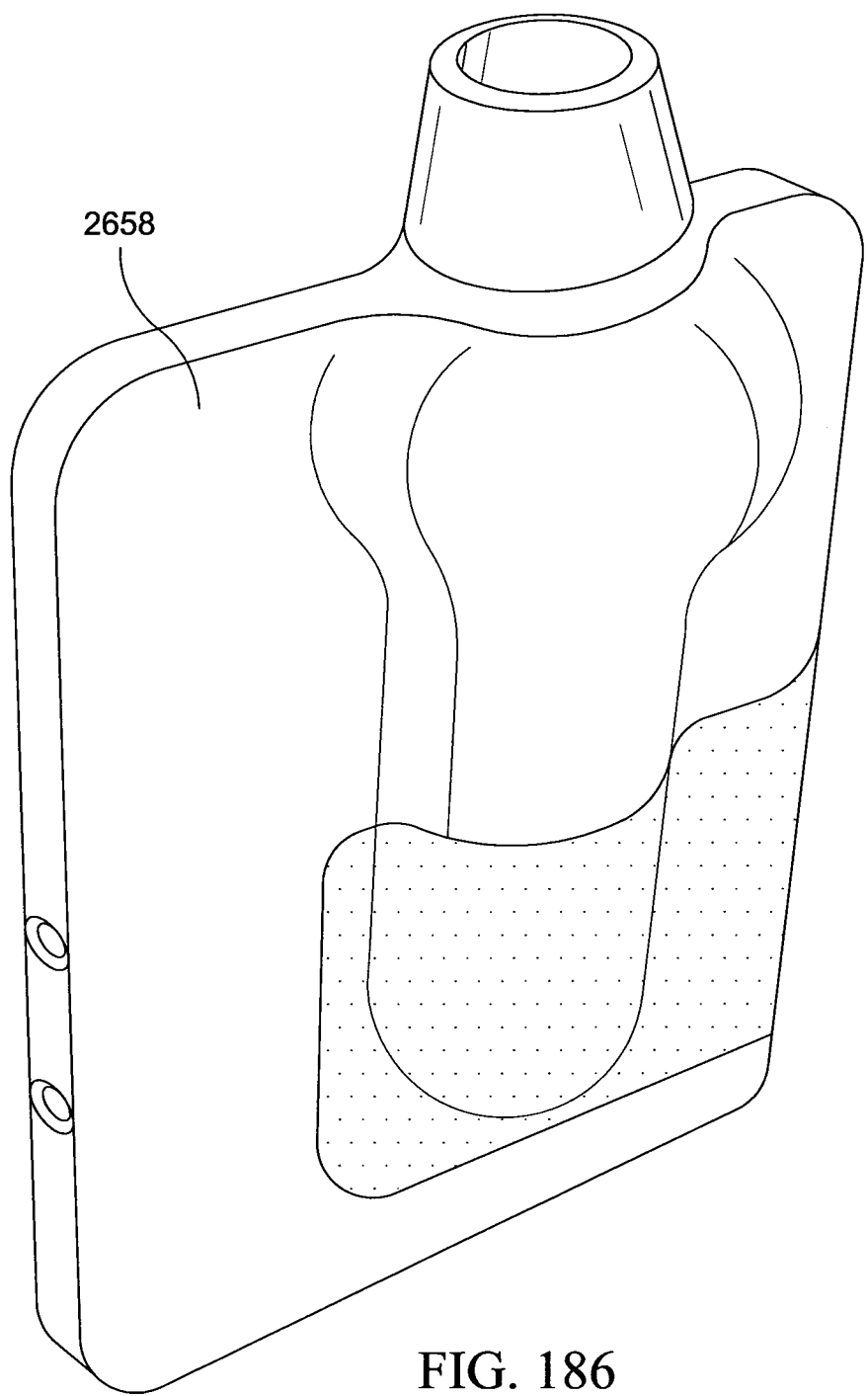
Figures 1, 187:
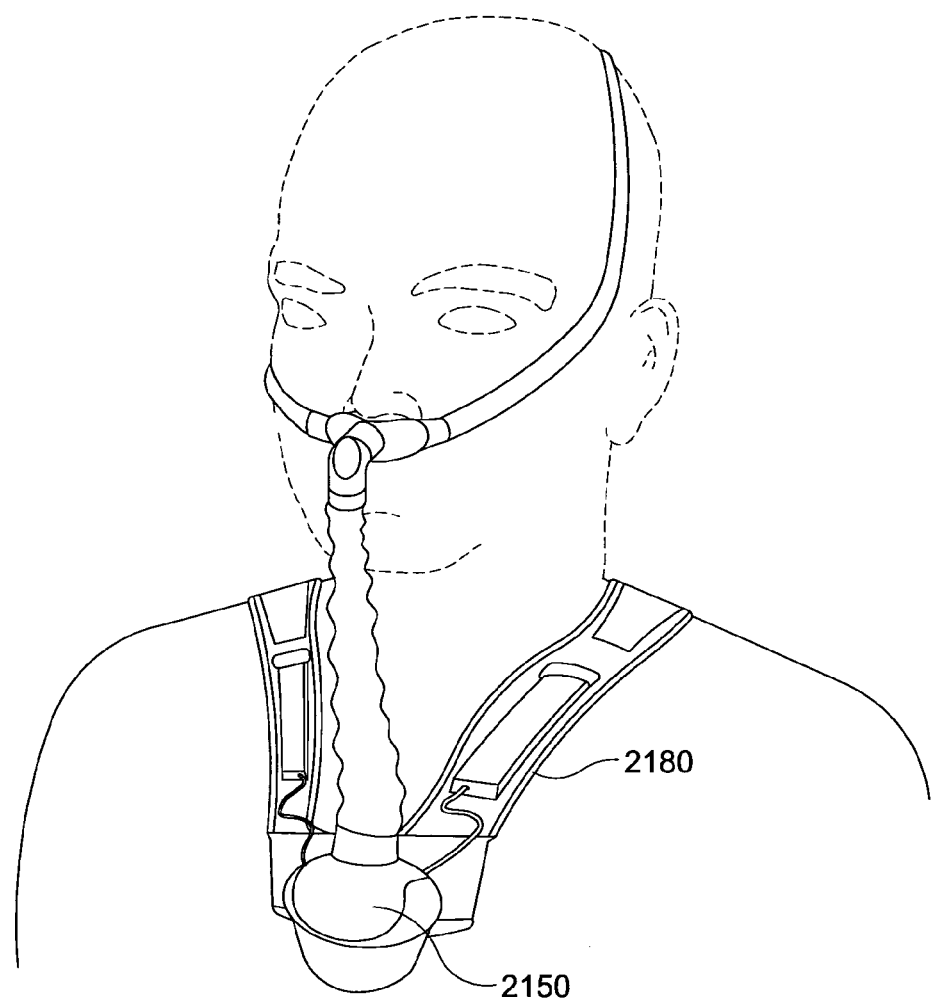
Figures 2, 187:
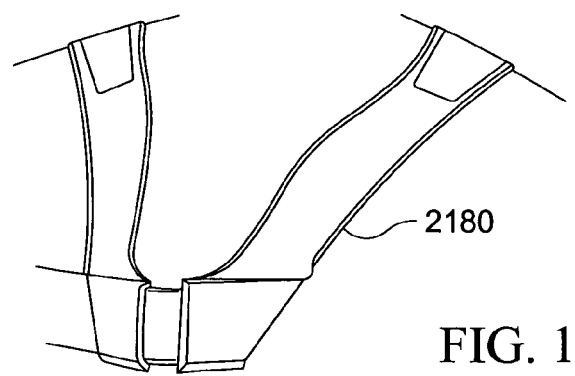
Figures 3, 188:
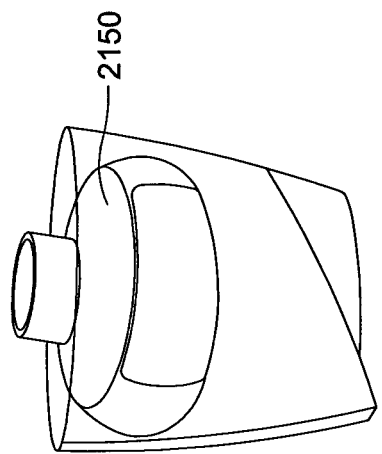
Figures 4, 188:
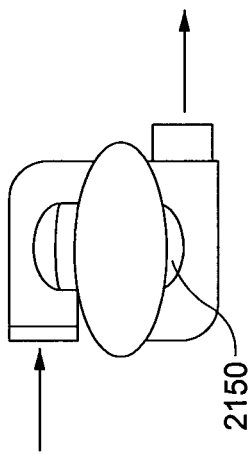
Figures 2, 188:
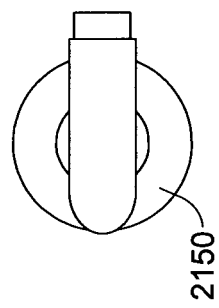
Figures 1, 188:
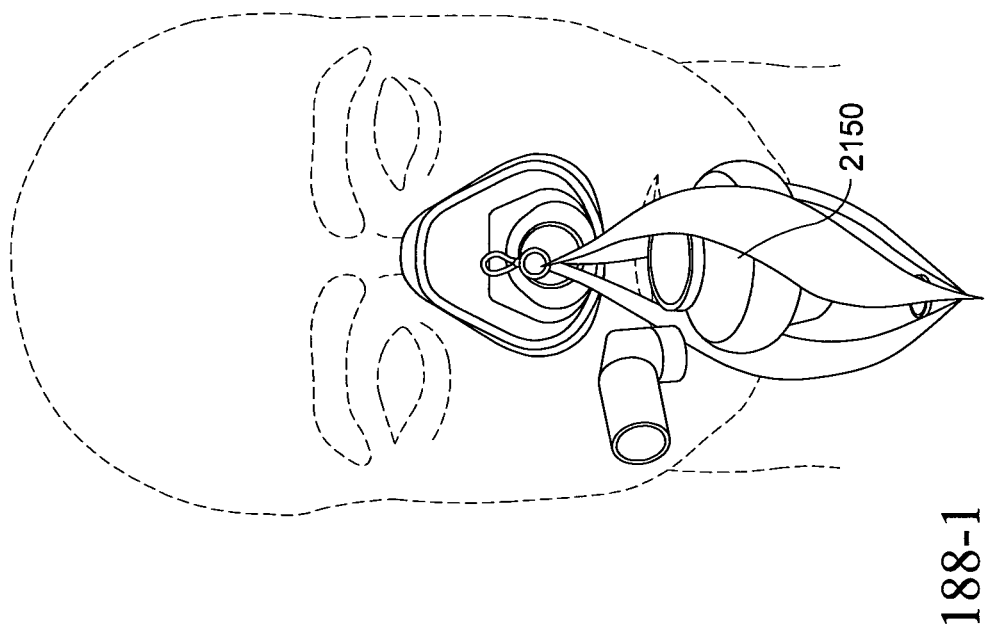
Figures 3, 189:
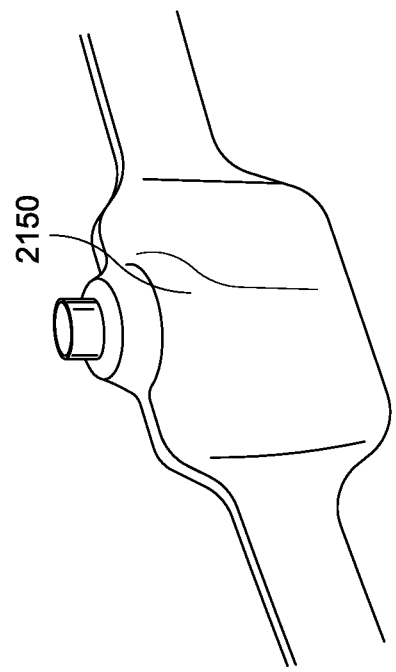
Figures 1, 189:
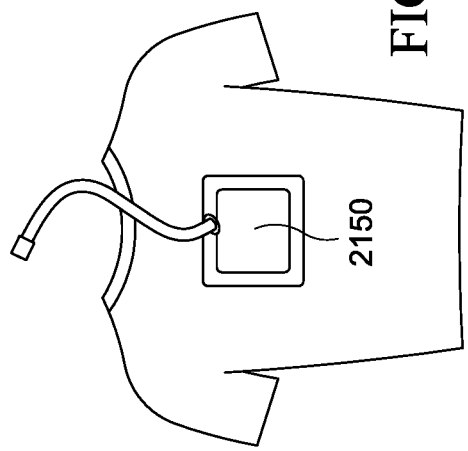
Figures 2, 189:
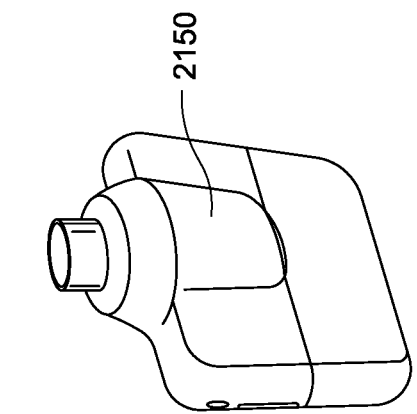
Figure 191:
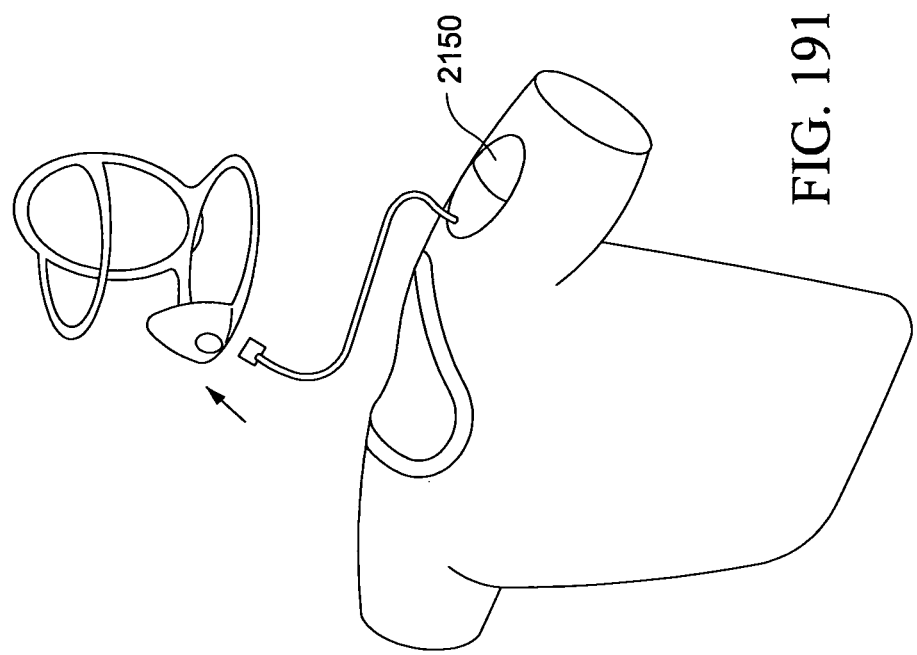
Figure 190:
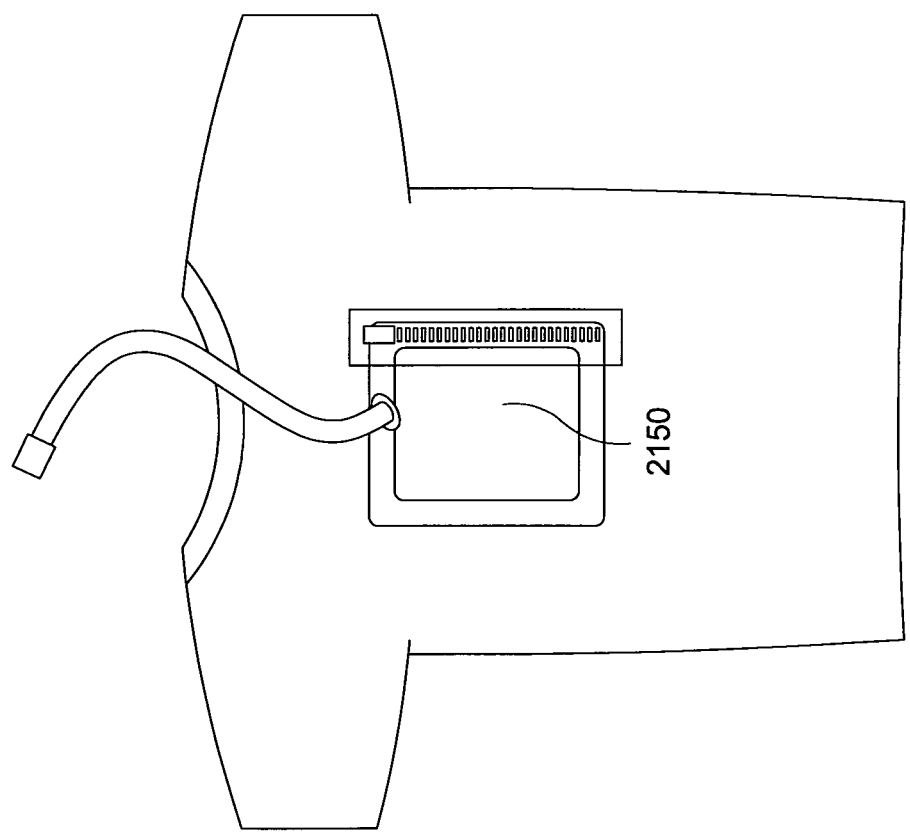
Figures 1, 2, 192:
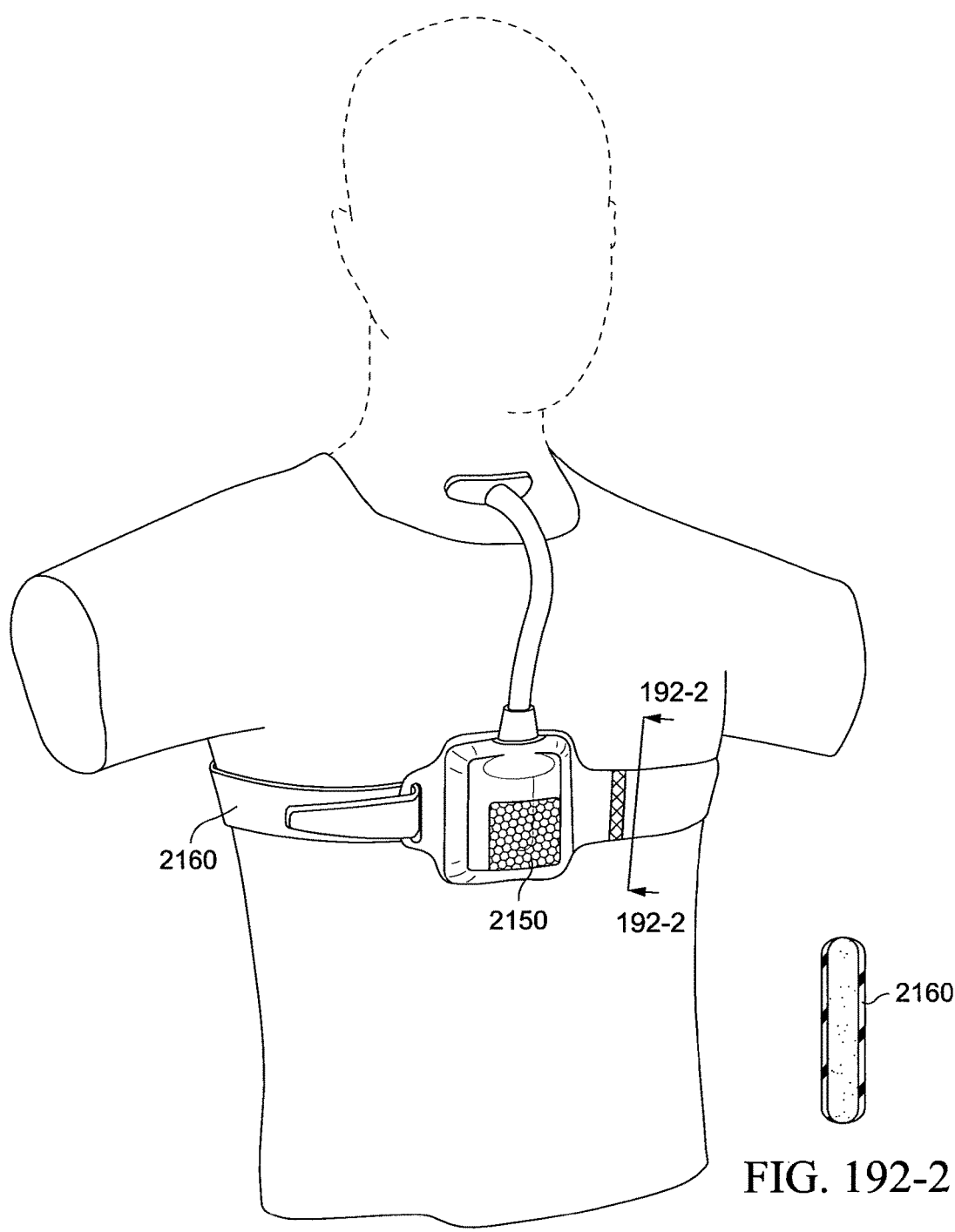
Figure 193:
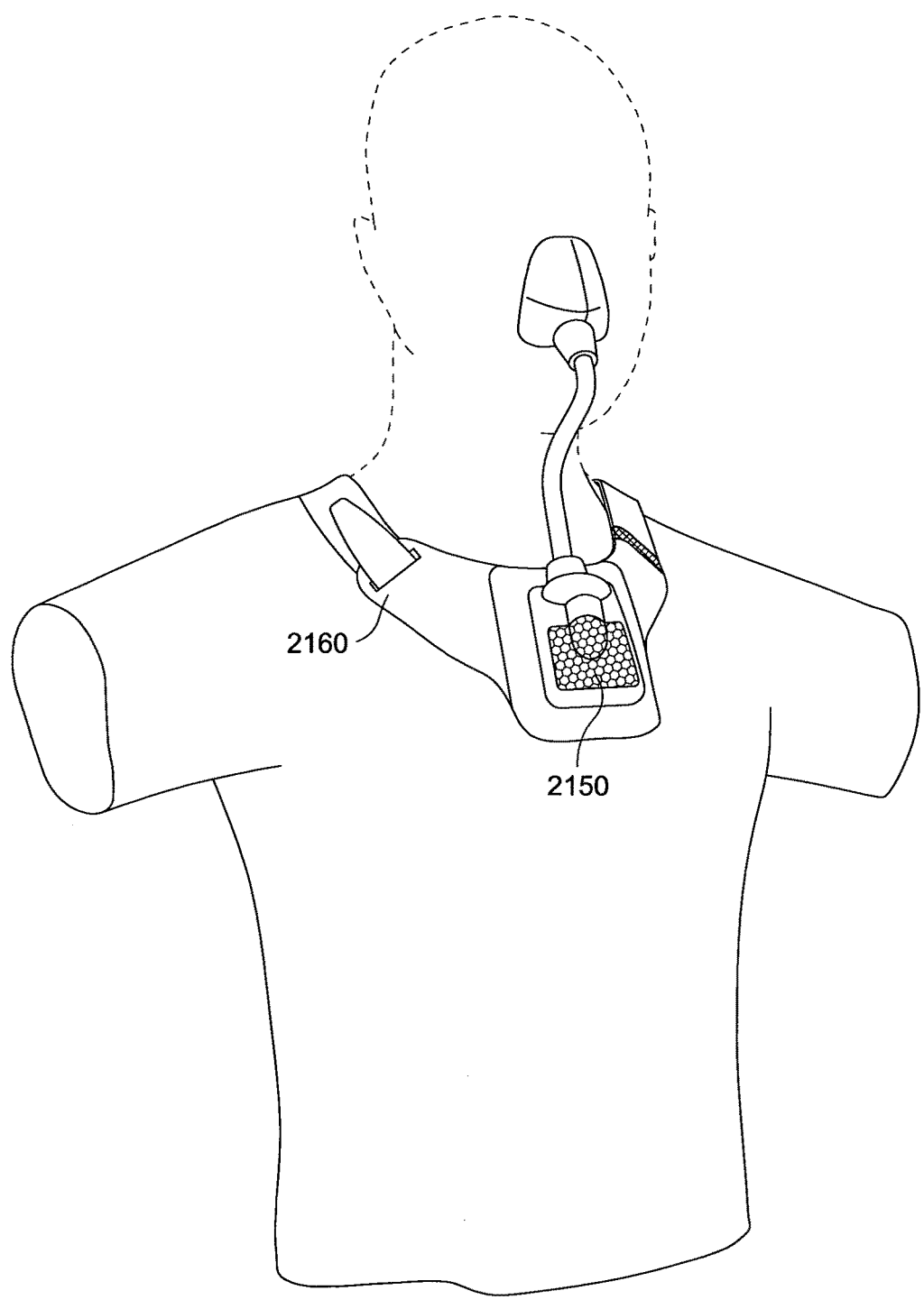
Figure 194:
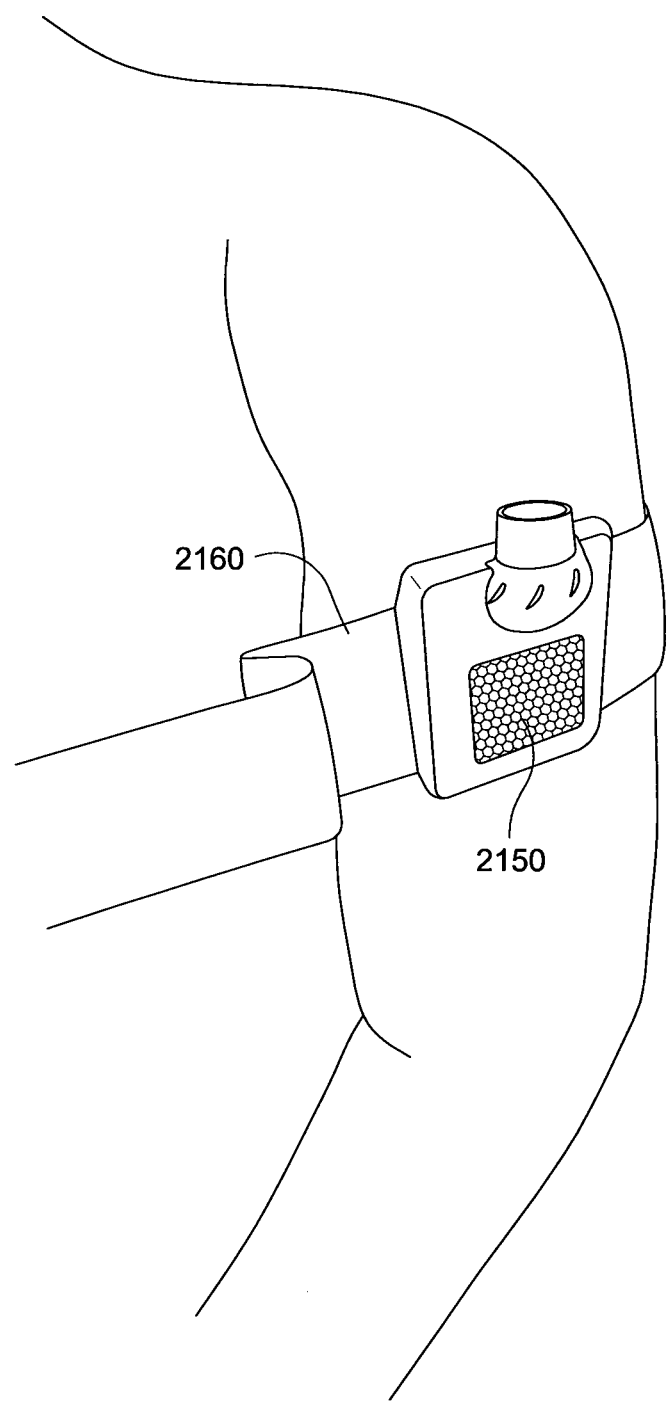
Figure 195:
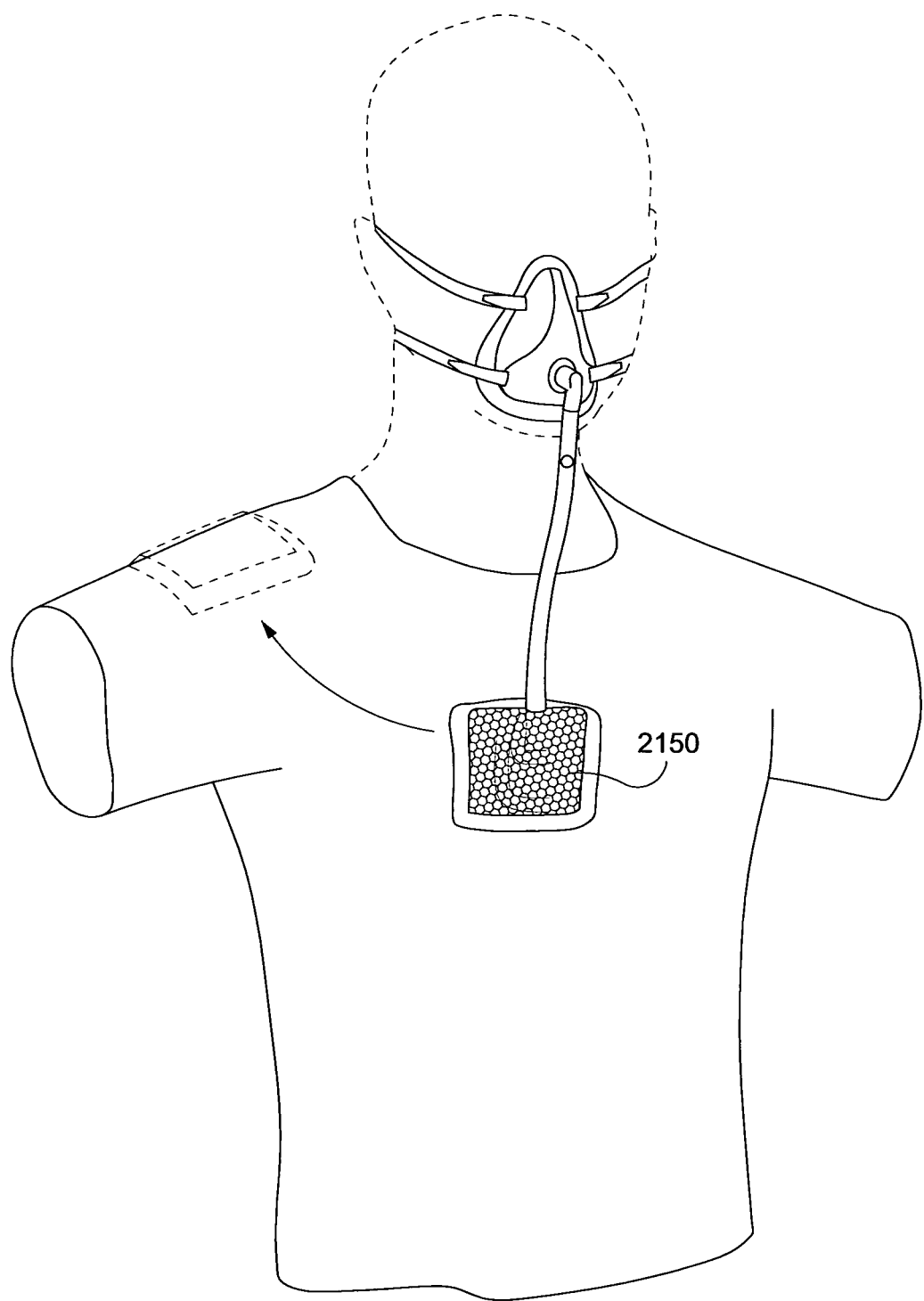
Figure 196:
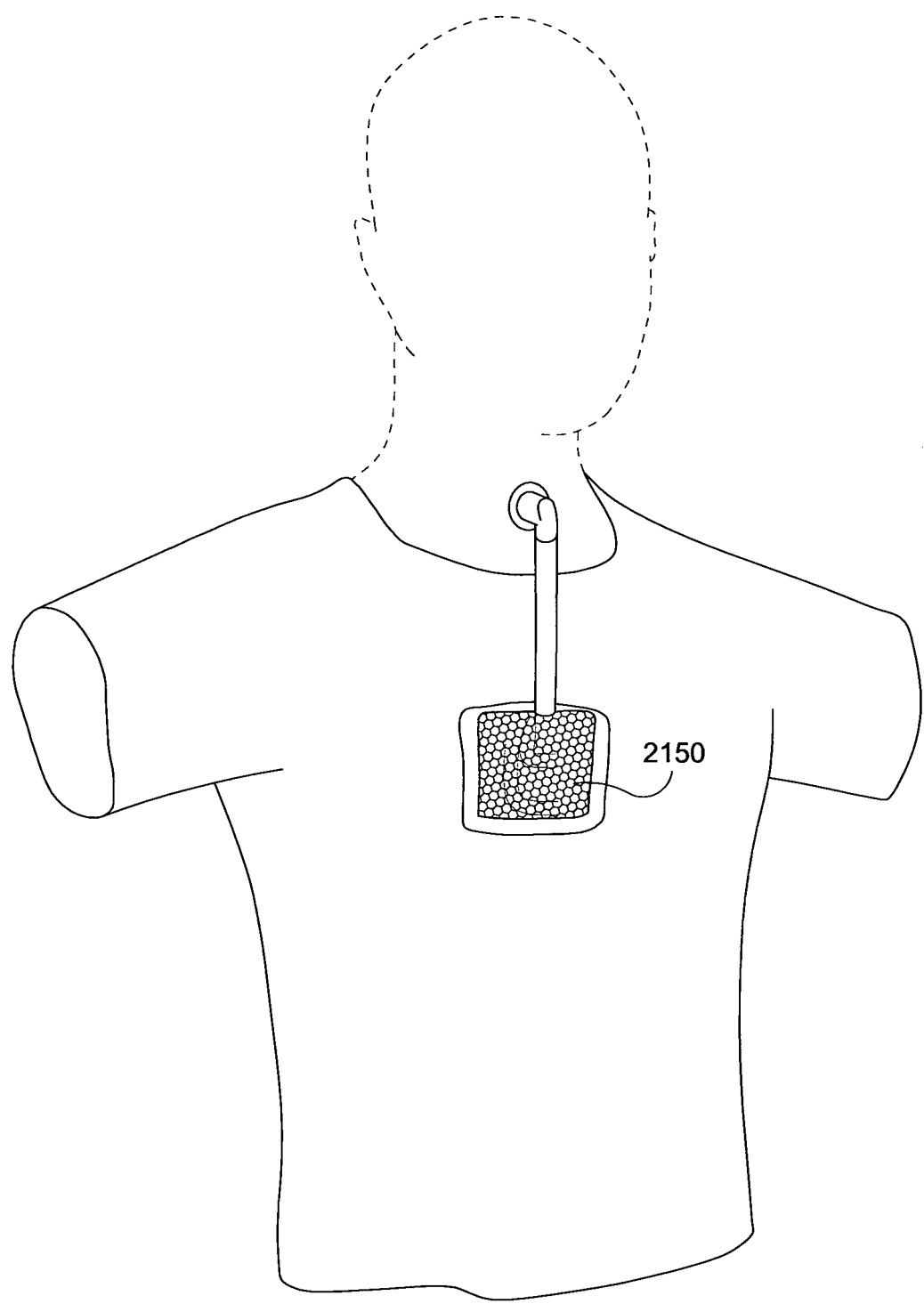
Figure 197:
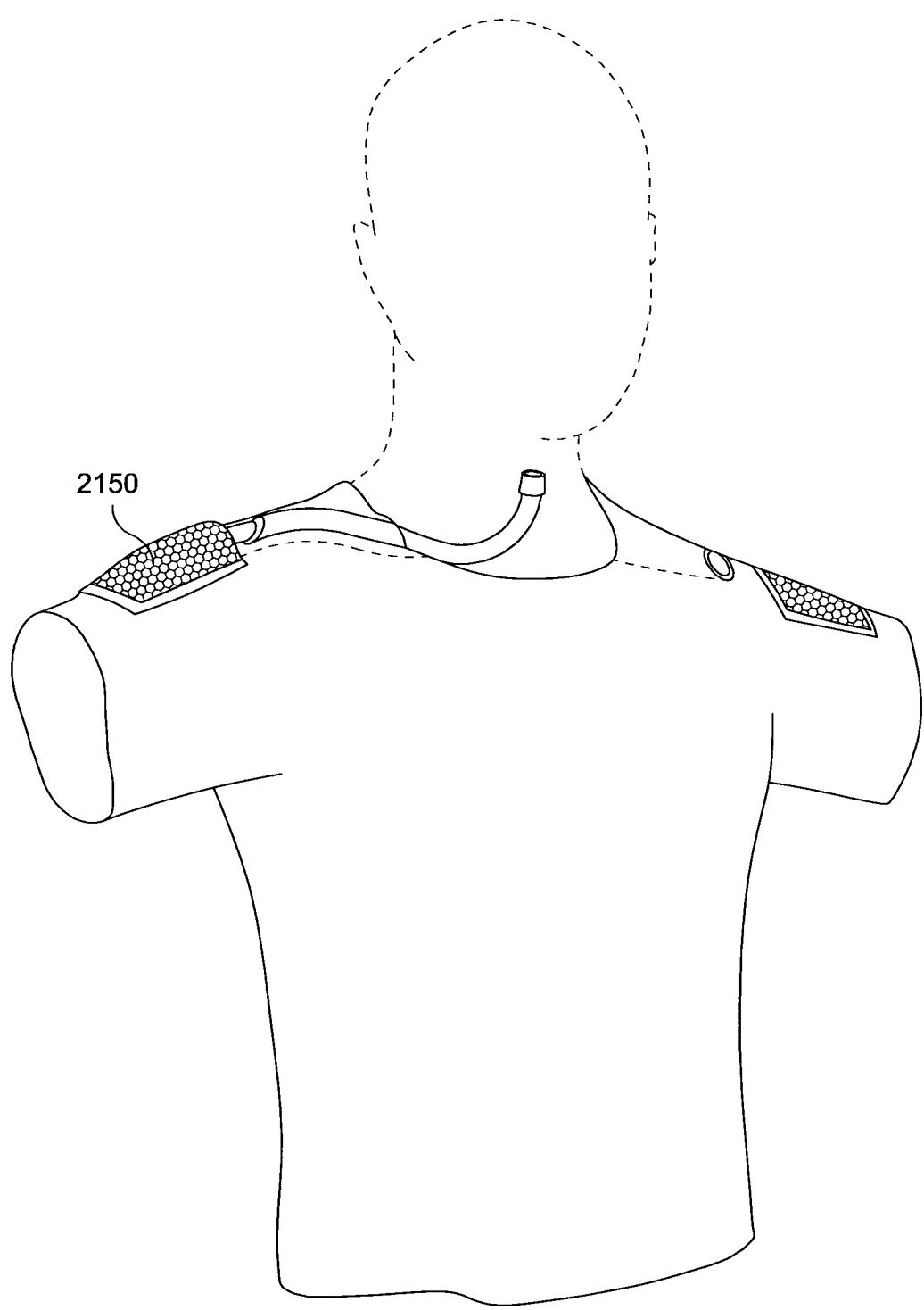
Figures 1, 198:
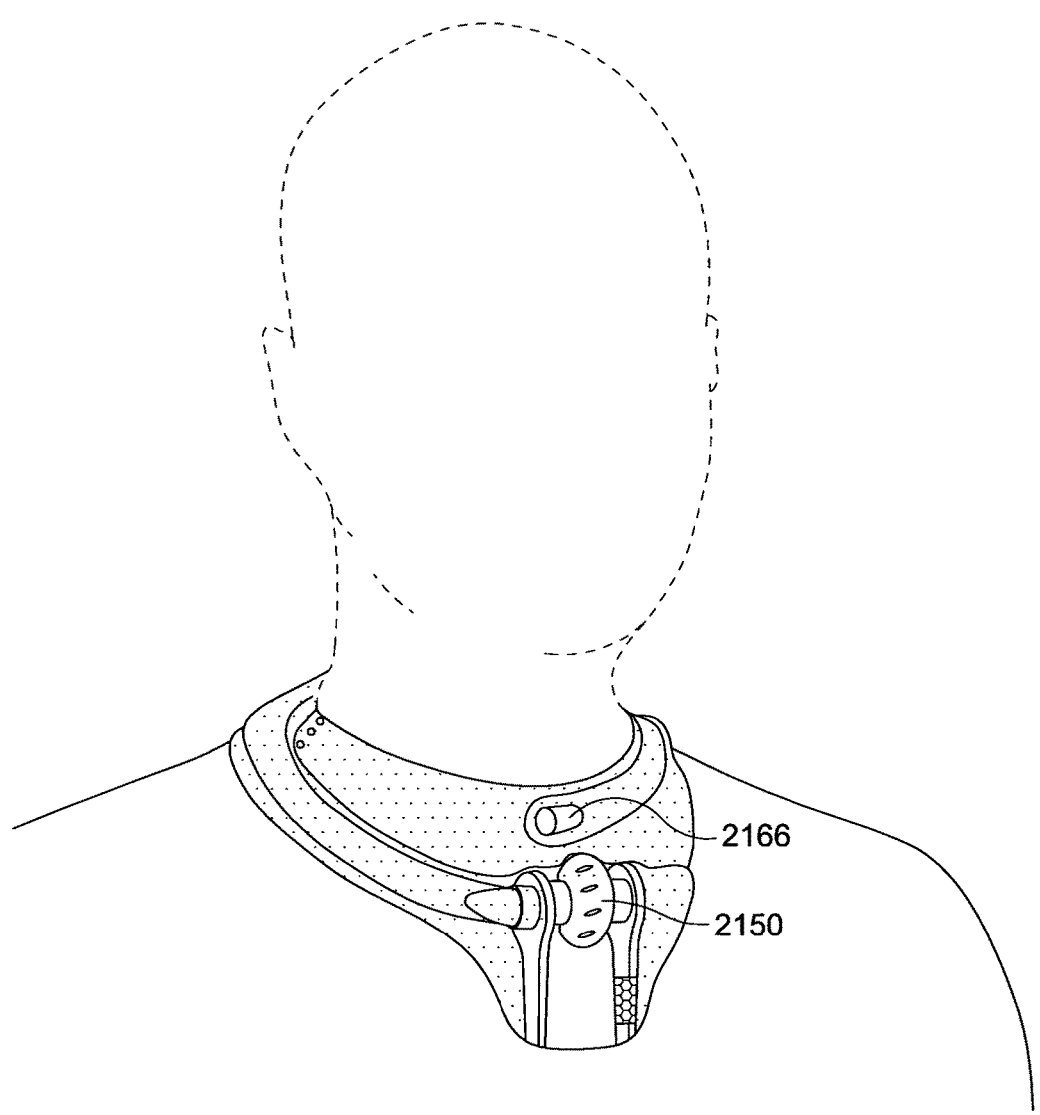
Figures 2, 198:
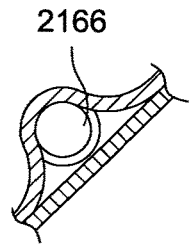

FIG. 176 shows a patient interface with a built-in blower according to an embodiment of the invention;

FIG. 177 shows a portable ventilator according to an embodiment of the invention;

FIG. 178 shows a portable ventilator according to an embodiment of the invention;

FIG. 179 shows a portable ventilator according to an embodiment of the invention;

FIGS. 180-1 and 180-2 show a portable ventilator according to an embodiment of the invention;

FIGS. 181-1 to 181-4 show a portable ventilator according to an embodiment of the invention;

FIG. 182 shows light-up tubing according to an embodiment of the invention;

FIG. 183 shows a portable ventilator according to an embodiment of the invention;

FIG. 184 shows a portable ventilator according to an embodiment of the invention;

FIG. 185 shows a portable ventilator according to an embodiment of the invention;

FIG. 186 shows a portable ventilator according to an embodiment of the invention;

FIGS. 187-1 and 187-2 show a wearable ventilator according to an embodiment of the invention;

FIGS. 188-1 to 188-4 show a wearable ventilator according to an embodiment of the invention;

FIGS. 189-1 to 189-3 shows a wearable ventilator according to an embodiment of the invention;

FIG. 190 shows a wearable ventilator according to an embodiment of the invention;

FIG. 191 shows a wearable ventilator according to an embodiment of the invention;

FIGS. 192-1 and 192-2 show a wearable ventilator according to an embodiment of the invention;

FIG. 193 shows a wearable ventilator according to an embodiment of the invention;

FIG. 194 shows a wearable ventilator according to an embodiment of the invention;

FIG. 195 shows a wearable ventilator according to an embodiment of the invention;

FIG. 196 shows a wearable ventilator according to an embodiment of the invention;

FIG. 197 shows a wearable ventilator according to an embodiment of the invention; and FIGS. 198-1 and 198-2 show a wearable ventilator according to an embodiment of the invention.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Aspects of the invention will be described herein in its application to invasive and non-invasive patient connections via patient interfaces and to positive airway pressure (PAP) devices, but it is to be understood that the aspects of the invention may have application to other fields of application where blowers are used such as ventilators, e.g., in both positive pressure and negative pressure applications.

In this specification, the words "air pump" and "blower" may be used interchangeably. The term "air" may be taken to include breathable gases, for example air with supplemental oxygen or heliox. It is also acknowledged that the blowers described herein may be designed to pump fluids other than air.

Also, each blower embodiment below is described as including a single stage design. However, it should be appreciated that aspects of the invention may be applied to multiple stage designs, e.g., two, three, four, or more stages.

1. Blower

FIGS. 1-6 illustrate a single stage blower 10 according to an embodiment of the present invention. As described below, the blower provides an arrangement that is compact, efficient, relatively quiet, low cost, low complexity, and provides laminar flow. In an embodiment, the blower may be structured to provide pressurized air in the range of 2-30 cmH$_2$O, and may be structured to provide pressurized air greater than 60 cmH$_2$O.

As illustrated, the blower 10 includes a housing 20 with first and second housing parts 22, 24, a stator component 30 including air directing grooves 35, a motor 40 positioned within the stator component 30 and adapted to drive a rotatable shaft or rotor 50, and an impeller 60 provided on one side of the stator component 30 and coupled to an end portion of the rotor 50. As illustrated, the blower provides a relatively simple, stacked assembly.

Figure 5:
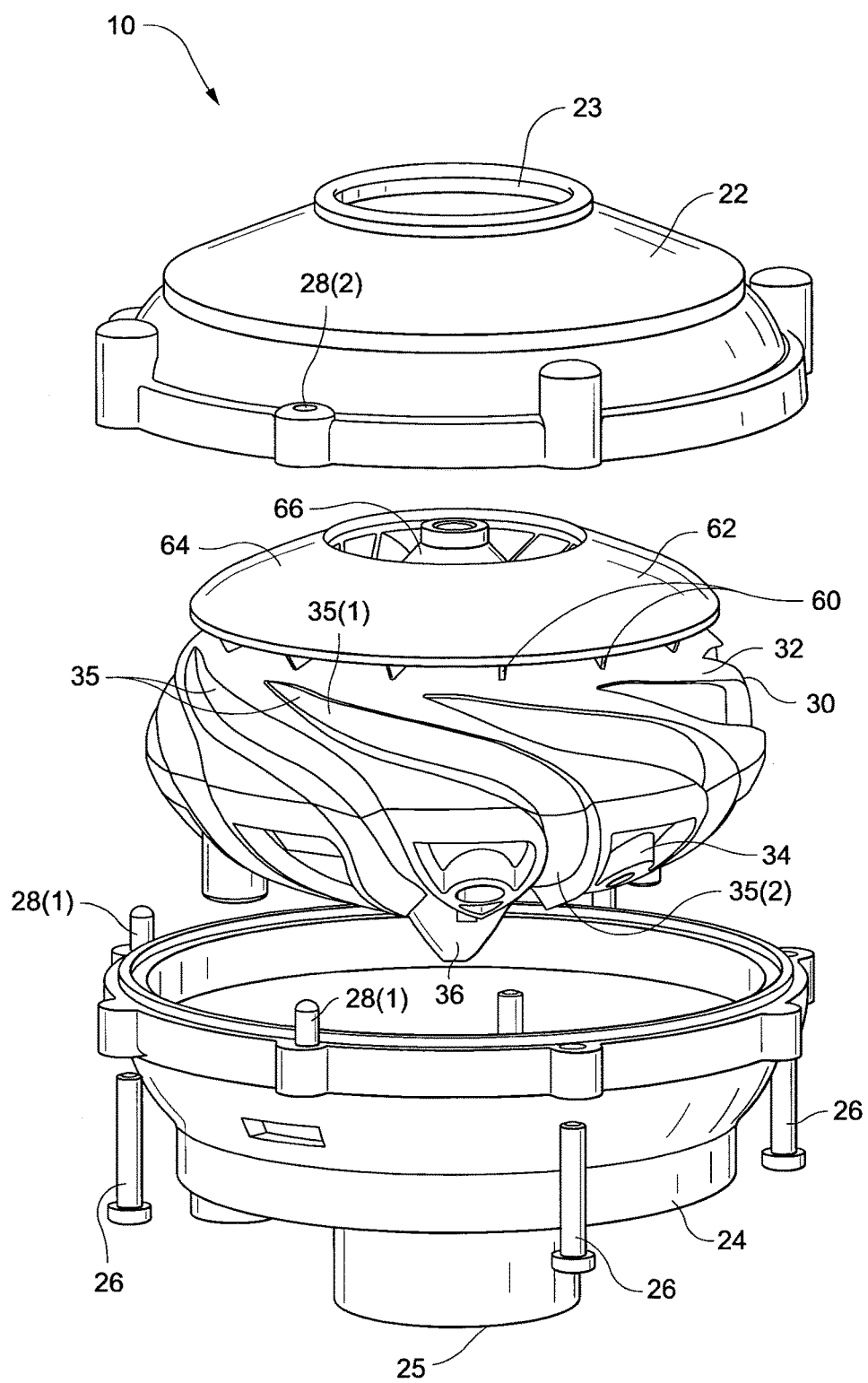
FIG. 5 is an exploded view of the blower of FIG. 4.

As best shown in FIG. 5, the first and second housing parts 22, 24 may be coupled to one another by one or more fasteners 26 (e.g., screws). In addition, the first and second housing parts 22, 24 may provide a joint (e.g., alignment pin 28(1) and receiving hole 28(2) arrangement as shown in FIG. 5) to facilitate alignment and connection. FIG. 2 shows an alternative joint for coupling the housing parts, e.g., annular protrusion 29 adapted to be received in annular groove.

The blower 10 has a proximal opening or proximal end 23 (e.g., patient side opening or opening proximal to the patient) provided by the first housing part 22 at one end and a distal opening or distal end 25 (e.g., ambient side opening or opening distal from the patient) provided by the second housing part 24 at the other end. The blower 10 is operable to draw a supply of gas into the housing 20 through the proximal opening 23 and provide a pressurized flow of gas at the distal opening 25.

The blower 10 has axial symmetry with both the proximal opening 23 and distal opening 25 co-axially aligned with an axis A of the blower (e.g., see FIG. 1). In use, gas enters the blower axially at one end and leaves the blower axially at the other end. Such arrangement may provide relatively low noise in use, e.g., due to axial symmetry and/or low volute turbulence. Exemplary embodiments of such blowers are disclosed in WO 2007/134405 A1, which is incorporated herein by reference in its entirety.

In the illustrated embodiment, as shown in FIG. 4, the blower may be relatively compact and have a diameter D of about 60-70 mm, e.g., 63 mm, and a height H of about 35-45 mm, e.g., 38.5 mm. However, other suitable sizes are possible.

1.1 Stator Component

Figure 6:
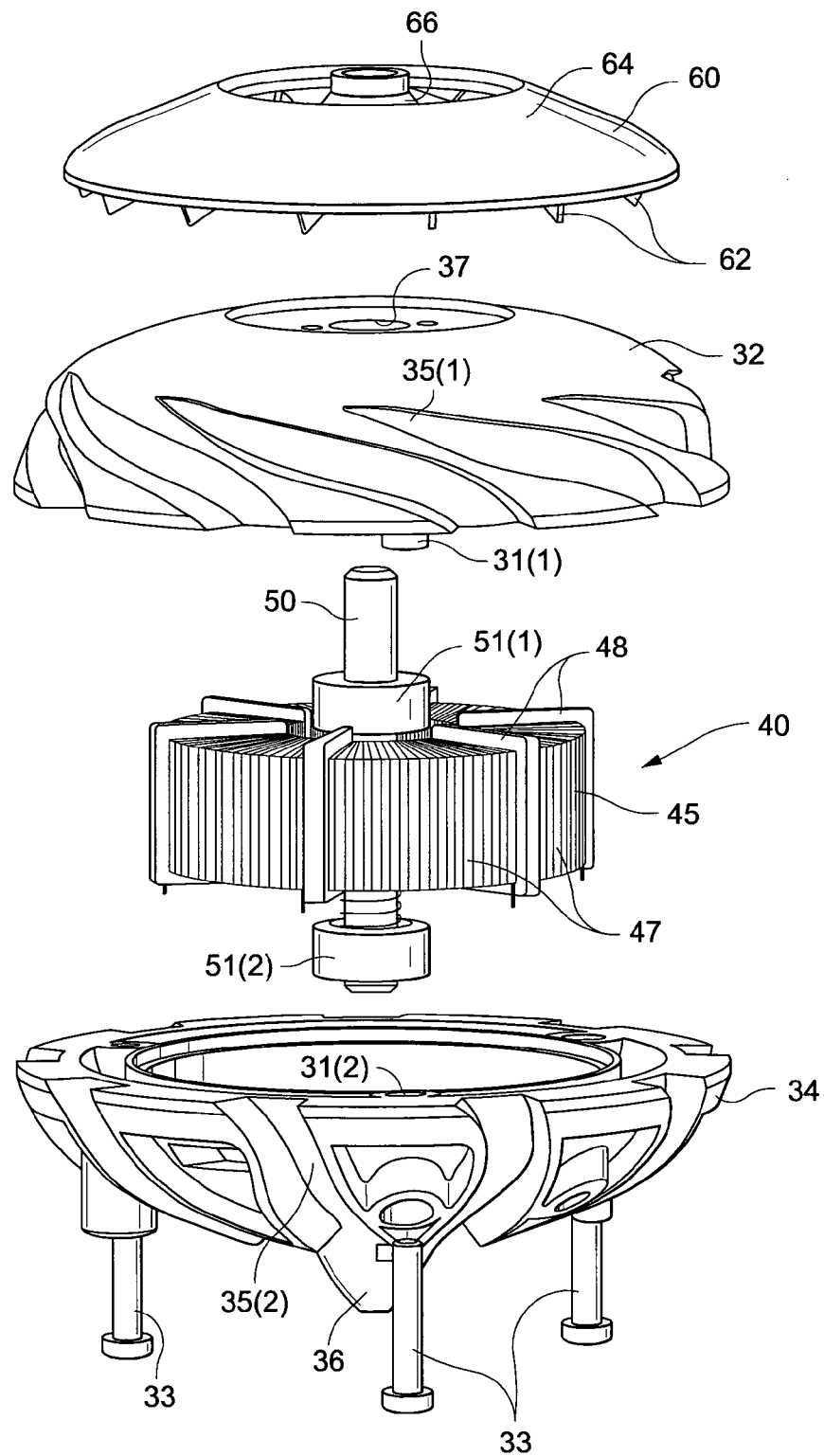
FIG. 6 is an exploded view of the stator component, motor, and impeller of the blower of FIG. 4.

As shown in FIGS. 2, 3, 5, and 6, the stator component 30 includes first and second parts 32, 34 that are coupled to one another, e.g., by one or more fasteners 33 as shown in FIG. 6. In addition, the first and second housing parts 32, 34 may provide a joint (e.g., alignment pin 31(1) and receiving hole 31(2) arrangement as shown in FIG. 6) to facilitate alignment and connection. The first and second parts 32, 34 cooperate to define a hollow interior adapted to support and maintain the motor 40 and rotor 50 in an operative position. In addition, the first and second parts 32, 34 cooperate to define a generally "turnip"-shaped exterior (e.g., generally bulbous shape) with a plurality of air directing grooves 35 that extend along the exterior surface of the parts.

As illustrated, the air directing grooves or volutes 35 are configured and arranged to collect and divide air from the impeller 60 and direct the air along a curved path towards the outlet 25 so that the airflow becomes laminar and minimizes volute turbulence along the length of the grooves. The leading edge of the air directing grooves 35 extend tangentially outwards from the outer tips of the impeller blades to prevent blade pass tonal noise being produced when the impeller blades pass the stator vanes. The leading edge of the stator vanes are configured to collect the air exiting the impeller blades and direct it from a generally tangential direction to a generally radial direction. Specifically, an inlet portion 35(1) of each groove extends generally tangentially from the outer perimeter or rim of the impeller 60 so that air exiting the impeller 60 can enter the groove. Preferably, the entry angle of the air entering the grooves is approximately between 5-10% away from the plane of rotation of the impeller. As illustrated, the inlet portion 35(1) extends from the rim of the impeller 60 to the maximum radial extent outer perimeter of the stator component. The groove curves downwards from the inlet portion 35(1) (e.g., at about) 80-90° into the outlet portion 35(2) of the groove which extends towards the cone-shaped base 36 of the stator component. As illustrated, the outlet portion 35(2) defines a laminar flow path that is positioned out of the line of sight of the impeller 60, i.e., outlet portion extends along lower side of the stator component. The grooves 35 all smoothly converge or rejoin at the generally cone-shaped base 36 to form an axial exit. The converging paths of the grooves create acoustic destruction for low noise.

In addition, the depth of each groove 35 increases or deepens as it extends from the inlet portion 35(1) towards the outlet portion 35(2), i.e., groove turns into more of a "tunnel" at the outlet portion. However, at the point where the air leaves the groove 35 and passes towards the outlet 25, the depth of the groove may be diminished by a ramp that angles the air path towards the outlet. Preferably, the depth of the groove is between 0-4 mm in this embodiment.

In the illustrated embodiment, nine air directing grooves 35 are provided to the stator component 30. However, it should be appreciated that more or less grooves are possible, e.g., 3, 4, 5, or more grooves.

In an embodiment, the blower provides a rising fan performance curve, e.g., which may be varied by changing the area provided by the grooves.

Preferably, the stator component may be constructed of a polymeric material or polycarbonate. Additionally, it may be preferred to construct the portion of the stator component contacting the motor out of aluminum. This aluminum portion of the stator component may function as an additional heat sink for the motor.

1.2 Motor

The motor 40 includes a magnet provided to rotor 50 and a stator assembly 45 to cause spinning movement of the rotor 50 via the magnet. The stator assembly 45 includes a stator core on which stator windings 47 are wound. In an embodiment, the stator core is in the form of a solid ferrite ring. However, the stator core may have a different arrangement, e.g., stack of sheet metal laminations. In an embodiment, the stator assembly may include a toroidal wound motor architecture (sensorless), e.g., based on common transformer windings.

In FIG. 6, the stator assembly 45 includes six windings 47 on the stator core, which provides a symmetric arrangement. However, the stator assembly may include alternative winding arrangements, e.g., 3 windings. Also, as illustrated, dividers 48 may be optionally provided between the windings 47.

As illustrated, exterior surfaces of the stator assembly 45 may be supported and retained by the first and second parts 32, 34 of the stator component 30, i.e., stator assembly encased or enclosed between the first and second parts.

Also, the first and second parts 32, 34 of the stator component 30 are structured to retain bearings 51(1), 51(2) that rotatably support the rotor 50. For example, the first part 32 may include a recess for supporting one bearing 51(1) and the second part 34 may include a recess for supporting the other bearing 51(2). The first and second parts 32, 34 may be structured to support bearings of the same or mixed bearing sizes.

In addition, the first part 32 provides an opening 37 along its axis that allows the end portion of the rotor 50 to pass therethrough for engagement with the impeller 60.

1.3 Impeller

Figure 7:
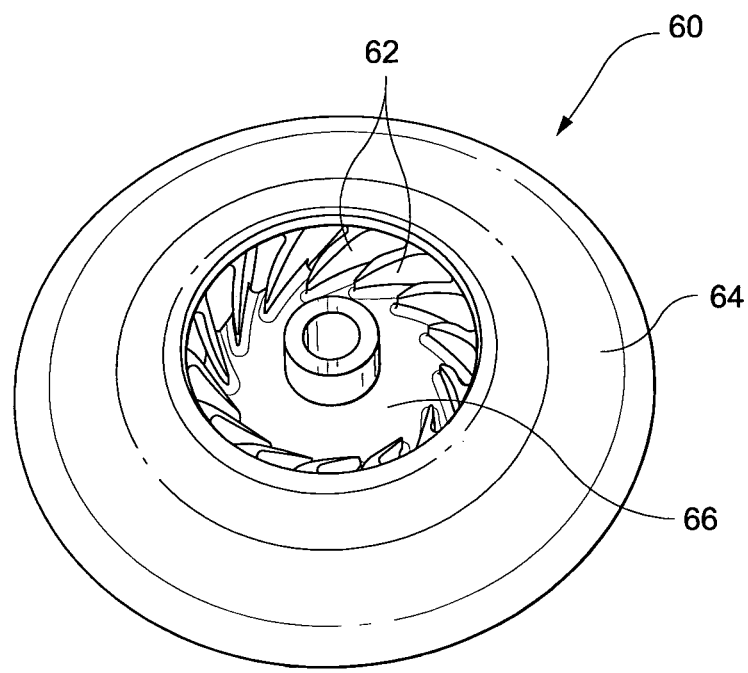
FIG. 7 is a top view of an impeller according to an embodiment of the present invention.
Figure 8:
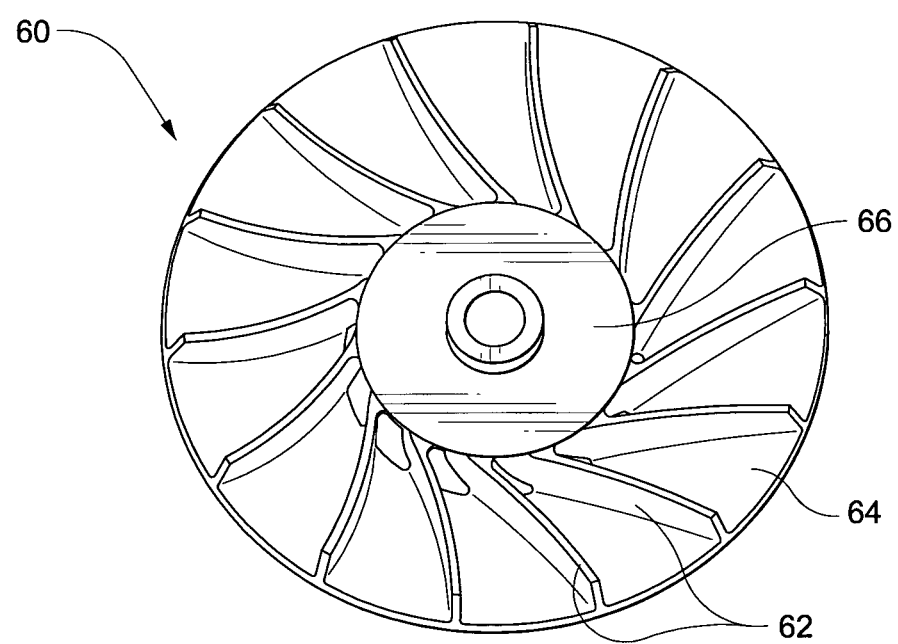
FIG. 8 is a bottom view of the impeller of FIG. 7.
Figure 9:
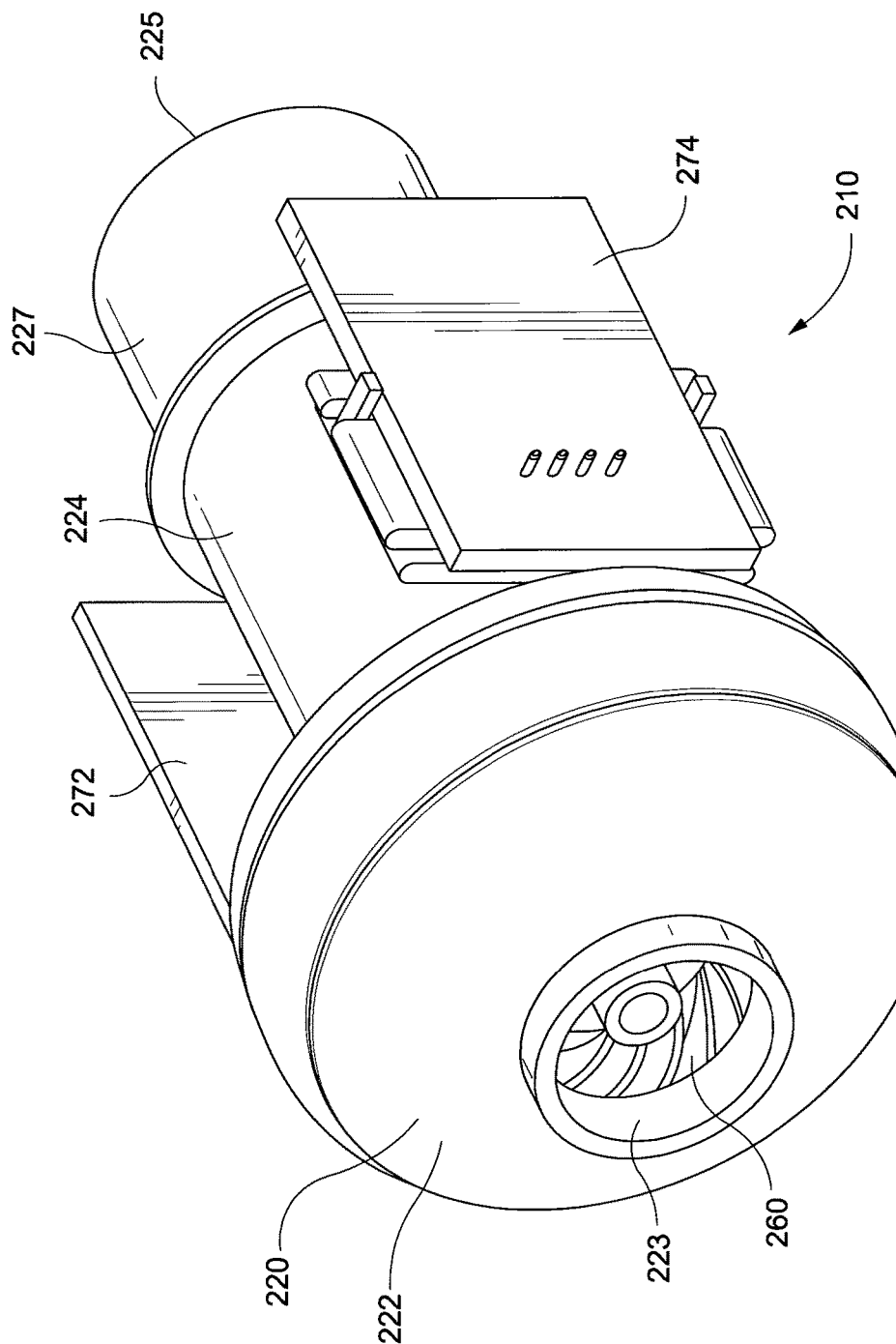
FIG. 9 is a perspective view of a blower according to another embodiment of the present invention.
Figure 10:
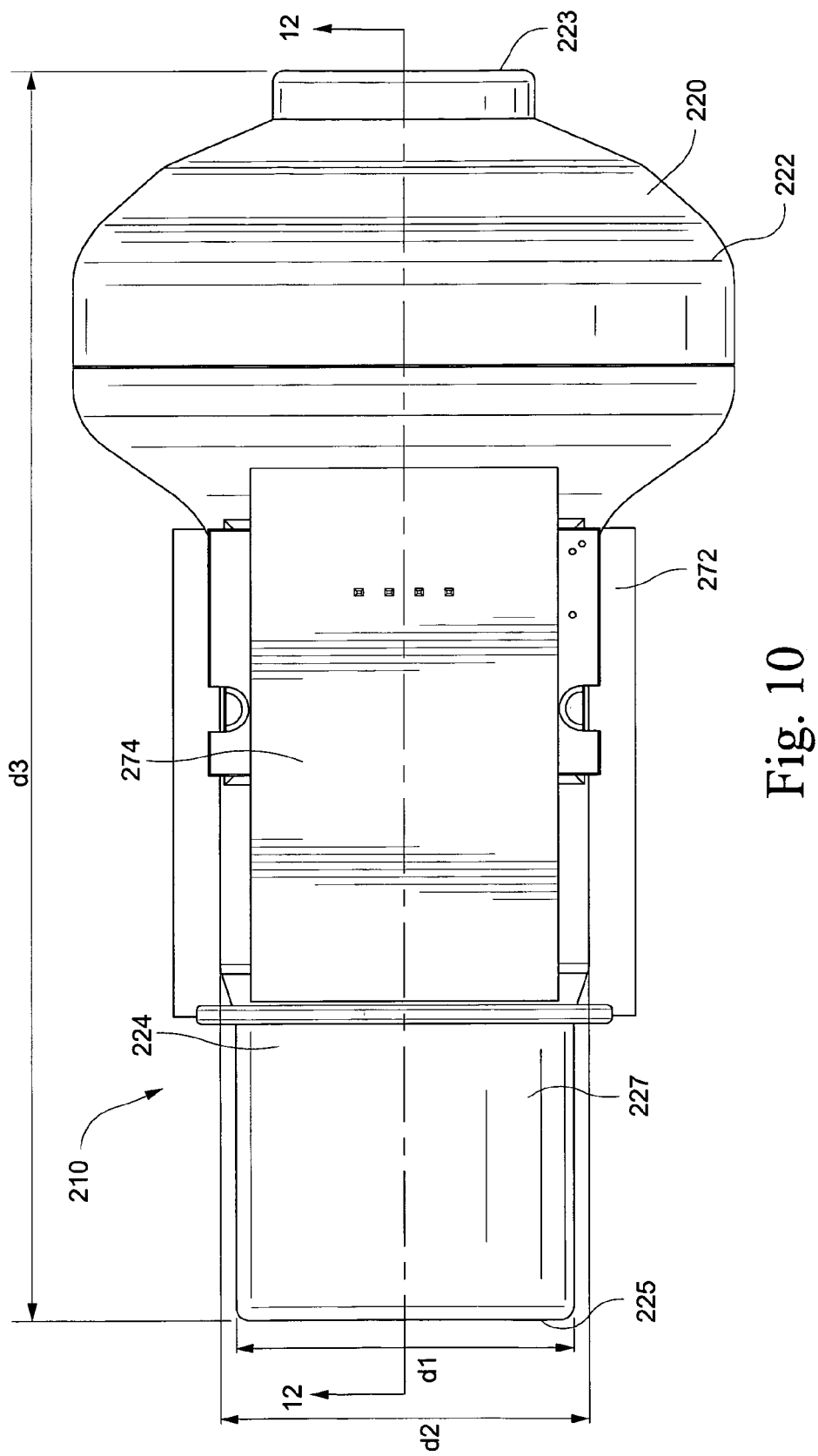
FIG. 10 is a side view of the blower of FIG. 9.
Figure 11:
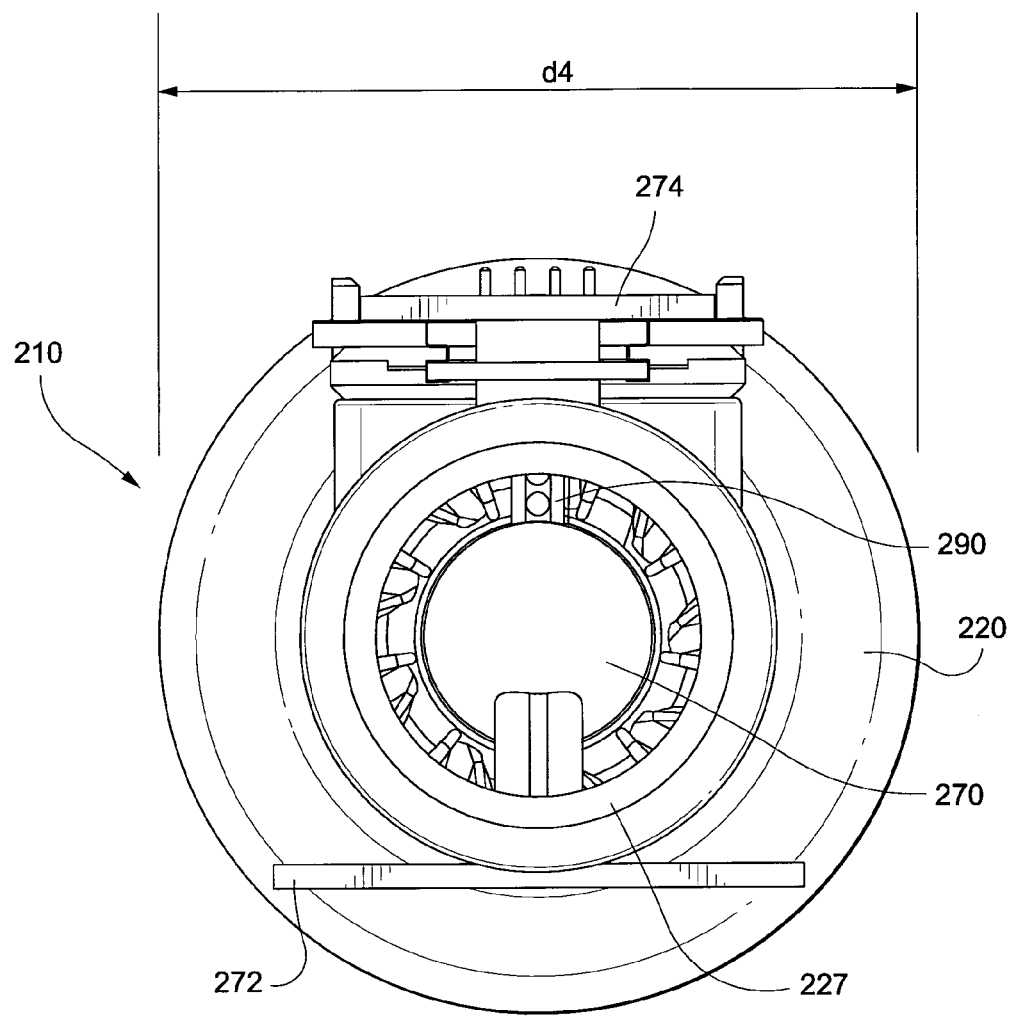
FIG. 11 is a top view of the blower of FIG. 9.

In the illustrated embodiment, as best shown in FIGS. 7 and 8, the impeller 60 includes a plurality of continuously curved or straight blades 62 sandwiched between a pair of disk-like shrouds 64, 66. The shrouds may help to reduce tonal noise in use. The lower shroud 66 incorporates the hub or bushing that is adapted to receive the rotor 50. Also, the impeller includes a tapered configuration wherein the blades taper towards the outer edge. Further details of impellers are disclosed in WO 2007/048206 A1, which is incorporated herein by reference in its entirety.

The shrouding of the impeller may also preferably at least partially cover the blades. This may have the benefit of preventing the blades from contacting the inner wall of the housing and breaking, e.g., if the blower suffers a shock while in operation.

As best shown in FIG. 8, the impeller includes 14 blades 62. In this arrangement, the ratio of impeller blades 62 to grooves 35 in the stator component 30 (i.e., 14:9) includes no common divisible number, which helps to avoid blade pass frequencies and tonal noises. However, it should be appreciated that more or less blades are possible. The blades are angled in a backwards direction relative to the direction of the flow to assist in reducing noise.

1.4 Fluid Flow Path

Air enters the blower 10 at the proximal opening 23 and passes into the impeller 60 where it is accelerated tangentially and directed radially outward. Air then flows into the air directing grooves 35 which direct the air downwardly along the stator component 30. Air from the grooves 35 then converges at the base 36 of the stator component and is directed towards the distal opening 25. Due to the air directing grooves 35, flow at the outlet 25 is substantially laminar which leads to relatively low conducted noise. In addition, the motor 40 driving the impeller 60 is shielded within the stator component 30 which leads to relatively low conducted noise.

Additionally, the air flow path may be encouraged to flow over the body of the motor to carry away heat produced from the motor.

2.0 "Mini" Blower

FIGS. 9-15 illustrate a blower 210 according to another embodiment of the present invention. In this embodiment, the blower 210 is relatively small with d1 about 22 mm (i.e., for connection to cuff of air delivery tubing), d2 about 22-25 mm (e.g., 24 mm), d3 about 80-100 mm, e.g., 82 mm, and d4 about 40-45 mm, e.g., 43 mm. However, other suitable sizes are possible.

As illustrated, the blower 210 includes a housing 220 (e.g., constructed of a polymeric material such as PEEK) with first and second housing parts 222, 224, a stator component 230 (e.g., constructed of a polymeric material such as PEEK) including air directing grooves 235, a motor 240 supported by the stator component 230 and adapted to drive a rotatable shaft or rotor 250, and an impeller 260 (e.g., constructed of a polymeric material such as PEEK) provided on one side of the stator component 230 and coupled to an end portion of the rotor 250. The impeller 260 has a small clearance above the stator component 230 and is adapted to rotate counterclockwise in use.

Figure 12:
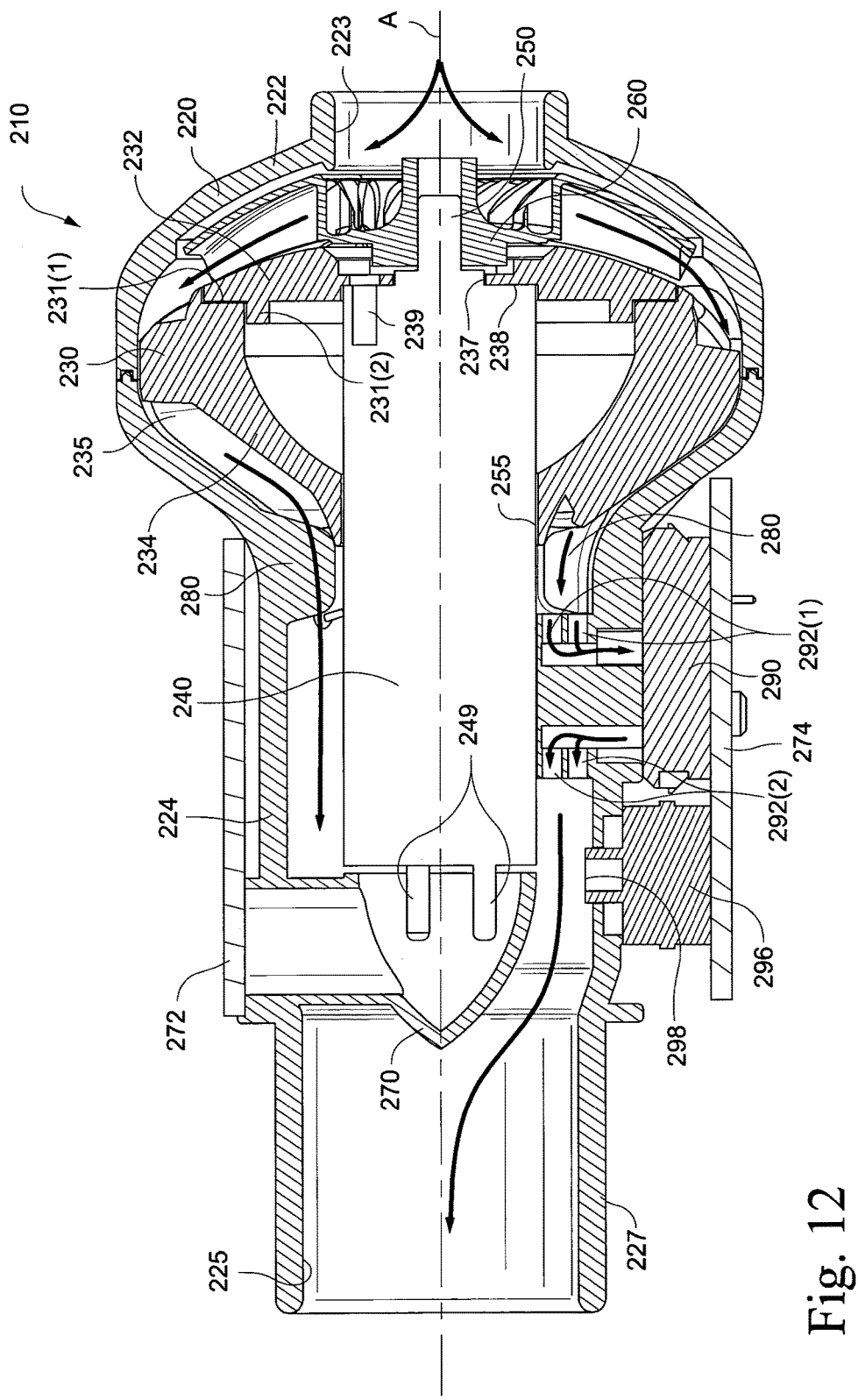
FIG. 12 is a cross-sectional view through line 12-12 of FIG. 10.

The blower 210 has axial symmetry with both the proximal opening 223 and distal opening 225 aligned with an axis A of the blower (e.g., see FIG. 12). In an embodiment, a filter may be connected to the proximal opening 223. Also, in an embodiment, the distal opening 225 may be connected to a moisture trap to prevent water or fluid from entering the housing.

Figure 15:
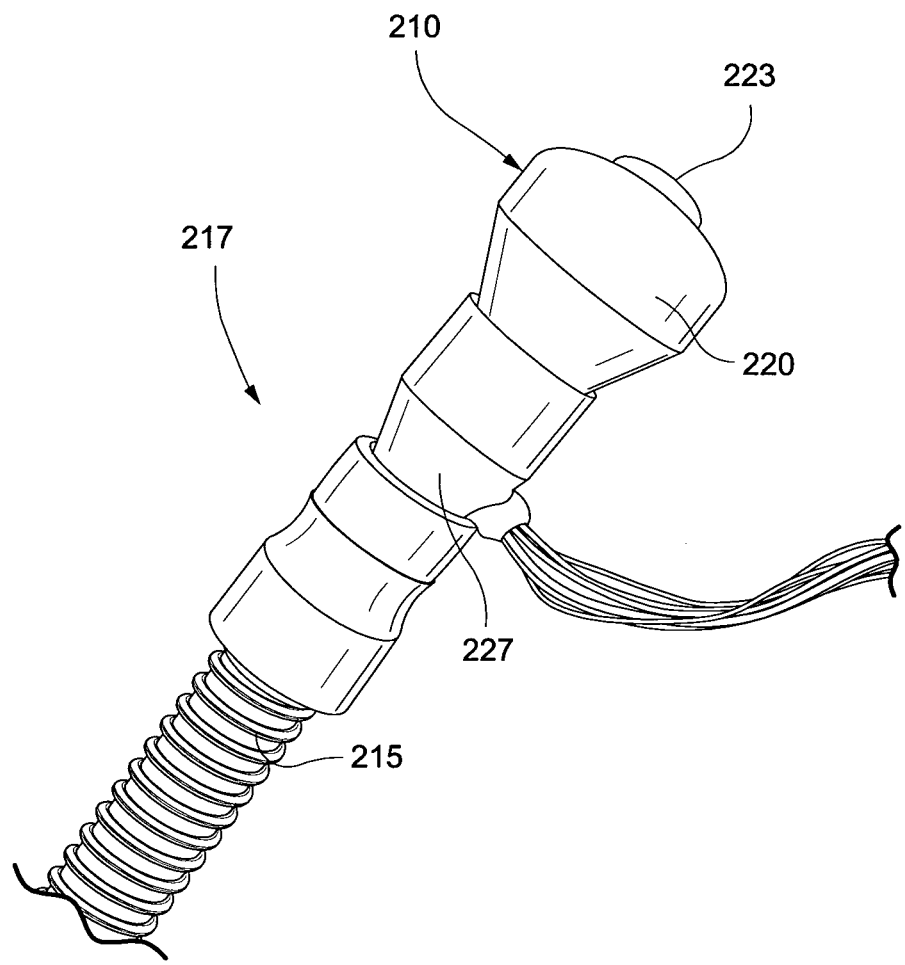
FIG. 15 is a perspective view of the blower of FIG. 9 attached to tubing.

In the illustrated embodiment, the outlet 225 is provided by an outlet tube 227 which allows ventilator tubing to be connected to the housing. FIG. 15 illustrates a PAP device 217 with the outlet tube 227 connected to ventilator tubing 215. A patient interface (not shown) is coupled to the other end of the tubing 215. The patient interface can be in the form of a nasal mask, a full face mask, a nasal cannula, nasal prongs, nasal pillows, or the like, which in turn may be supported on the patients head via headgear. The headgear may support the blower 210.

In an embodiment, the blower 210 may be structured to provide pressurized air greater than 60 cmH$_2$O at flow rates of up to 215 L/min.

2.1 Stator Component

Figure 13:
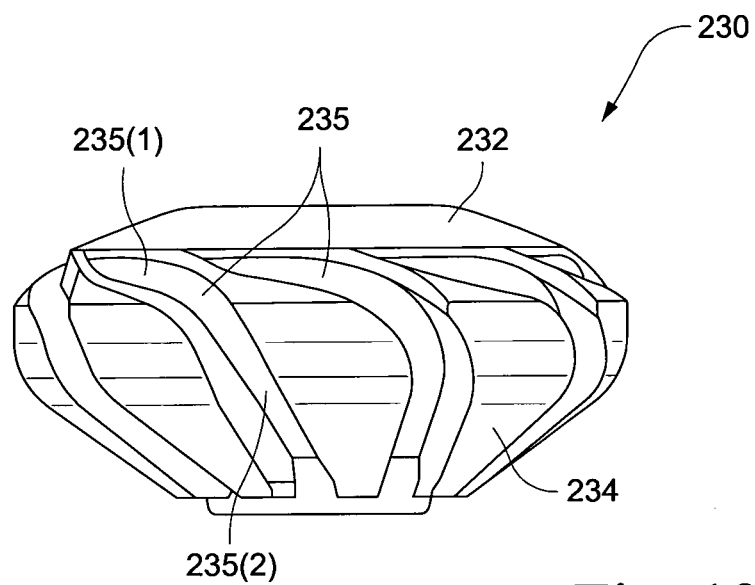
FIG. 13 is a side view of the stator component of the blower of FIG. 9.
Figure 14:
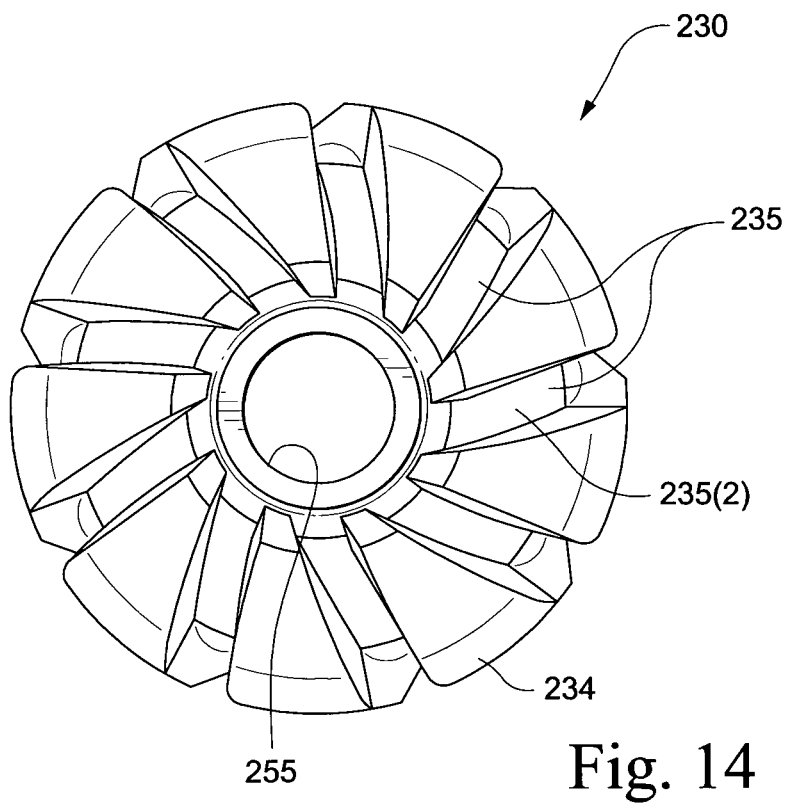
FIG. 14 is a bottom view of the stator component of FIG. 13.

As shown in FIGS. 12-14, the stator component 230 includes first and second parts 232, 234 that are coupled to one another. The first and second parts 232, 234 may be coupled to one another by one or more fasteners (e.g., screws) or by an adhesive (e.g., glue)). In addition, the first and second parts may provide a joint (e.g., second part includes recess 231(1) to receive first part, and first part includes one or alignment pins 231(2) to engage within hollow interior of second part) to facilitate alignment and connection.

The first and second parts 232, 234 cooperate to define a hollow interior and are adapted to support the motor 240 and rotor 250 in an operative position. In addition, the first and second parts 232, 234 cooperate to define a plurality of air directing grooves 235 (e.g., nine air directing grooves) including an inlet portion 235(1) and outlet portion 235(2) as described above.

The stator component 230 may be attached to the housing 220 by one or more fasteners, e.g., three mounting screws. However, the stator component may be attached to the housing in other suitable manners. Alternatively, the stator component may not be attached to the housing but retained by a friction fit. The hollow interior of the stator component 230 aids in the molding process and reduces the weight of the stator component. The hollow interior of the stator component 230 may be filled and sealed from the air path to reduce the deadspace within the ventilator.

Figure 17:
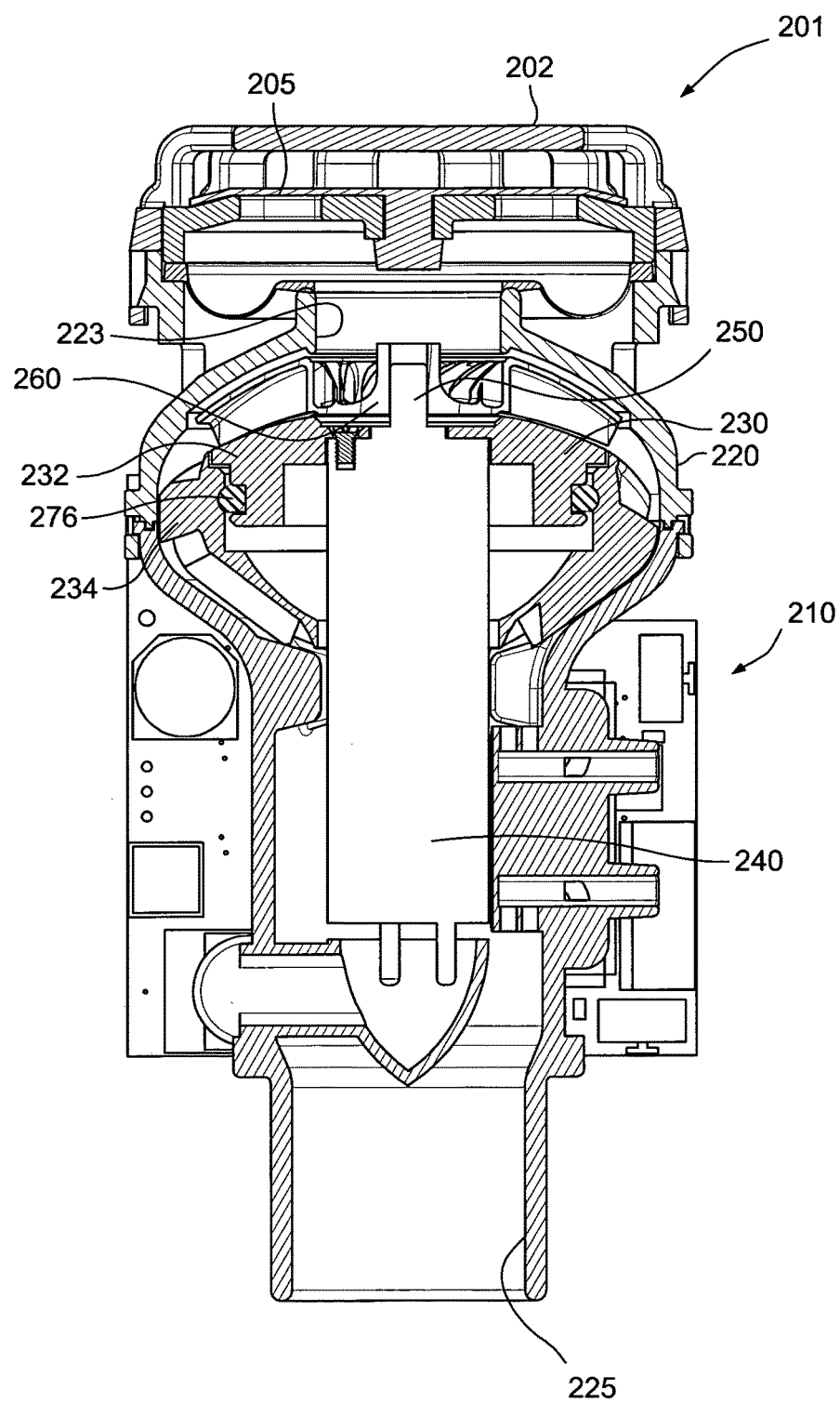
FIG. 17 is a cross-sectional view of the blower of FIG. 16.
Figure 18:
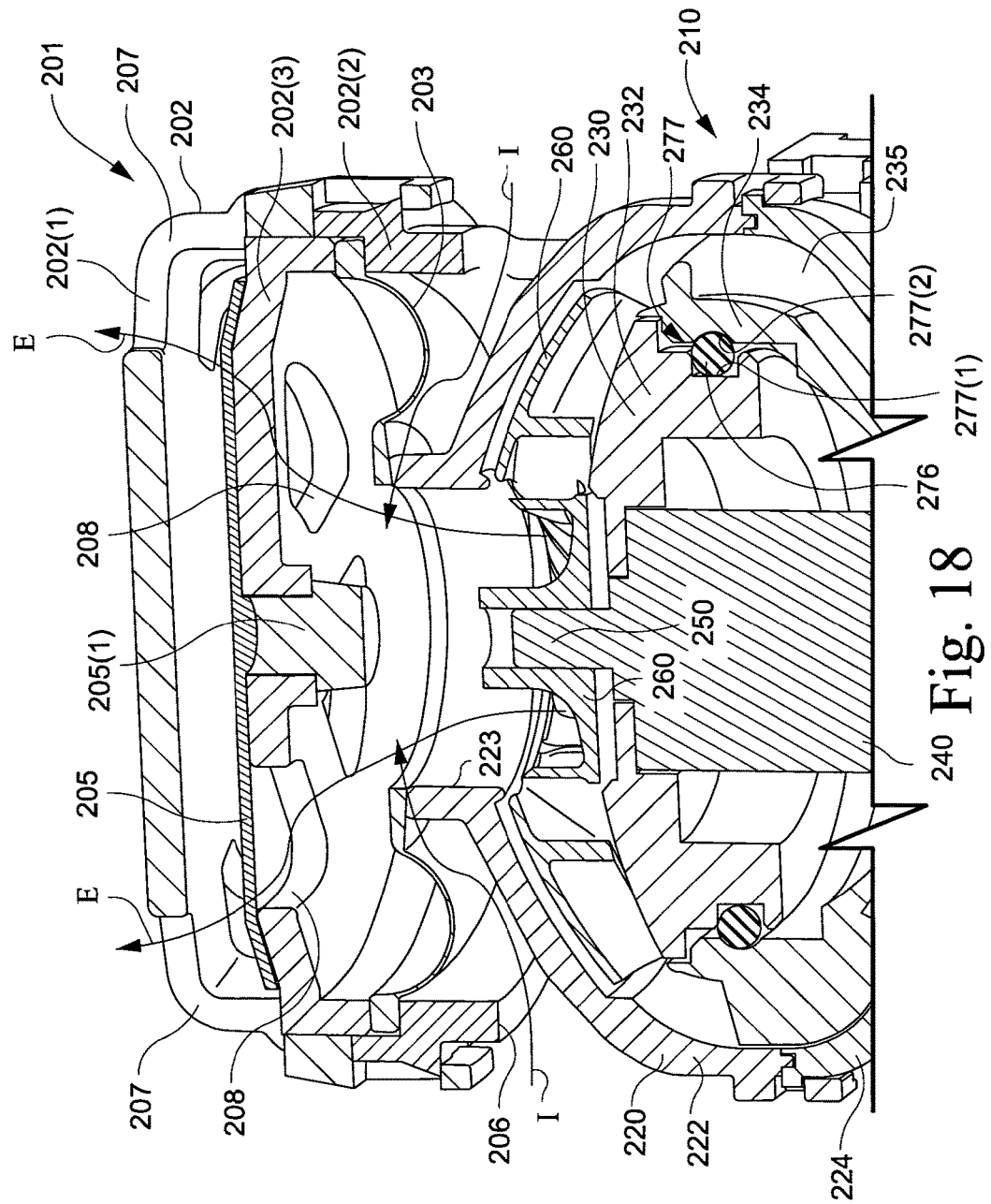
FIG. 18 is an enlarged cross-sectional view of the blower of FIG. 16.
Figure 19:
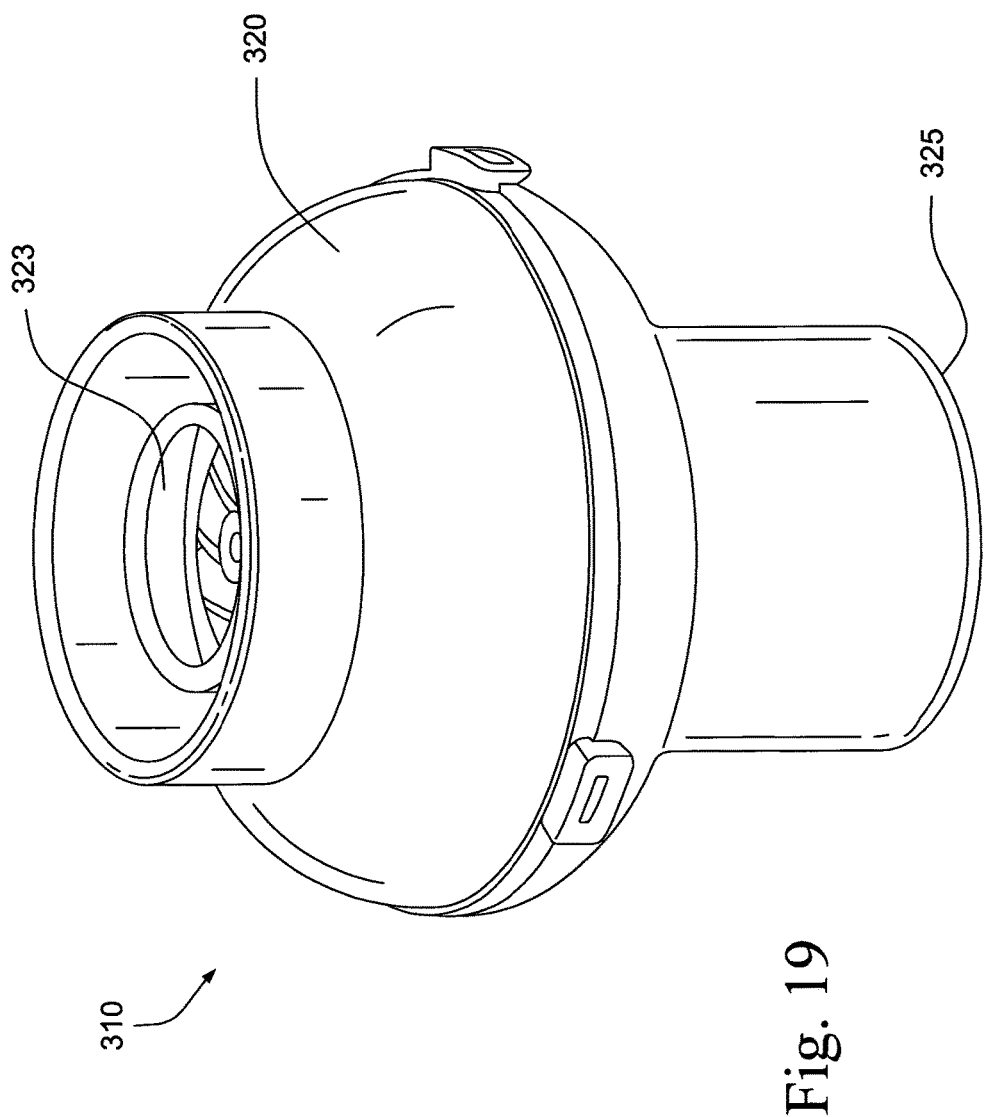
FIG. 19 is a perspective view of a CPAP version of a blower according to an embodiment of the present invention.
Figure 20:
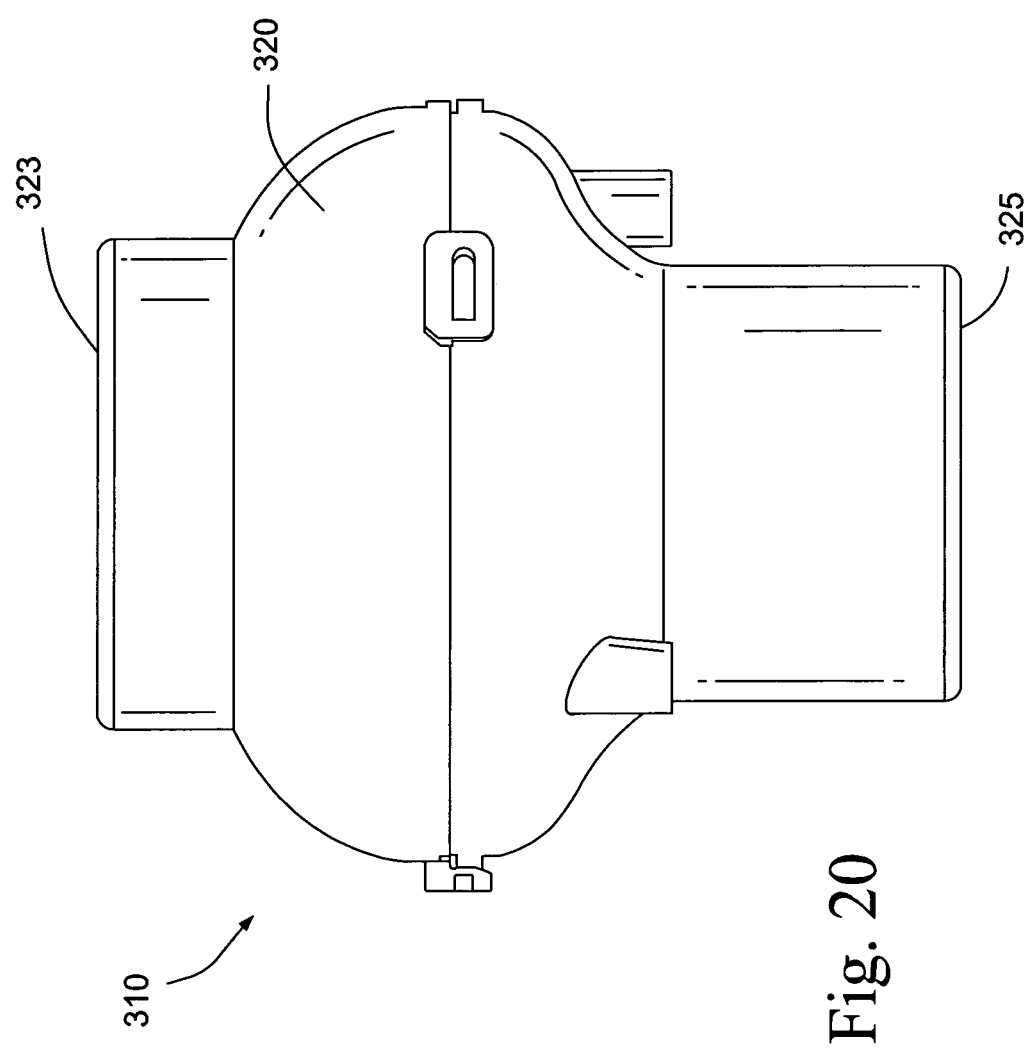
FIG. 20 is a side view of the blower of FIG. 19.
Figure 21:
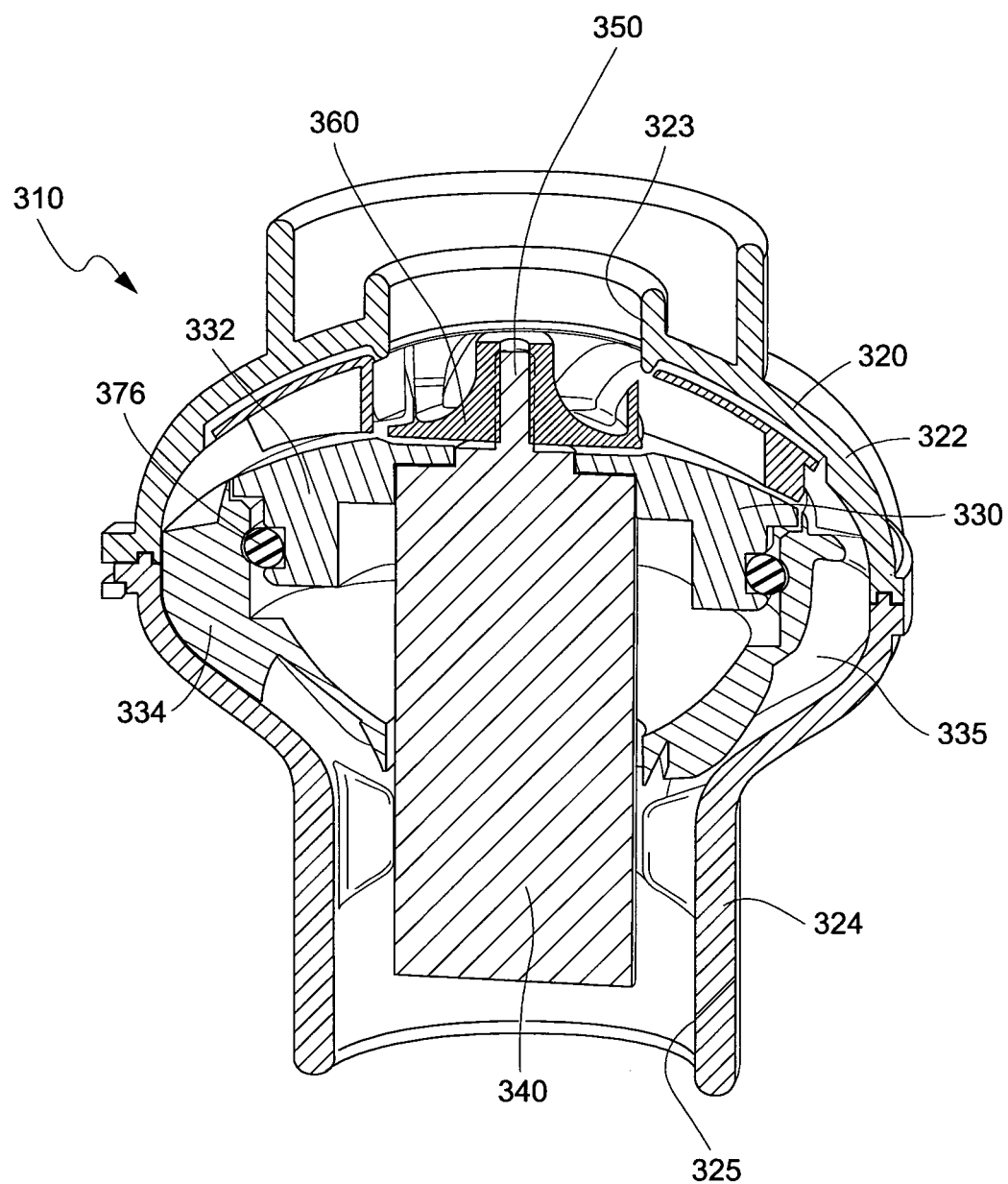
FIG. 21 is a cross-sectional view of the blower of FIG. 19.

In an alternative embodiment as shown in FIGS. 17-18, instead of using fasteners to couple the first and second parts 232, 234 to one another, fasteners may be replaced with an O-ring 276 adapted to be inserted into a gap 277 between the first and second parts 232, 234 of the stator component. In this example, each part 232, 234 may include a respective groove or ring-shaped recess 277(1), 277(2) that cooperate to define the gap 277 adapted to receive the O-ring 276. The O-ring 276 may be adapted to sit within the respective recesses and resist forces pulling apart the first and second parts 232, 234. Additionally, the O-ring has advantages including easier assembly during manufacture (e.g., fewer fasteners), vibration isolation, and shock resistance, and may also additionally reduce noise generated by high speed vibration during use.

2.2 Motor

The motor 240 is in the form of a brushless DC motor structured to cause spinning movement of the rotor 250. In an embodiment, the motor may be a 13 mm diameter motor with 30 watt power consumption and up to 80,000 rpm. However, different size motors such as a larger motor is possible, e.g., 16 mm diameter motor. Also, the motor may be sterilisable and sealed. The sealing feature may prevent or limit corrosion of the motor caused by exposure to high relative humidities or bodily fluids.

As illustrated, the first part 232 of the stator component 230 includes a recess 238 to receive the end of the motor 250 and an opening 237 to allow the rotor 250 to pass therethrough for engagement with the impeller 260. The motor 240 is attached to the first part 232 of the stator component 230 by one or more mounting screws 239, e.g., three mounting screws.

The second part 234 of the stator component 230 includes an opening 255 that allows the lower end of the motor 240 to pass therethrough. The opening of the second part 234 may also help to support and retain the motor, e.g., friction fit.

The base of the motor 240 includes one or more power connection points 249 (e.g., three power connection points) for connecting power wiring. As illustrated, a cone or bullet shaped piece 270 is supported by the second housing part 224 and is configured and positioned to cover or protect the connection points 249 so they are separate from the air path, i.e., wiring and power connection points are shielded or enclosed by the cone-shaped piece.

A printed circuit board assembly (PCBA) 272 is mounted to the housing to control the motor. The PCBA may contain one or more sensors to enhance control, e.g., Hall sensors, thermal sensors.

In an embodiment, the motor may be connected to multiple metallic heat sinks, and/or the air path may be encouraged to flow over the motor to aid in heat exchange.

Additionally, the motor may be encapsulated in a thin jacket to reduce motor noise. In an embodiment, the jacket may be constructed of a soft polymer or silicone.

2.3 Flow and Pressure Sensors

A flow sensor 290 and a pressure sensor 296 may be provided along the air flow path. As shown in FIG. 12, the flow sensor 290 includes inlet tubes 292(1) and outlet tubes 292(2) in fluid communication with the air flow path that allow air to enter and exit the sensor. Flow straighteners 280 are provided to the housing adjacent the outlet of the stator component 230 and upstream of the flow sensor 290 (e.g., see FIG. 12). The flow straighteners 280 are configured and arranged to straighten the air flow exiting the stator component 230 to prevent tangential air flow across the flow sensor inlet tubes 292(1), which provides a more accurate flow estimate from the flow sensor.

The pressure sensor 296 includes a flexible membrane 298 in fluid communication with the air flow path, wherein displacement of the flexible membrane provides an indication of pressure of the air in the air flow path.

A second PCBA 274 is mounted to the housing (on an opposite side to the first PCBA 272) to control and receive data from the flow sensor 290 and pressure sensor 296.

2.4 Fluid Flow Path

Air enters the blower 210 at the proximal opening 223 and passes into the impeller 260 where it is accelerated tangentially and directed radially outward. Air then flows into the air directing grooves 235 of the stator component 230 which direct the air along the stator component 230. Air from the grooves 235 then exits the stator component 230 and passes along a channel defined between the second housing part 224 and the lower end of the motor 240 towards the distal opening 225. Due to the air directing grooves 235 and the flow straighteners 280, flow at the distal opening 225 is substantially laminar which leads to relatively low conducted noise. The air directing grooves 35, 235, 535 have a substantially constant cross-sectional area so that the resistance for airflow in both directions is reduced. In particular, expiratory impedance is reduced by having a uniform cross-sectional area for the fluid flow path.

3. Ventilator

In an embodiment, the blower may be used as a ventilator blower. When the blower is used as a ventilator blower, the proximal opening of the blower may be connected to a passive air valve assembly. Alternatively, the valve assembly may be provided (e.g., integrally molded) to the outflow or outlet of the blower. The valve assembly can minimize deadspace when the device is employed as a ventilator.

Figure 16:
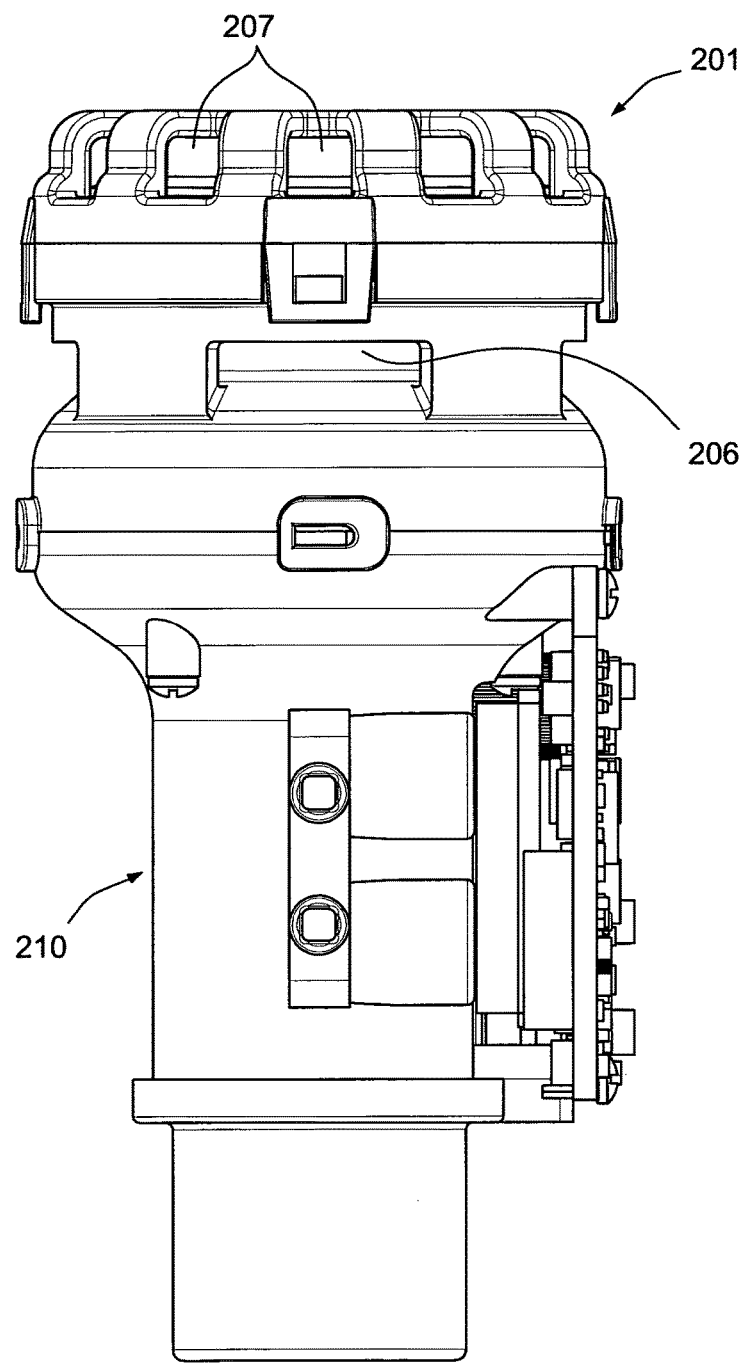
FIG. 16 is a side view of a blower including a passive air valve assembly according to an embodiment of the present invention.

FIGS. 16-18 illustrate a blower 210 including a passive air valve assembly 201 according to an embodiment of the present invention. The blower 210 includes a housing 220 with first and second housing parts 222, 224 defining a proximal opening 223 and distal opening 225, a stator component 230 including air directing grooves 235, a motor 240 supported by the stator component 230 and adapted to drive a rotatable shaft or rotor 250, and an impeller 260, as described above. The first and second parts 232, 234 of the stator component are coupled using an O-ring 276 as described above.

In the illustrated embodiment, the valve assembly 201 is provided to the proximal opening 223 of the blower 210. The valve assembly 201 includes a housing 202 adapted to support a first valve 203 and a second valve 205. The first valve 203 is in communication with atmosphere and positioned and arranged to allow air to flow into the blower via the proximal opening 223 during an inhalation phase of the patient's breathing cycle (as indicated by the arrows I). The second valve 205 is in communication with atmosphere and positioned and arranged to allow air to exit the blower via the proximal opening 223 during an exhalation phase of the patient's breathing cycle (as indicated by the arrows E).

The housing 202 includes first and second housing parts 202(1), 202(2) (e.g., coupled to one another by a clip structure) and an intermediate housing part 202(3) that retains the valves 203, 205 within the housing. As illustrated, the intermediate housing part 202(3) cooperates with the first and second housing parts to sandwich an edge of the valve 203. The valve 205 includes a hub 205(1) that is secured within an opening provided to the intermediate housing part 202(3).

The second housing part 202(2) includes openings 206 to allow communication with atmosphere via valve 203, and the first housing part 202(1) and the housing part 202(3) include respective openings 207, 208 to allow communication with atmosphere via valve 205.

3.1 Mobile or Portable Ventilator System

Another aspect of the present invention relates to a small, portable ventilator adapted for use at a location proximal to the patient. In one embodiment, the ventilator may be used for non-invasive ventilation that is delivered to a patient via a mask or nasal prongs. In an alternative embodiment, the ventilator may be used for invasive ventilation via connection to a tracheotomy tube or endotracheal tube. Some exemplary advantages of having a proximal ventilator include reducing the length of the tubing required to deliver the ventilation to the patient (i.e., allows the use of a short breathing circuit which provides minimal circuit resistance to enhance compliance), and a smaller, lighter device that may enhance mobility for a patient. In one embodiment, the ventilator may be configured as a wearable system as described in greater detail below.

In one embodiment, the ventilator is placed close to the patient and used with a non-vented patient interface device such as a non-vented mask, non-vented mouthpiece, tracheotomy tube or endotracheal tube. Thus, the patient breathes in and out through the ventilator. Consequently, a deadspace within the device that is compatible with the tidal volume of the patient should be achieved. The deadspace is minimized by the internal dimensions of the blower and possibly by the passive valve assembly incorporated into the ventilator inlet. In such a non-vented proximal system, the heat generated from the motor needs to be managed within the limitations of the motor's specification. A ventilator commonly includes two sets each of a flow element and a flow sensor to measure inspiratory and expiratory flow respectively to monitor and/or control ventilation. A non-vented ventilator in such close proximity to the patient allows direct monitoring of bidirectional respiratory flow, but may suffer condensation on the flow element caused by the patient's exhaled gas, and so may affect the accuracy of flow/volume measurements. The ventilator is a highly ergonomic ambulatory ventilator with excellent electro-pneumatic efficiency, promoting battery life or allowing a small battery pack. Advantageously, the patient is not required to be tethered to a bulky unit via bulky hoses. An associated advantage is that the ventilator is not required to overcome the resistive losses of a long breathing circuit, nor correct volume measurements for the compliance of long breathing systems. The ventilator can sit directly at the end of the cannula, potentially underneath clothing, with only a thin flexible electrical cable to the handset (battery and user interface). Disconnection hazard is reduced, because the patient can be moved together with the ventilator rather than separately.

In an alternative embodiment the ventilator may used with a vented patient interface, either invasive for example with a tracheotomy having a vent, or non-invasive for example using a vented mask, vented mouthpiece, vented nasal prongs, etc. In this configuration, the ventilator may be located proximal or distal from the patient as desired because in a system with a proximal vent, where the patient's exhalate is flushed from the circuit, the circuit length and deadspace of the ventilator does not impose additional deadspace. To adequately flush exhalate from the circuit, a minimum vent flow is required, achieved by a minimum PEEP and the vent's dimensions. Thus, the passive exhalation valve relevant to the non-vented embodiment would not be necessary in a dedicated vented implementation. Furthermore, heat management of the motor is simplified in a vented system due to the presence of a bias flow and no condensation forms on the flow element as minimal expired air is flowing over the flow element. It may be preferable to avoid passing the heat to the gas and thence to the patient. Accordingly, it may be decided to pass the heat to ambient. In such a vented ventilator arrangement, the small size, weight and battery operating time of the ventilator according to an embodiment of the invention would increase the portability of the device. It allows for a compact ambulatory device, say belt mounted or holster mounted, applicable to rehabilitation or as an emergency respirator. Alternatively the ventilator may be mounted on the head or on the body and used with a short breathing tube as described in more detail later.

Also, for non-invasive, the ventilator may be used with a non-vented mask, since a passive exhalation valve is provided to the ventilator. Moreover, the ventilator may also be designed for use with an external or third party expiratory valve under the ventilator's control, such as an intersurgical valve or a proximal solenoid valve if a non-vented mask is used such as that described in co-owned pending PCT application no. PCT/AU2010/000708, filed Jun. 9, 2010. In such a case, the passive exhalation valve may not be necessary but an inlet filter may still be advantageous.

Overall Ventilator System

Figure 25:
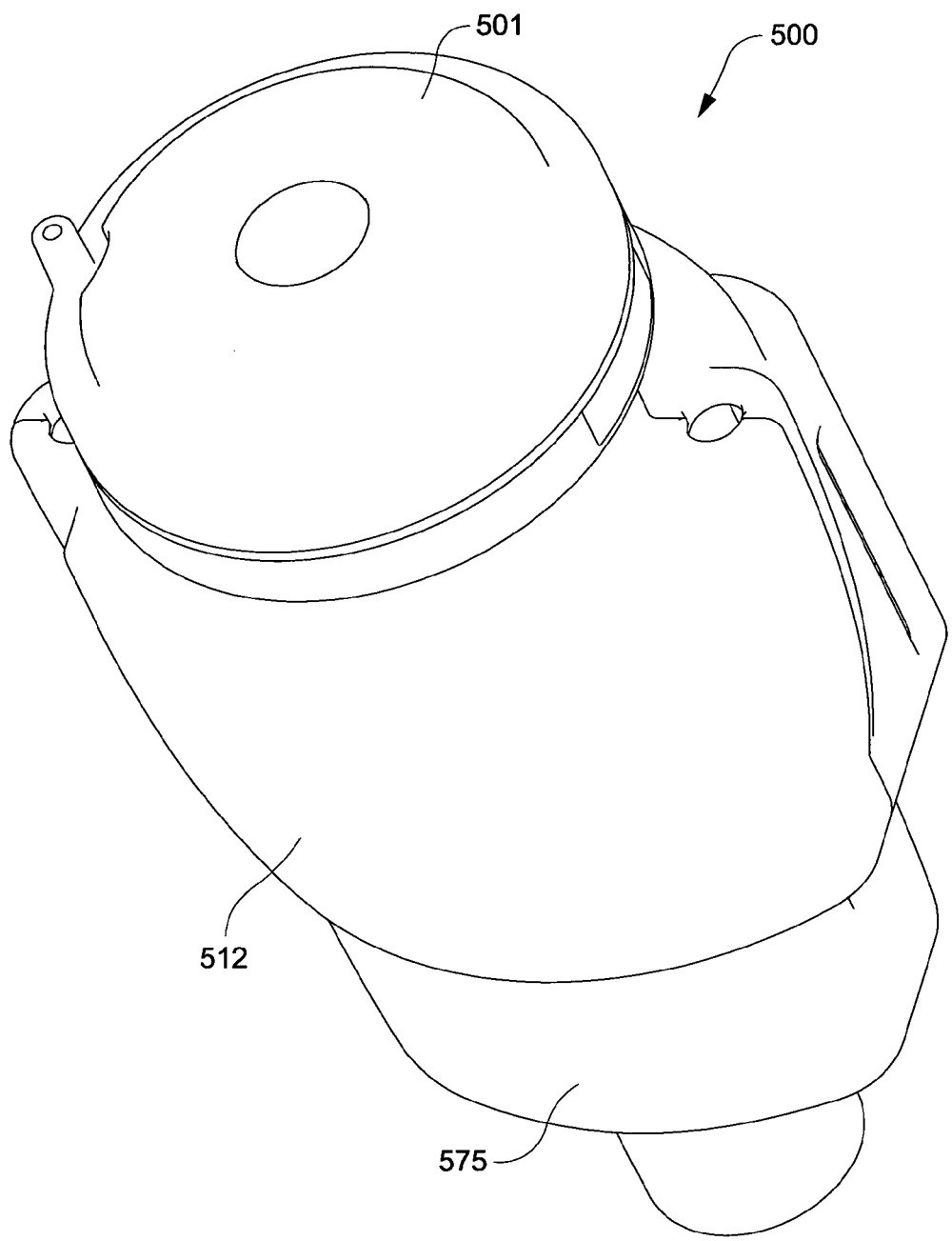
FIG. 25 is a perspective view of a ventilator system according to an embodiment of the invention.
Figure 26:
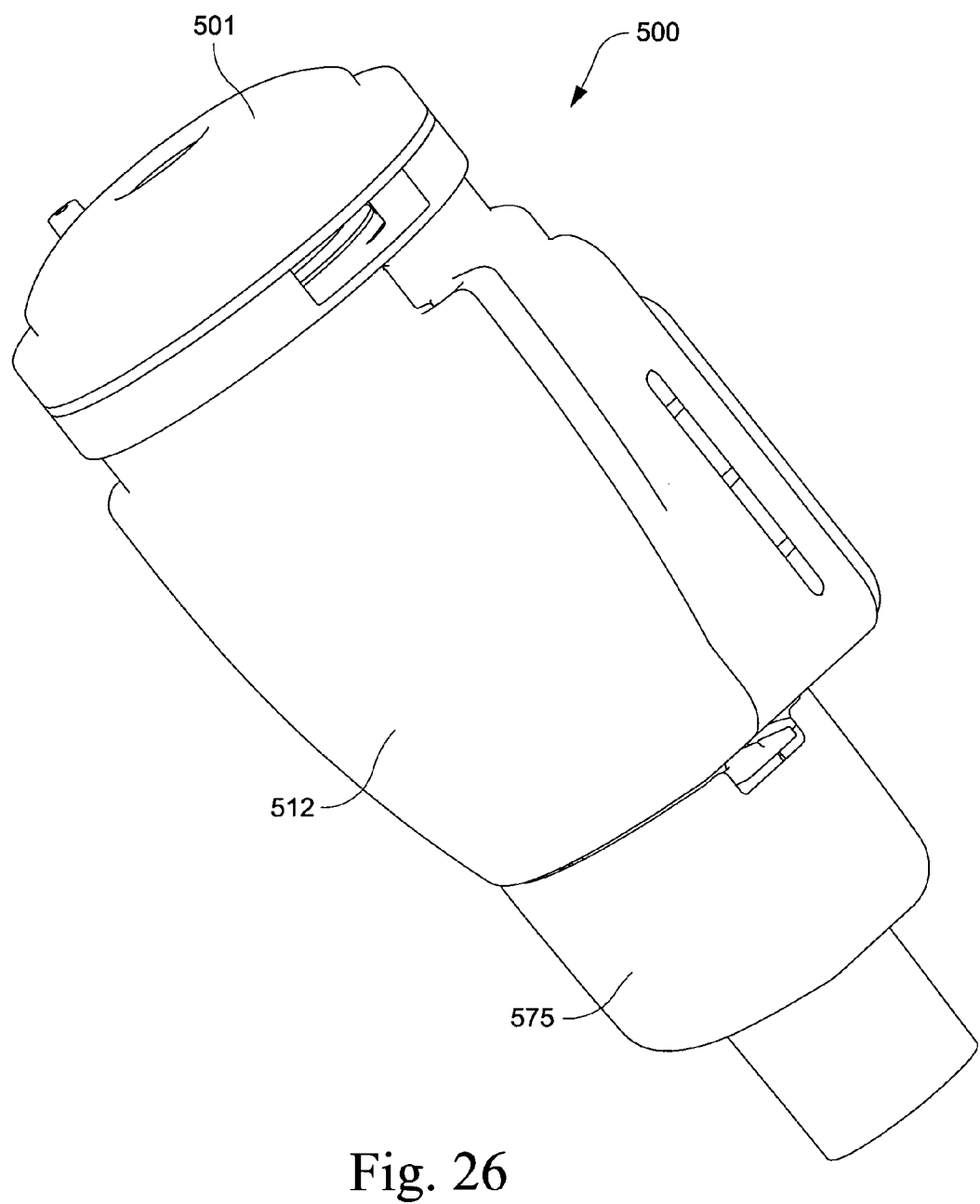
FIG. 26 is another perspective view of the ventilator system of FIG. 25.
Figure 27:
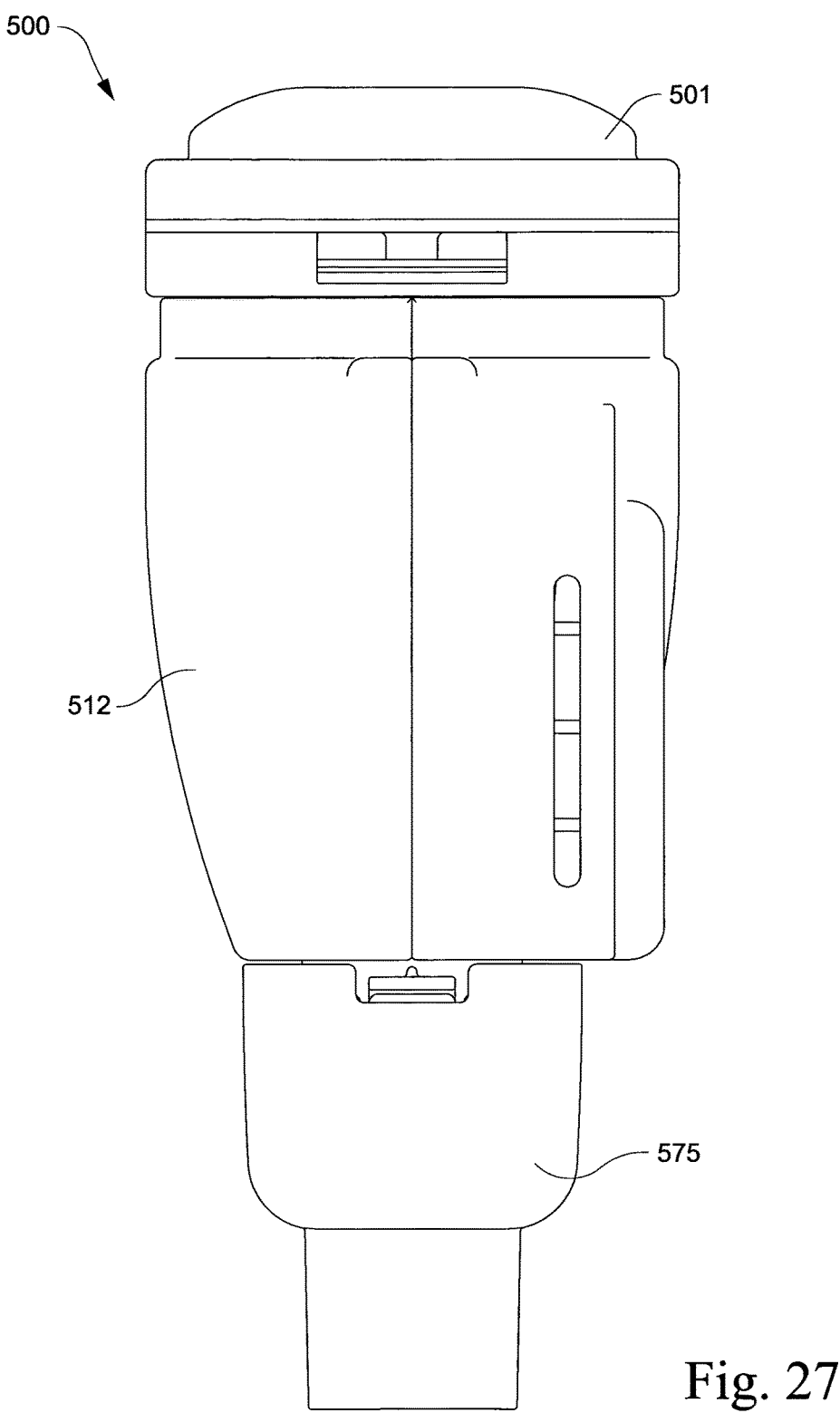
FIGS. 27-31 are side, front, rear, bottom, and top views of the ventilator system of FIG. 25.
Figure 28:
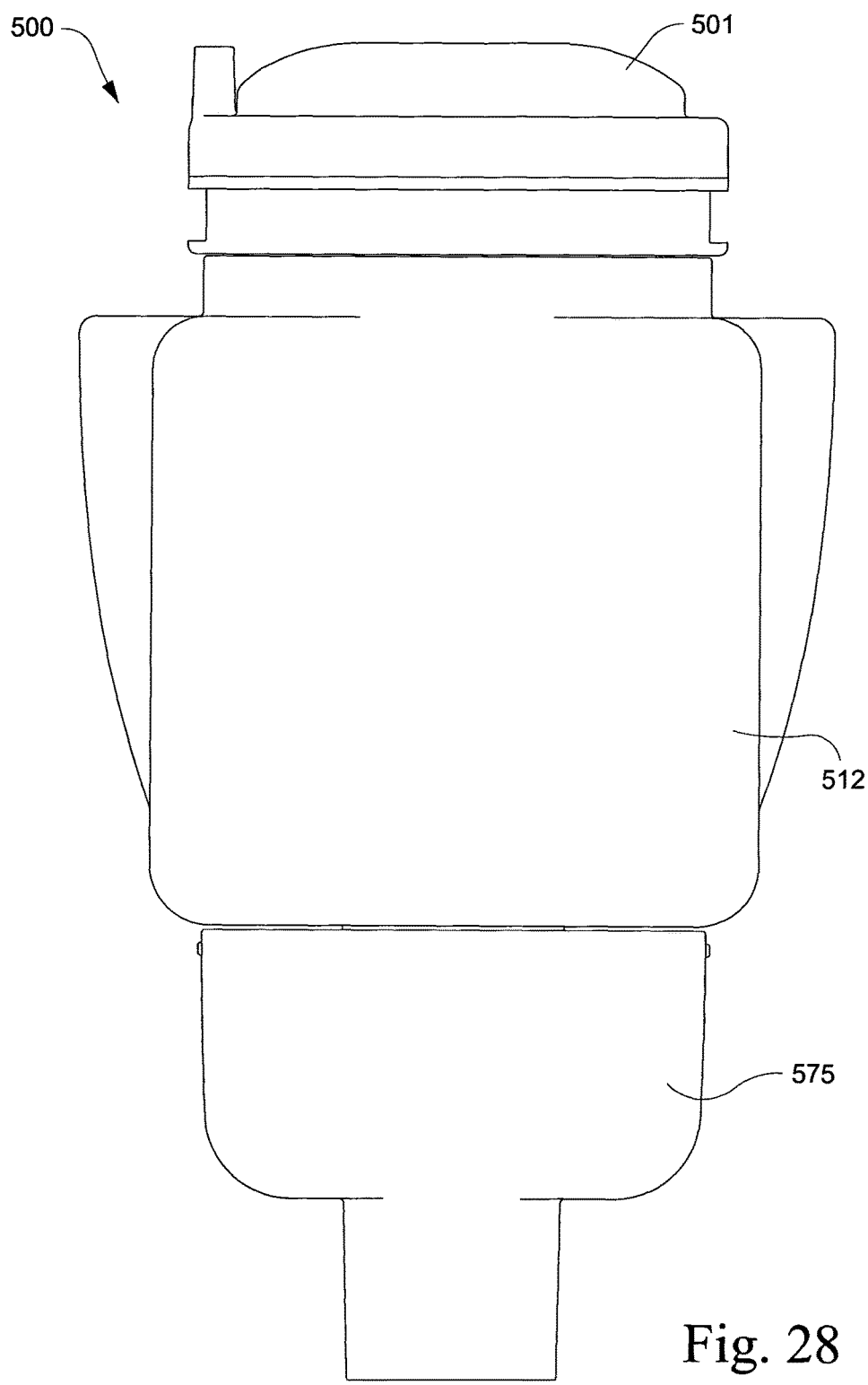
Figure 29:
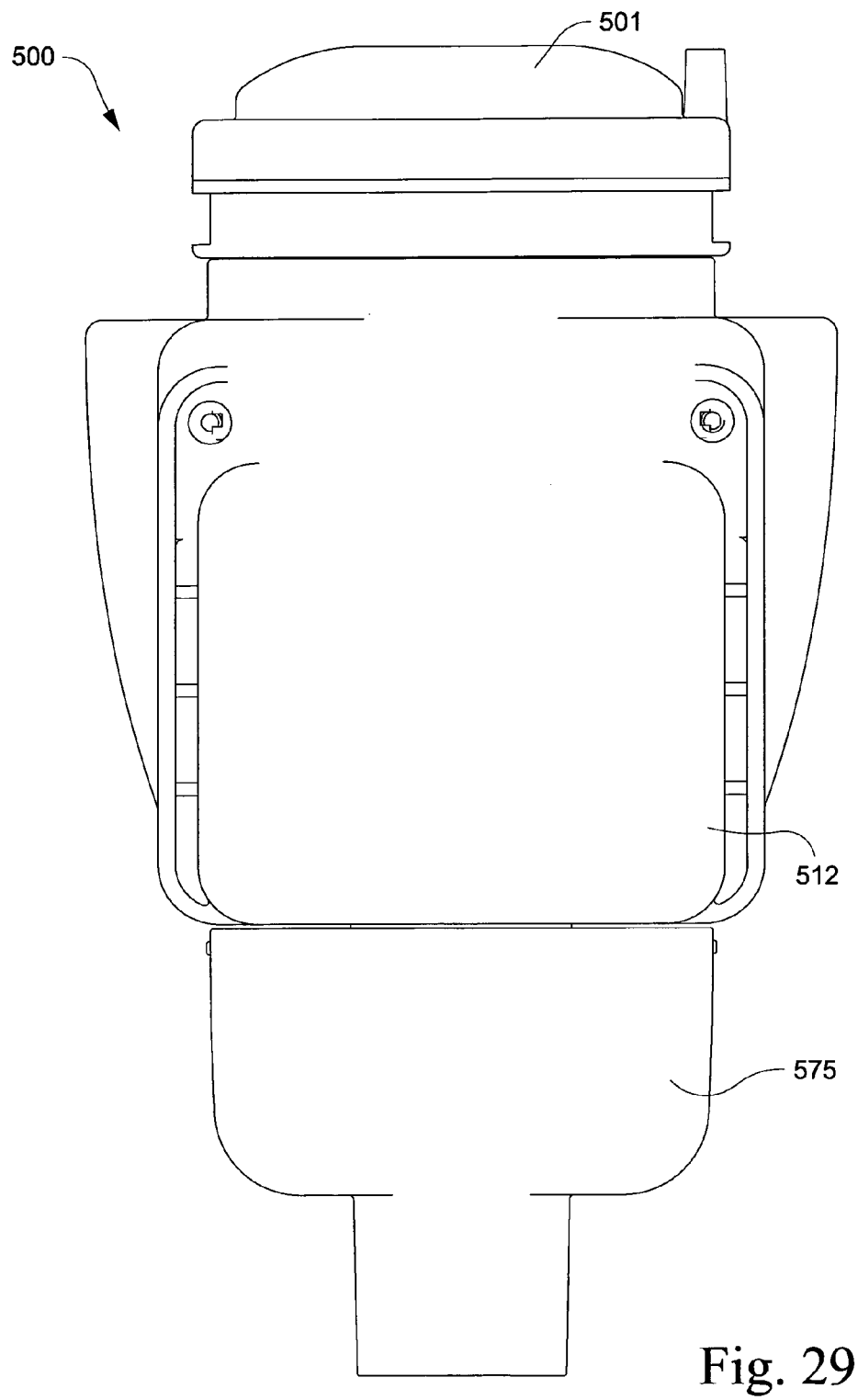
Figure 30:
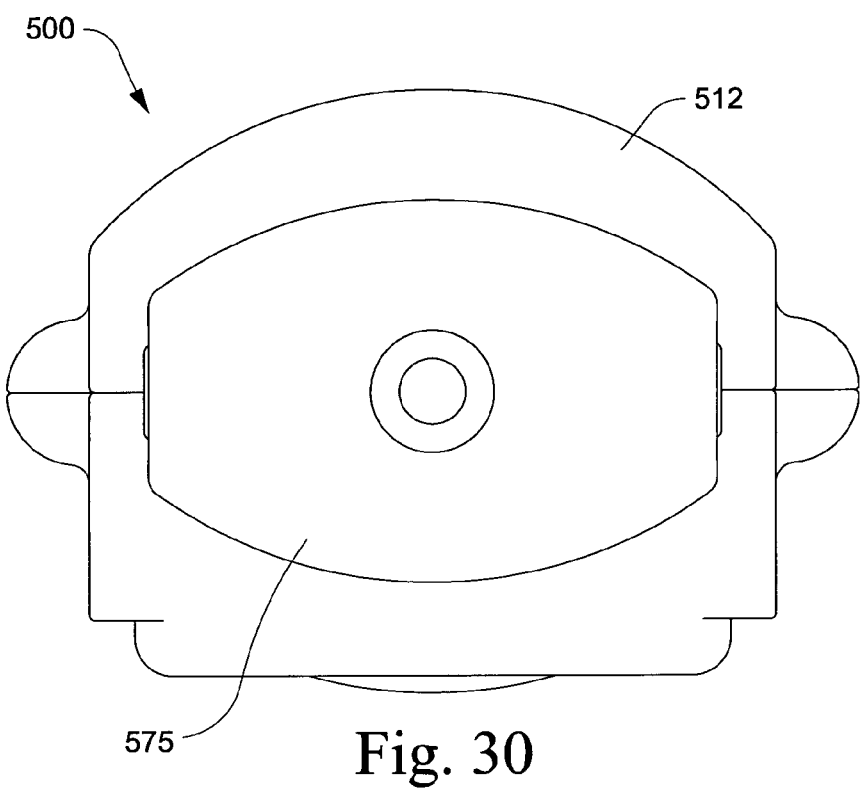
Figure 31:
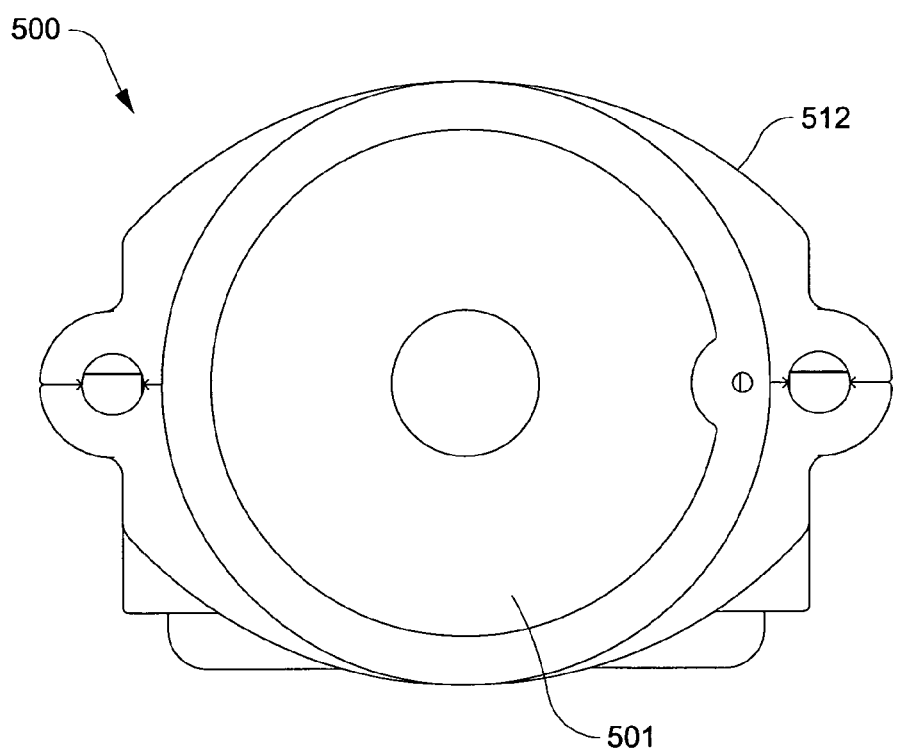
Figure 110:
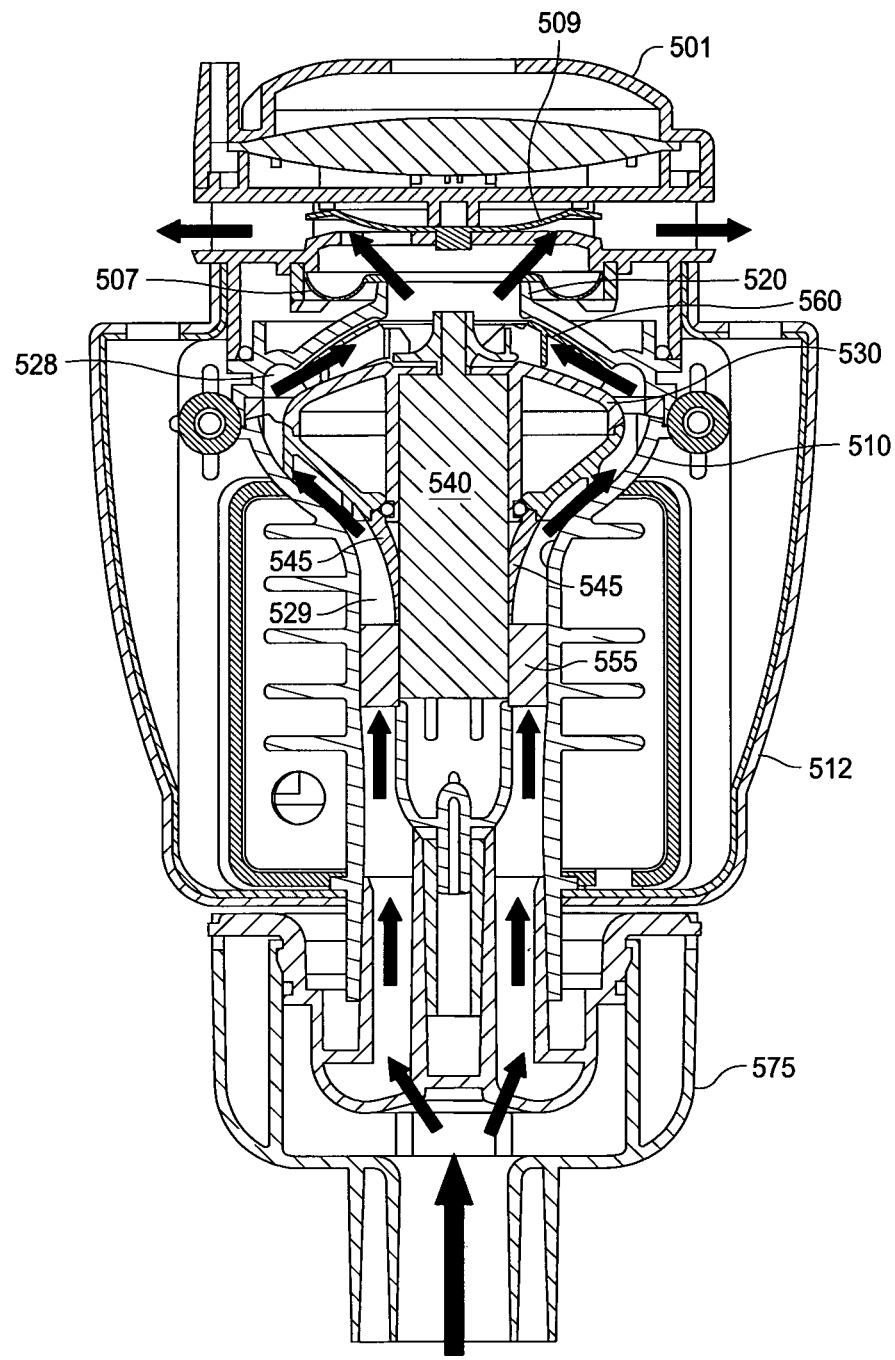
FIG. 110 is a cross-sectional view of the ventilator system of FIG. 25 showing air flow during expiration.
Figure 111:
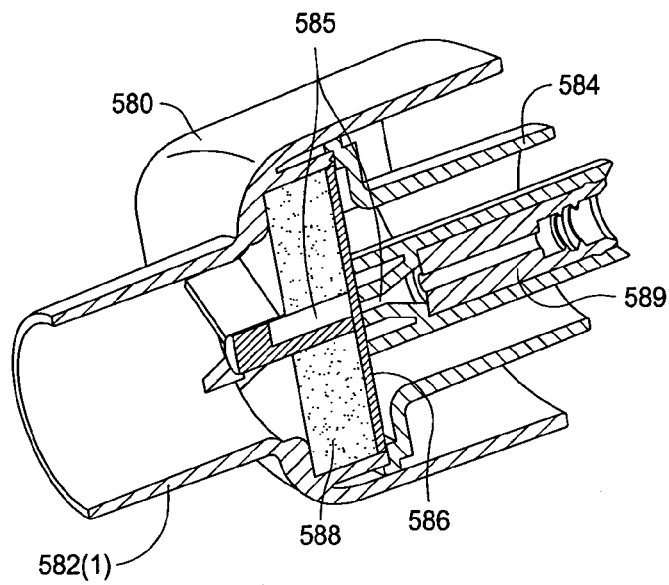
FIG. 111 is a cross-sectional view of a heat moisture exchange filter (HMEF) according to an embodiment of the invention.
Figure 112:
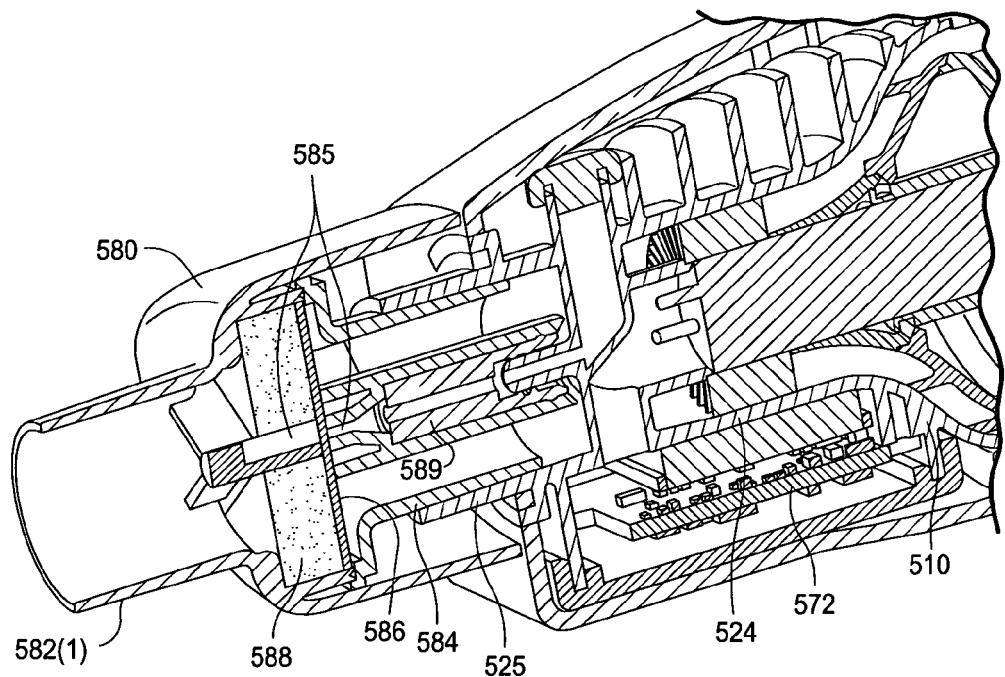
FIG. 112 is a cross-sectional view of the HMEF of FIG. 111 provided to a ventilator system.
Figure 113:
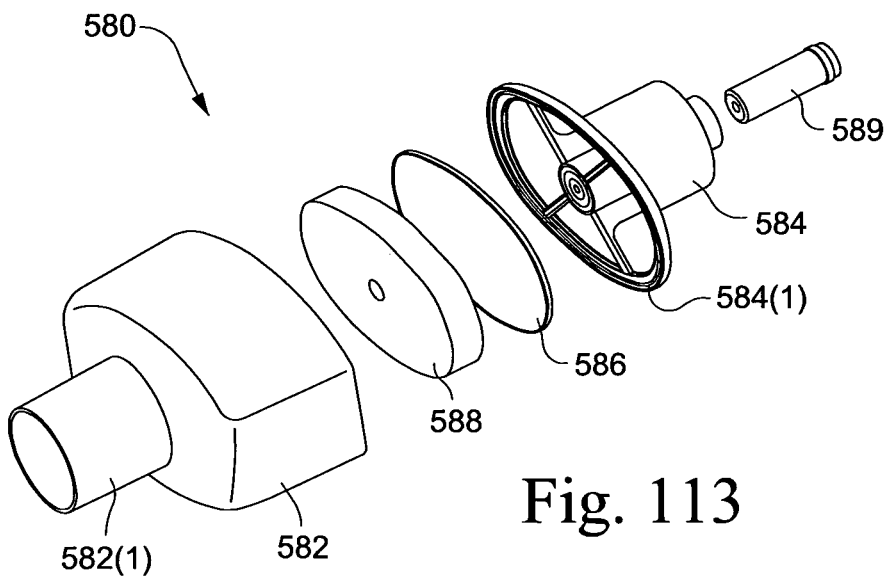
FIG. 113 is an exploded view of the HMEF of FIG. 111.
Figure 114:
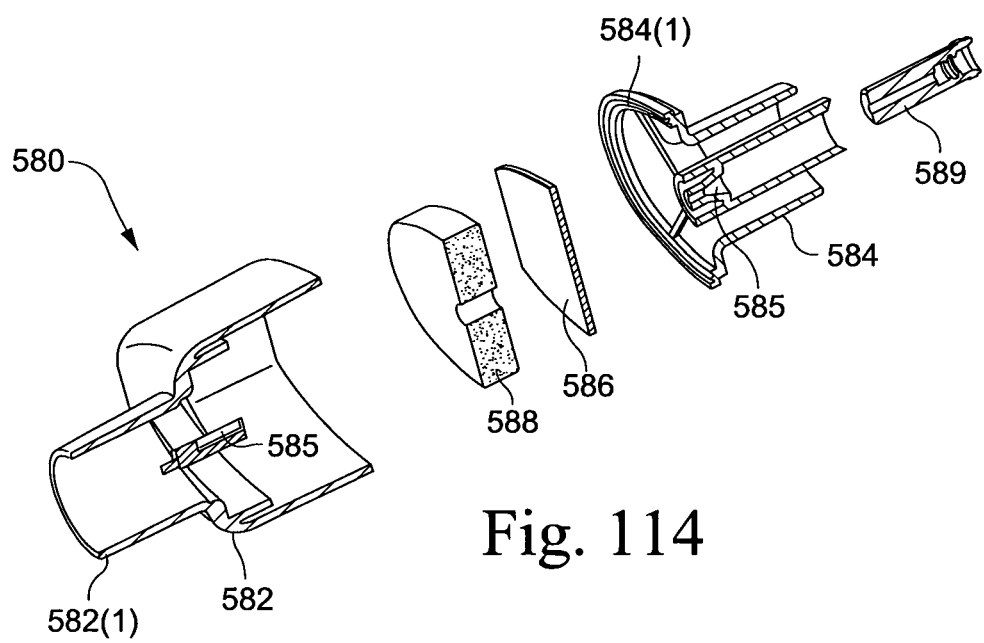
FIG. 114 is an exploded cross-sectional view of the HMEF of FIG. 111.
Figure 115:
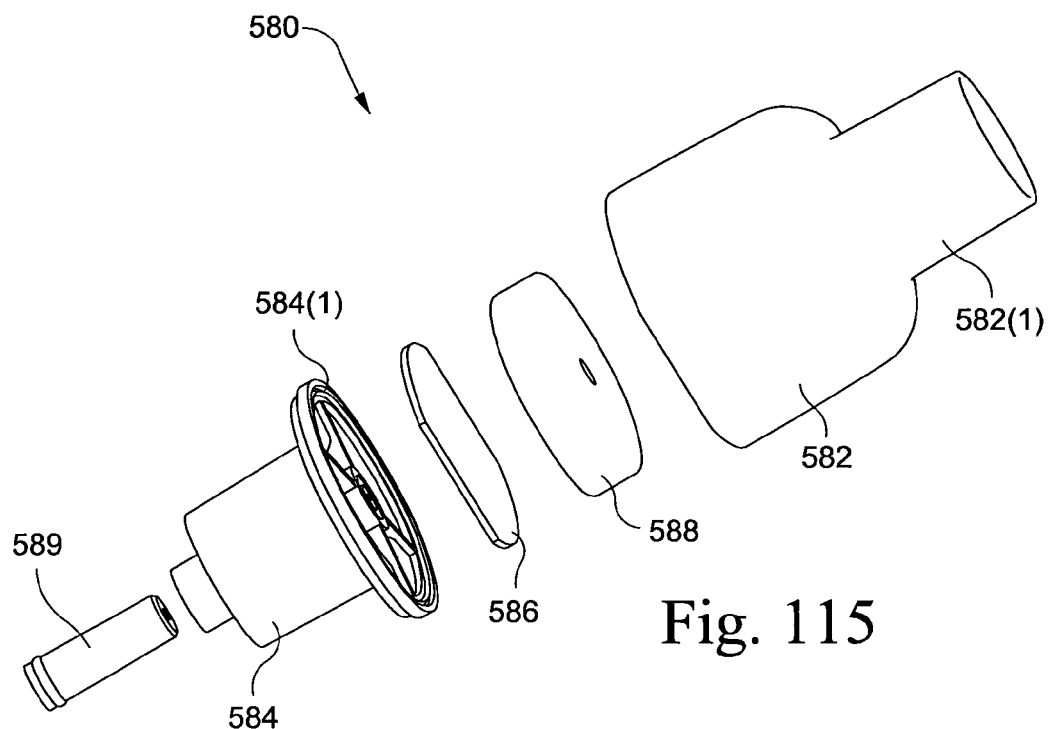
FIG. 115 another exploded view of the HMEF of FIG. 111.
Figure 116:
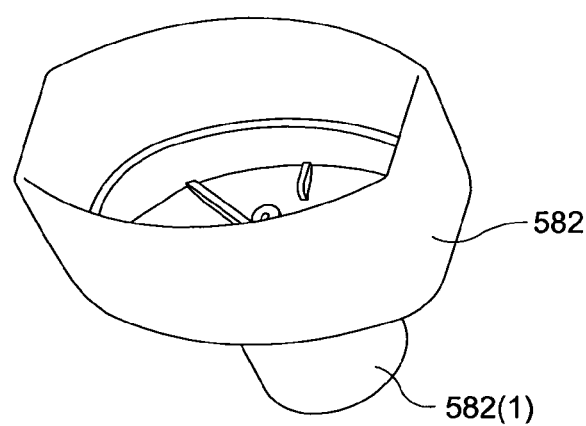
FIG. 116 is a perspective view of an outer casing of the HMEF according to an embodiment of the invention.
Figure 117:
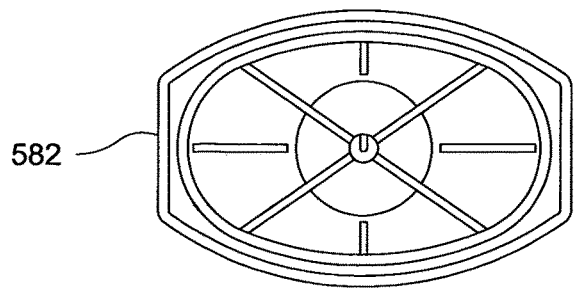
FIGS. 117-119 are bottom, top, and side views of the outer casing of FIG. 116.
Figure 118:
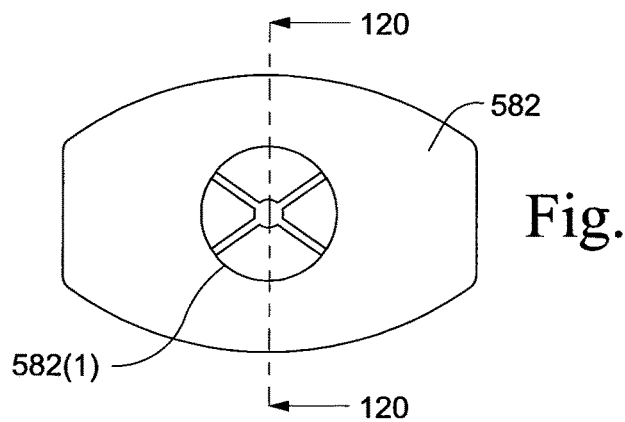
Figure 119:
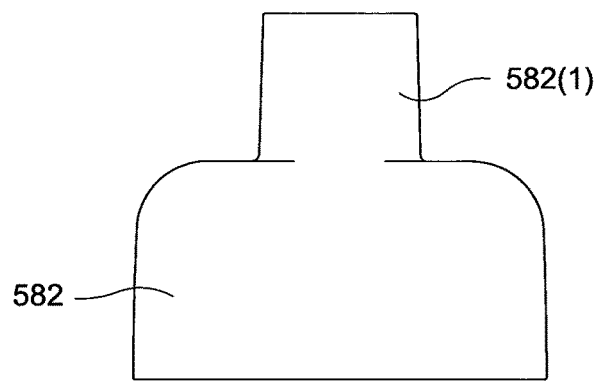
Figure 120:
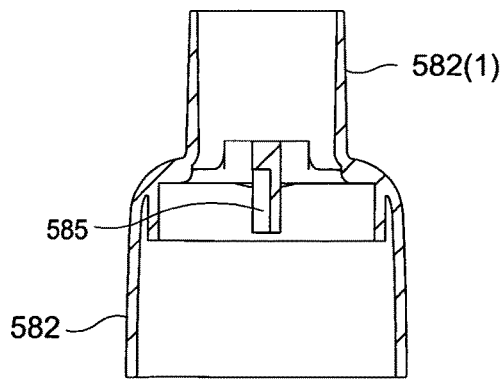
FIG. 120 is a cross-sectional view of the outer casing of FIG. 116.

FIGS. 25-110 illustrate a ventilator system 500 according to an embodiment of the present invention. As illustrated, the ventilator system 500 includes a blower 510, a filter/valve assembly 501 provided to the proximal opening of the blower, and a mucous trap 575 provided to the distal opening of the blower. The mucous trap is an optional component and may be replaced with a standard 15/22 mm conical connector, or a heat moisture exchange filter (HMEF), for example, as described below.

Blower

The blower 510 includes a housing 520, a stator component 530 including air directing grooves 535, a motor 540 adapted to drive a rotatable shaft or rotor 550, and a low inertia centrifugal impeller 560. A printed circuit board assembly (PCBA) 572 is mounted to the housing to control the motor. The PCBA 572 may be encapsulated or covered by a cap 573. In addition, a casing 512 including first and second parts 512(1), 512(2) may be provided to enclose the blower.

As best shown in FIGS. 32-50, the housing 520 includes a first or top housing part 522 (e.g., see FIGS. 41-44) defining a proximal opening or proximal end 523 (e.g., patient side opening or opening proximal to the patient) and a second or bottom housing part 524 (e.g., see FIGS. 45-50) defining a distal opening or distal end 525 (e.g., ambient side opening or opening distal from the patient). It should be appreciated that the proximal opening acts as an inlet for airflow to the patient for inspiration and acts as an outlet for expired air from the patient during expiration. Likewise, the distal opening acts as an outlet for airflow to the patient for inspiration and acts as an inlet for expired air from the patient during expiration.

Figure 36:
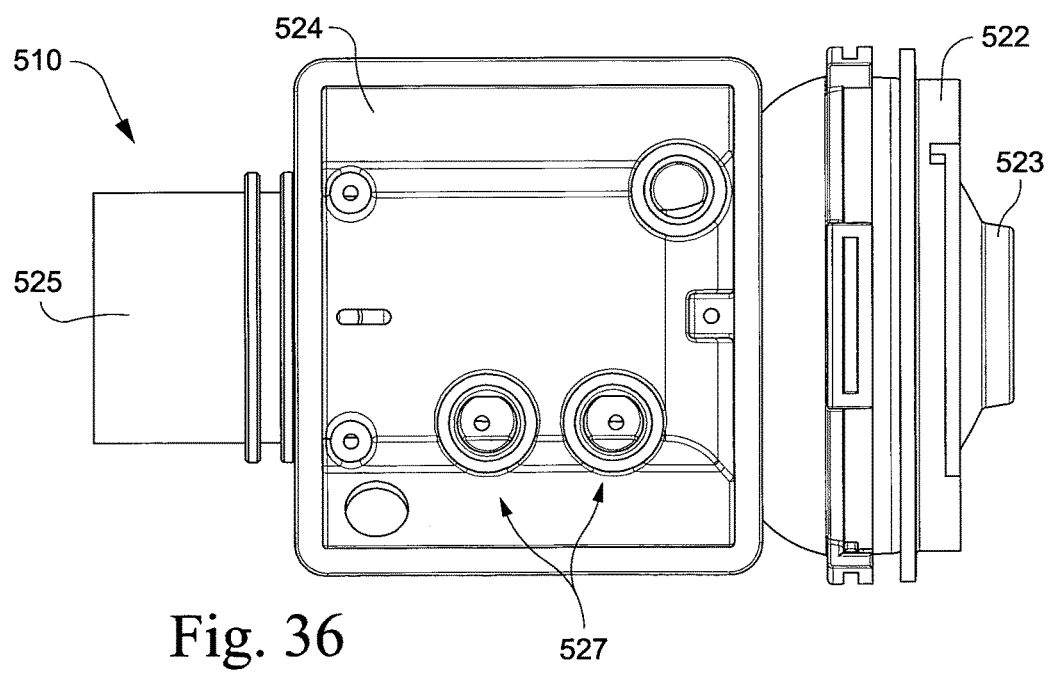
FIGS. 36-39 are rear, side, bottom, and top views of the blower of FIG. 35.
Figure 37:
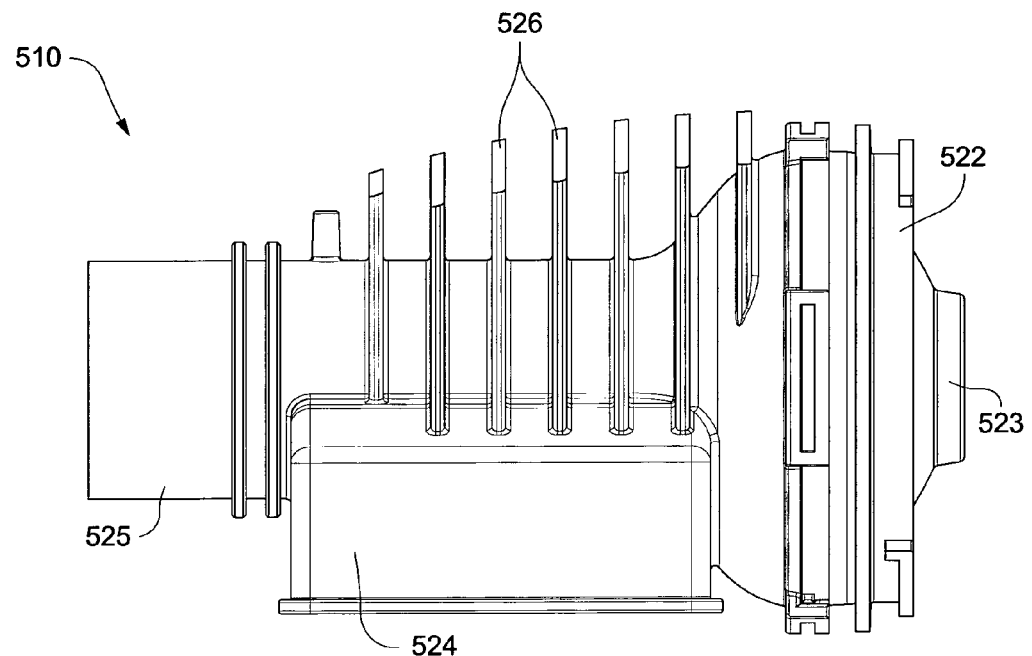
Figure 38:
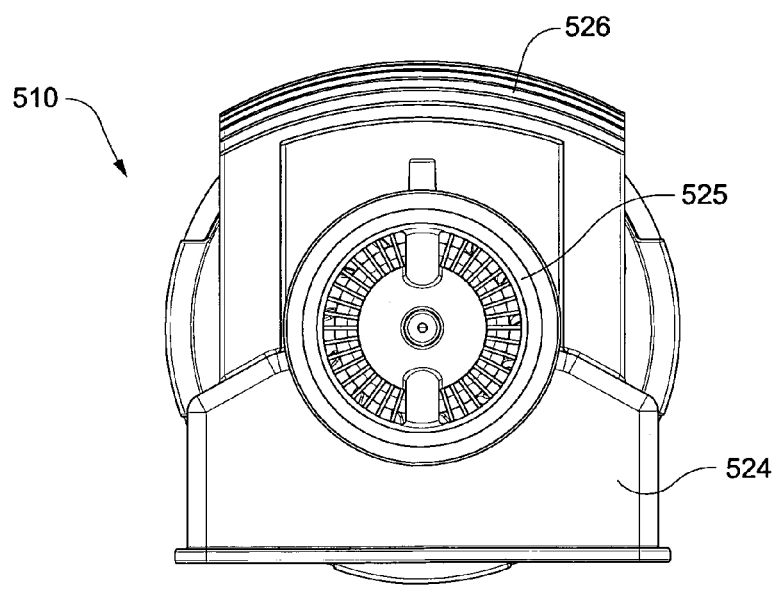
Figure 39:
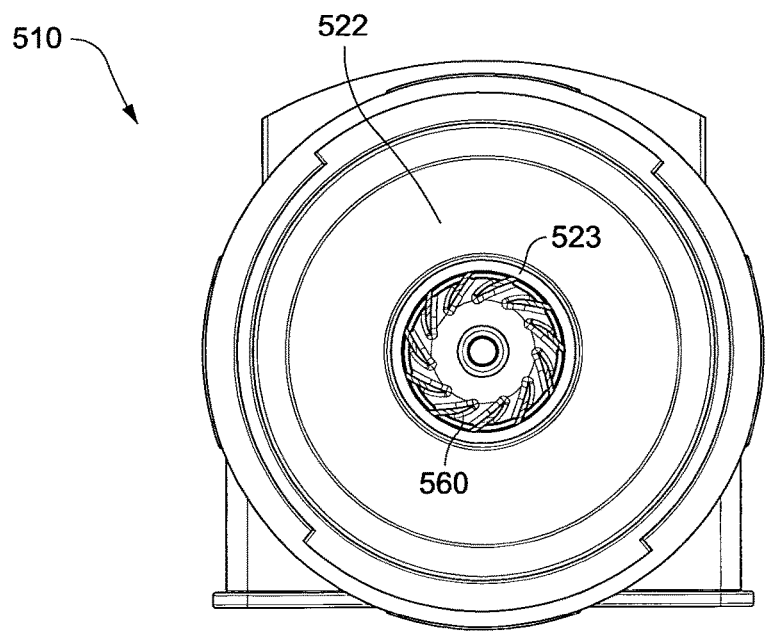
Figure 40:
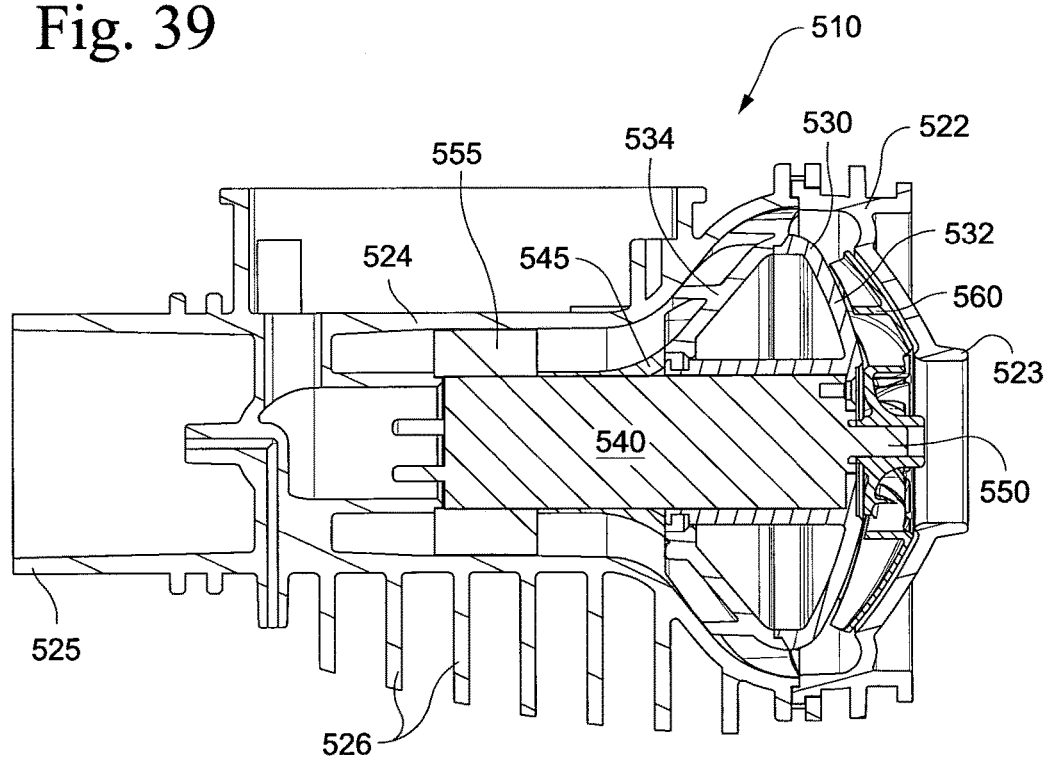
FIG. 40 is a cross-sectional view of the blower of FIG. 35.
Figure 48:
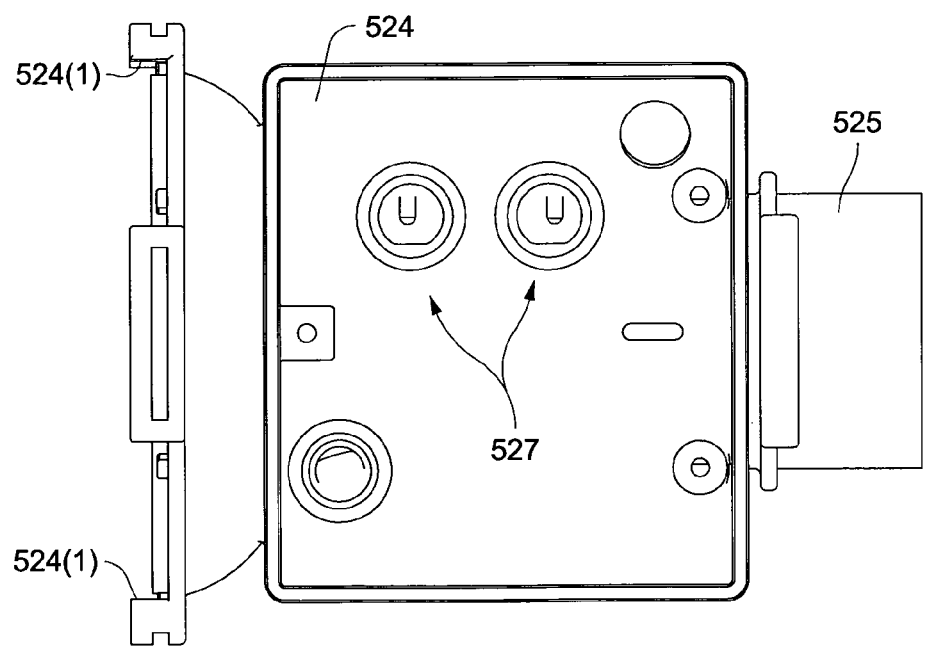
Figure 49:
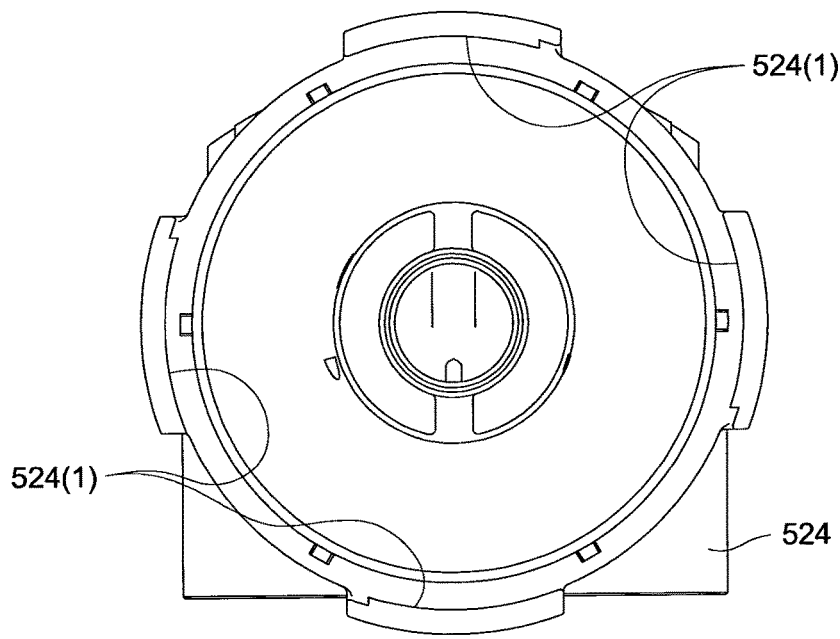
Figure 50:
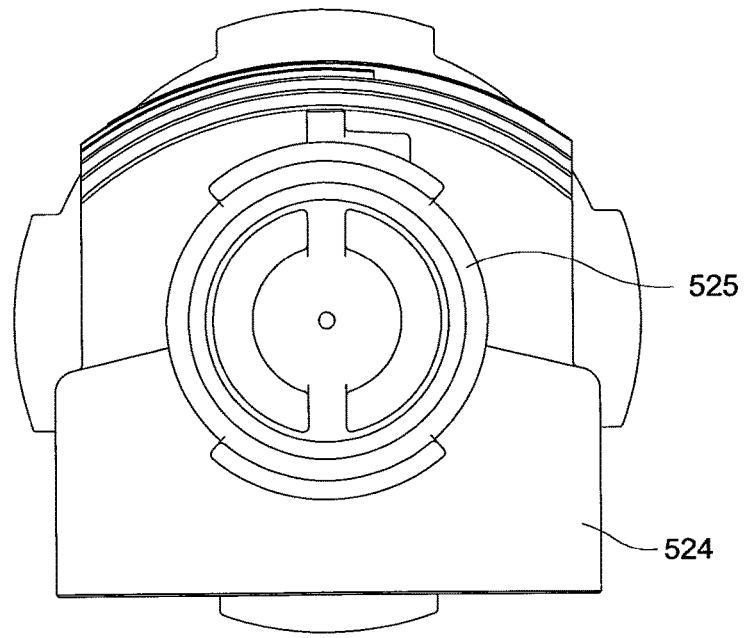
Figure 51:
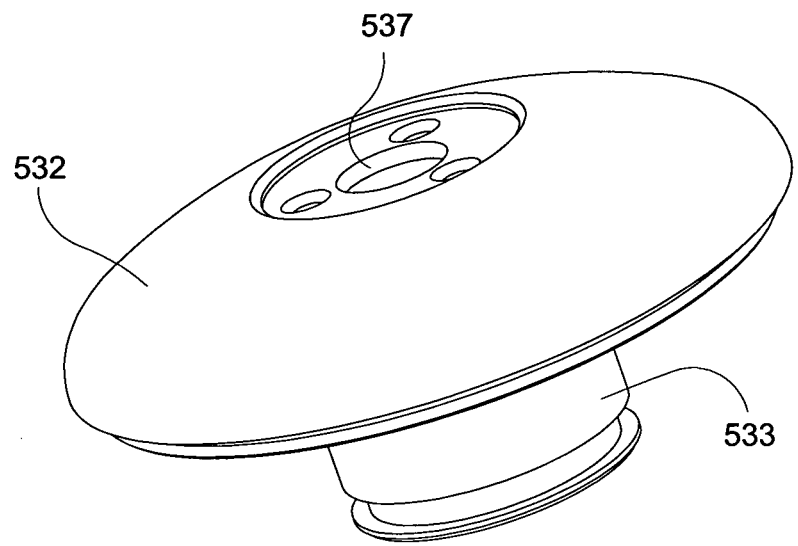
FIG. 51 is a perspective view of a first part of the stator component of the blower according to an embodiment of the invention.
Figure 52:
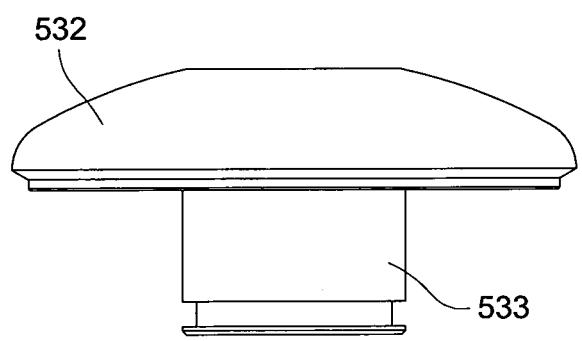
FIGS. 52-54 are side, top, and bottom views of the first part of FIG. 51.
Figure 53:
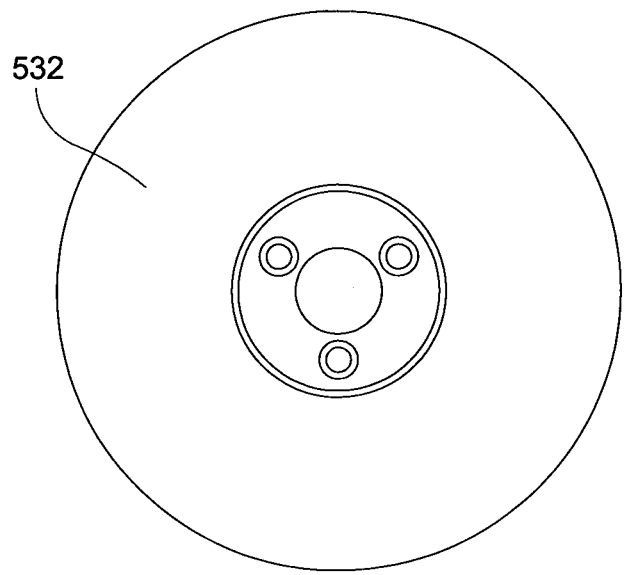
Figure 54:
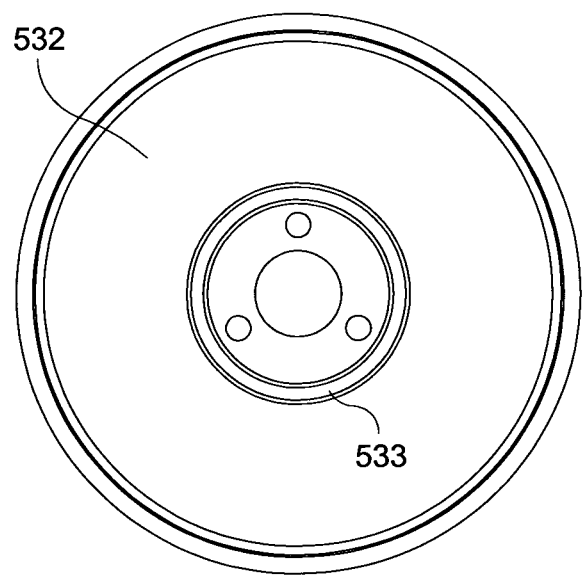
Figure 55:
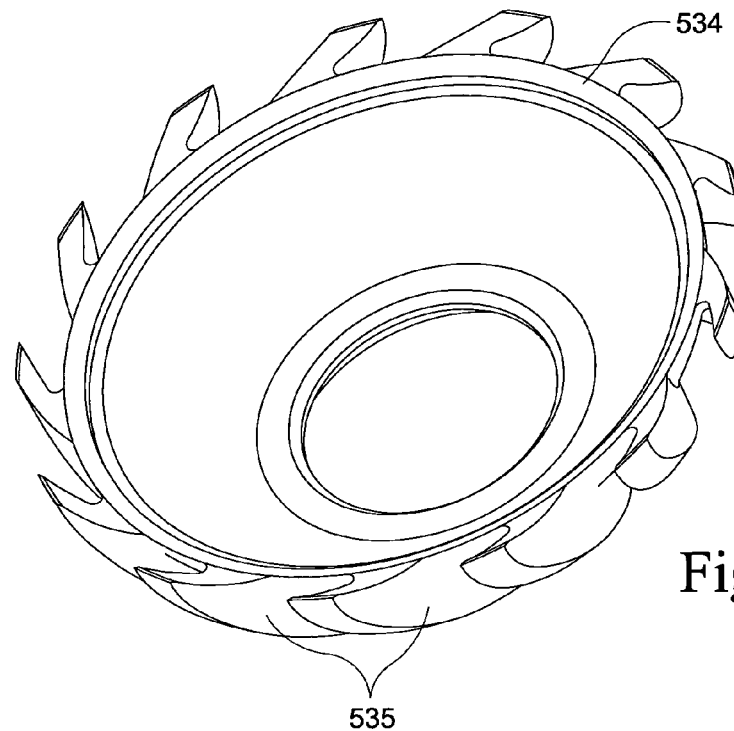
FIG. 55 is a perspective view of a second part of the stator component of the blower according to an embodiment of the invention.
Figure 56:
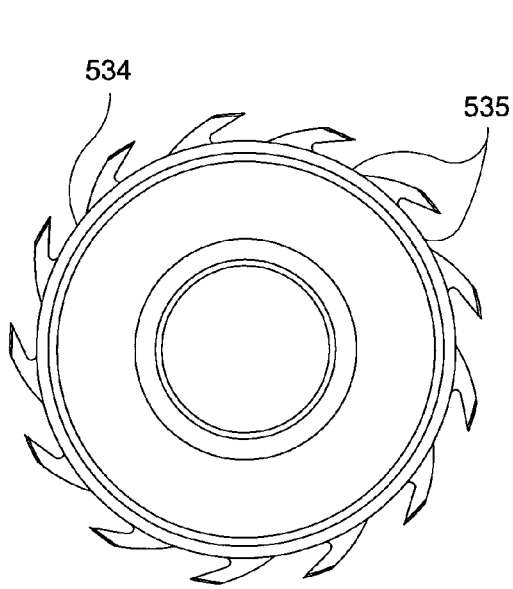
FIGS. 56-58 are top, bottom, and side views of the second part of FIG. 55.
Figure 57:
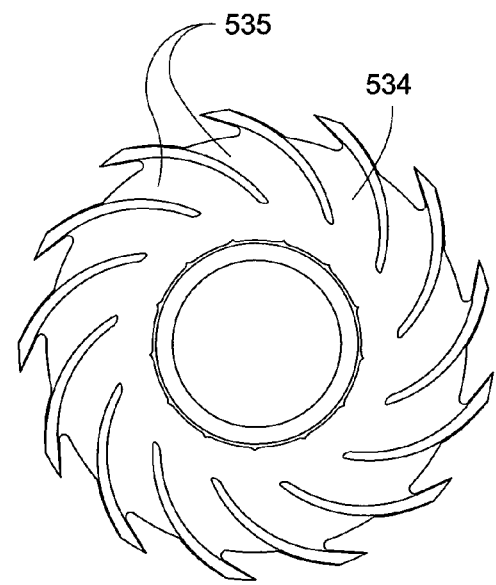
Figure 58:
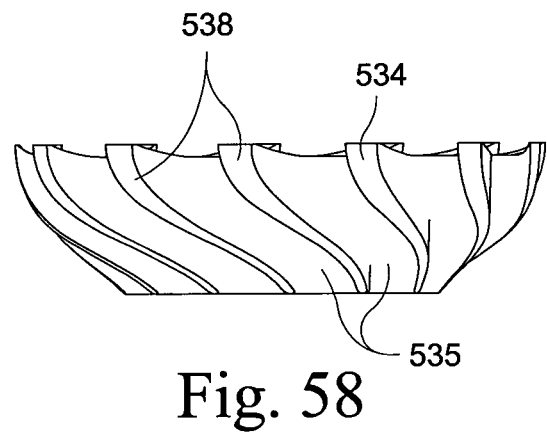
Figure 59:
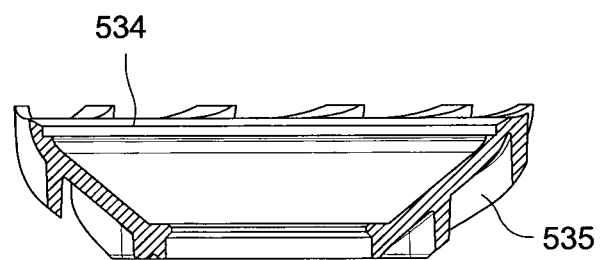
FIG. 59 is a cross-sectional view of the second part of FIG. 55.
Figure 60:
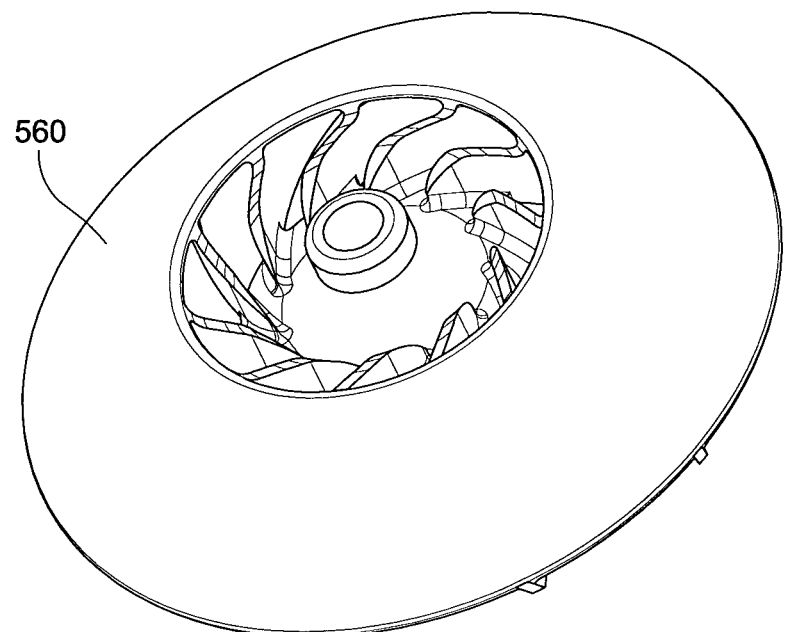
FIG. 60 is a perspective view of an impeller of the blower according to an embodiment of the invention.
Figure 61:
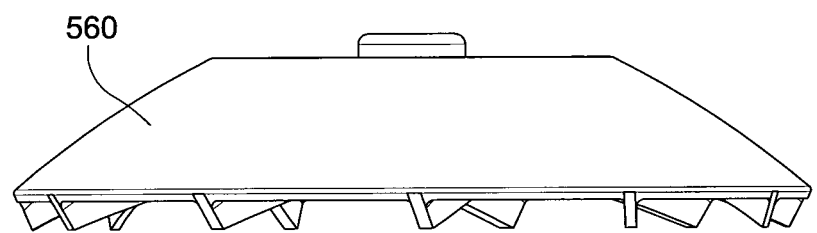
FIGS. 61-63 are side, top, and bottom views of the impeller of FIG. 60.
Figure 62:
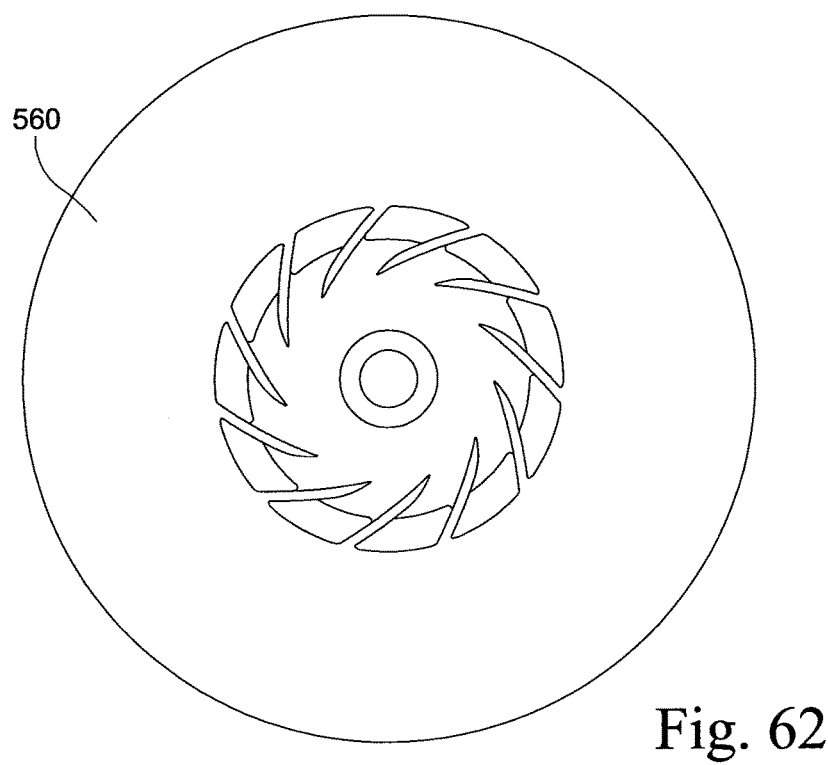

As shown in FIGS. 36 and 48, the bottom housing support 524 includes one or more openings 527 that allow sensors of the PCBA 572 to communicate with the air flow path within the blower. The bottom housing part 524 also includes multiple heat sinks or fins 526 to assist with removing heat.

In the illustrated embodiment, the first and second housing parts 522, 524 may be coupled to one another by a bayonet type connection (see FIGS. 41-44), e.g., protrusions 522(1) provided on first housing part 522 adapted to slidably engage within respective slots 524(1) provided on the second housing part 524. However, it should be appreciated that the first and second housing parts may be secured to one another in other suitable manners, e.g., fasteners, etc.

As best shown in FIGS. 32-34 and 51-59, the stator component 530 includes a first part 532 (e.g., see FIGS. 51-54) and a second part 534 (e.g., see FIGS. 55-59) that are coupled to one another. The first part 532 (e.g., constructed of a heat conducting material such as aluminum) provides a tube or motor flange 533 adapted to support the motor 540 in an operative position. The first part 532 includes an opening 537 to allow the rotor 550 to pass therethrough for engagement with the impeller 560. The second part 534 (e.g., constructed of a heat conducting material such as aluminum) defines the plurality of air directing grooves or channels 535 as described above to direct air from a centrifugal flow to an axial flow. The stator component may act as a heat conductive element or heat sink to dissipate heat from the motor. A rubber component 536 is provided within the stator component to assist with heat dissipation.

A non-electrically conducting motor sleeve 545 (e.g., constructed of plastic) is provided to the motor 540 below the stator component along a central segment of the motor. The sleeve 545 prevents inductive losses from the motor 540.

A flow element 555 (e.g., constructed of a heat conducting material such as aluminum) is provided in the air flow path between the motor 540 and the bottom housing part 524. The flow element 555 acts a flow sensor and includes a plurality of vanes 555(1) (e.g., 20-60 vanes, e.g., 40 vanes) that measures flow in both directions and provides a heat conducting function for the motor, i.e., acts as a heat sink for the motor (e.g., see FIGS. 68-70).

The housing 520 and stator component 530 cooperate to define a plenum chamber 528 (e.g., see FIGS. 32 and 33) for air flow from the impeller 560. Also, the housing 520 and sleeve 545 cooperate to define a downstream chamber 529 (e.g., see FIGS. 32 and 33) to allow flow recirculation through the stator component without affecting the flow sensor, i.e., downstream chamber allows flow to develop fully laminar and reduce turbulence before the flow element. Furthermore, having a plenum chamber 528 for the air flow from the impeller reduces the occurrence of blade pass tonal noise as the impeller blades 562, particularly the tips of the impeller blades, are shielded from the stator vanes 535. Thus, there is no line of sight between the tips of the impeller blades 562 and the stator vanes 535.

Figure 32:
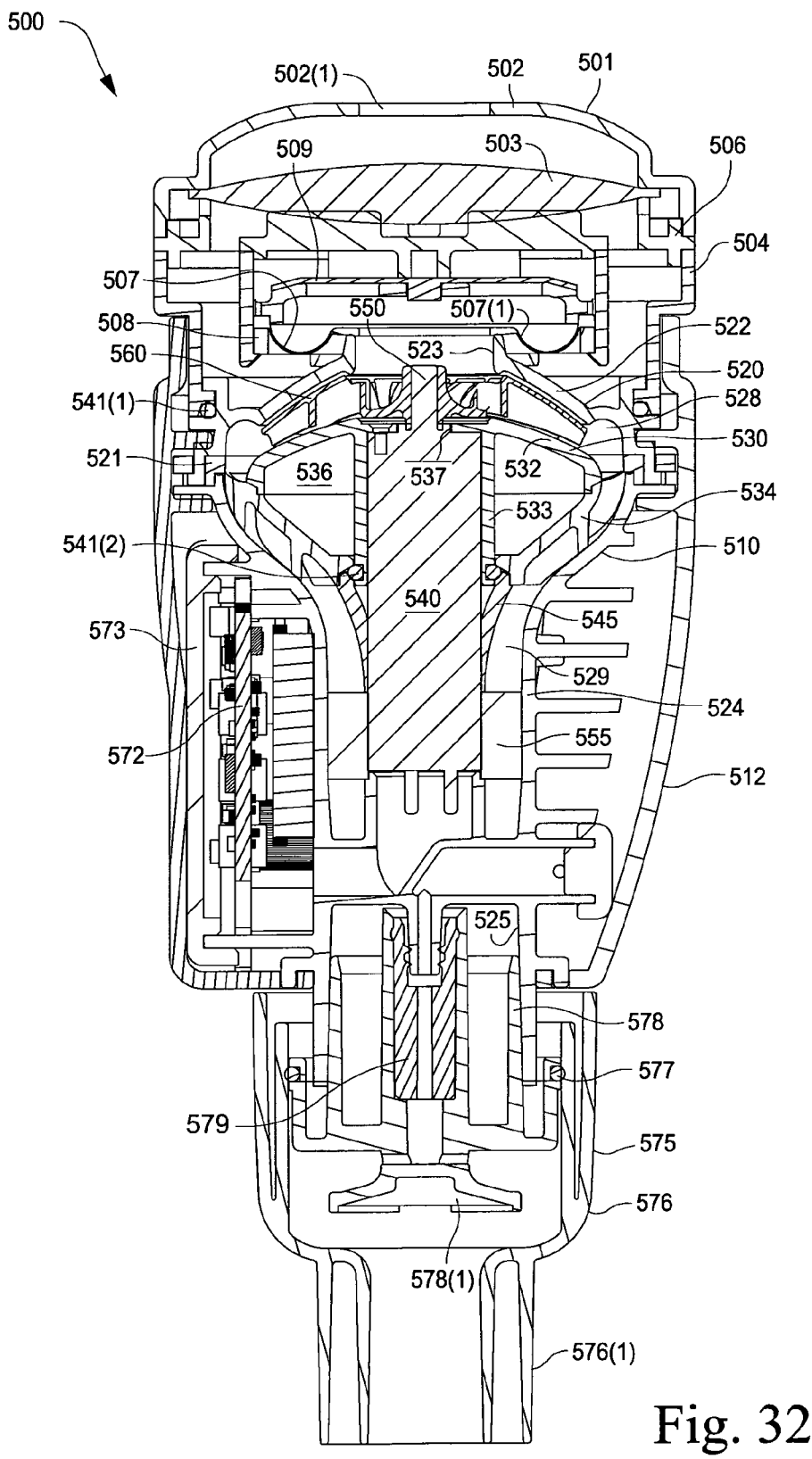
FIG. 32 is a cross-sectional view of the ventilator system of FIG. 25.
Figure 33:
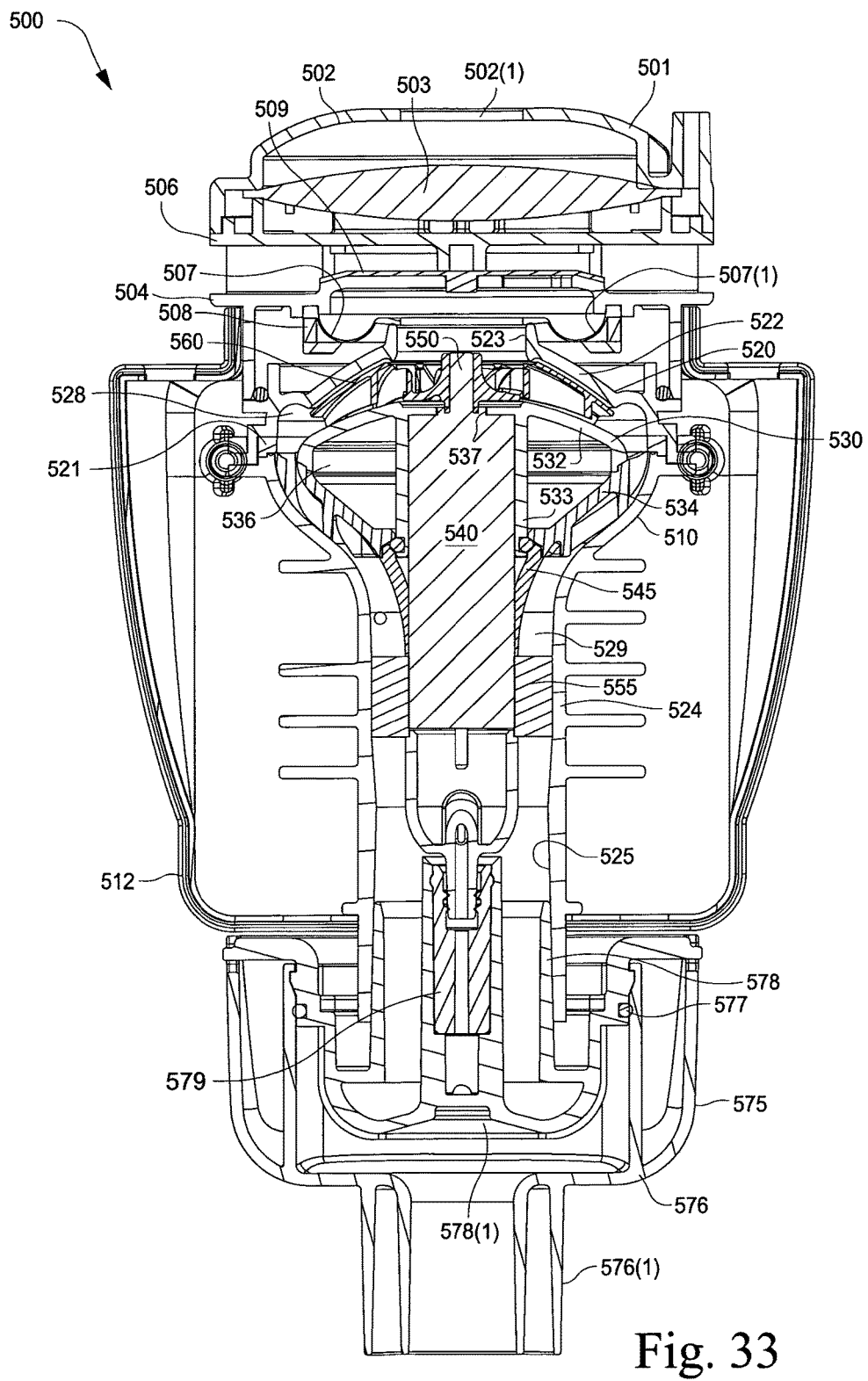
FIG. 33 is another cross-sectional view of the ventilator system of FIG. 25.
Figure 34:
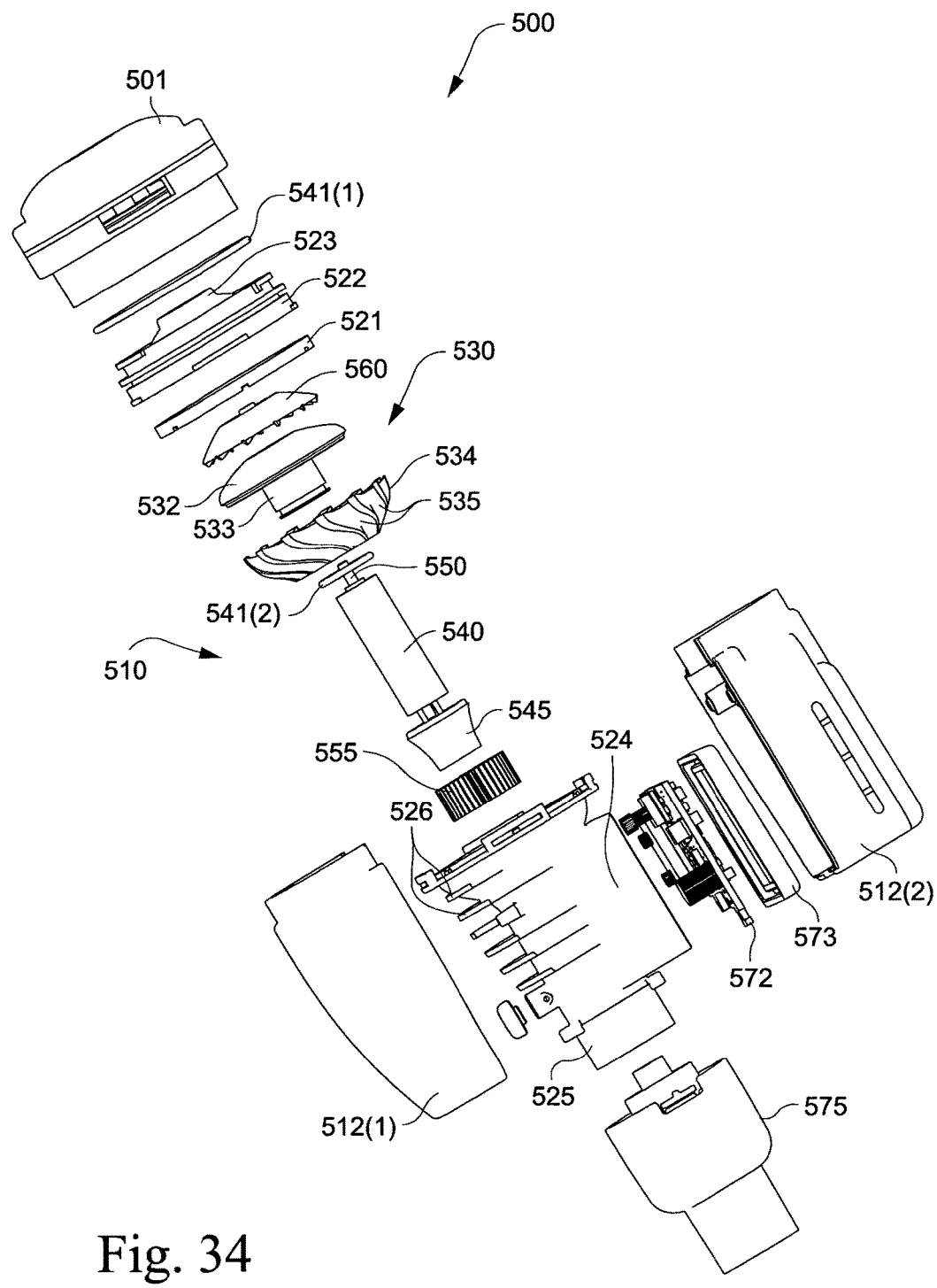
FIG. 34 is an exploded view of the ventilator system of FIG. 25.
Figure 35:
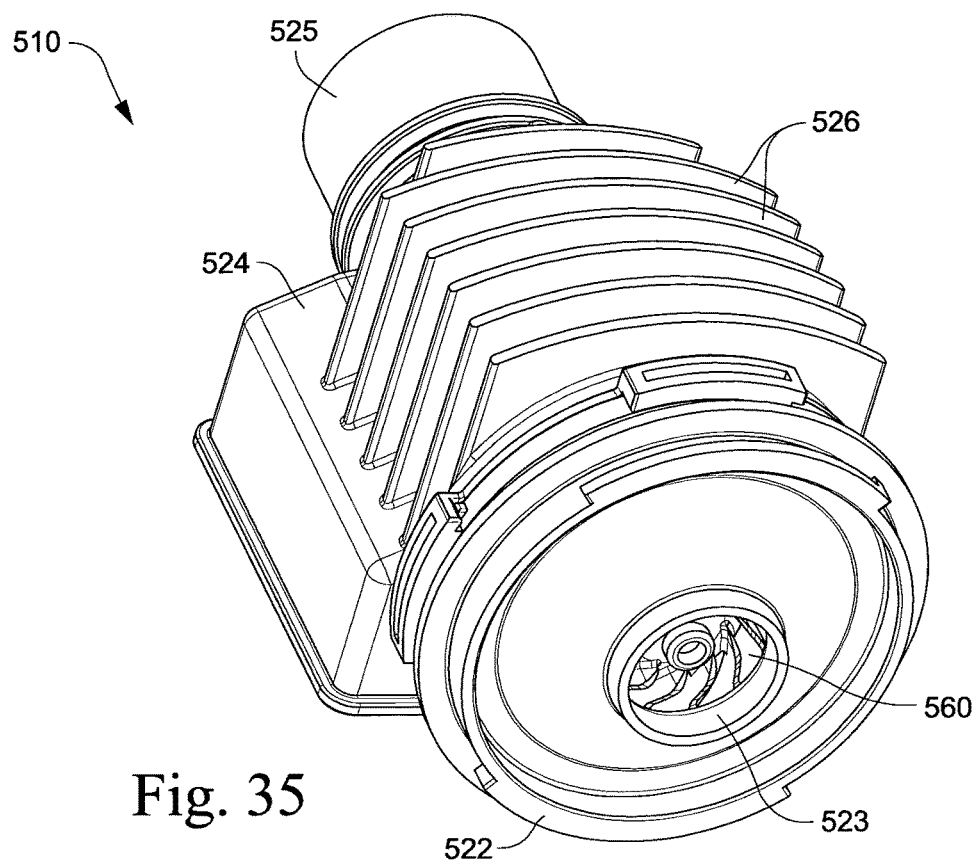
FIG. 35 is a perspective view of a blower of the ventilator system according to an embodiment of the invention.

As shown in FIGS. 32-34, a gasket 521 (e.g., constructed of silicon) may be provided between the first and second housing parts 522, 524, e.g., for sealing, vibration isolation, shock resistance, reduce noise. In addition, as shown in FIGS. 32-34, an o-ring 541(1) may be provided between the first housing part 522 and the filter/valve assembly 501 and an o-ring 541(2) may be provided between the first and second parts 532, 534 of the stator component 530 and the sleeve 545, e.g., for sealing, vibration isolation, shock resistance, reduce noise. The o-ring 541(2) seals the internal volume of the stator component to prevent airflow into the stator component and thus reduce the deadspace volume.

Filter/Valve Assembly

As best shown in FIGS. 32, 33, and 71-96, the filter/valve assembly 501 includes a filter cover 502 (e.g., see 77-80) defining an air inlet 502(1) and an auxiliary port 502(2) (e.g., for auxiliary oxygen), an air flow diverter/manifold 504 (e.g., see FIGS. 81-84) defining air inlets 504(1) and expired air outlets 504(2) and outlet channels 504(3), an air flow diverter cap 506 (e.g., see FIGS. 85-88), an air inlet membrane valve or inhale valve membrane 507 (e.g., see FIGS. 89-92) to control airflow into the blower proximal opening for inspiration and airflow out of the blower for expiration, an inlet valve ring 508, an air outlet membrane valve or exhale valve membrane 509 (e.g., see FIGS. 93-96) to allow air to be expired, and a filter 503 to filter the inlet airflow.

Figure 41:
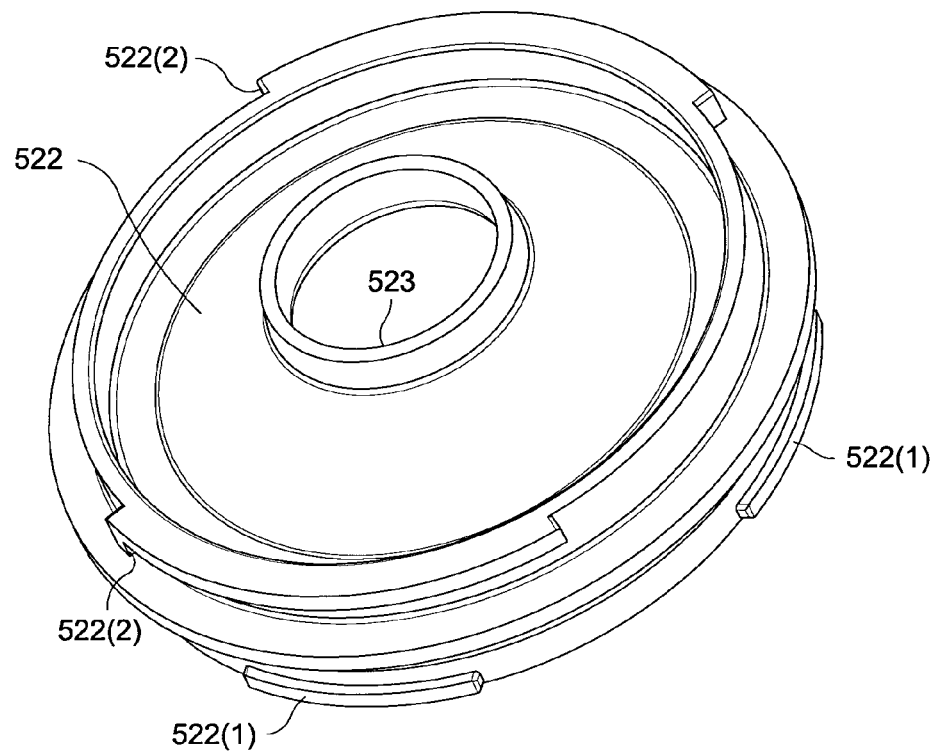
FIG. 41 is a perspective view of a top housing part of the blower according to an embodiment of the invention.
Figure 42:
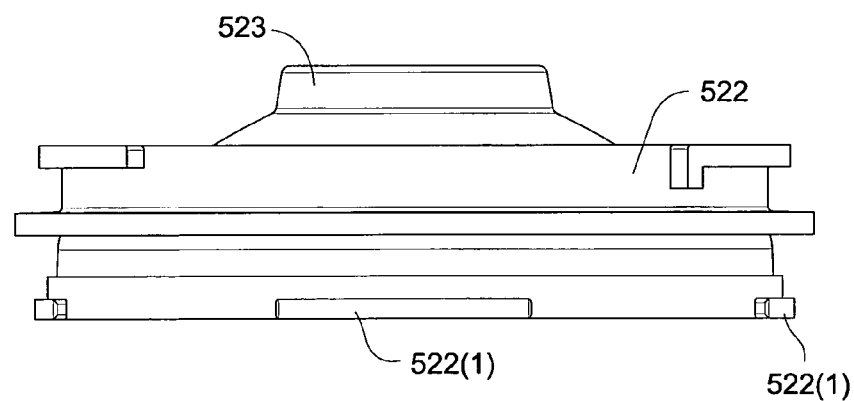
FIGS. 42-44 are side, top, and bottom views of the top housing part of FIG. 41.
Figure 43:
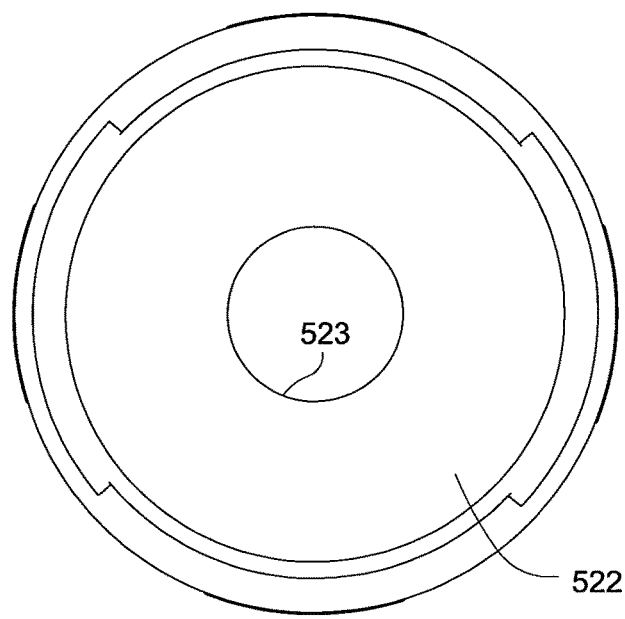
Figure 44:
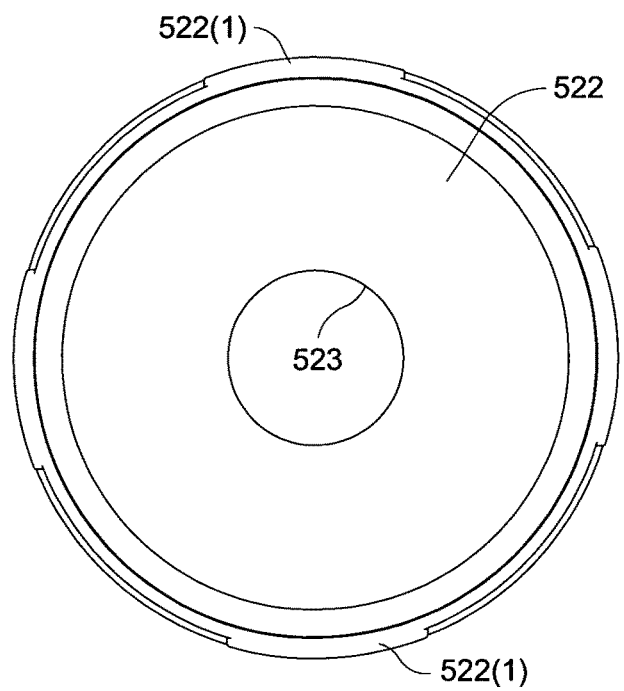
Figure 45:
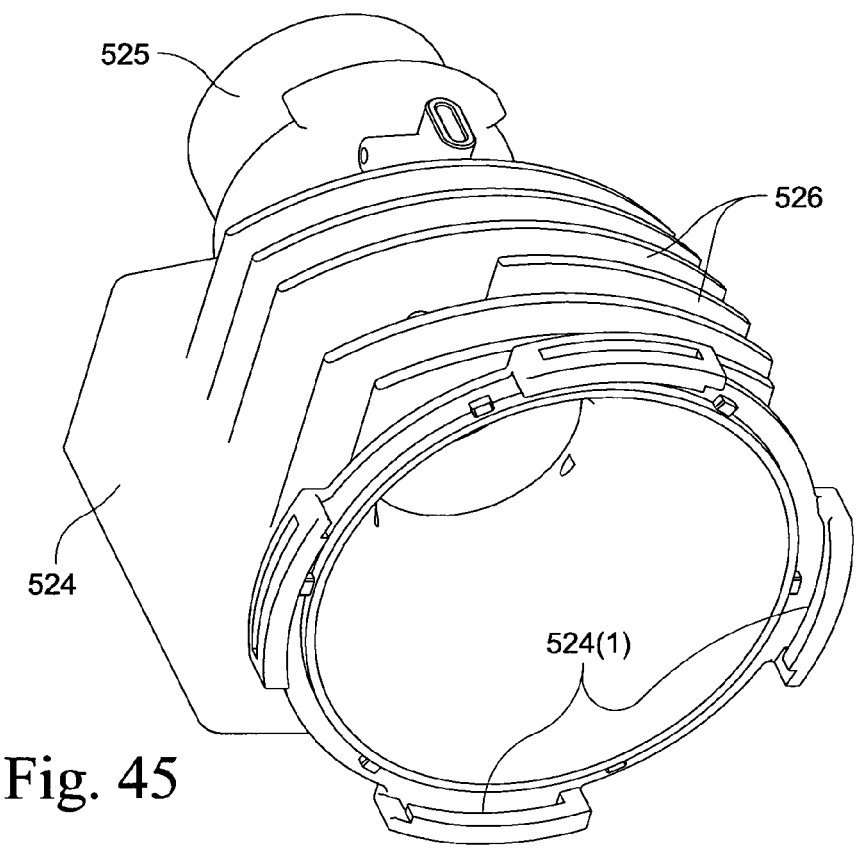
FIG. 45 is a perspective view of a bottom housing part of the blower according to an embodiment of the invention.
Figure 46:
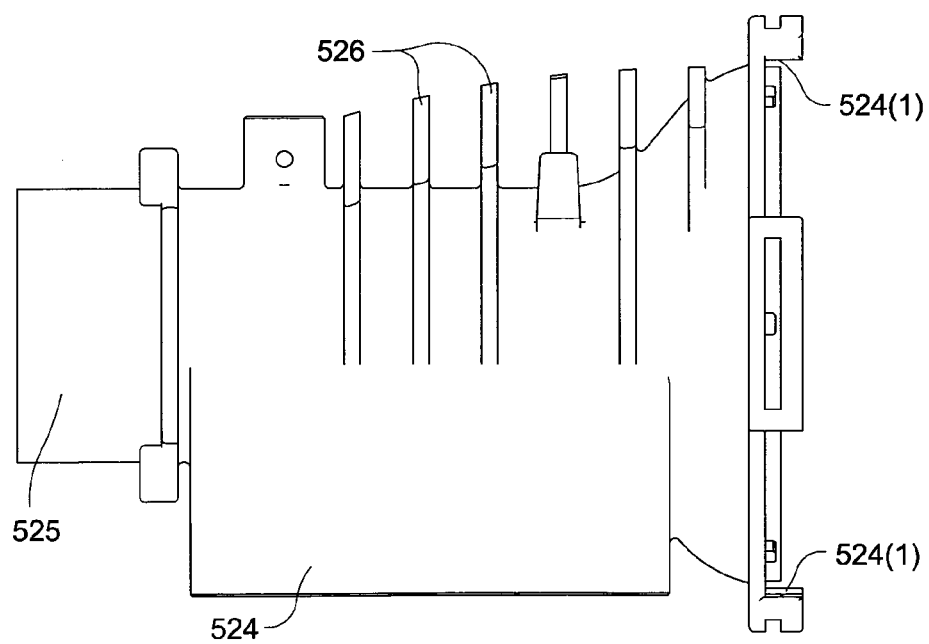
FIGS. 46-50 are left side, right side, rear, top, and bottom views of the bottom housing part of FIG. 45.
Figure 47:
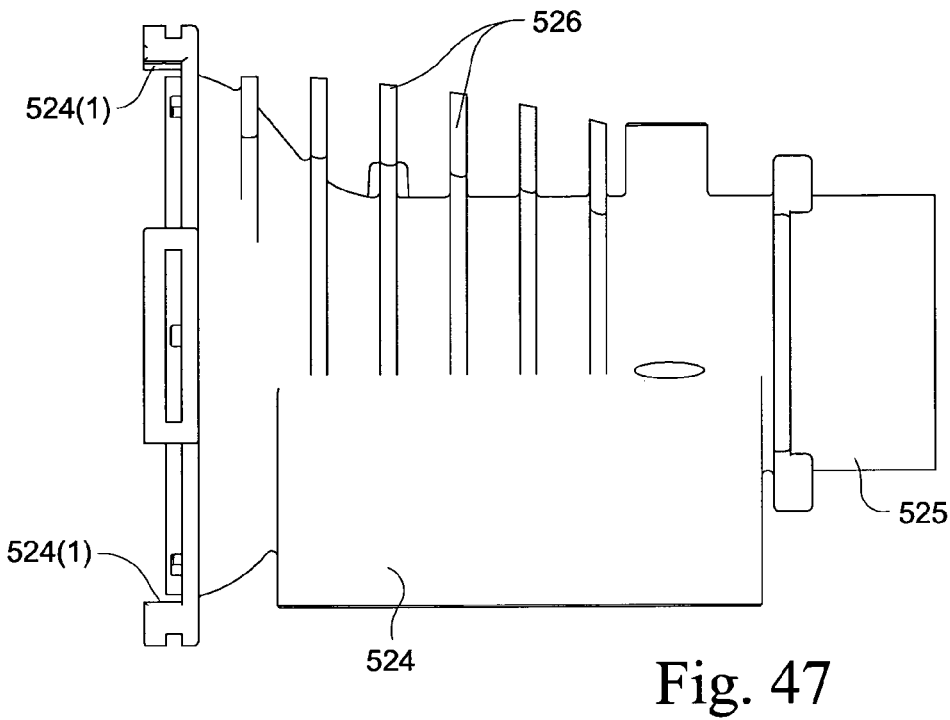

In the illustrated embodiment, the filter/vale assembly may be coupled to the blower by a bayonet type connection, e.g., protrusions 504(4) provided on base of the air flow diverter/manifold 504 (e.g., see FIGS. 74 and 84) adapted to slidably engage within respective slots 522(2) provided on the top of the first housing part 522 (e.g., see FIG. 41). However, it should be appreciated that the filter/valve assembly and the blower may be secured to one another in other suitable manners.

Figure 75:
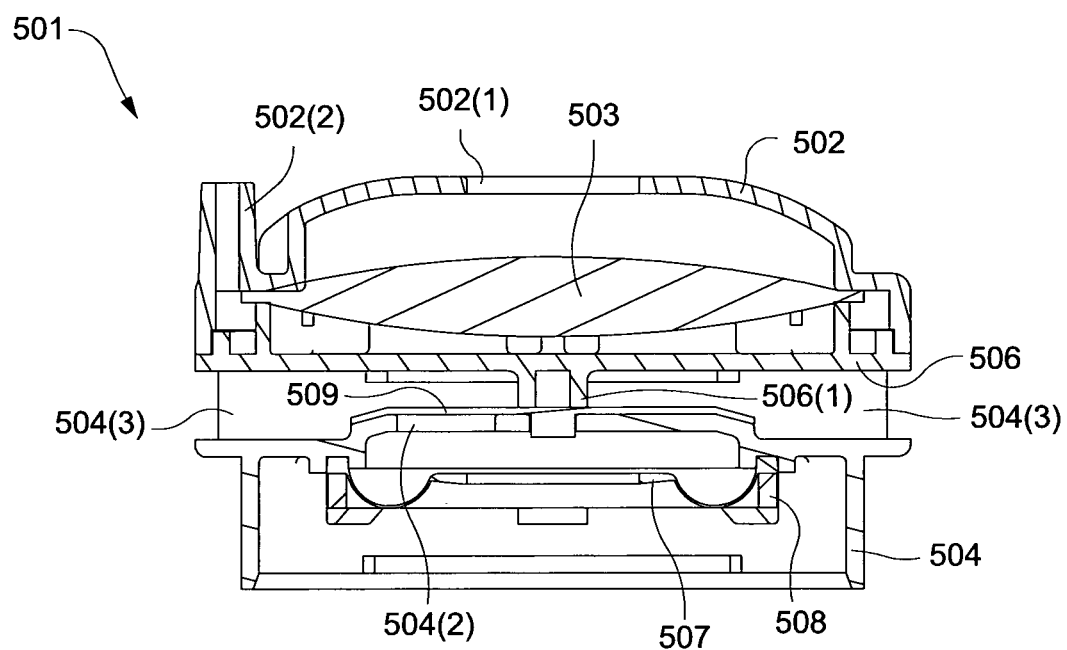
FIG. 75 is a cross-sectional view of the filter/valve assembly of FIG. 71.
Figure 76:
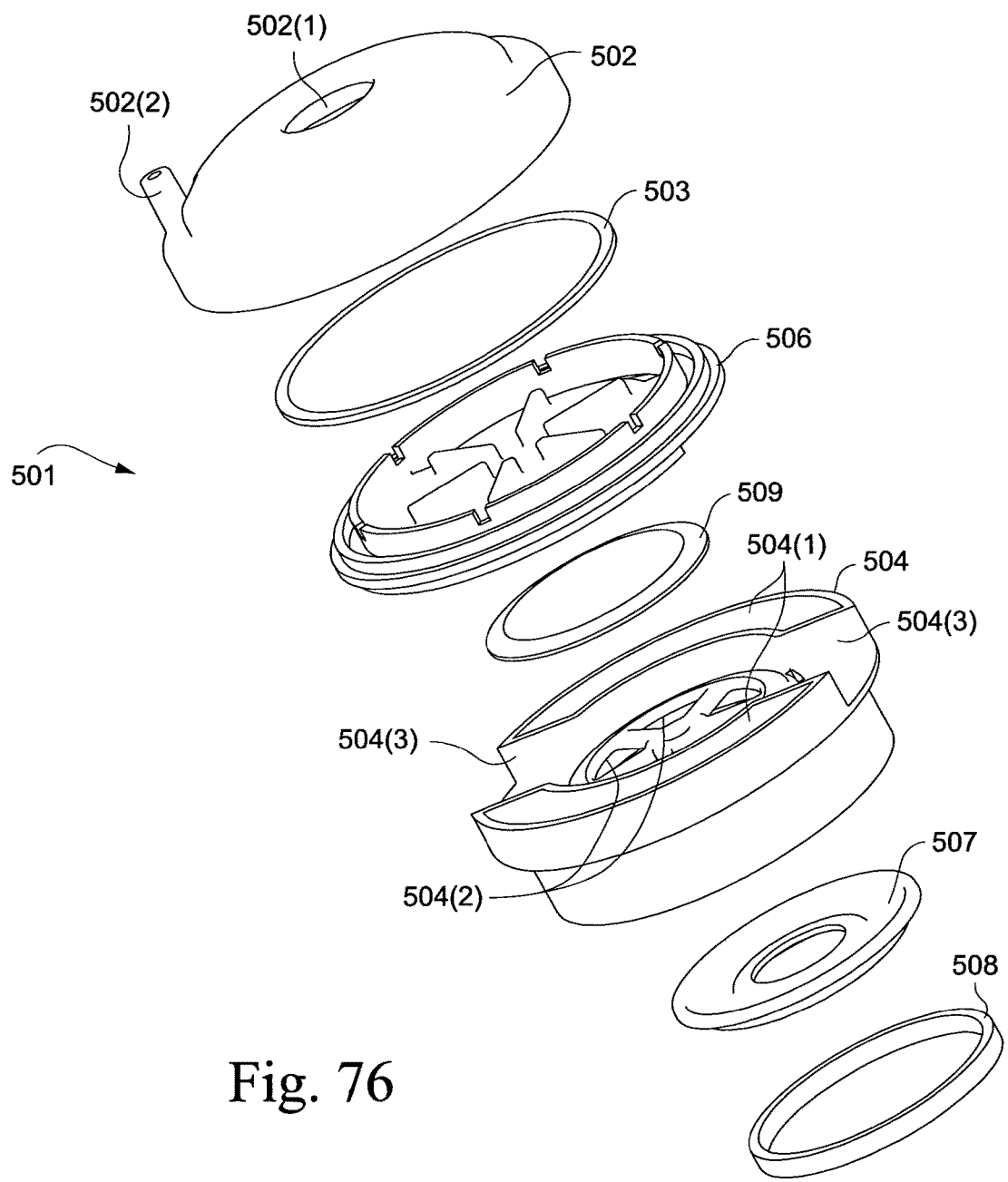
FIG. 76 is an exploded view of the filter/valve assembly of FIG. 71.
Figure 77:
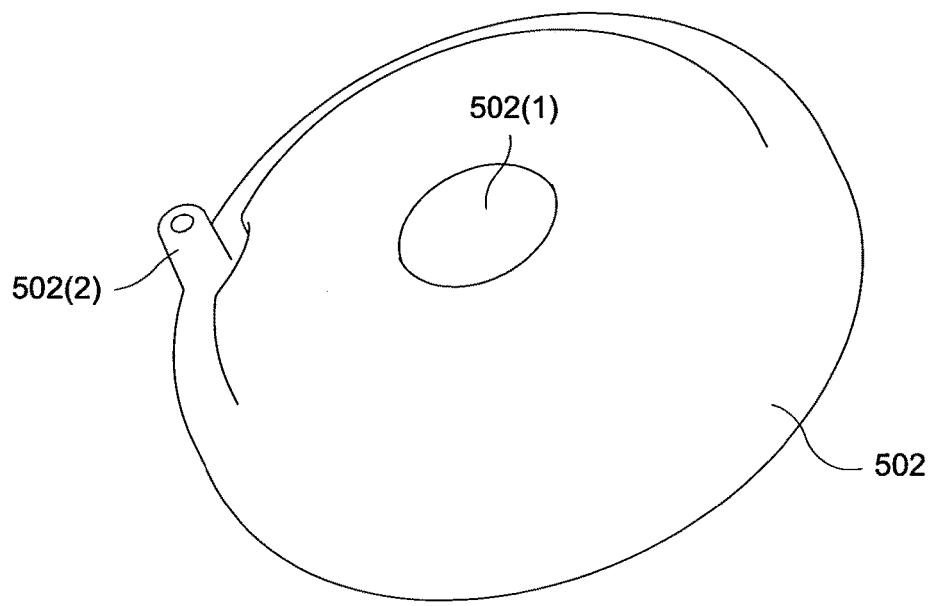
FIG. 77 is a perspective view of a filter cover of the filter/valve assembly according to an embodiment of the invention.
Figure 78:
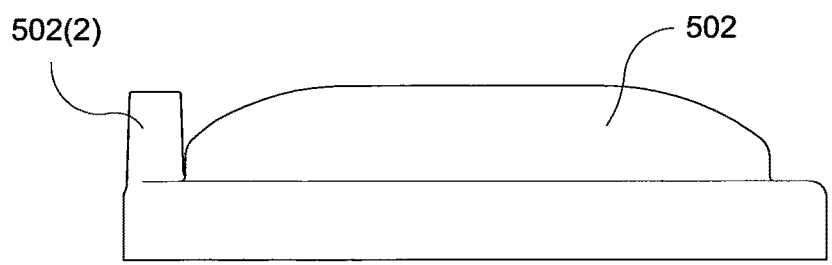
FIGS. 78-80 are side, top, and bottom views of the filter cover of FIG. 77.
Figure 79:
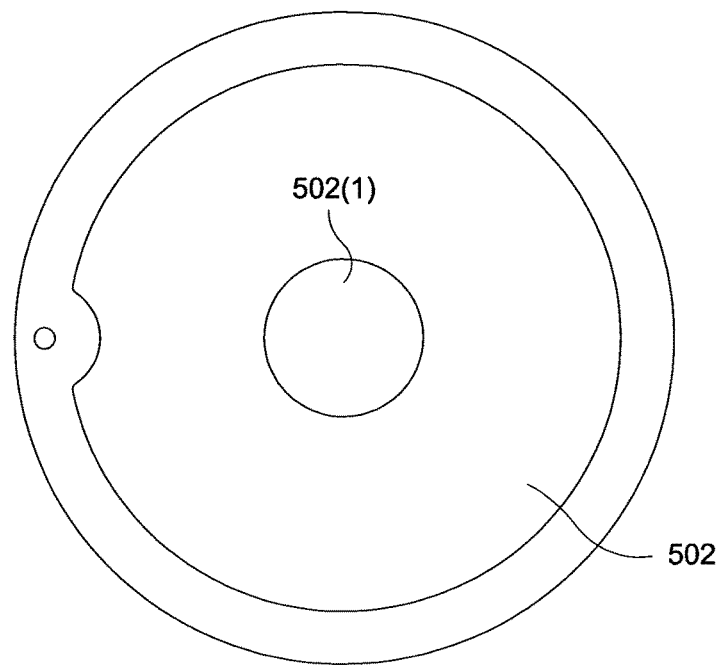
Figure 80:
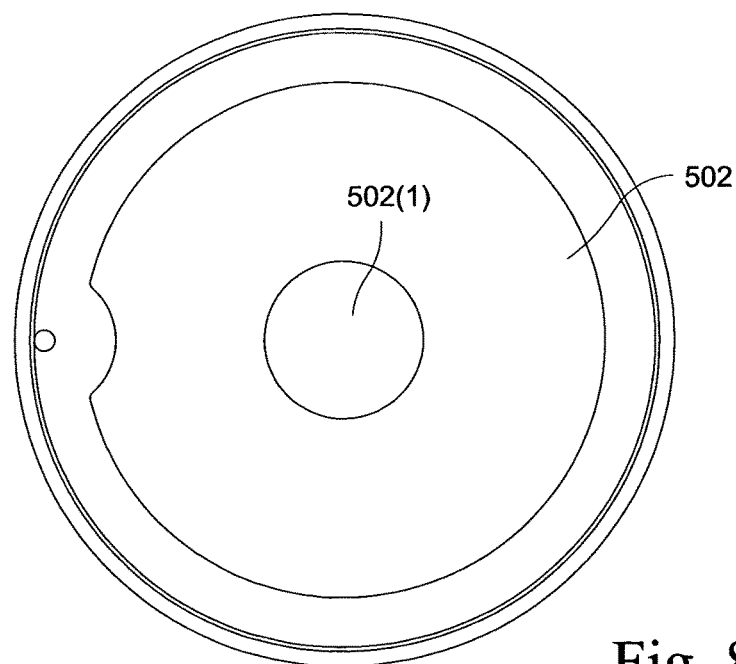
Figure 81:
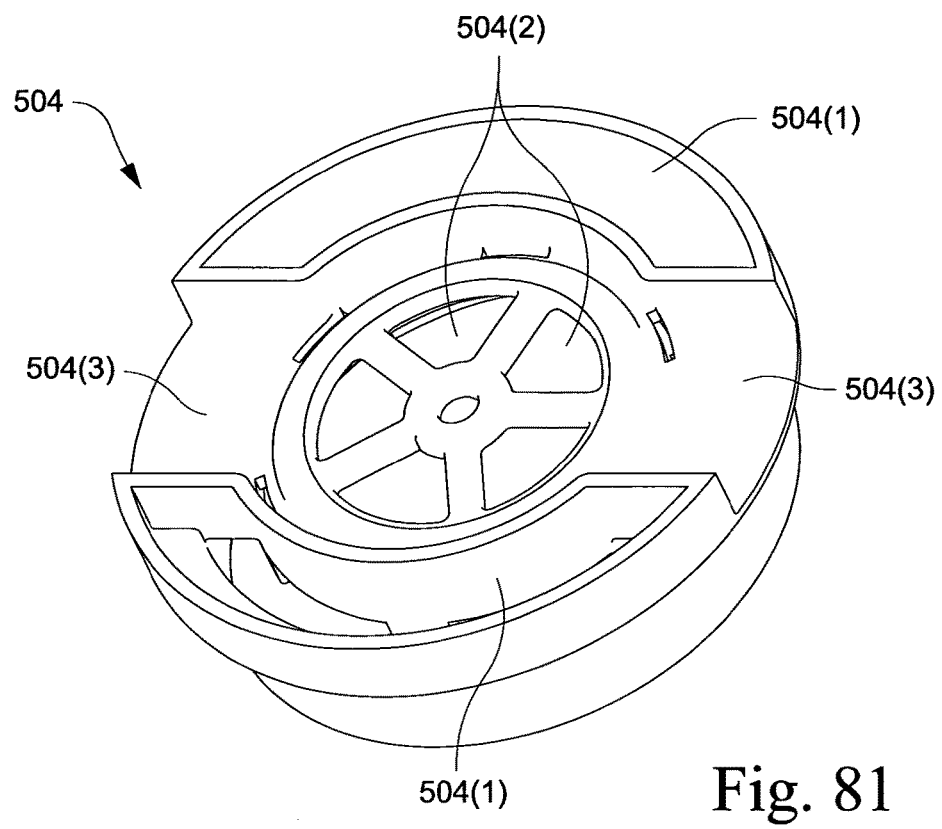
FIG. 81 is a perspective view of an air flow diverter/manifold of the filter/valve assembly according to an embodiment of the invention.
Figure 82:
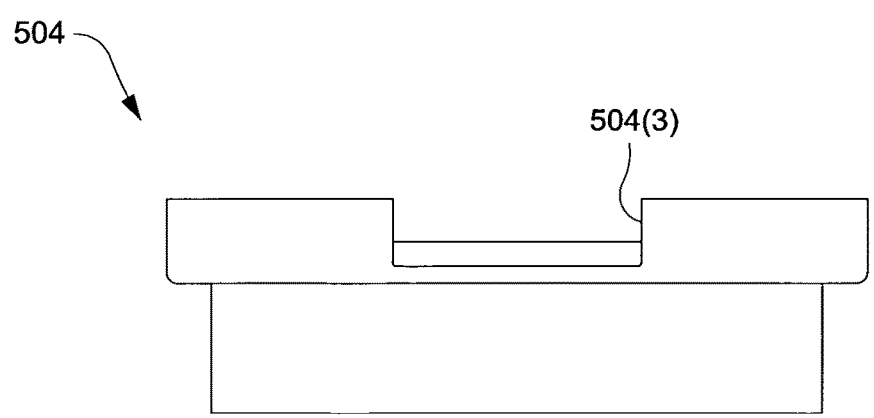
FIGS. 82-84 are side, top, and bottom views of the air flow diverter/manifold of FIG. 81.
Figure 83:
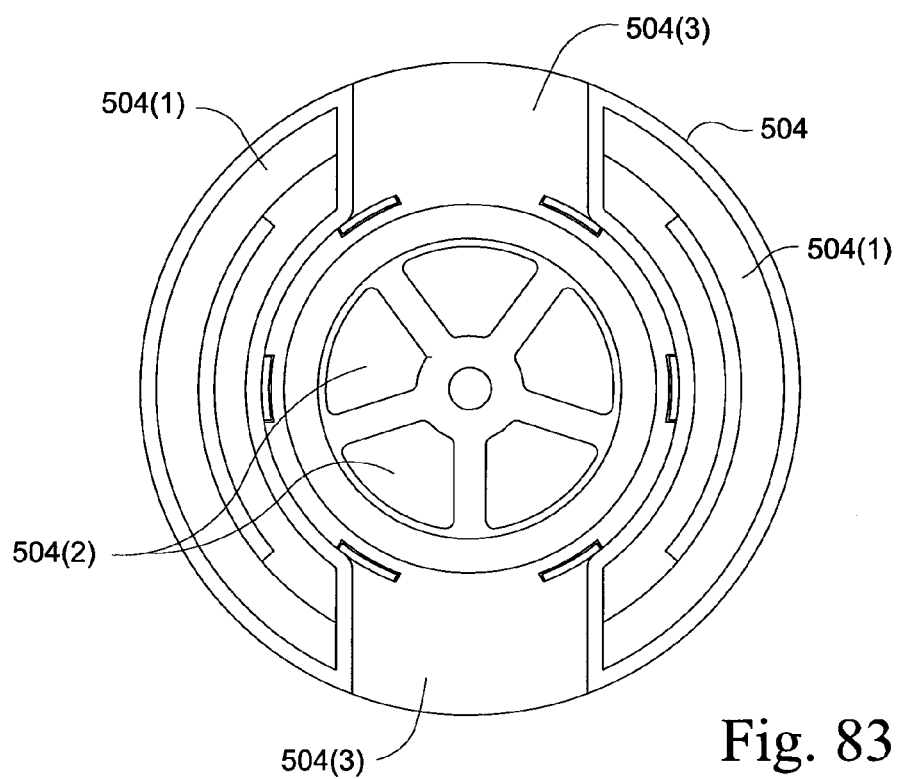
Figure 84:
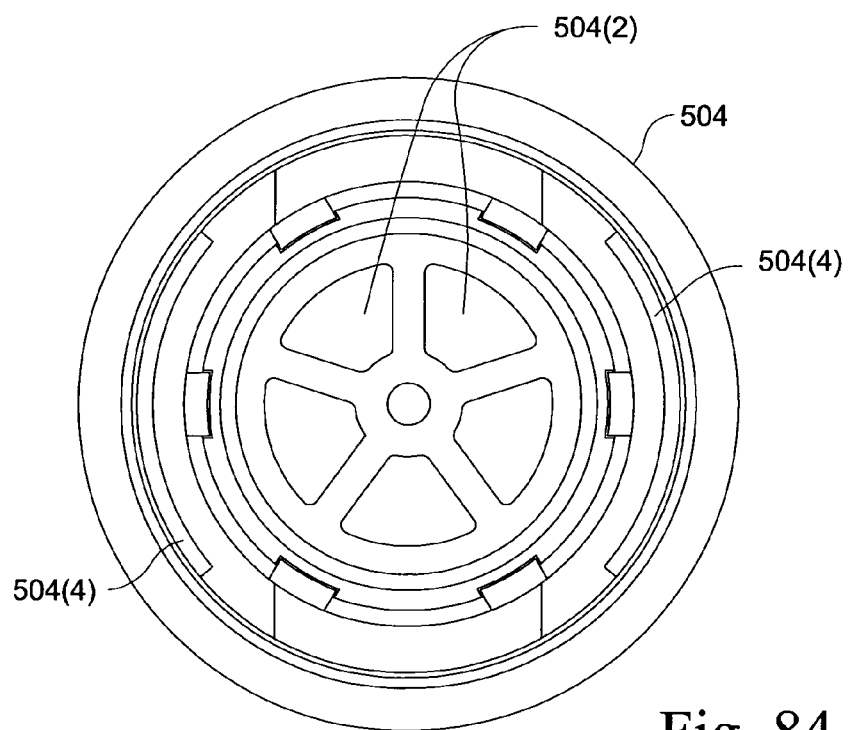
Figure 85:
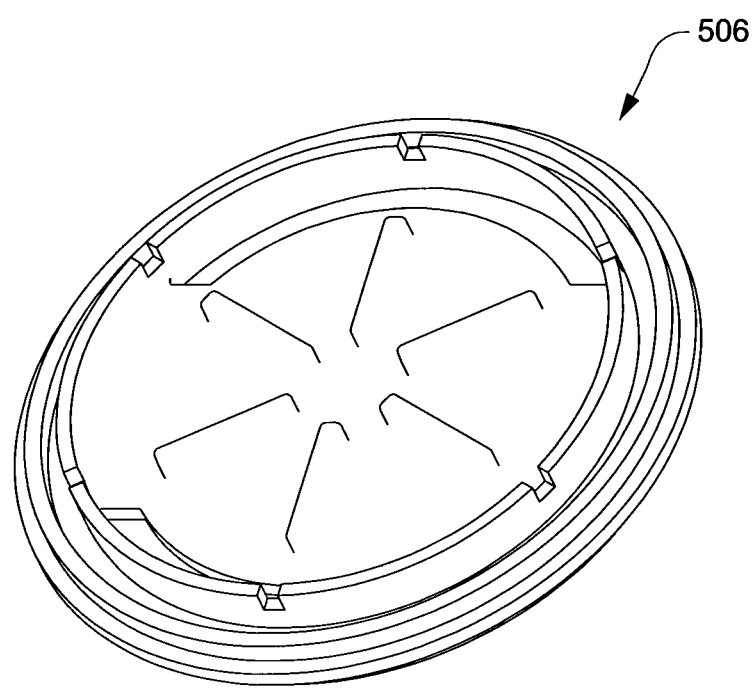
FIG. 85 is a perspective view of an air flow diverter cap of the filter/valve assembly according to an embodiment of the invention.
Figure 86:
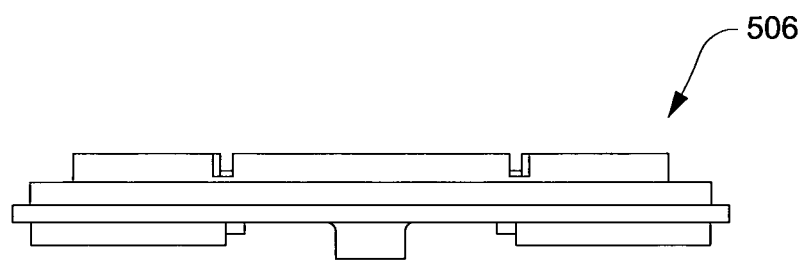
FIGS. 86-88 are side, top, and bottom views of the air flow diverter cap of FIG. 85.
Figure 87:
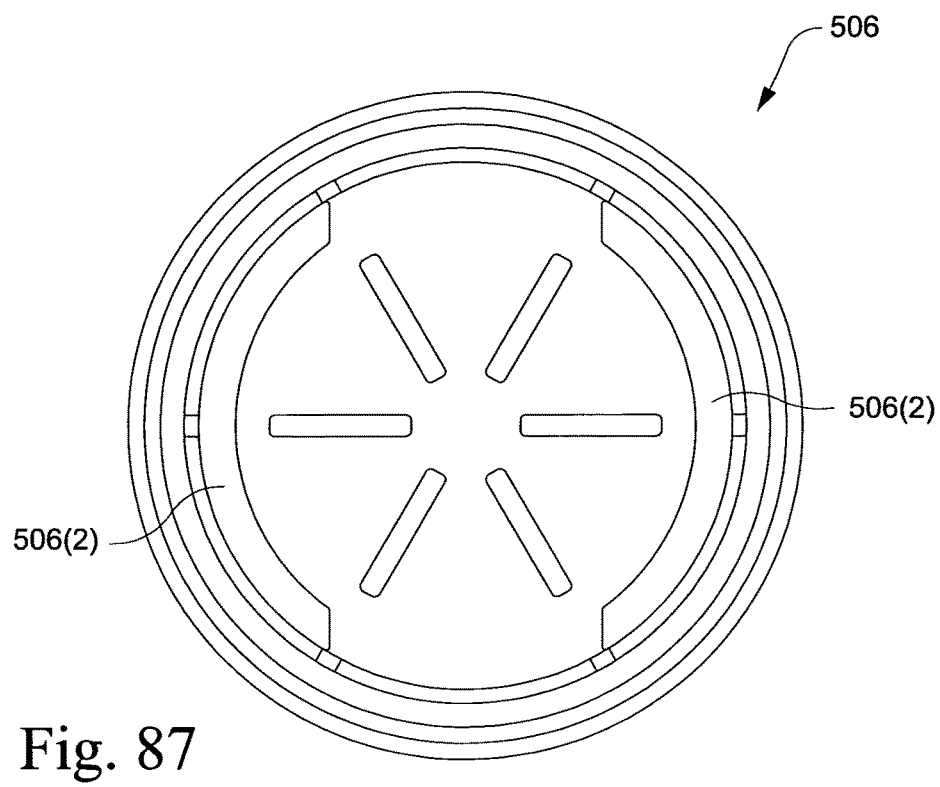
Figure 88:
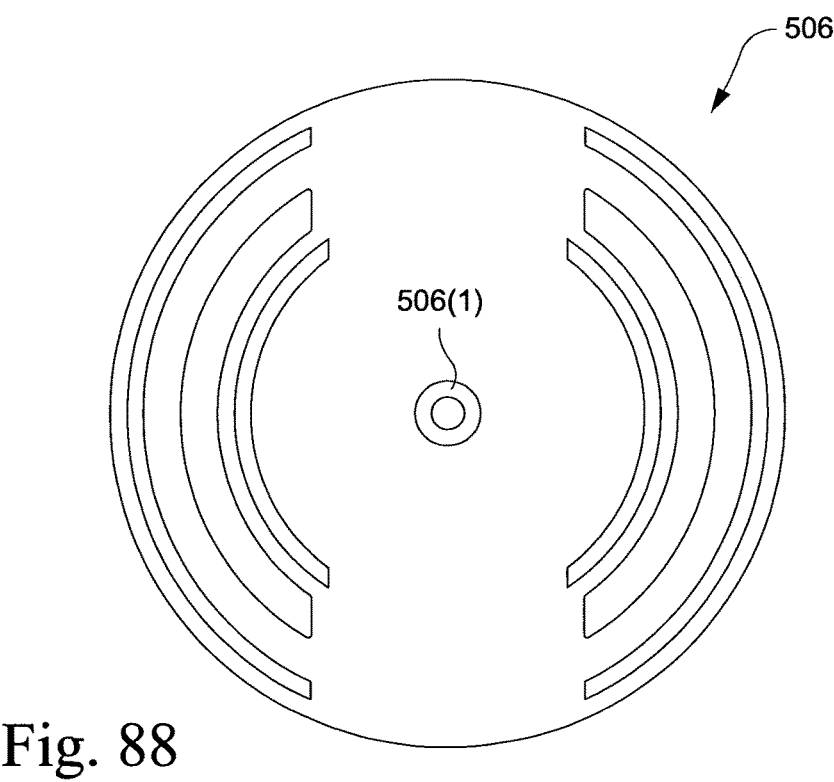
Figure 89:
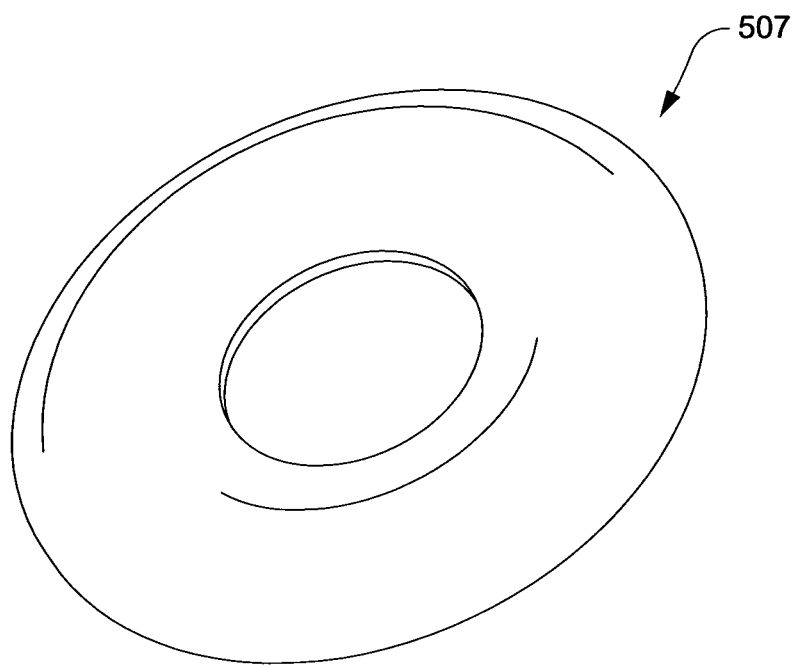
FIG. 89 is a perspective view of an air inlet membrane valve of the filter/valve assembly according to an embodiment of the invention.
Figure 90:
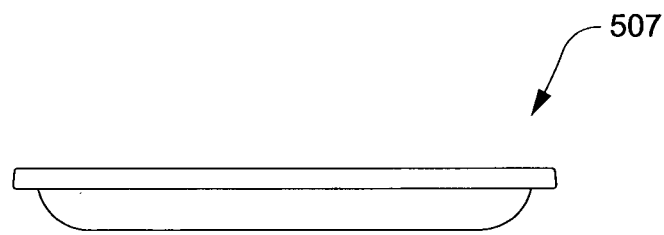
FIGS. 90-92 are side, top, and bottom views of the air inlet membrane valve of FIG. 89.
Figure 91:
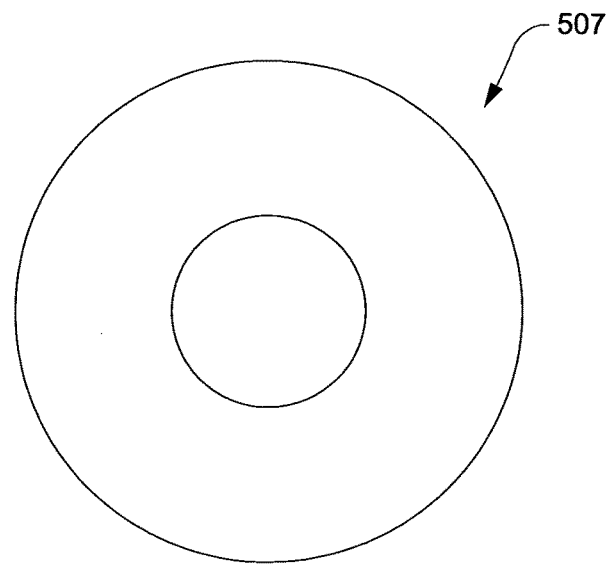
Figure 92:
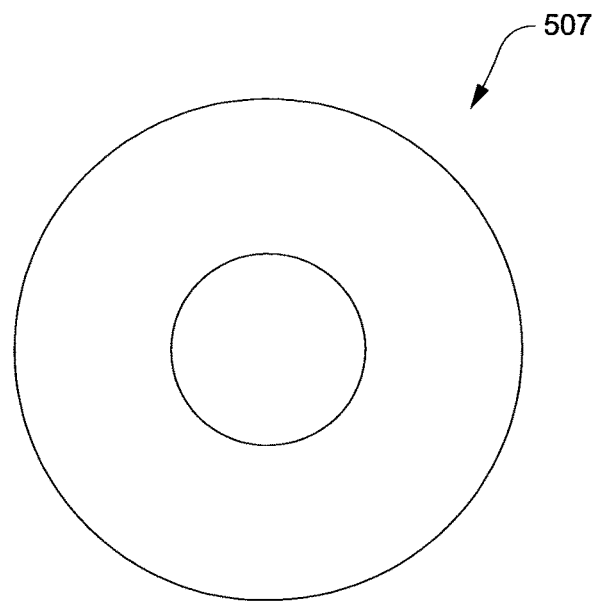
Figure 97:
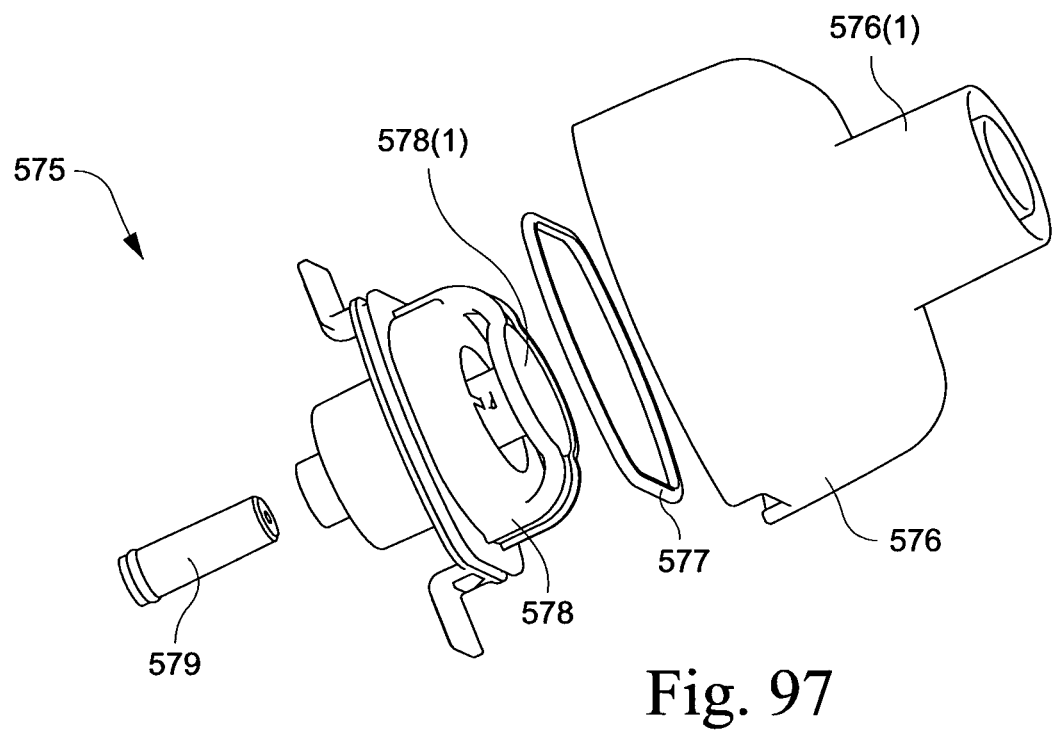
FIG. 97 is an exploded view of a mucous trap according to an embodiment of the invention.
Figure 98:
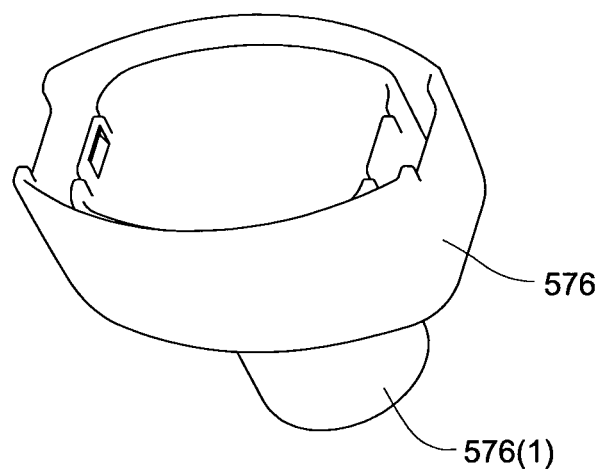
FIG. 98 is a perspective view of an outer case of the mucous trap according to an embodiment of the invention.
Figure 99:
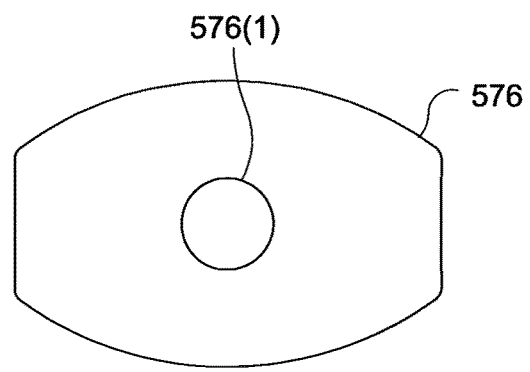
FIGS. 99-101 are top, bottom, and side views of the outer case of FIG. 98.
Figure 100:
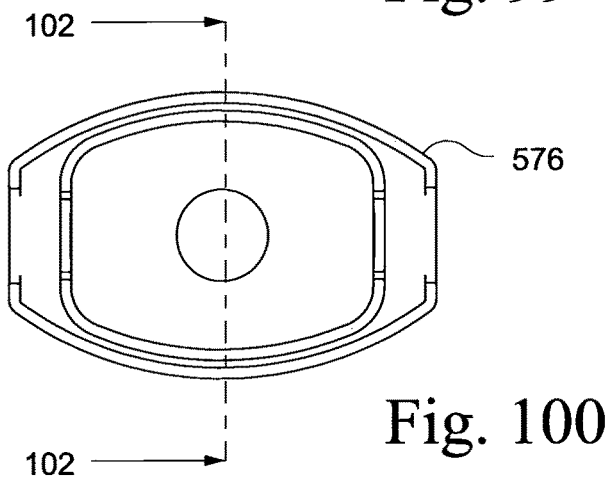
Figure 101:
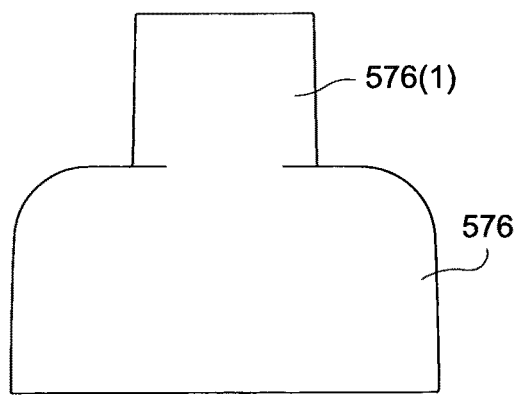
Figure 102:
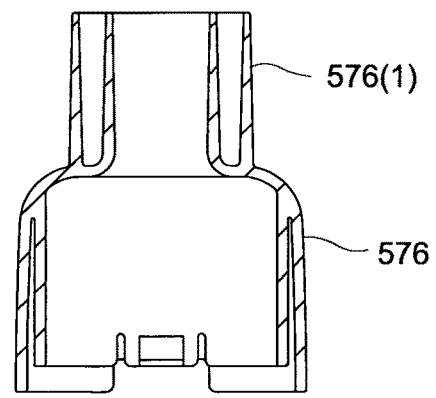
FIG. 102 is a cross-sectional view of the outer case of FIG. 98.
Figure 106:
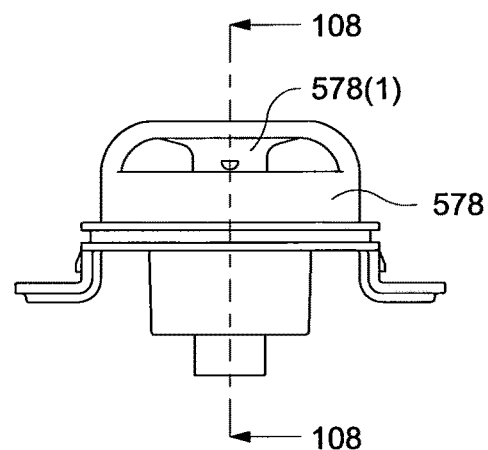
Figure 107:
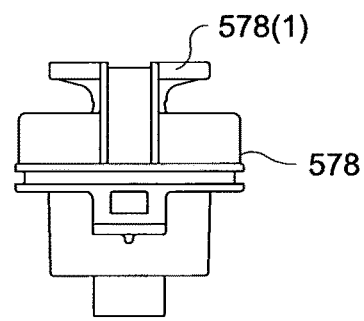
Figure 108:
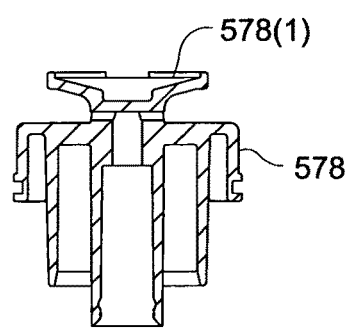
FIG. 108 is a cross-sectional view of the inner case of FIG. 103.
Figure 109:
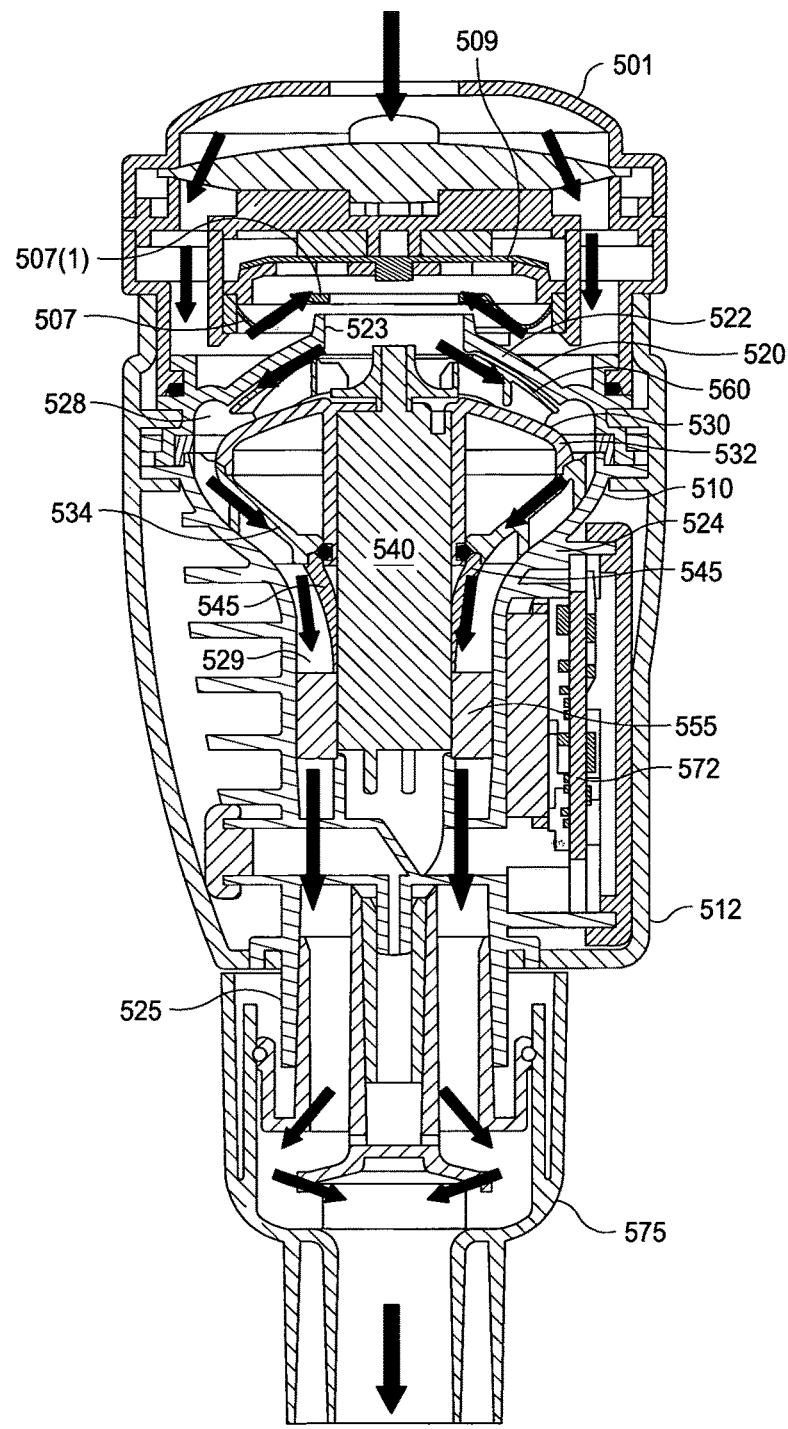
FIG. 109 is a cross-sectional view of the ventilator system of FIG. 25 showing air flow during inspiration.

The air flow diverter cap 506 provides structure 506(1) to maintain positioning of the outlet valve 509, e.g., see FIG. 75. Also, the air flow diverter cap 506 cooperates with the filter cover 502 to support the filter 503 adjacent the inlet of the filter cover. In addition, the air flow diverter cap 506 provides openings 506(2) (e.g., see FIG. 87) that communicate with air inlets 504(1) for inlet air flow therethrough. Operation of the filter/valve assembly 501 is described in more detail below.

Mucous Trap

As best shown in FIGS. 32, 33, and 97-108, the mucous trap 575 may be provided, e.g., to protect the flow element 555. The mucous trap 575 includes an outer case 576, an inner case 578, a seal ring 577 between the outer and inner cases, and a port seal 579. The outer case 576 provides a tube 576(1) for connecting tubing communicated with the patient, e.g., via a mask. The tube acts as an outlet for airflow to the patient for inspiration and acts as an inlet for expired air from the patient during expiration. The inner case 578 provides a capture section or capture plate 578(1) in the middle of the flow path, e.g., to capture any particulate matter expired by the patient. The outer and inner cases 576, 578 may be coupled to one another via a snap-fit, e.g., inner case includes snap-fit tabs adapted to interlock with recesses provided to the outer case.

Figure 133:
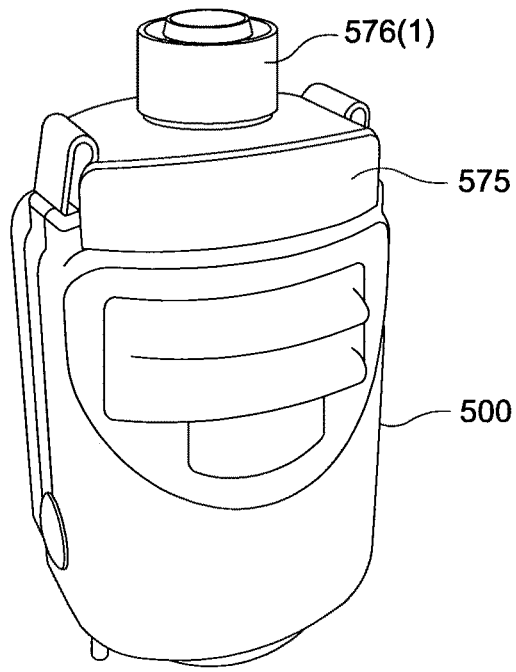
FIG. 133 is a perspective view of a ventilator system with a mucous trap according to an embodiment of the invention.

FIG. 133 is a perspective view of a ventilator system 500 with an integrated mucous trap 575. Operation of the mucous trap is described in more detail below.

Heat Moisture Exchange Filter (HMEF)

Figure 134:
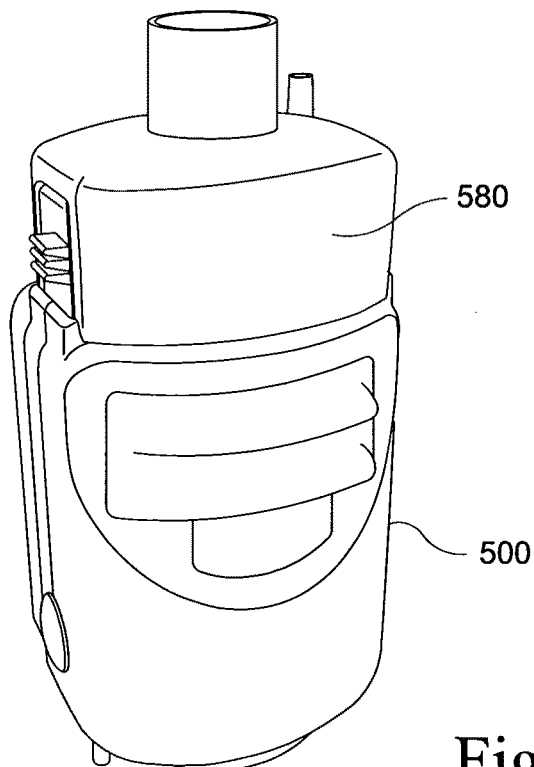
FIG. 134 is a perspective view of a ventilator system with a HMEF according to an embodiment of the invention.

In an embodiment, a heat moisture exchange filter 580 (HMEF) may be provided to the ventilator (e.g., in lieu of the mucous trap or of a standard conical connector) to provide a level of humidification and protection for the patient's airway, e.g., conditioning the inhaled air and/or protect the ventilator from exhaled particulates. The HMEF may be a replaceable accessory, but includes an integrated and tailored appearance with respect to the ventilator. For example, FIG. 134 is a perspective view of a ventilator system with an integrated HMEF 580.

As shown in FIGS. 112-125, the HMEF 580 includes an outer casing 582, an inner casing 584, a filter pad or filter media 586, a heat and moisture exchange pad 588 (e.g., foam sponge), and a port seal 589 (e.g., constructed of silicone). The outer casing 582 provides a tube 582(1) for connecting tubing communicated with the patient, e.g., via a mask. The tube acts as an outlet for airflow to the patient for inspiration and acts as an inlet for expired air from the patient during expiration. An ultrasonic weld line 584(1) is provided to the inner casing 584 to attach the inner and outer casings. The inner and outer casings cooperate to define an internal pressure port 585 for measuring pressure on the patient side of the filter media 586. The internal pressure port 585 uses the filter media 586 to protect the pressure sensor from bacteria, etc.

Figure 126:
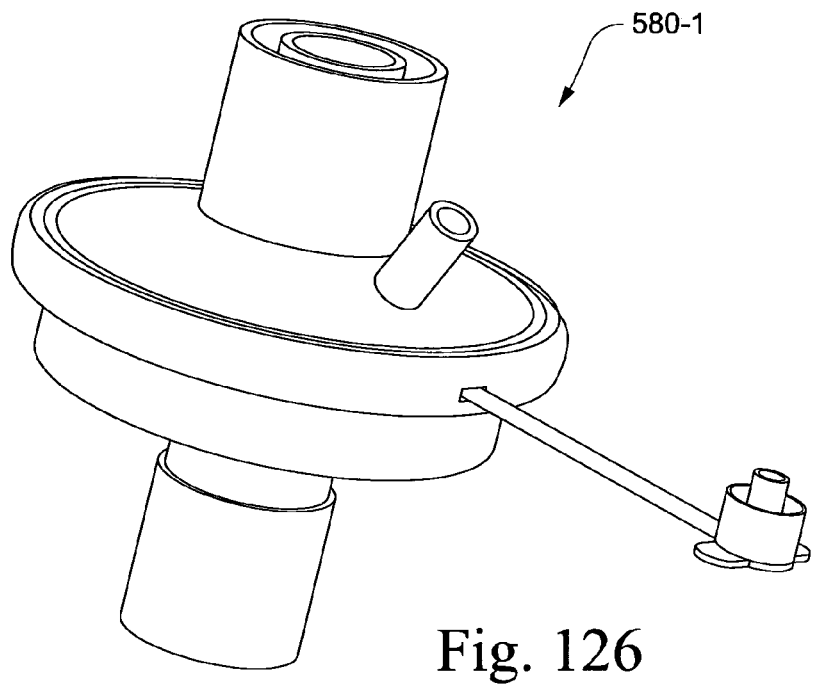
FIGS. 126 and 127 are perspective and side views of a HMEF according to another embodiment.
Figure 127:
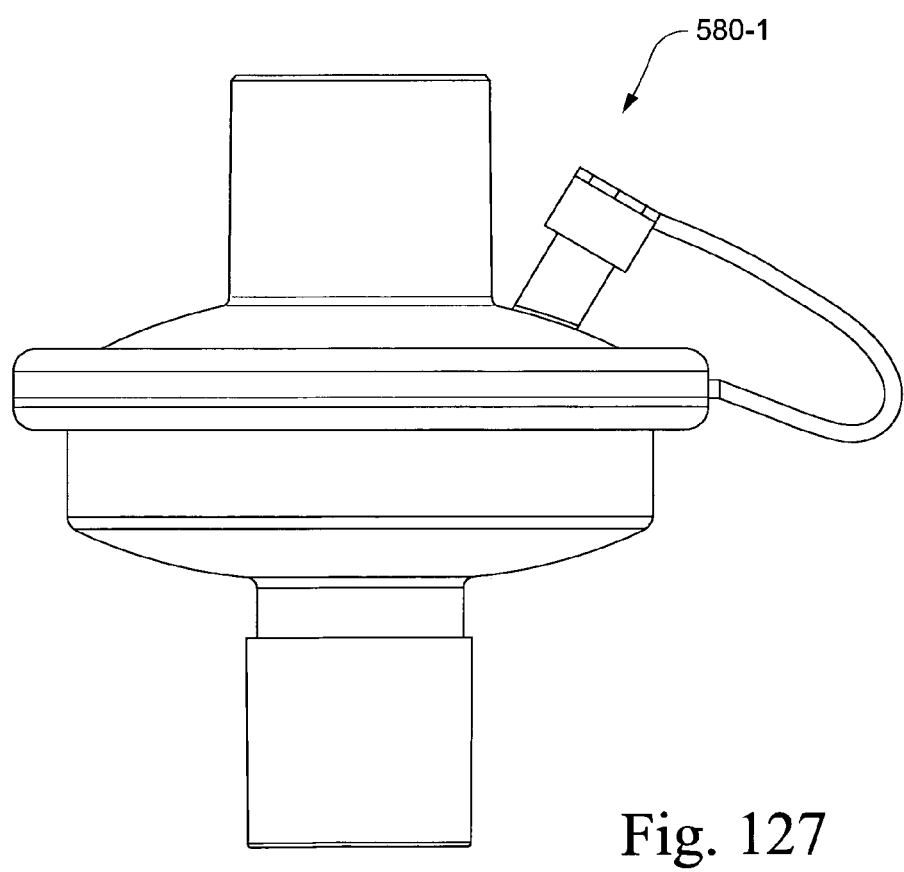
Figure 128:
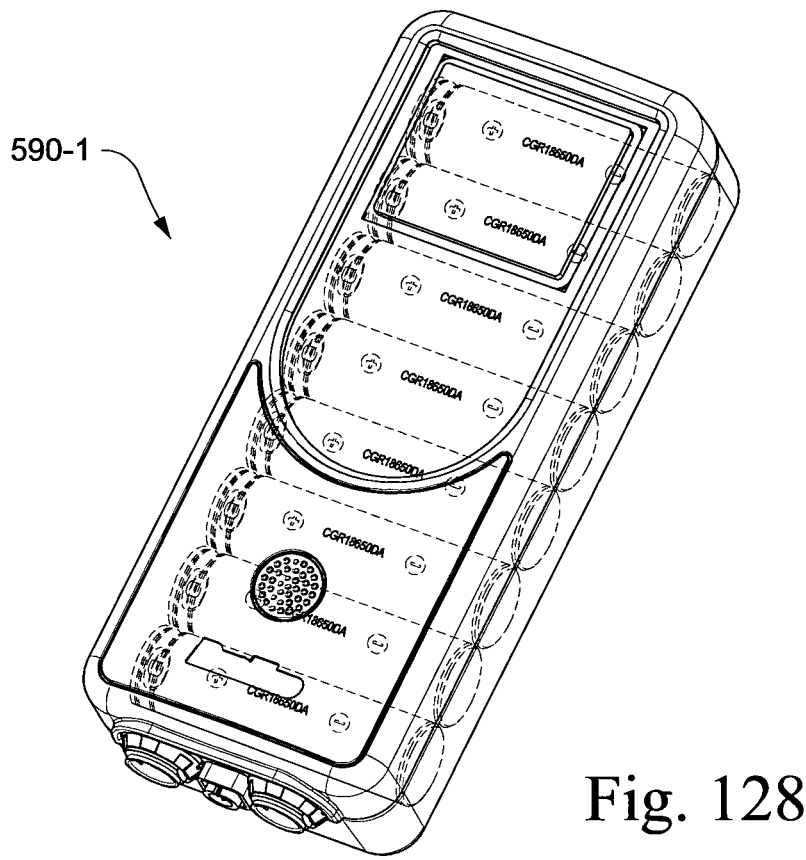
FIG. 128 is a perspective view of a remote for the ventilator system according to an embodiment of the invention.
Figure 129:
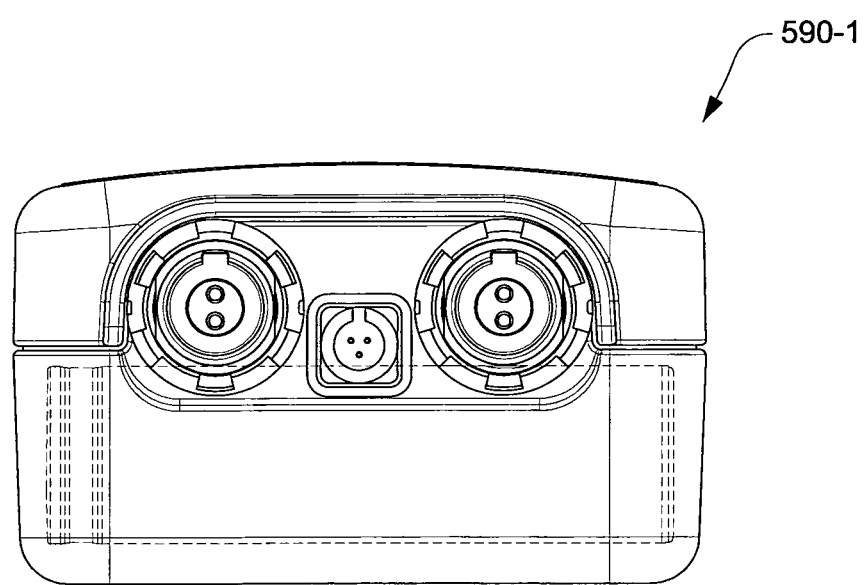
FIGS. 129-132 are front, top, left side, and right side views of the remote of FIG. 128.
Figure 130:
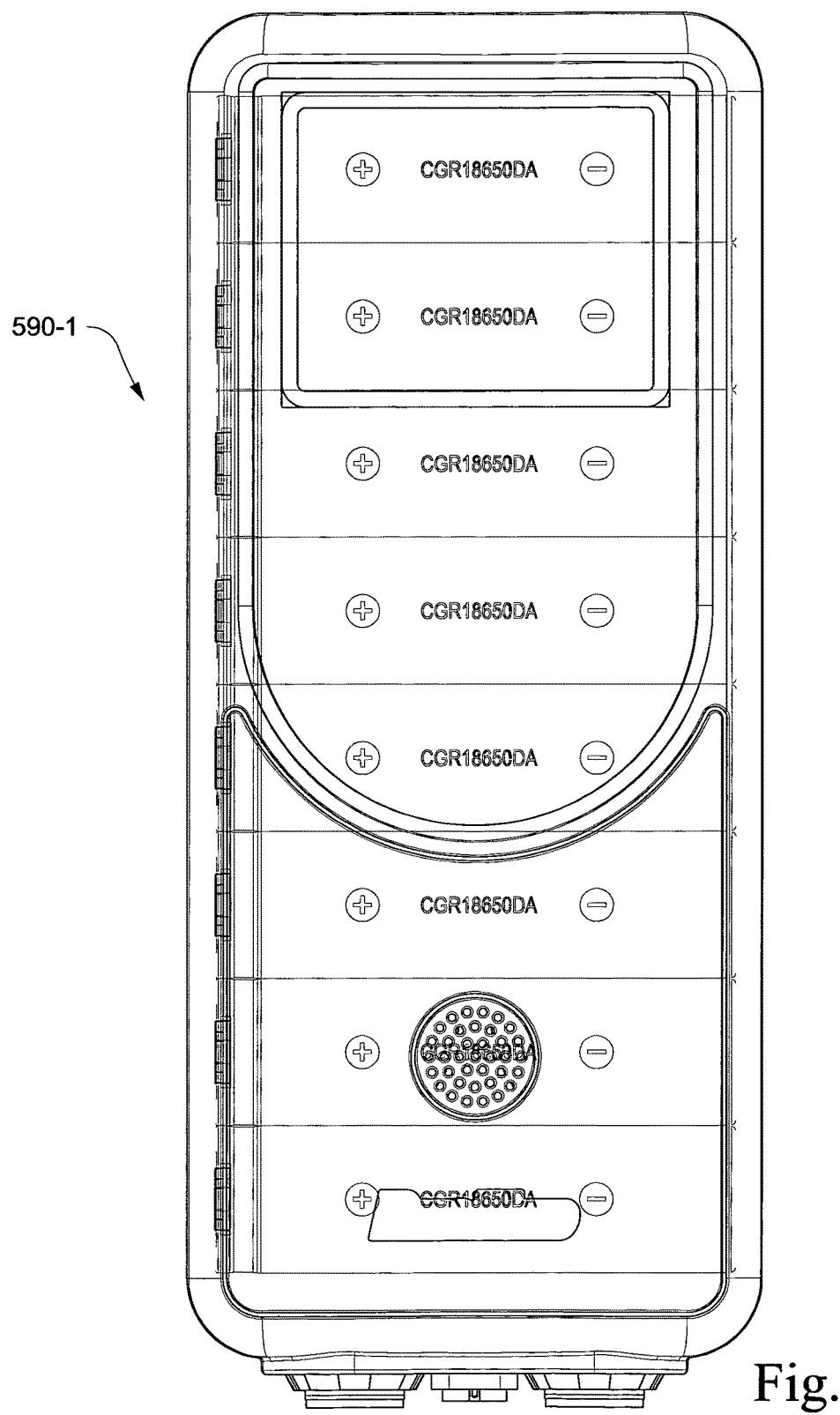
Figure 131:
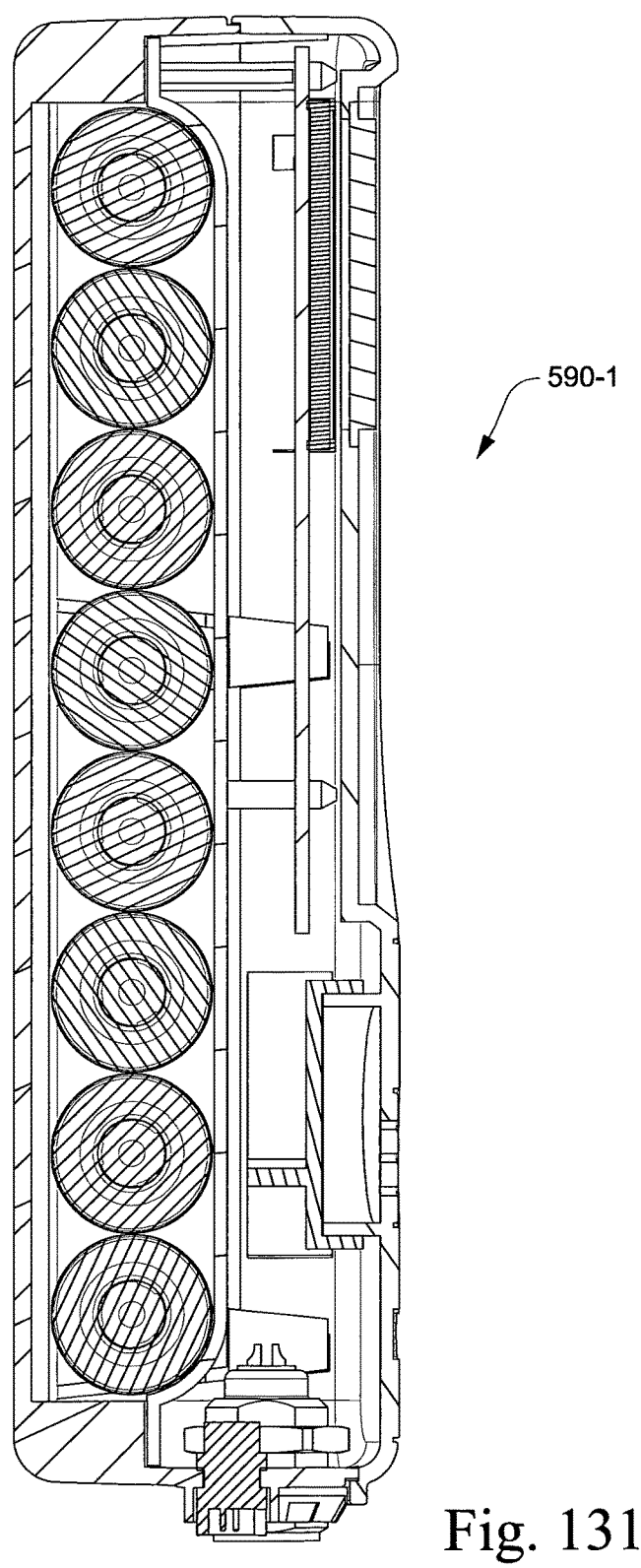
Figure 132:
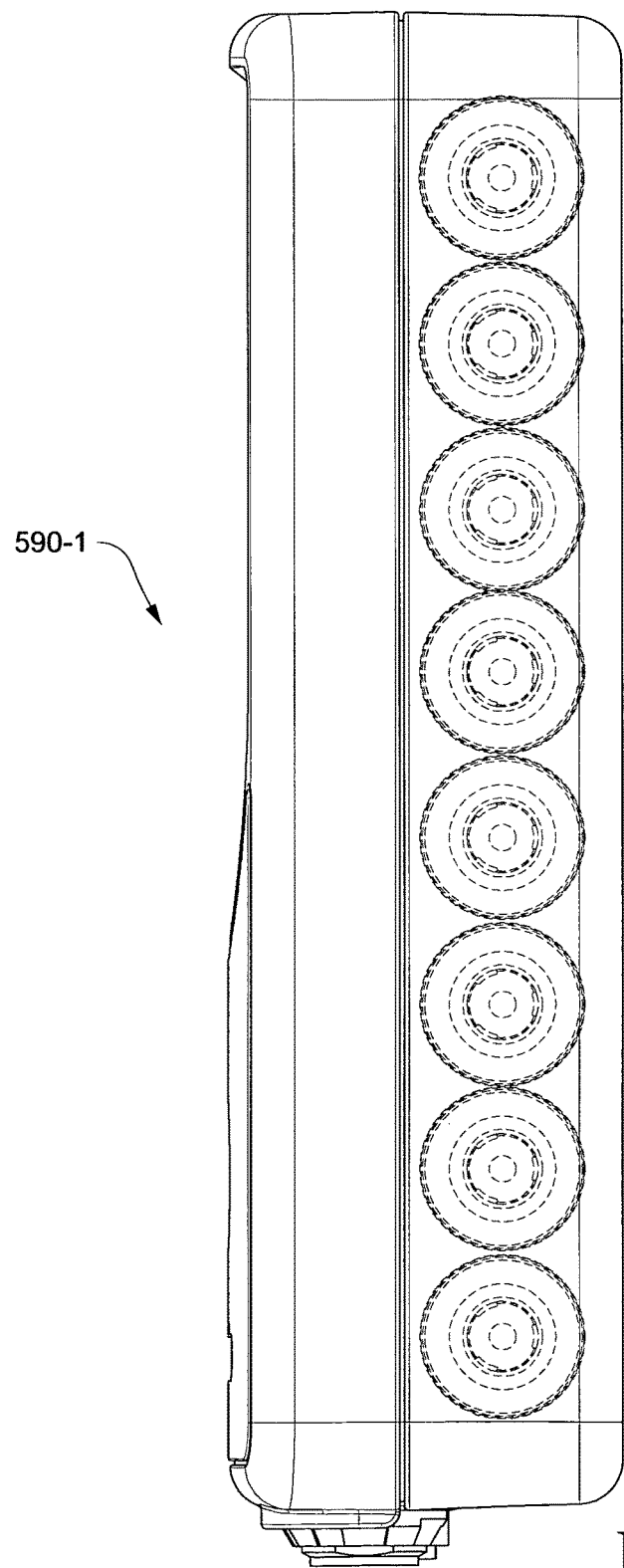

In an alternative embodiment, an off-the-shelf HMEF may be used with the device. For example, FIGS. 126 and 127 show an off-the-shelf HMEF 580-1 (e.g., ECO MAXI heat moisture exchange filter) that possibly could be used with the ventilator.

In another alternative embodiment, the same functionality of the HMEF could be incorporated into the patient interface (e.g., mask, tube) as opposed to a unit inline with the ventilator as described above.

Wearable System

As noted above, the ventilator may be configured as a wearable system. The wearable ventilator may be embodied as a single unit, with power storage and control interface built in, or may be embodied as a divided unit where the electro-pneumatic transducer (or blower/filter/sensing assembly) is as small and as proximal as is practicable, and components that are able to be segregated from electro-pneumatic transducer (such as power and/or control components) are conveniently located elsewhere (such as on the patient (e.g., vest, belt, etc.), or near the patient (e.g., wheelchair, seat, pillow, bed, bedside, or operated by carer). The power/control unit may include a battery to power the device and a user interface to allow the adjustment of the parameters for therapy. It can also accommodate the ventilator alarm.

FIGS. 135-1 and 136 show a remote or handset 590 (e.g., power/control unit) for the ventilator according to an embodiment of the invention. The handset 590 may include an optional extension battery 599 that is releasably connected to the handset (e.g., see FIGS. 135-2 and 135-3).

As illustrated, the handset 590 includes a housing 591 (e.g., constructed of PC/ABS), a bumper strip 592 (e.g., constructed of TPU) that provides a seal between housing parts of the housing, a membrane keypad 593, a display screen 594 (e.g., color LCD screen), a ventilator connection 595 for attaching the electrical cable communicated with the ventilator, a remote alarm connector 596, a communications connection 597, an alarm buzzer 598, and an SD card reader 587.

In the illustrated embodiment, the keypad 593 includes a start/stop ventilation button 593(1), a menu selection button 593(2), an up/increase button 593(3), a down/decrease button 593(4), an ok/validate/accept button 593(5), a manual breath button 593(6), an audio pause button 593(7), alarm indicators 593(8), and a DC input connected indicator 593(9). However, it should be appreciated that such keypad arrangement is only exemplary and other suitable buttons and button arrangements may be provided to the keypad.

Figure 137:
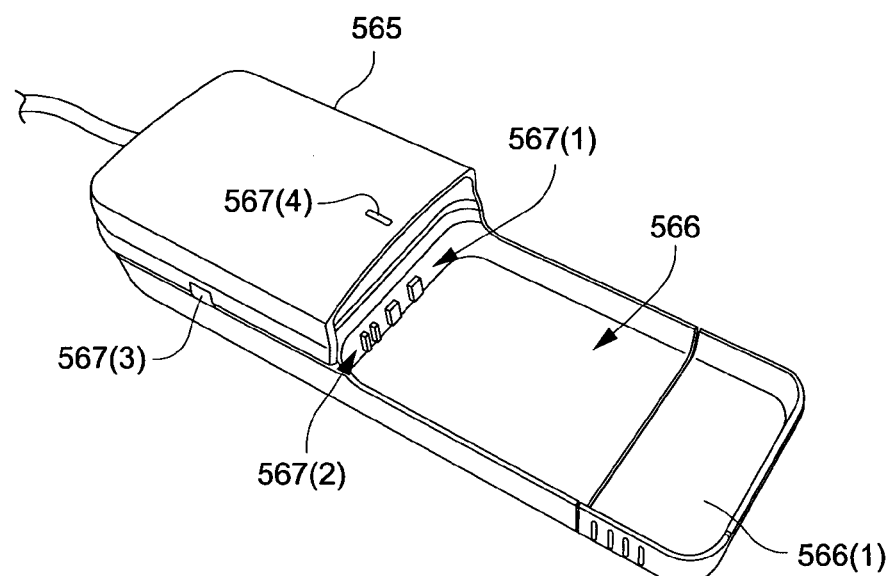
FIG. 137 is a perspective view of a docking station or dock according to an embodiment of the invention, the dock in a first position.
Figure 138:
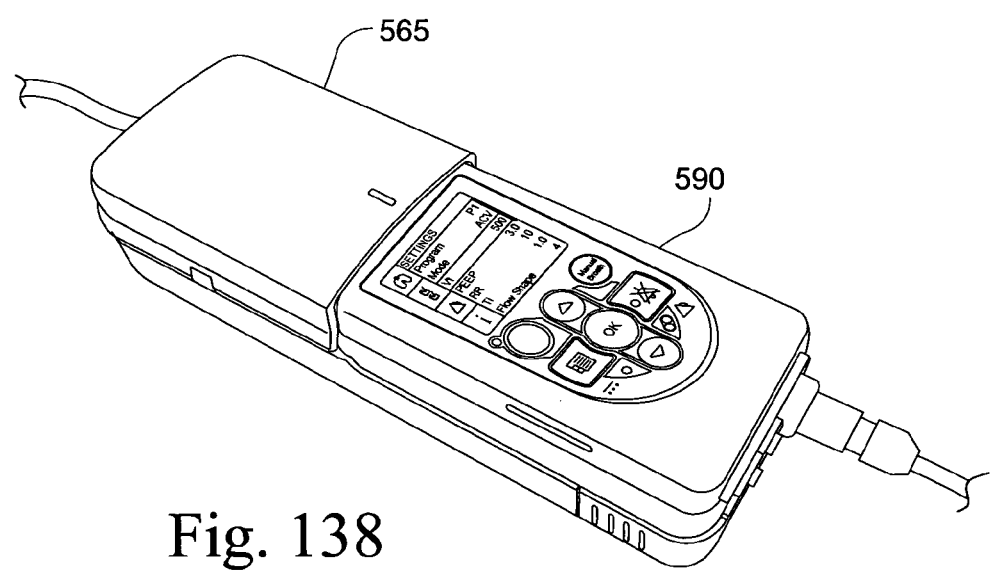
FIG. 138 is a perspective view of the handset of FIG. 135-1 within the dock of FIG. 137.

FIG. 137 shows a docking station or dock 565 according to an embodiment of the invention. The dock 565 defines a cradle 566 to support the handset 590 and contacts for charging the handset. The dock includes DC charging contacts 567(1), remote alarm contacts 567(2), a remote alarm connection 567(3), and a power indicator 567(4). FIG. 138 shows the handset 590 in a docked position within the dock 565.

Figure 139:
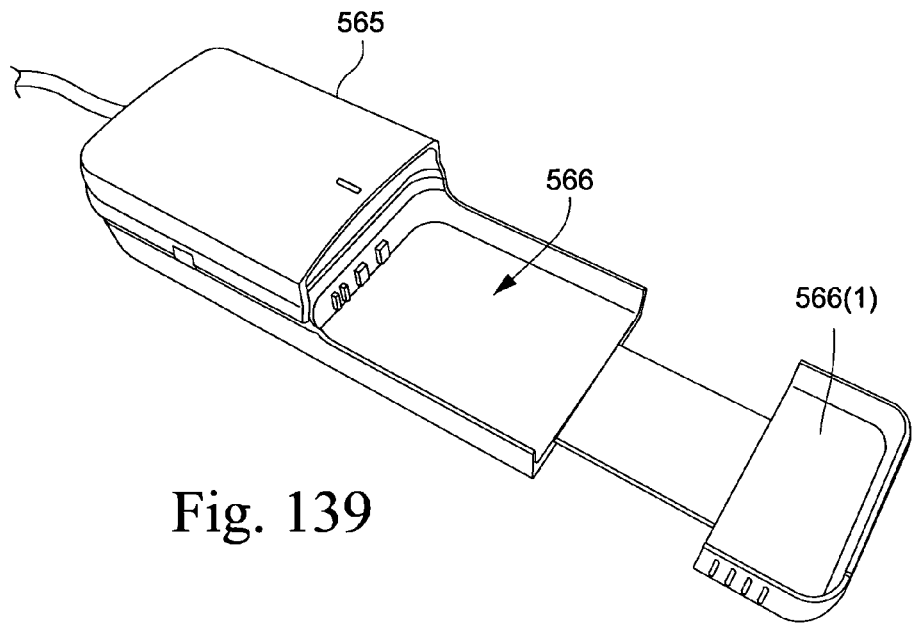
FIG. 139 is a perspective view of the dock of FIG. 137 in an extended second position.
Figure 140:
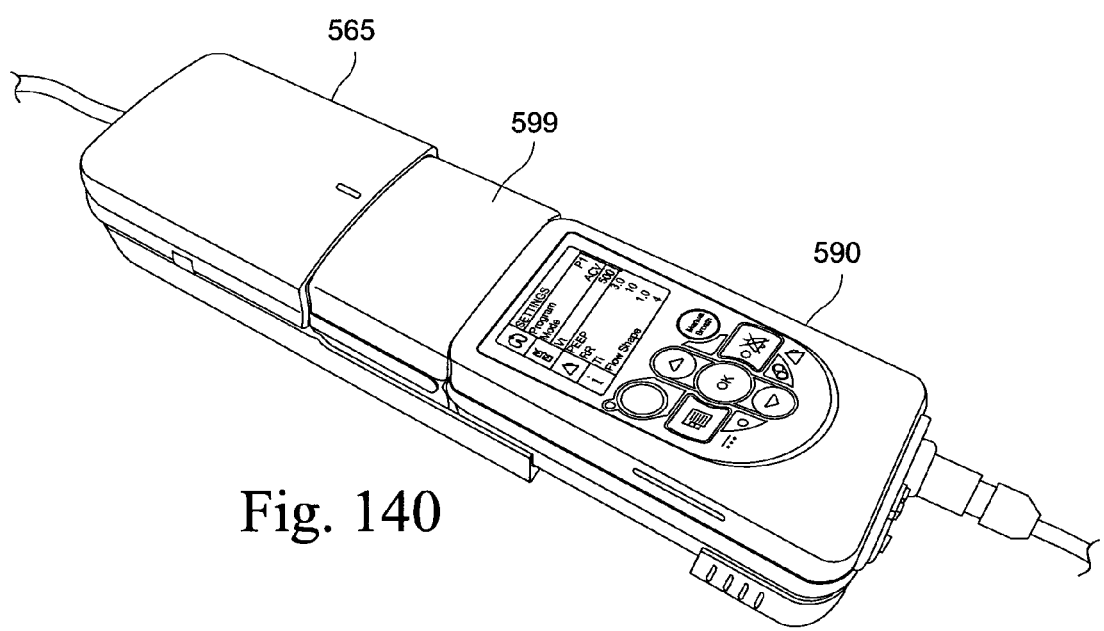
FIG. 140 is a perspective view of the handset and extension battery of FIG. 135-3 within the dock of FIG. 139.

As best shown in FIG. 139, the cradle 566 includes a slidable cradle member 566(1) that allows the size of the cradle to be enlarged to accommodate the handset 590 with an extension battery 599. FIG. 139 shows the dock with the cradle member 566(1) moved to an extended position. FIG. 140 shows the handset 590 with extension battery 599 in a docked position within the enlarged cradle.

Figure 141:
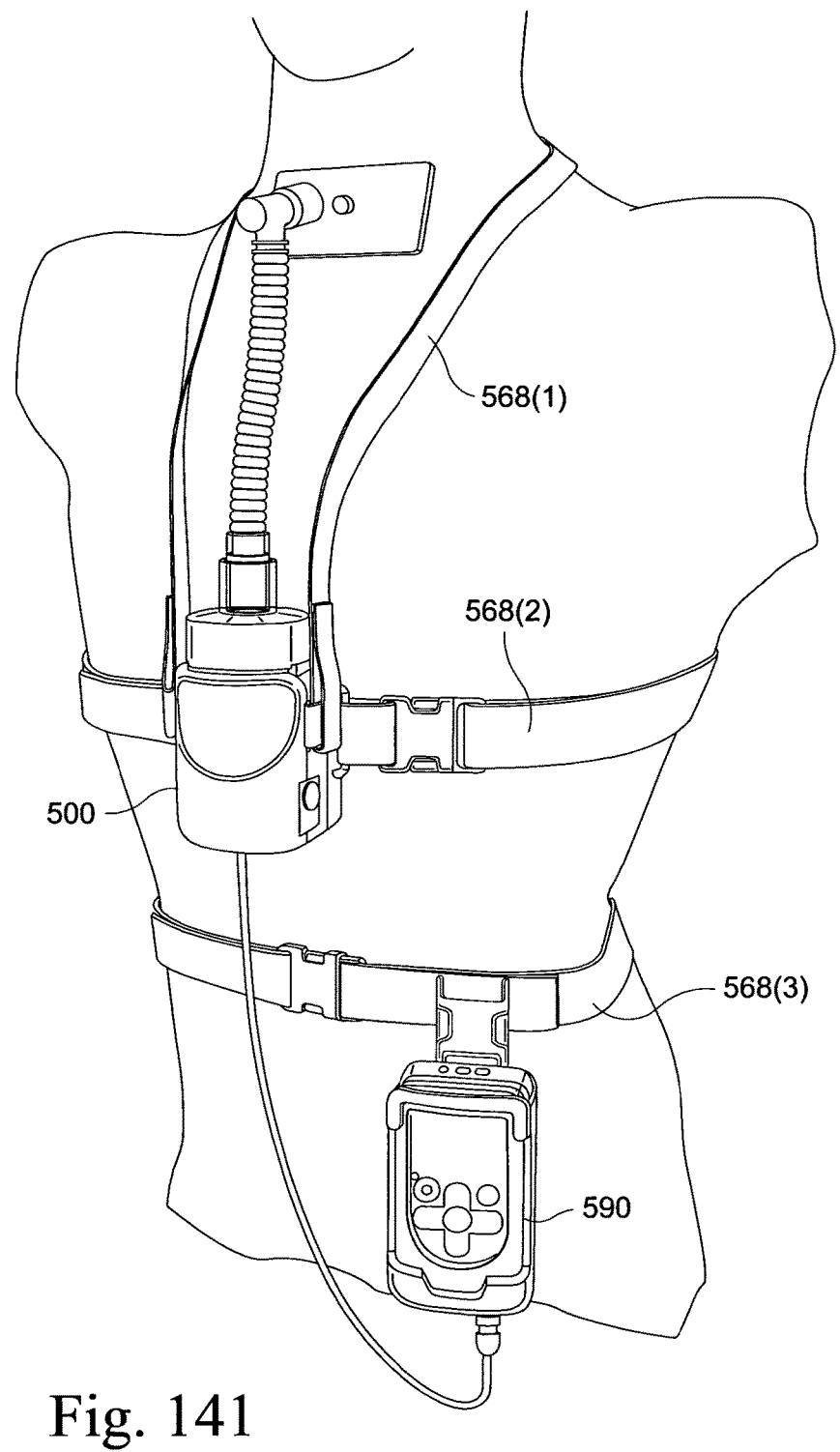
FIG. 141 shows a ventilator adapted for tracheotomy ventilation, a handset, a handset harness, and a stabilizing strap according to an embodiment of the invention.
Figure 142:
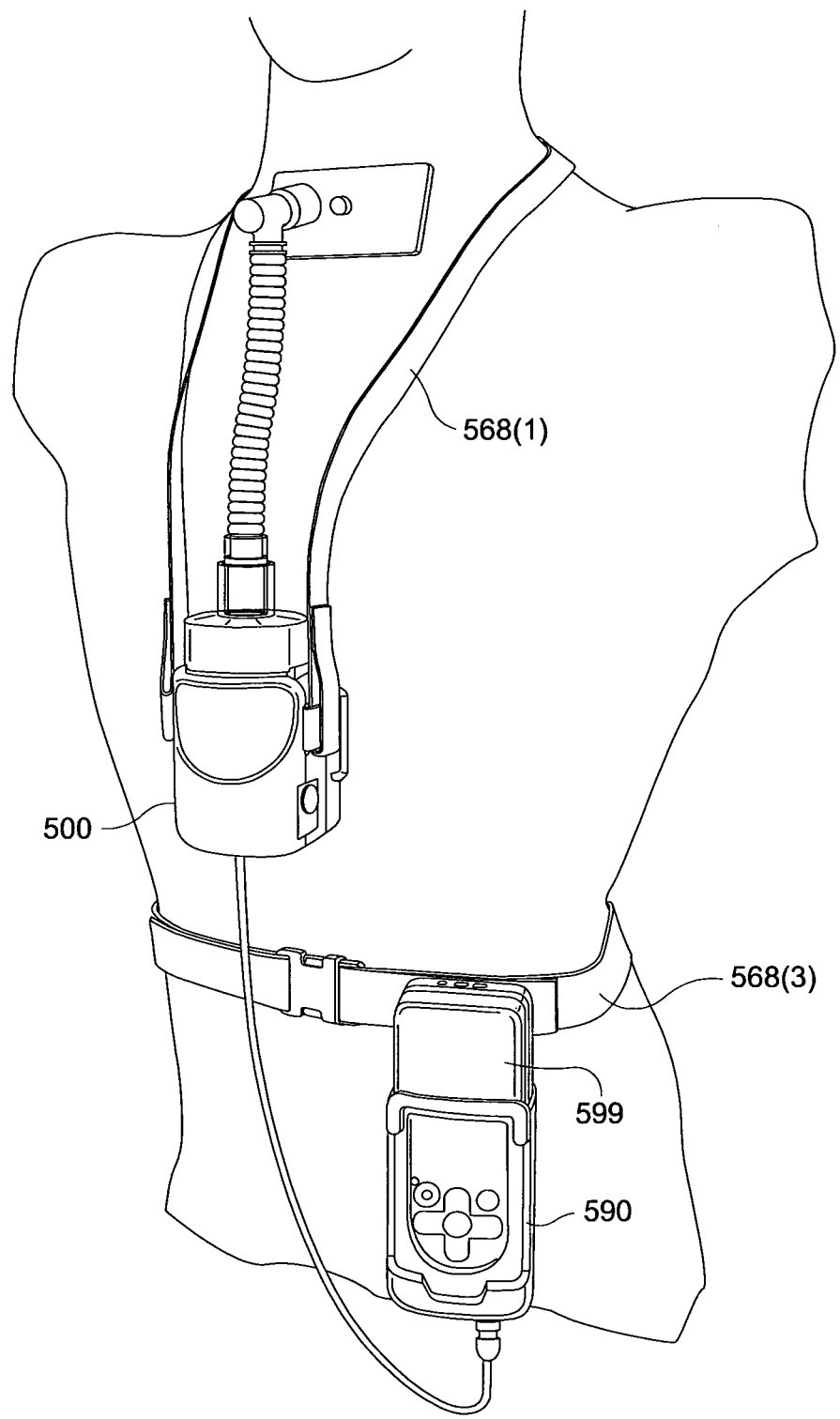
FIG. 142 shows a ventilator adapted for tracheotomy ventilation, a handset with extension battery, and a handset harness according to an embodiment of the invention.
Figure 143:
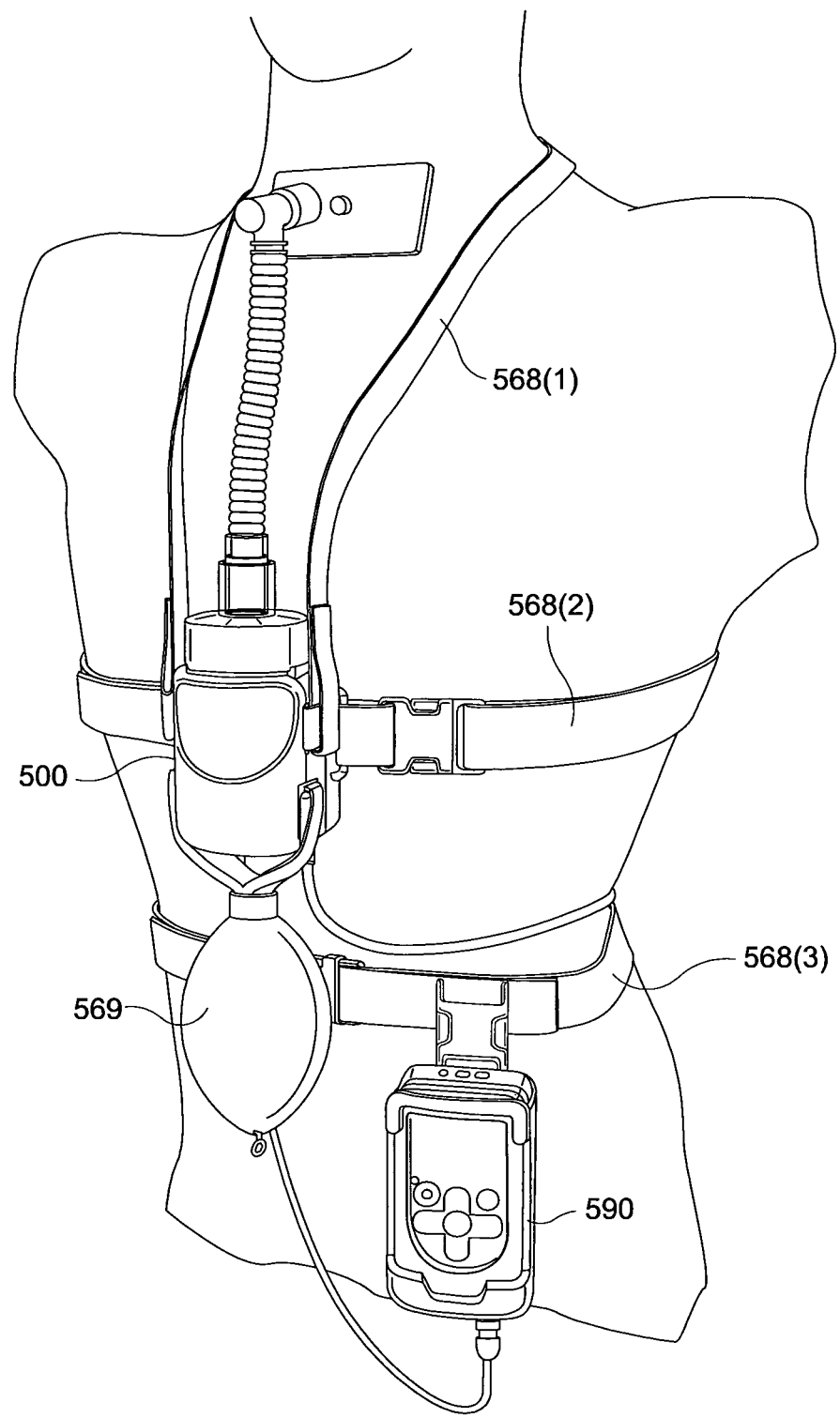
FIG. 143 shows a ventilator adapted for tracheotomy ventilation, a handset, a handset harness, a stabilizing strap, and an oxygen conservation accessory according to an embodiment of the invention.

FIGS. 141 to 143 show various arrangements of the portable ventilator 500 and handset 590 in use as a wearable system. For example, FIG. 141 shows a ventilator 500 adapted for tracheotomy ventilation, a neck strap 568(1) for supporting the ventilator near the patient's chest, a stabilizing strap 568(2) for stabilizing the ventilator near the patient's chest, and a handset 590 supported on the patient's waist by a handset harness and strap 568(3). The stabilizing strap 568(2) may be optional, e.g., FIG. 142 shows the ventilator supported by the neck strap 568(1) without a stabilizing strap. Also, FIG. 142 shows the handset harness and strap 568(3) supporting a handset 590 with an extension battery 599. FIG. 143 shows an arrangement similar to FIG. 141, with an oxygen conservation accessory 569 provided to the ventilator.

FIGS. 128-132 show another embodiment of a battery operated remote 590-1 for controlling the ventilator.

Operation

Operation and additional aspects of the ventilator are described in more detail with specific reference to FIGS. 32, 33, 109, and 110.

The ventilator may optionally include the filter/valve assembly 501 having an air inlet 502(1) that allows air to be drawn in from the atmosphere into the system. The air is preferably passed through the filter 503 to remove any particulate matter. However the filter/valve assembly may not be required if there was no concerns about filtering the air, or with muffling noise, or with oxygen enrichment, then the blower could simply communicate with atmosphere. Optionally, the filter 503 may be an anti-bacterial (AB) filter. In the illustrated embodiment, the AB filter is provided on the proximal side to: (1) protect the ventilator and the ambient environment from pathogens, (2) protect the flow meter from secretions, and/or (3) act as a heat moisture exchange (HME).

The filter/valve assembly 501 includes 2 one-way valves (i.e., air inlet valve 507 and air outlet valve 509) configured "back-to-back" to separate inhaled flow from exhaled flow. The air inlet valve 507 is in the form of a first membrane including an annular portion 507(1) that lifts up due to the resulted vacuum around the blower proximal opening during inspiration. This opens the air inlet valve 507 and allows air to flow into the blower proximal opening 523 during inspiration (e.g., see FIG. 109). The air inlet valve 507 has a central aperture that allows air to flow therethrough. The air outlet valve 509 is in the form of a second membrane and air will not exit through the air outlet valve during inspiration because of the vacuum created here. The air outlet valve 509 is closed during inspiration in order to prevent air being drawn into the blower through the expired air outlets or outlet channels 504(3) directly. Two exemplary reasons for not drawing air through the expired air outlets include: (1) air at the outlets has relatively rich $CO_2$, and (2) air drawn from the expired air outlets will not pass the filter.

During expiration, the air flows back through the ventilator to the air outlet valve 509. The air inlet valve 507 remains closed around the perimeter of the blower proximal opening sealing the inlet flow path from the exhaled air, and the air outlet valve 509 is pushed upwards to allow the expired air to exit out the expired air outlet channels 504(3) (e.g., see FIG. 110). There may be one or more expired air outlet channels 504(3) provided to the filter/valve assembly, e.g., two expired air outlets as illustrated. Thus, the exhaled air is separated from the inhaled air in the filter/valve assembly. It is noted that the impeller and rotor are still running during expiration to maintain a positive end expiratory pressure (PEEP) or prevent stall.

Figure 63:
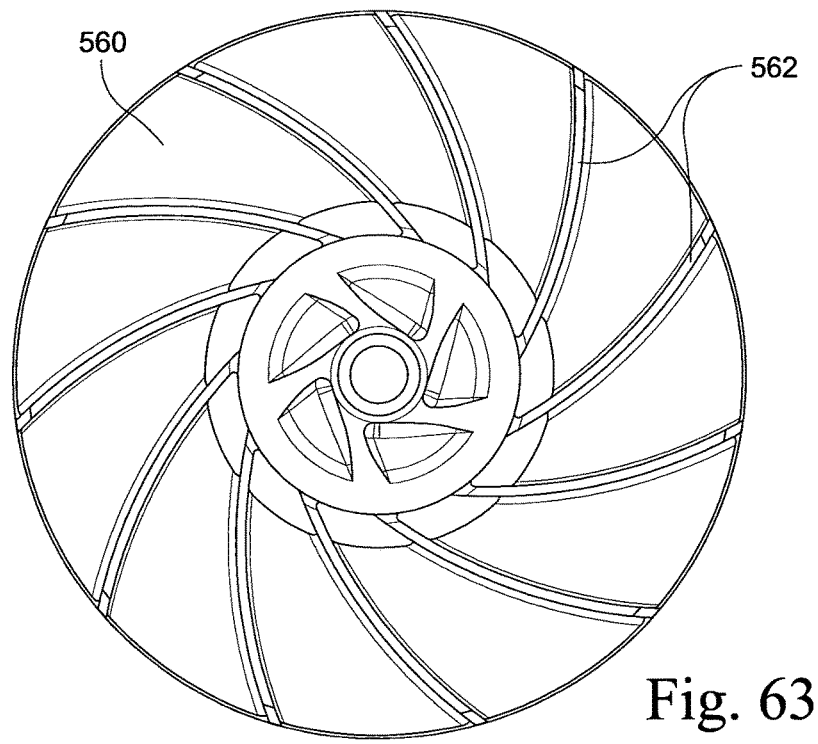
Figure 64:
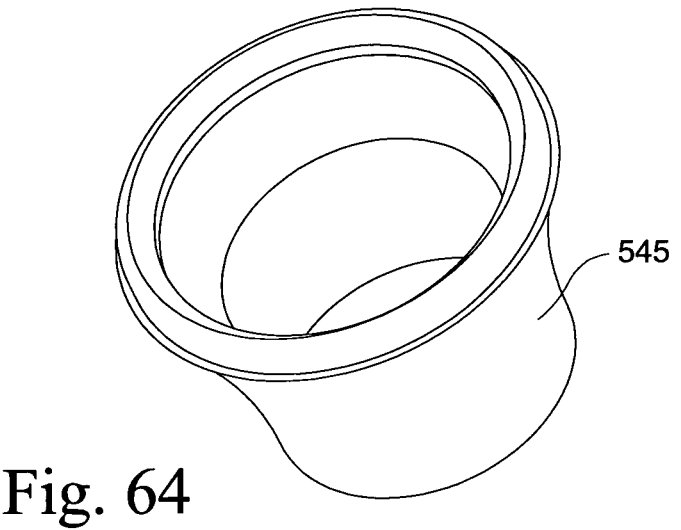
FIG. 64 is a perspective view of a sleeve of the blower according to an embodiment of the invention.
Figure 65:
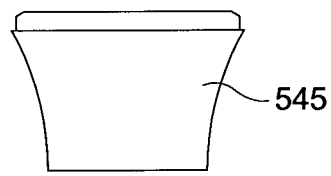
FIGS. 65-67 are side, top, and bottom views of the sleeve of FIG. 64.
Figure 66:
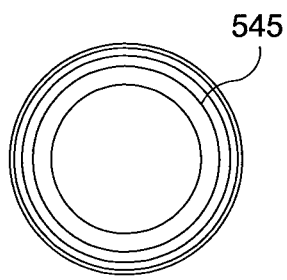
Figure 67:
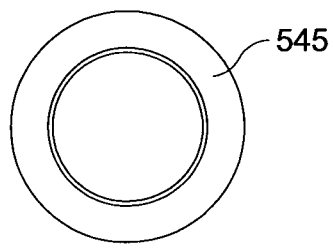

Air enters the blower proximal opening 523 and flows into the impeller 560. In the illustrated embodiment, the impeller has 11 vanes 562 (e.g., see FIG. 63). The number of impeller blades is preferably a prime number to reduce tonal noise. Also, the number of impeller blades may be selected to provide sufficient pneumatic performance as well as sufficient expiratory resistance, provide relatively low inertia, and/or provide a strong structure that results in low deformation during high speed revolution. However, it is noted that the impeller may include a different number of blades such as 9 or 13 depending upon the blower requirements. The number of impeller blades may be balanced against the flow impedance and the efficiency, where too many blades may increase the flow impedance and too few blades may reduce the efficiency. The impeller may be a mixed flow, low inertia impeller that is attached to the rotor of the motor. The impeller has an alternating shroud arrangement as described in co-pending U.S. application Ser. No. 12/083,350, which is incorporated herein by reference in its entirety. The blades of the impeller may be curved backwards in relation to the rotation of the impeller. This facilitates a reduction in acoustic noise. Backward curving impeller blades also facilitates a decreasing pressure flow curve which may be advantages for volume-control ventilation as it providers finer resolution for controlling the flow throughout the inspiratory cycle. However, for embodiments focused on pressure-target ventilation or for non-invasive ventilation (where higher inspiratory flow rates are helpful), then radial or forward-facing blades may be preferable.

The motor 540 is a powerful, relatively quiet, miniature and efficient motor, such as a Maxon EC13 motor (30 W or 50 W). It may be preferred that the motor be fully sealed and autoclavable to allow sterilization of the system. A narrow diameter facilitates the low deadspace of the non-vented embodiment. However, the minimal dimensions of the motor, particularly around the motor windings, permits the motor's magnetic flux to interact with any closely-adjacent conductive structures, and in doing so reducing the motor's efficiency. Also, the pneumatic work done by the motor inherently produces heat, even with such an efficient motor, which for a small motor with small surface area may need specific design treatments to target thermal management of the motor. In an embodiment, the motor couples thermally conductive parts of high surface area to the motor in the interest of heat management, but specifically avoids electrically conductive parts around that section of the motor producing strong magnetic flux to avoid loss of motor efficiency. Specifically, the flow meter and the stator and the base of the housing may all be thermally conductive elements coupled intimately with the motor body, while the region between the flow meter and stator may be electrically non-conductive.

The impeller 560 rotates and directs the airflow tangentially outwards from the impeller. The air from the impeller enters the plenum chamber 528 that surrounds the impeller. The plenum chamber is a constant volume chamber having a constant diameter. The plenum chamber allows a uniform or stable pressure to be produced, especially at low flow rates. The plenum chamber acts as a reservoir or a buffer for flow exiting the impeller. The volume that the plenum chamber provides suppresses the offset and reduces noise in flow measurement at low flow, especially at zero flow. This stable pressure reduces or minimizes the pressure variation around the circumference of the stator inlet, which if uncontrolled can promote offset error in the flow sensing: this pressure variation can induce localized flow from say a high-pressure zone, through a segment of the flow element, then circulating back through another segment of flow element to a low pressure zone around the circumference of the stator inlet. The plenum chamber also discourages pressure impulses being developed, that can lead to impulse noise in the flow sensing. Having the plenum chamber radial outwards from the impeller and the stator vanes or air directing grooves 535 starting from this plenum chamber also reduces blade pass tonal noise as the tips of the impeller blades are shielded from the stator vanes.

From the plenum chamber 528, the air flow is directed through the stator component 530 including part 534 with air directing grooves 535. The stator component includes a plurality of channels or air directing grooves 535 that assist in directing the airflow from a generally tangential direction to a generally axial direction and encouraging a laminar flow. In an exemplary embodiment, the part 534 of the stator component has a cross-sectional area of about 170-180 $mm^2$, divided substantially equally between 13 channels of the part. However, the cross-sectional area and number of channels may be varied depending upon the patient use and size of the system. For example, a ventilation system for pediatrics may have a smaller cross-sectional area, e.g., less than 170 $mm^2$. The number of channels may be selected to: include a prime number, avoid coupling with the impeller, and/or balance between the deadspace and resistance. The cross-sectional area is substantially maintained through the channels to reduce turbulence despite variation in width and depth of the vanes. The stator vanes 538 (e.g., see FIG. 58) that define the channels 535 are wider closer to impeller with a shallower depth and proceed down with a reducing width and expanding depth. A substantially constant cross-section assists in maximizing laminar flow through the channels.

The substantially constant cross-section also reduces expiratory impedance for the exhaled airflow. The shapes of the channels assist with the moldability of the stator part.

The channels in the stator are separated from each other, e.g., such that air does not flow between channels in use. The stator channels have an upper curved profiled with an angle at the tip, e.g., about 20-40°, e.g., about 30°. However, the stator channels may have other suitable tip angles. The tip angle may be selected with the consideration of flow and rotating speed the blower is likely to have when in normal use, the resistance, and/or moldability, for example. The stator component 530 is assembled within the blower housing 520 via a drop in assembly and is sandwiched between the top and bottom housing parts 522, 524. The blower housing parts may be molded from thermally conductive polycarbonate (e.g., Coolpoly E4501).

In an embodiment, the stator component is molded from a heat conducting material such as aluminum. The aluminum assists in dissipating heat from the motor as it acts as a heat sink. It is noted that different size stators with a different number of vanes may be used depending upon the desired tidal volume required. However, as mentioned above, it may be desired to limit the deadspace within the blower to maintain a desired tidal volume for the patient.

Due to the both the inspiratory and expiratory flow passing through the blower, the cross-sectional area of the blower, i.e. deadspace volume, should be balanced against the desire to minimize any imposed respiratory resistance on the patient. Thus, the system is optimized to reduce the impedance for the expiratory flow through the system while also minimizing the deadspace volume.

Below the stator component 530 is a downstream chamber 529 that provides a volume between the end of the stator component 530 and the flow element 555. This downstream chamber helps to reduce flow turbulence and allows airflow recirculation through the stator without affecting the flow sensing through the flow element 555 at zero flow or a very low flow, further diminishing the recirculation effect discussed for the plenum chamber above. This ensures that the air flowing through the flow element is more stable and more uniform to ensure a smooth flow signal is obtained. The downstream chamber also helps to remove the flow measurement offset at zero and very low flow.

The non-electrically conductive sleeve 545 (e.g., formed from a non-electrically conductive material such as a plastic) surrounds the motor 540 within the downstream chamber 529. The sleeve surrounds the central portions of the motor and is adapted to prevent or substantially reduce the formation of eddy currents that lead to inductive losses in the motor and reduced motor efficiency, e.g., sleeve has a profile following the stator component to create a smooth flow transition. The sleeve also assists in maintaining the correct alignment of the stator component. The o-ring 541(2) between the top of the sleeve 545 and the bottom of the stator component 530 seals the internal space within the stator reducing the deadspace volume. A heat-conductive elastomer component or rubber component 536 is also located within the stator component to assist with dissipating heat from the motor. The rubber component has a complementary shape to the stator component.

Figure 68:
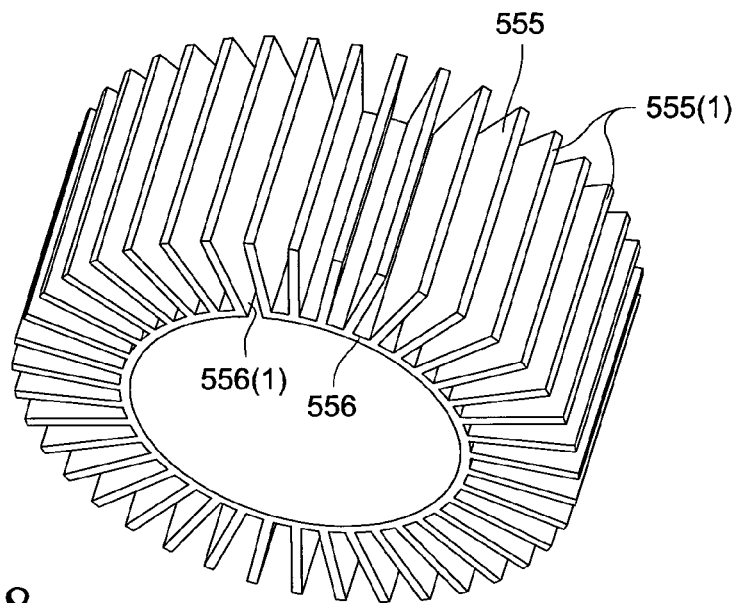
FIG. 68 is a perspective view of a flow element of the blower according to an embodiment of the invention.
Figure 69:
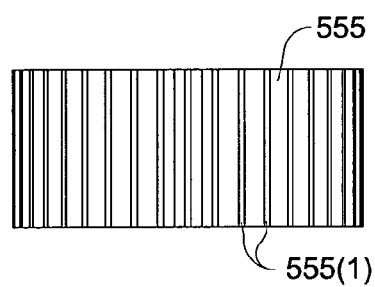
FIGS. 69 and 70 are side and bottom views of the flow element of FIG. 68.
Figure 70:
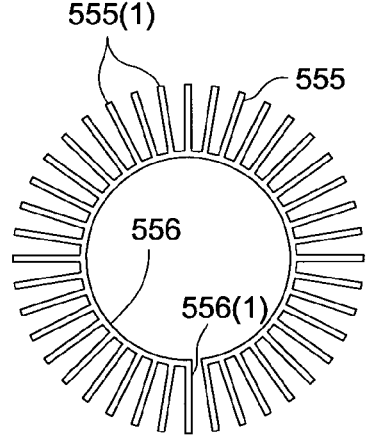
Figure 71:
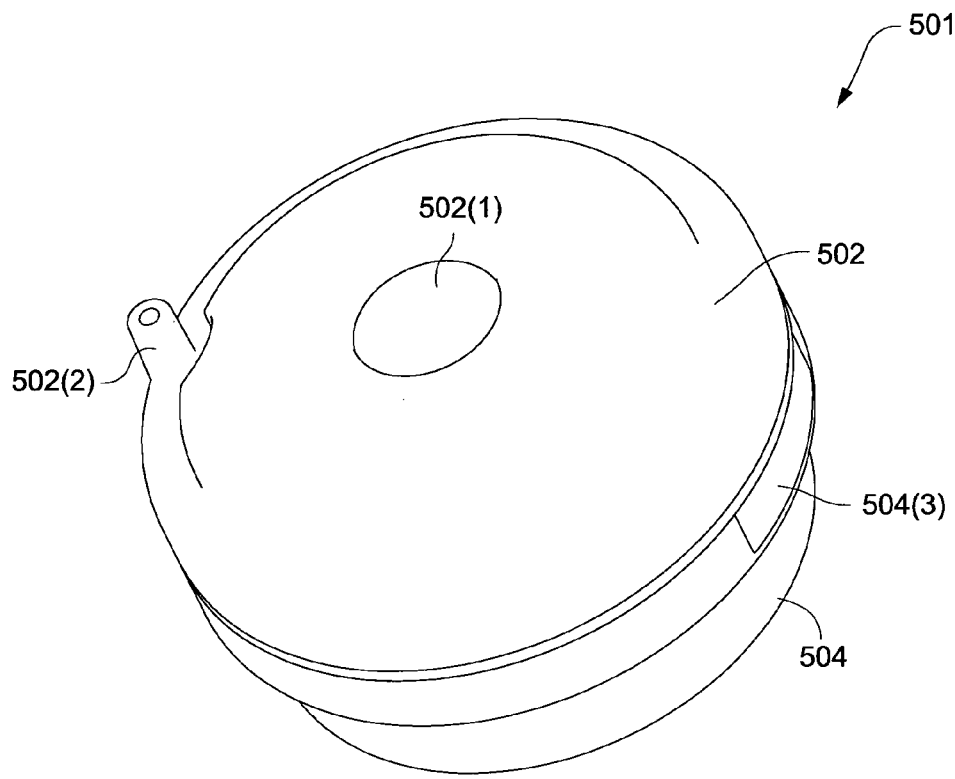
FIG. 71 is a perspective view of a filter/valve assembly according to an embodiment of the invention.
Figure 72:
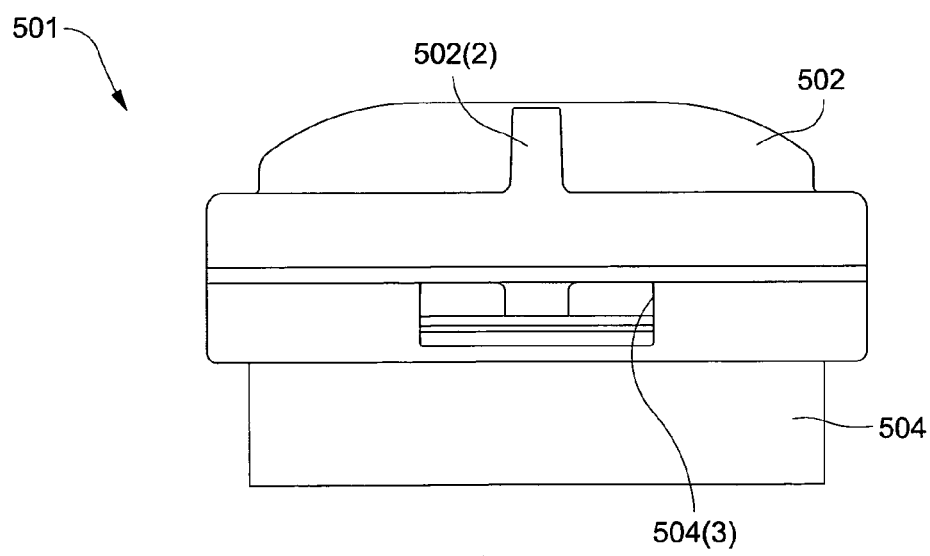
FIGS. 72-74 are side, top, and bottom views of the filter/valve assembly of FIG. 71.
Figure 73:
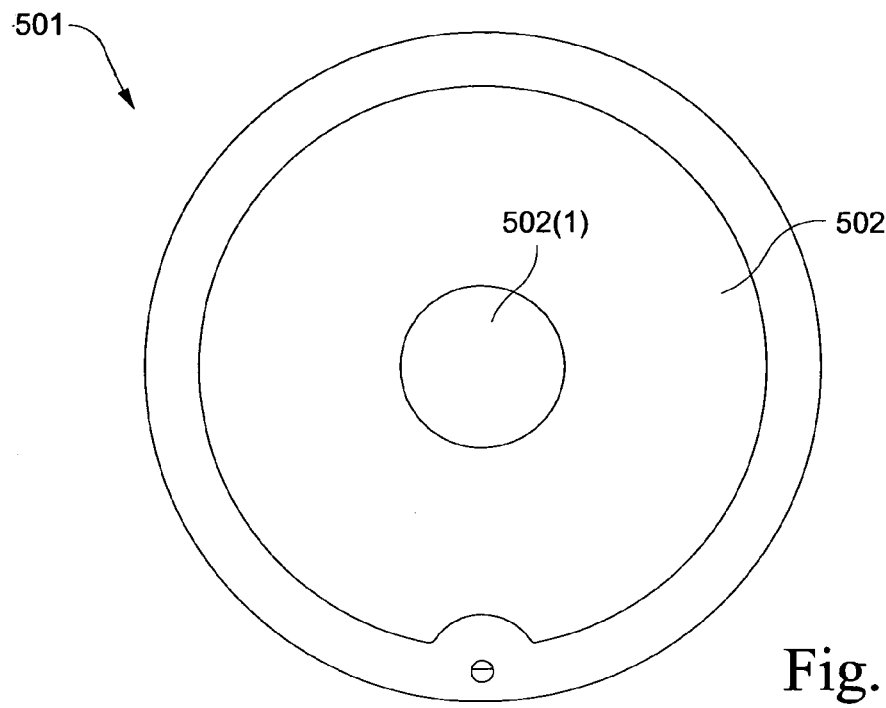
Figure 74:
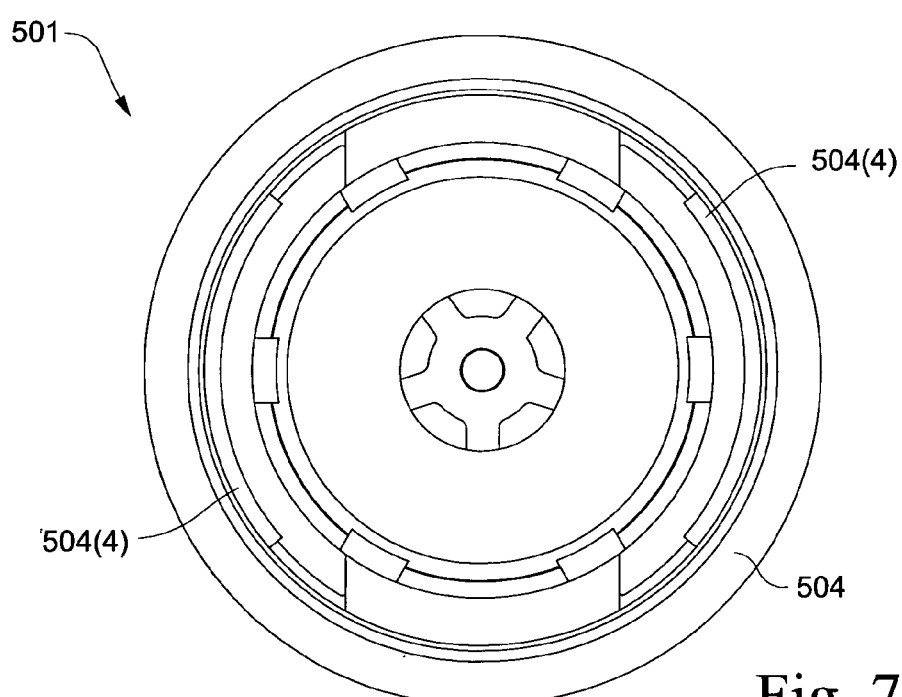

The flow element 555 is located below the downstream chamber 529. The sleeve 545 also provides a stop for the locating of the flow element 555. The flow element (e.g., constructed from a heat conducting material such as aluminum) provides an additional heatsink for the motor 540, assisting in dissipating heat from the motor. This advantageously also warms the flow element minimizing condensation on the flow element which may adversely effect flow measurement. The flow element is a circular component adapted to fit around the end of the motor. As best shown in FIGS. 68-70, the flow element includes 20-60 vanes, e.g., 40 vanes. The number of vanes is designed to ensure good resolution at low flow while also accommodating the measurement of maximum flows as dictated by the alternate applications of the ventilator. In the embodiment that combines both vented and non-vented applications the flow element can measure a relatively high maximum flow, for example 180 L/min. The flow element 555 has a split inner core 556 (from which the vanes 555(1) extend as best shown in FIGS. 68 and 70) with split 556(1) to allow the flow element to be a spring-fit around the bottom of the motor and to expand and contract with the changes in heat of the motor. In an exemplary embodiment, the flow element may be Honeywell flow sensor X202705.

After the flow element 555, the air flow path proceeds through the system to the outlet flow tube to the patient. The cross-sectional area in the flow path is maintained substantially constant to reduce the generation of the turbulence through the flow path. Turbulence can lead to undesirable noise or losses in the system. It may be advantageous to include a mucous trap 575 (e.g., as described above with respect to FIGS. 32, 33, and 97-108) proximal to the ventilator to catch any expired particulate matter expired by the patient, for example mucous. A capture plate 578(1) is located within the central region of the outlet flow tube to the patient. It is the capture plate that catches any particulate matter expired. During inspiration, the airflow travels through the mucous trap and around the capture plate to the outlet flow tube 576(2) to the patient. During expiration, the air entering the outlet flow tube hits the capture plate 578(1) which catches any expired particulate matter, the air can then flow around the capture plate and back through the ventilator to the filter/valve assembly 501 as discussed above. Alternatively to the mucous trap 575, a filter element may be used, to provide anti-bacterial or anti-viral filtration, and/or act as a heat/moisture exchanger which can be of physiological beneficial by conditioning the inhaled air, and/or protect the ventilator from exhaled particulates. For example, the HMEF 580 as discussed above may be provided to the ventilator in lieu of the mucous trap.

The chamber space provided by the filter/valve assembly 501 acts as a type of muffler to assist in reducing conducted noise from travelling back through the system.

The filter/valve assembly 501 also includes port 502(2) to allow oxygen to be attached to the inlet to enable the supply of oxygen enriched air to the patient. The oxygen is directed into the inlet flow path area of the filter/valve assembly. In one embodiment, the volume of the chamber at the air inlet of the filter/valve assembly may be increased to provide an oxygen reservoir that will be filled by the oxygen supply during expiration to allow a boost of oxygen to be supplied upon the switch to inspiration.

Optionally, the filter/valve assembly may provide attachments for $3^{rd}$ party filters, as a user preference or for special-purpose filtration (e.g., smoke, dust, contaminants, toxins, toxic gas absorption).

It may be advantageous for the ventilator to know which inlet accessory is in use, for example to calculate an estimated $FiO_2$ (i.e., fraction of inspired oxygen). Means may be provided to detect which of the inlet accessories in use, either as user-input to the controller (menu), or automatic detection. Automatic detection may be achieved by a variety of established means, e.g., embedded magnets with hall-sensor detection, optical reflectors, microswitch and mechanical key, inductance loop, etc.

The segregated power/control assembly (e.g., handset 590 as discussed above) provides several features. For example, the segregated power/control assembly may act as a renewable power source. If the power/control assembly is removable, it can be replaced quickly with another power/control assembly with a fresh battery charge. The assembly includes a mechanism where the ventilation configuration is stored within the electro-pneumatic transducer assembly, courtesy of a local microcontroller and sensor unit within the transducer. An alarm may be included in the electro-pneumatic transducer assembly, instead of or in addition to the power/control unit. The segregated power/control assembly may also act as a mobile programming unit, in that the ventilation configuration is duplicated within the power/control handset, so the choice exists whether to accept the configuration of the electro-pneumatic transducer, or the configuration of the power/control unit. This allows rapid "pasting" of settings to a new patient or a new ventilator, for instance as may be of value in an institutional setting such as a hospital, or as may be of value in allowing a dependent patient to carry a redundant electro-pneumatic transducer assembly in case of mechanical failure, with rapid changeover.

The power/control assembly, whether integrated with the electro-pneumatic transducer or whether segregated, also includes features of use in an ambulatory device. It possesses in internal accelerometer (can be single or multiple-axis), and allows peripheral sensors to also be connected such as a pulse oximeter or $CO_2$ monitor (trans-cutaneous or end-tidal). Together or in isolation this can allow: accelerometer monitoring of rehabilitation parameters, such as pedometer estimation of six-minute walk distance, which can improve clinical management patients during of ventilator-assisted exercise programs; accelerometer monitoring of patient falls, which may optionally utilize the ventilator's alarm function in drawing attention to the patient fall; accelerometer detection free-fall of the ventilator, allowing blower operation to be suspended (for self-protective reasons) in anticipation of an impending impact; accelerometer detection of extreme ambient vibration, which may interfere with the ventilator's ability to correctly sense patient breathing activity (trigger/cycle): if ambient vibration is detected, a mandatory ventilation regime may be instituted until the external influence has been removed; accelerometer detection of increased patient activity, which alone or in concert with oximeter-sensed heart-rate or oxygen saturation, may be used to alter ventilation parameters in anticipation of increased ventilatory demand; accelerometer-driven user input for changing ventilation parameters: in certain environments, such as extreme glare, noise, motion, etc, traditional medical device user interfaces such as electronic displays and button navigation may be challenged: an accelerometer interface allows a sensed rhythm and vigor of motion (acceleration) to be used to drive parameters such as breath rate and amplitude; separate means of confirming the user's intention may be required, to separate ambient or incidental movement from an instructional movement; a sensed CO2 driven regulation of ventilation: in field ventilators, used by emergency personnel or even users without any medical training, simplicity of operation is key, and automation is one way of maximizing simplicity: allowing the ventilator to perform limited automation of control, for instance closed loop adjustment of tidal volume to maintain CO2 target, is one potential approach: and/or an oximeter combined with adjustable oxygen flow allows the user to adjust oxygen guided by blood oxygen saturation.

In emergency ventilation, it may be advantageous to offer an estimate of fraction of inspired oxygen. Oxygen sensing cells provide this directly, but are large. An aspect of the invention includes a calculated $FiO_2$, based on the supplemental oxygen flow rate (either user-input or sensed with a flow meter) and knowledge of the delivered tidal volume and the internal dimensions of the ventilator.

For hospital transport ventilators, operation within an MRI environment is advantageous. Most ventilators possess ferrous or magnetic components, which may limit the proximity of the ventilator to the magnet bore. However a small, efficient micromotor ventilator platform with minimal ferrous components may permit closer proximity than traditional devices. It may be advantageous to for such a ventilator to monitor ambient magnetic field strength, so that an alarm may be raised if it is being used with an excessive magnetic field. An aspect of the invention may optionally include a magnetic field strength sensor, such as a Hall-effect sensor, to sense ambient field strength and provide appropriate feedback to the user.

The power and control unit for an embodiment of the ventilator is formed as a separate unit to the pneumatic components described above. The control unit may be designed as a handset (e.g., handset 590 as discussed above). The control unit may comprise a power unit such as a battery unit or the power or battery unit may be made as separate unit that is adapted to attach to the control unit. The control unit and the ventilator unit both include a micro-controller capable of recording the patient data. In this manner, different control units may be interchanged with different ventilator units and the exchange of patient details may be exchanged from the ventilator to a new handset or vice versa. Thus, in an embodiment where the power or battery unit is incorporated within the control unit, then when the battery gets low a new charged control unit may be connected to the ventilator and the patient and therapy details exchanged from the ventilator to the new control unit to proceed with therapy. Alternatively, if a patient is moved from one location to another and the ventilator unit is to be exchanged then the control unit may send the patient and therapy data to the new ventilator to maintain the appropriate treatment.

The control unit also comprises the user interface system to allow the setting, input and adjustment of patient details and therapy parameters. The benefit of having a separate control unit from the proximally located ventilator unit is an increase in usability in adjusting parameters. It allows the user to see the user interface more easily than if it was attached to the proximal ventilator unit. Furthermore, the clinician or nurse may be able to adjust the parameters while the user is being mobilized rather than having to stand in front of the user.

In an alternative embodiment the ventilator unit may comprise a simple user interface and/or battery to allow the simple adjustments of the ventilator.

Alternative Arrangements

In an alternative embodiment of the invention, a ventilator system may include a headworn system. In this embodiment, the blower may be mounted on the patient's head (e.g., on the crown of the patient's head or on the front portion of a patient's head).

In an embodiment, the elbow and external tubing may be removed as the tubing may run through the headgear.

In an embodiment, the blower may be mounted on a foam cushion to prevent or limit transmission of vibration and noise. The foam cushion may include multiple layers of foam of differential hardnesses or densities.

The blower may be mounted at an angle normal to the patient's (e.g., in an orientation such as ear to ear). Alternatively, the blower may be aligned in direction between the rear of the head and the patient's nose.

The blower may be mounted on a front portion of a patient's head between the crown and the forehead, preferably closer to the patient's forehead.

In an embodiment, the headgear may include an air channel with no or limited turns in the air path and a 90° turn may be avoided.

Additionally, one or more headgear straps (e.g., constructed of fabric) may be adapted to function as a vent for the system.

Figures 1, 144:
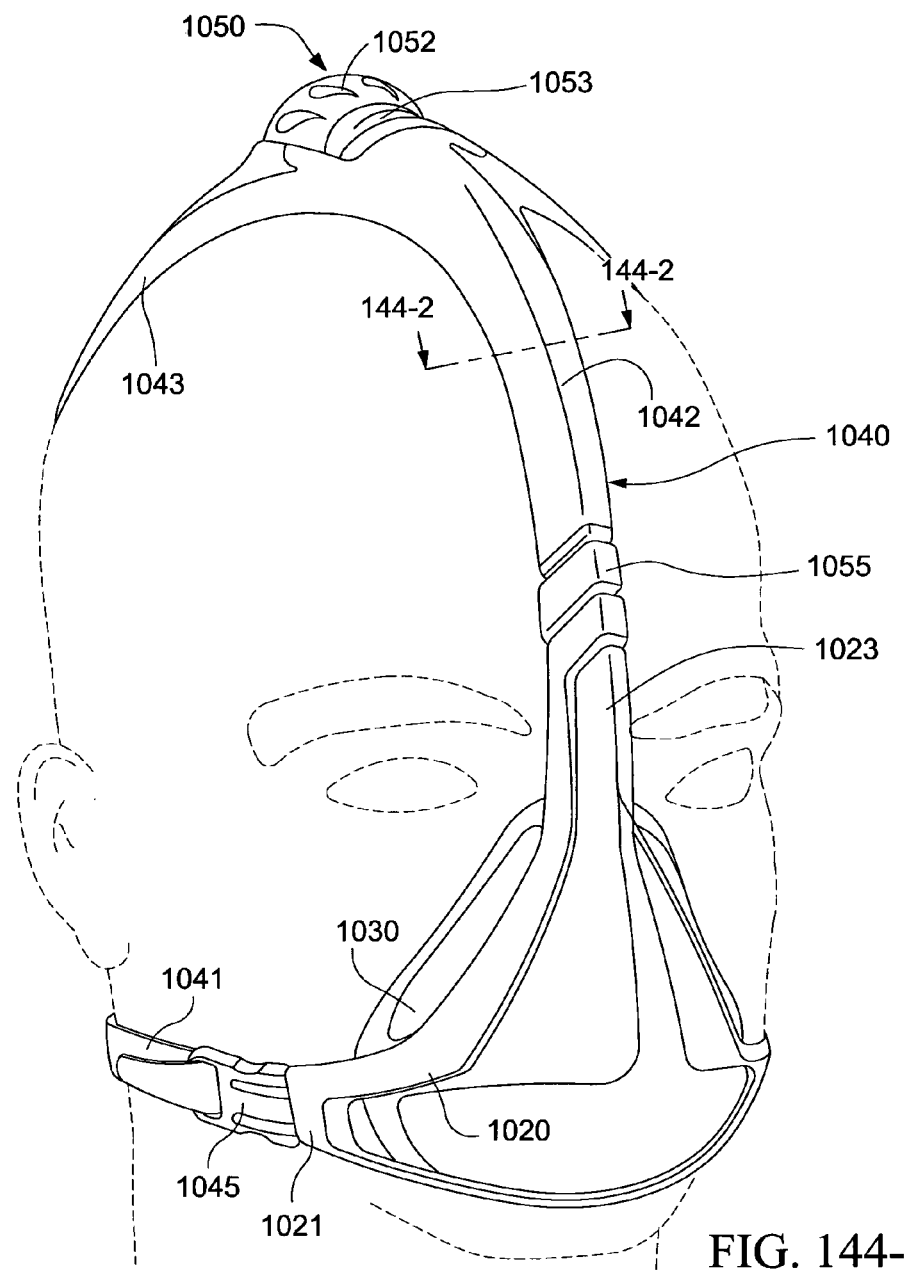
Figures 2, 144:
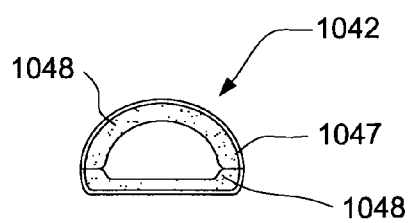
Figures 3, 144:
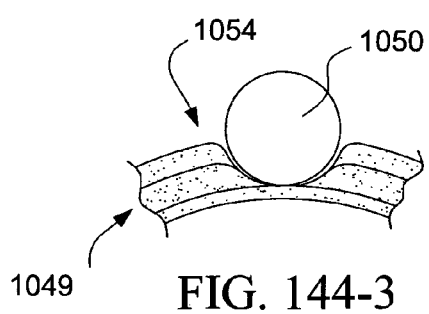
Figure 158:
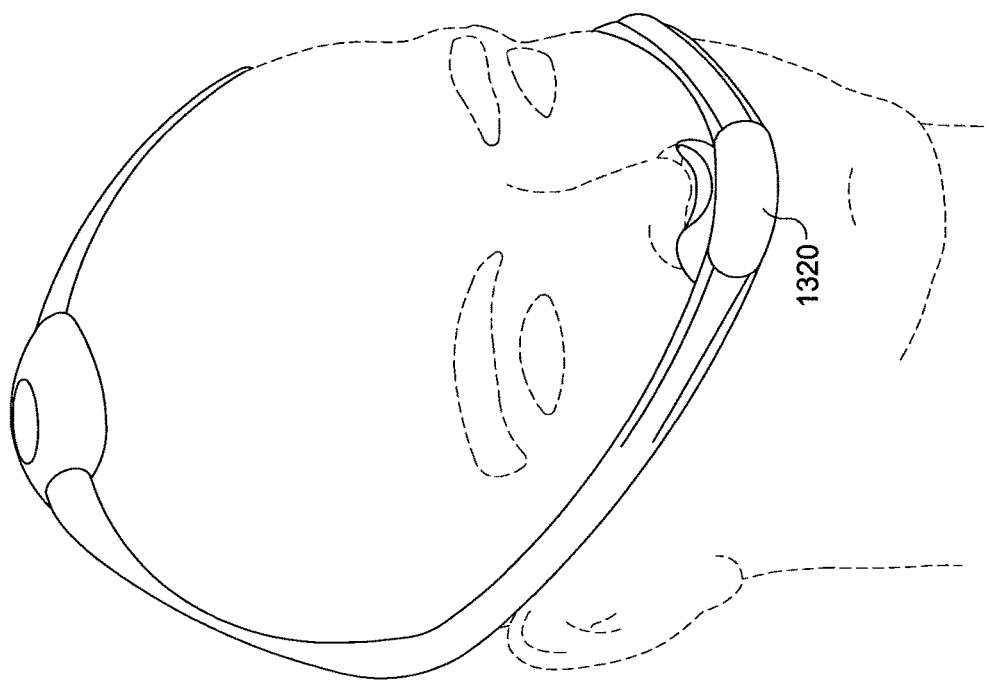
FIG. 158 shows a headworn ventilator system according to an embodiment of the invention.

FIGS. 144-1 to 158 show headworn ventilator systems according to alternative embodiments of the present invention. As illustrated, the blower may rest on the top and/or side of the patient's head in use.

In FIGS. 144-1 to 144-3, the patient interface or mask includes a frame 1020, a cushion 1030 provided to the frame and adapted to form a seal with the patient nose and mouth, and headgear 1040 to support the mask in position on the patient's head. The headgear 1040 includes side straps 1041, 1043 and an over-the-head strap 1042 that passes between the patient's eyes towards the top of the patient's head. As illustrated, the headgear 1040 supports a blower 1050 in position on the crown of the patient's head. The over-the-head strap 1042 forms a duct to communicate pressurized air from the blower to the breathing chamber defined by the cushion. In addition, the headgear includes multi layer foam and/or dampening material 1049 to support the blower 1050 and limit vibration/noise. In an embodiment, the mask may include one or more aspects as described in PCT Application PCT/AU2009/000241, filed Feb. 27, 2009, which is incorporated herein by reference in its entirety.

Frame 20 is arranged such that it connects with cushion 30 adjacent its perimeter or outer most edge. This is so that the appearance of the mask is less obtrusive as the visual impact of the mask will be reduced. It also enables a clear line of sight to the patient's nares and/or mouth when viewed from the front. A short tube 1023 is coupled with the cushion 1030 to deliver the pressurized air from the blower 1050 via the headgear flexible tubing 1042 to the cushion 1030. The short tube 1023 may be integrally moulded with the cushion 1030. The short tube 1023 may be made from a sealing material such as silicone. Frame 1020 may include headgear connection portions 1021 for interfacing with headgear straps 1041. As shown in FIG. 144-1, headgear straps 1041 may be connected to the frame using clips 1045. Alternative connection means are possible, such as hooks or slots for receiving headgear straps, push fit, hook and loop connections, magnets, or any other connecting means. Headgear may also be provided with a cuff or interfacing means that is able to be push fit or otherwise connect with the frame. As shown in FIG. 144-1, over-the-head strap 1042 is provided with a cuff 1055, the cuff being stitched, glued, ultrasonically welded, radio frequency welded, or connected by any other means, to the end or connecting portion of over-the-head strap 1042. This interfacing means then connects to the frame.

Flexible tubing may be molded within the over-the-head strap 1042 and interfacing means to connect with the mask. The flexible tubing may alternatively be molded with the mask, for example as one part with the cushion, and inserted within the cuff 1055 and over-the-head strap 1042.

Over-the-head strap 1042 may be constructed of more than one layer of material. Preferably, the outer most layer 1047 may be a fabric, textile or other soft material for providing comfort when in contact with the patient's skin. An inner layer 1048 may be foam, gel, 3D woven fabric, or any other dampening material to absorb noise from the air delivery tube. Another inner layer may be a polymer sheet or film 1046 (e.g., FIG. 146-2-3) to seal the inner portion of the duct so as to prevent air leakage. The polymer sheet may be polyurethane, polyvinyl or another suitable polymer. Alternatively, the inner portion may be sealed using silicone spraying or a separately attachable duct 1052 (FIG. 146-2-2). In a further alternative, a skinned foam may be inserted within the outer layer. Preferably, the portion of the over-the-head strap contacting the user's face may include additional layers or thicker regions of the dampening layer so as to absorb more vibration and noise.

At the blower connecting end of the over-the-head strap 1042, a second cuff or connecting means 1053 may be provided to connect the blower outlet to the headgear 1040. The second cuff 1053 may be formed from a polymer material. The polymer may be a thermoplastic elastomer, thermoplastic urethane, polyester, polypropylene or any other suitable material. The cuff may be glued or integrally formed with the over-the-head strap 1042.

The blower mounting portion 1054 of the headgear may include a cradle or positioning means to capture the blower, stabilise it in position, and preferably absorb noise and vibration. The blower mounting portion 1054 of the headgear may include additional layers of dampening materials 1049 such as foam, silicone, gel, 3D textiles or any other suitable dampening materials.

The blower may have an air intake or inlet portion 1052 positioned parallel to the top portion of the patient's head (as shown in FIG. 144-1). Alternatively, the inlet may be positioned normal or perpendicular to the top portion of the patient's head.

Figure 145:
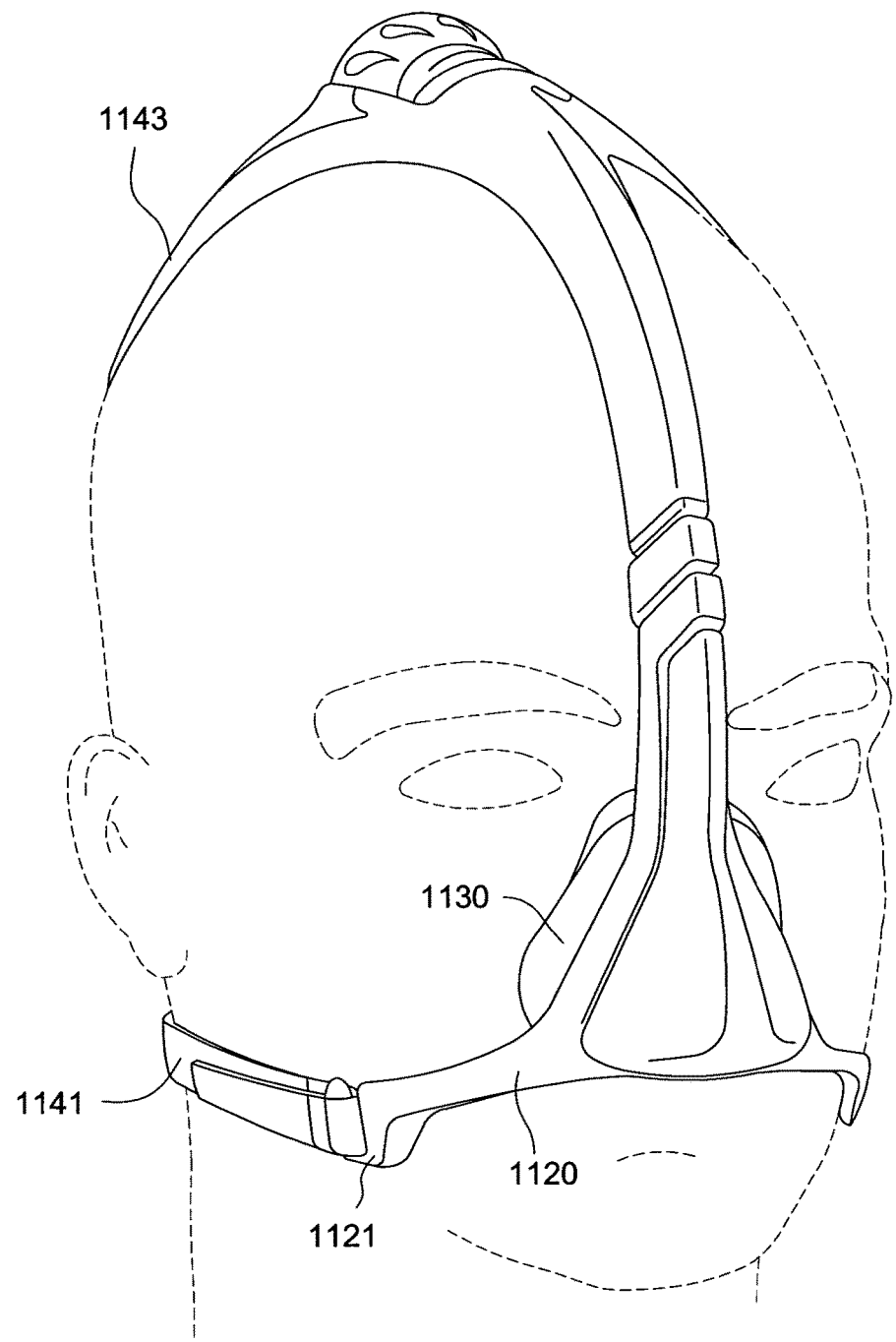
FIG. 145 shows a headworn ventilator system according to an embodiment of the invention.

FIG. 145 shows a mask similar to the mask of FIG. 144-1. In contrast, the patient interface of FIG. 145 includes a nasal cushion 1130 and the frame 1120 includes an alternative configuration for attaching lower headgear straps 1141.

Lower headgear connectors 1121 may be slots or loops to receive loops of headgear straps 1141. Preferably, slots may be connected to arms or wings that may move the connection point of the headgear to the frame away from the patient's line of sight.

In FIGS. 146-1 to 146-4, the patient interface includes a nasal prong or pillow arrangement 1230 adapted to form a seal with the patient's nares. The headgear 1240 includes side straps 1244 that form ducts to communicate pressurized air from the blower to the nasal prong arrangement. In an embodiment, the headgear and/or mask may include one or more aspects as described in WO 2009/052560 A1, U.S. Patent Application Publication 2009/0044808 A1, or U.S. Pat. No. 7,318,437, each of which is incorporated herein by reference in its entirety.

Cushion 1230 may include a plug or vent clip 1231 to seal the cushion. In order to manufacture the pillows on cushion 1230, the core may be removed through the aperture shown in FIG. 146-3. Alternatively, the plug may include vent holes if using a vented system to provide venting to the mask arrangement. Alternatively a plug may be solid for use in a non-vented system. FIG. 146-3 shows the cushion 1230 with the floating core and the aperture from which the core has been removed as indicated by the arrow.

Headgear straps 1244 may be attachable to the cushion 1230. Headgear straps 1244 may be ducted or hollowed to enable the passage of gas through the straps. The cushion connecting ends of the headgear straps 1244 may include cuffs or connecting means to enable removal of the cushion from the headgear. The cuffs may be molded, glued, radio frequency welded, ultrasonically welded or otherwise attached to the cushion connecting ends of the headgear straps 1244.

The headgear may include more than one layer as shown in FIGS. 146-2-1 to 146-2-3. The outer most layer 1047 will preferably include a soft, comfortable material such as fabric, foam, frosted polymers or any other suitable material. Preferably, an inner layer 1048 may comprise a dampening material such as foam, gel, silicone, 3D textiles or any other suitable material. Preferably, the headgear straps 1244 may be constructed using ultrasonic welding or thermoforming or a combination thereof. An inner most portion 1046 of the headgear straps 1244 may include a sealed, ducted portion for transmitting gases from the blower to the cushion. This may be constructed from an extruded silicone tube, a helical tube, or a polyurethane tube.

The top portion of the headgear may include a transition portion or connecting portion 1245 for joining the headgear straps 1244 to the blower (e.g., see FIG. 146-4). Transition portion may include a generally W-shaped portion as shown in FIG. 146-4, wherein there are two outer portions for connecting with the side straps or ducts within headgear straps, and a central connecting portion for connecting with the blower. This transition portion may be integrally formed with the headgear, for example by thermoforming, ultrasonic welding, gluing or any other connecting means. In an alternative embodiment, the transition portion may be positioned within or on the headgear without permanent fixation. The transition portion may be made of any sealed material, such as silicone, TPE, TPU, polypropylene, polycarbonate, or any other suitable material. Preferably, transition portion may sealingly engage with headgear ducts and the blower. The transition portion and headgear ducts may sealingly engage by interference fit. Alternatively, they may be formed in one piece. The transition portion and blower may sealingly engage by interference fit, such as push fit.

FIGS. 147-158 show alternative configurations for communicating pressurized air from the blower to the mask, alternative frame configurations for attaching headgear, alternative headgear arrangements, and/or alternative cushion or sealing arrangements.

Figure 147:
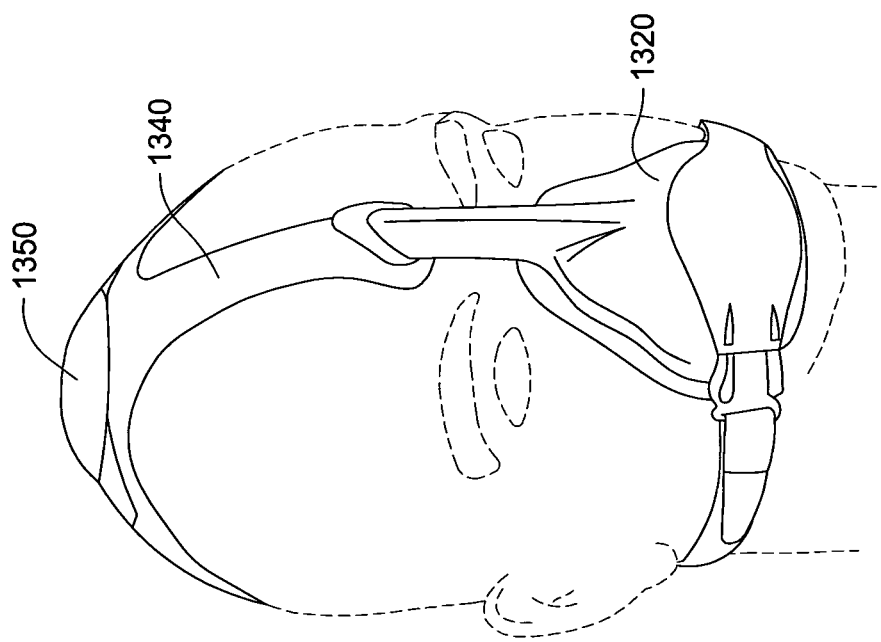
FIG. 147 shows a headworn ventilator system according to an embodiment of the invention.

FIG. 147 shows a blower 1350 mounted on the top or at the apex of the patient's head that is held in position by a headgear 1340. The headgear may include a securing portion for maintaining the blower in position on the headgear. The securing portion may include a formed region that holds the blower in compression to maintain it in position. Alternatively, the securing portion may include a sock, clip, wrap or any other structure to maintain the blower in position. The headgear may further include a channel or hollow region to pass a tube from the blower outlet to the mask 1320. The channel or hollow region may extend along the length of the tube or a portion thereof. The channel may maintain the heat within the tube and make the system appear more streamlined. The channel may further dampen or prevent the flow of noise from the blower to the mask. The mask may include a cushion and a frame. The mask may further include lower headgear connection points. The lower headgear connection points may include clips, loops or other headgear connection mechanism.

Figure 148:
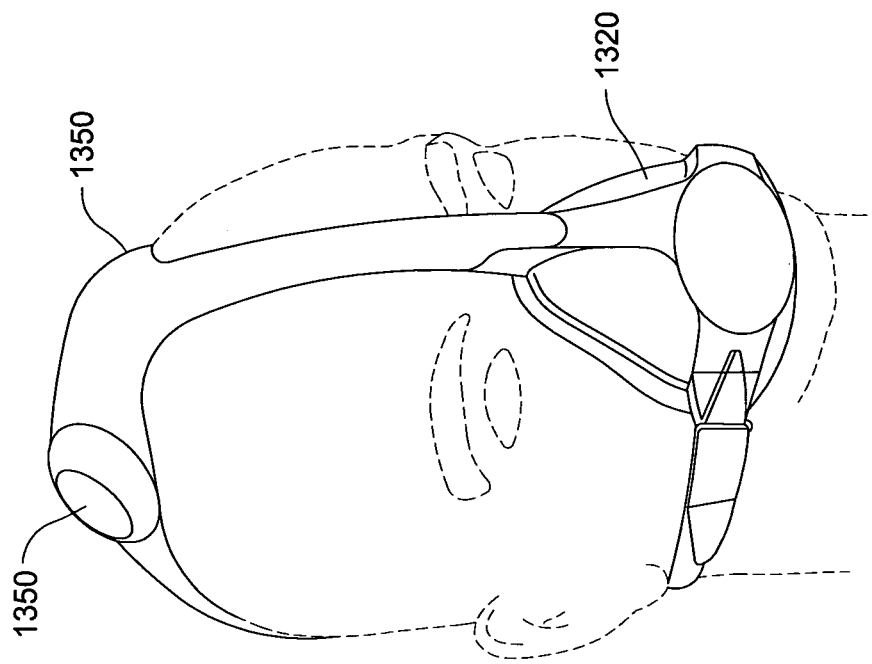
FIG. 148 shows a headworn ventilator system according to an embodiment of the invention.

FIG. 148 further demonstrates an arrangement for mask and blower system, where there are two blowers 1350 mounted at the top or apex region of the patient's head. Each blower may connect to a tube, where the tube then connects to the mask system 1320. Preferably, the tubes connecting the blowers and the mask are positioned under or encapsulated within the headgear straps. The embodiment shows two blowers, however it is possible for more than two blowers to be positioned on the headgear.

Figure 149:
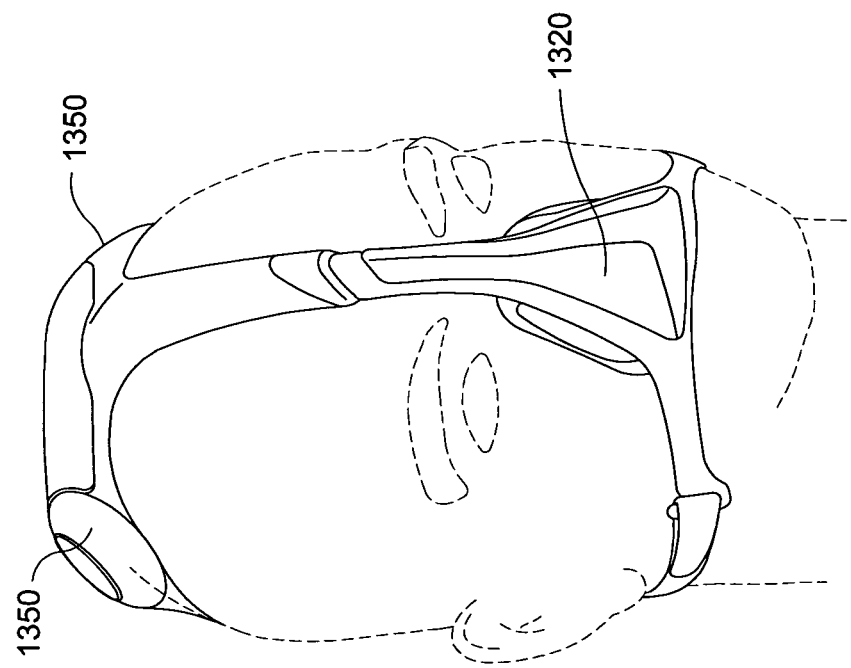
FIG. 149 shows a headworn ventilator system according to an embodiment of the invention.

FIG. 149 shows an alternative arrangement to the embodiment shown in FIG. 148. FIG. 148 shows a full face mask or mask that seals around at least the nose and mouth of a patient. The embodiment shown in FIG. 149 shows a mask 1320 that seals around a nose region of a patient. In addition, the mask includes a frame, where the frame may be a skeleton frame or a frame that surrounds the perimeter of the mask without shrouding or covering the central portion of the mask. This may make it easier to see the patient's nares when the system is in use. Such an arrangement may be beneficial in a clinical setting where a view to the patient's nares is desirable. In addition, the frame includes outriggers or slender extensions from the frame to the headgear connecting portions to reduce the visual bulk of the mask and also to enable greater flexibility at the headgear connecting portions. Such flexibility may be desirable to enable greater sealing engagement of the mask with the patient.

Figure 150:
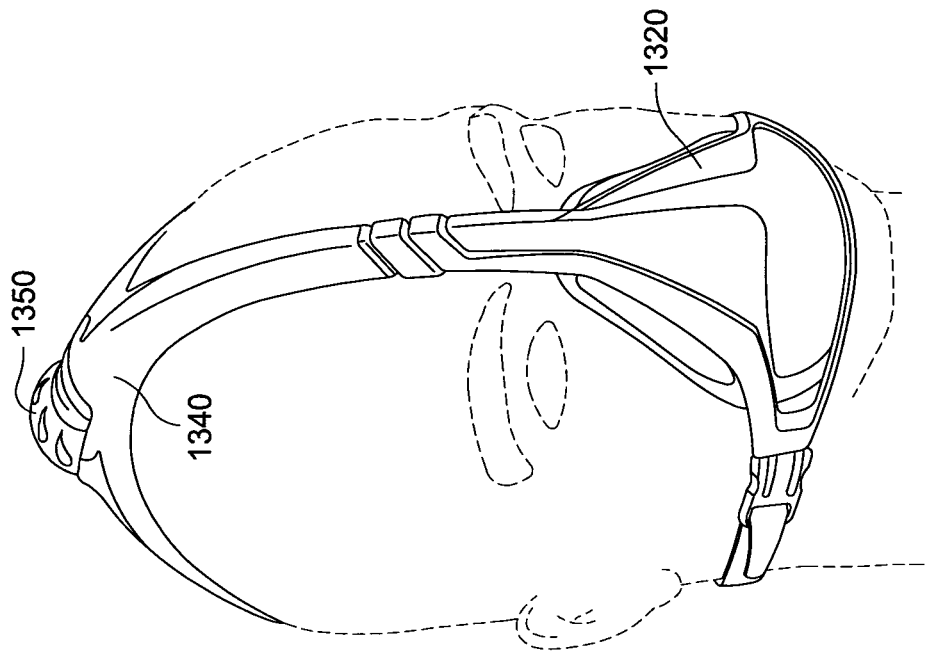
FIG. 150 shows a headworn ventilator system according to an embodiment of the invention.

FIG. 150 shows a full-face mask 1320 according to a further embodiment of the present invention. The blower 1350 is positioned at the top or apex of the patient's head. The intake of the blower housing is rearward facing, that is, facing in a horizontal direction away from the patient's face. It may also be possible for the intake of the blower housing to be positioned in alternative orientations such as directly vertical. The headgear 1340 may include a channel or hollow region for positioning of a tube, the tube being attached to the outlet of the blower housing and the mask. The headgear channel may terminate at a cuff or connecting region, where the mask frame having an opposition cuff or connection region for engagement with the headgear channel. The connection may be a mechanical connection such as a snap fit or taper lock. Alternatively the connection may be a permanent chemical connection or may be molded in one piece. The frame may be of a skeleton or perimeter arrangement similar to that shown in FIG. 149.

FIGS. 151-1 to 151-3 show an alternative arrangement of the present invention, where the patient interface 1320 is a pillows or prongs type mask. The patient interface is fluidly connected or a part of a tube arrangement 1340, where the tubes are routed or positioned on each of the patient's cheeks and between the patient's eyes and ears. The tubes terminate or connect to a blower or blower housing 1350, positioned at the top or apex of the patient's head. The headgear may encapsulate or otherwise surround the tubes as shown in FIG. 151-3. The headgear may be formed with the tubes or may be retrospectively fit or placed around the tubes. As shown in FIG. 151-2 the tubes may be radio frequency welded within a thermoformed fabric, for example.

FIGS. 152-1 and 152-2 show an alternative pillows or prongs type mask 1320, where the tube is routed directly vertical or upwards of the patient's head. That is, the tube is positioned in use between the patient's eyes. The mask may connect to the headgear 1340 on its lateral sides by push fit tabs, hook and loop, or any other engagement mechanism. Preferably, for vented systems the mask may have an orifice for venting on its lower portion, directly opposite the position or attachment points of the prongs or pillows. This may be to facilitate manufacture by allowing the core to be removed from the pillow or prong mask as described above in relation to FIG. 146.

Figure 153:
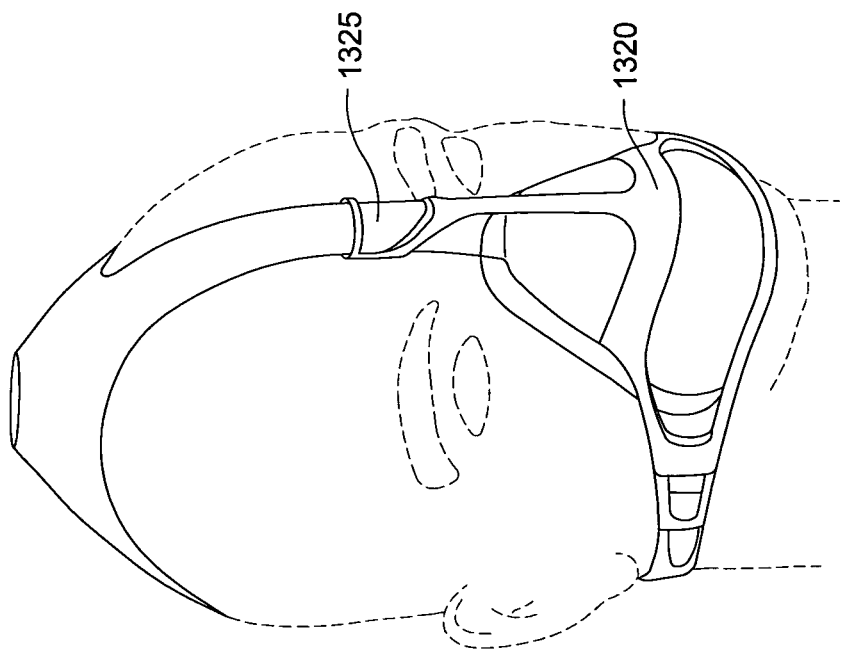
FIG. 153 shows a headworn ventilator system according to an embodiment of the invention.

FIG. 153 shows a further embodiment of the present invention. This embodiment includes many attributes of the system described in FIG. 150. The skeleton or minimized frame 1320 in this embodiment has a top portion that is generally upsidedown T-shaped. The upper stem of the T-shaped portion loops or wraps around the tube 1325. Lower headgear connectors are positioned on the lower portion of the minimized frame.

Figure 154:
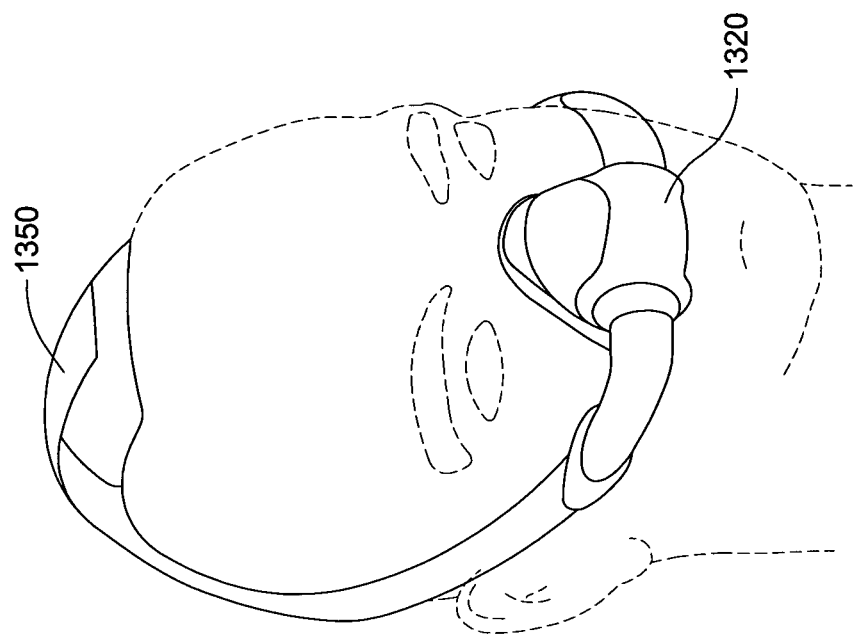
FIG. 154 shows a headworn ventilator system according to an embodiment of the invention.

FIG. 154 shows an alternative embodiment of the present invention. The mask 1320 may have side connectors to a tube or tubes, where the tubes are directed or positioned along the patient's cheeks and between the patient's eyes and ears. The tubes terminate or connect at the blower 1350, and connect to the rear or inferior side of the blower or blower housing. The rear or inferior side of the blower is generally opposite the side of the blower facing the same direction as the face of the patient. This may enhance the stability of the system by cupping or embracing the rear of the patient's head in use.

Figure 155:
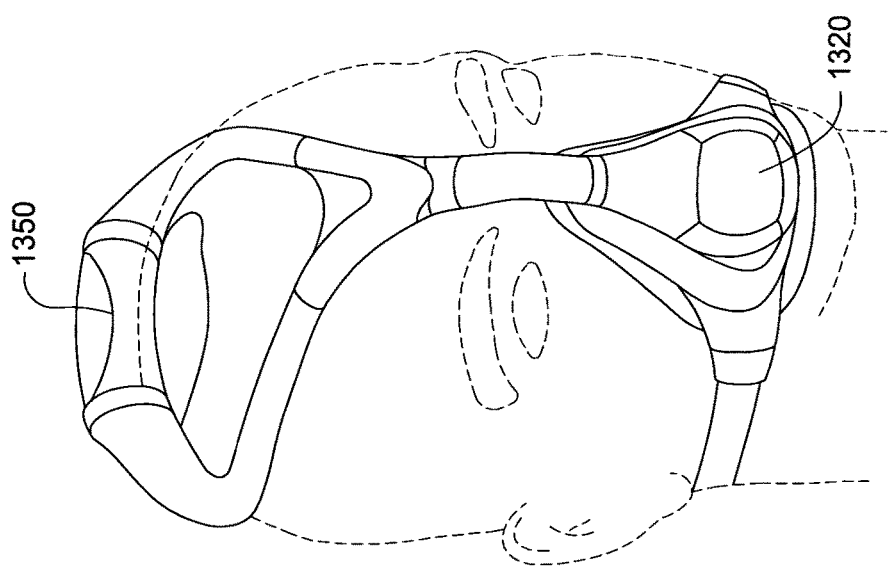
FIG. 155 shows a headworn ventilator system according to an embodiment of the invention.

FIG. 155 shows a further alternative embodiment of the present invention. The mask 1320 may have a tube connecting portion at the top or apex of the mask. The tube may bifurcate at the general forehead region of the patient. There may be a webbing or mesh at the junction or separation point of the tube to prevent the bifurcated tube from splaying to far outward. The bifurcated tubes may then enter or connect to the outlet of the blower or blower housing 1350.

Figure 156:
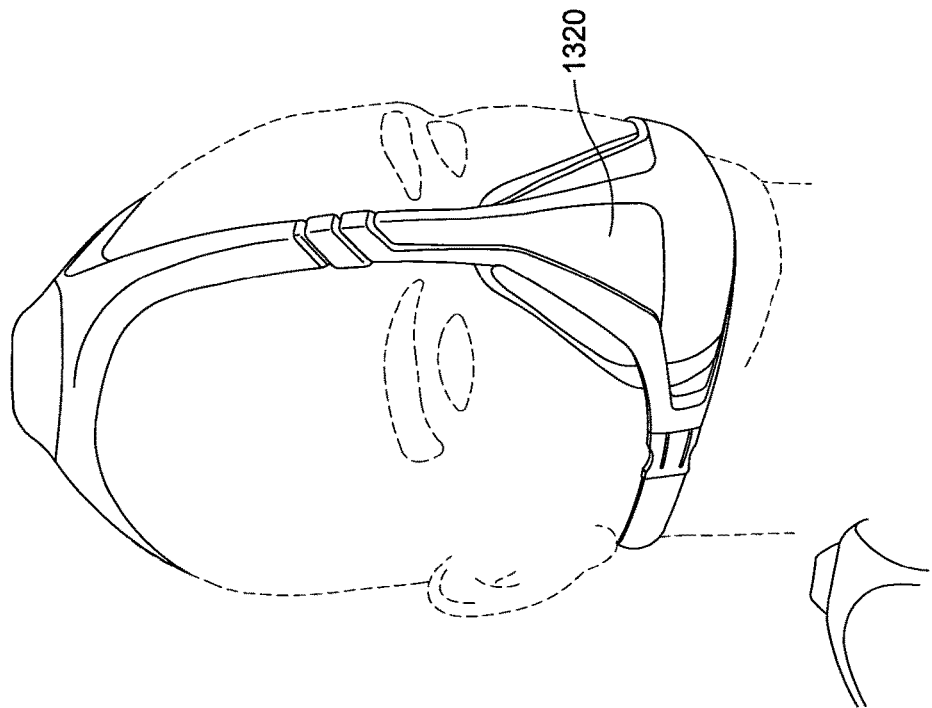
FIG. 156 shows a headworn ventilator system according to an embodiment of the invention.

FIG. 156 shows a further alternative embodiment of the present invention. The mask 1320 is a full face mask having an alternative configuration for attaching lower headgear straps.

Figure 157:
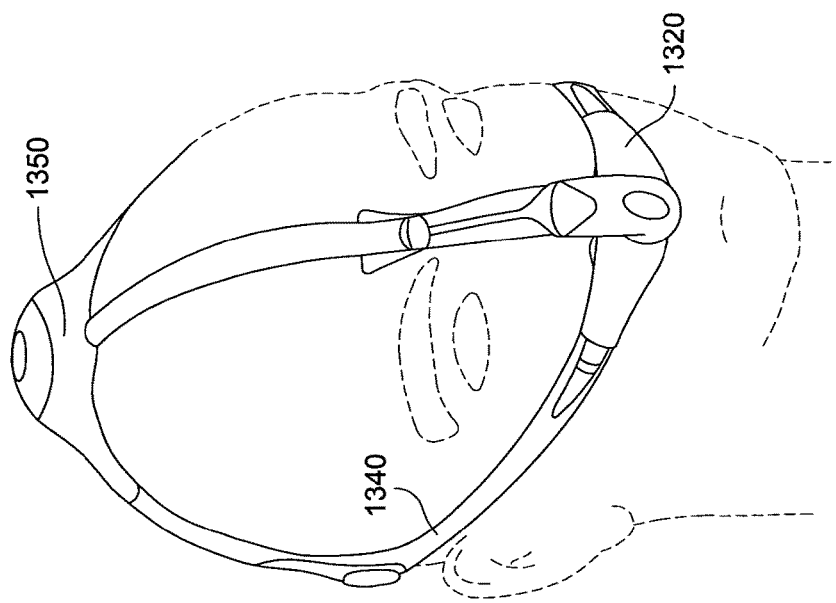
FIG. 157 shows a headworn ventilator system according to an embodiment of the invention.

FIG. 157 shows an alternative patient interface 1320, being a nasal cradle. The nasal cradle may have a tube connecting portion at the front of the nasal cradle cushion that delivers the pressurized air from the blower 1350 directly into the front of the nasal cushion. A tube is routed directly vertical or upwards of the patient's head from tube connecting portion to the blower positioned on the patient's head. That is, the tube is positioned in use between the patient's eyes. Headgear side straps 1340 support the positioning of the nasal cradle on the patient's nares.

FIG. 158 shows an alternative patient interface 1320, being a nasal cradle. The nasal cradle may include a single orifice to deliver breathable gas to both nares of the patient, with the outer walls engaging an outer region of the nose of the patient.

As noted above, mounting the blower on the patient's head (e.g., on the patient's crown) may allow vibration noise to be transmitted directly to the skull of the patient. Also, the headgear straps may transmit noise to the patient's skull in use. Thus, blower support structures may be used to decouple or isolate the blower from the patient's skull so as to dampen vibrations in use.

Preferably, the blower may not radiate heat to a level that the patient cannot tolerate or is dangerous. Preferably, the blower may not produce temperatures over 60° C. Preferably, the blower may not produce temperatures over 30° C.

Another aspect of the invention relates to a ventilator system in which the blower is built into or incorporated into the patient interface or mask. In an embodiment, the blower may be divided into two or more smaller blowers. Miniature blowers such as the small 8 W blowers manufactured by Maxon having a diameter of approximately 8 mm and a length of approximately 30 mm may be utilized or other commercially available miniature blowers. In one embodiment, the stator and air path features such as volute or plenum chamber may be build into the internals of the mask.

FIGS. 159-176 show masks with a built in blower according to alternative embodiments of the present invention.

Figure 159:
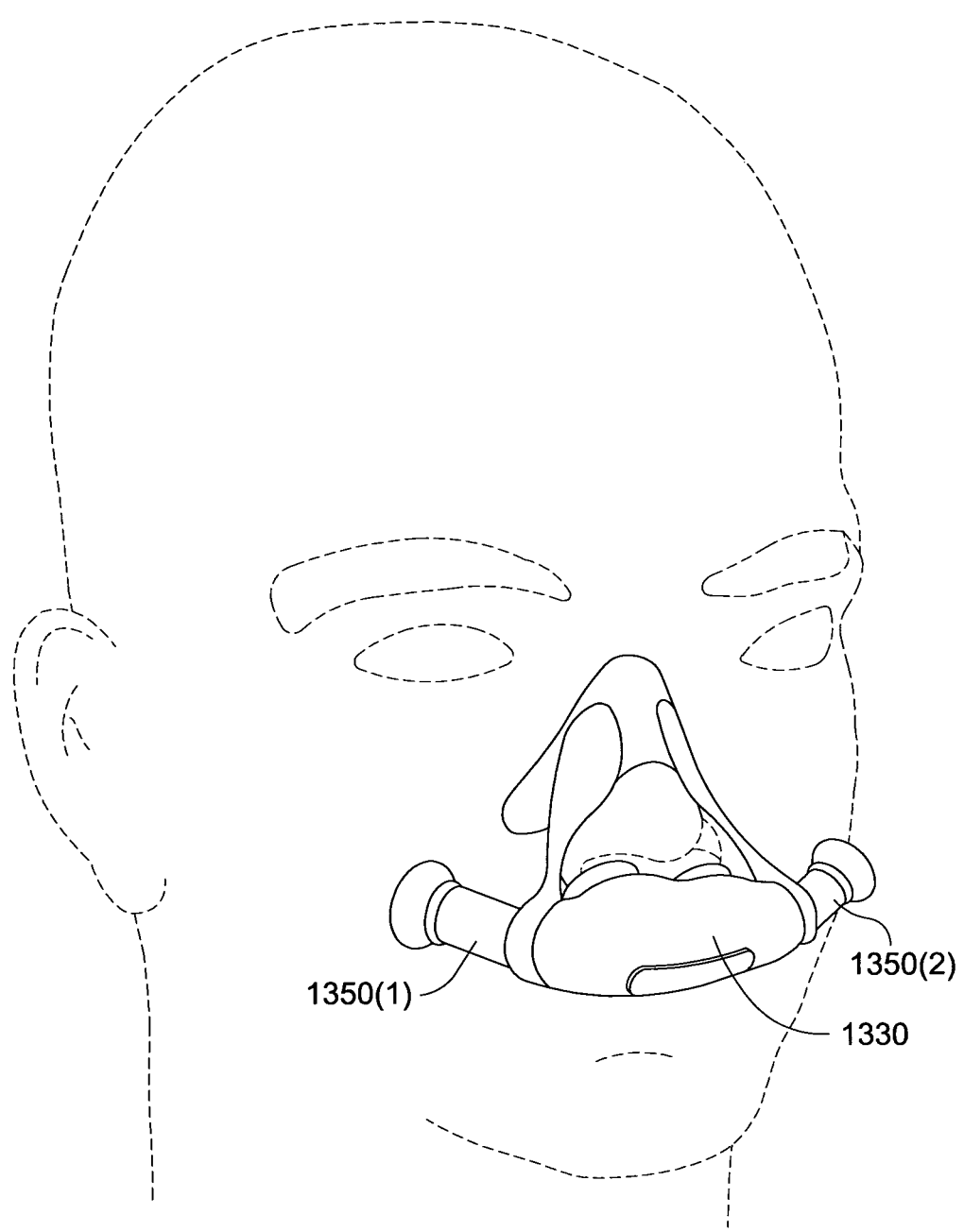
FIG. 159 shows a patient interface with a built-in blower according to an embodiment of the invention.

In FIG. 159, the patient interface or mask includes a nasal prong or pillow arrangement 1330 adapted to form a seal with the patient's nares. First and second blowers 1350(1), 1350(2) are provided to respective ends of the nasal prong arrangement to provide pressurized air to the nasal prong arrangement. The mask may be attached to the patient's face by a combination of hook and loop (e.g., Velcro) tabs and adhesive. In an embodiment, one blower may be used.

Blowers 1350(1) and 1350(2) may be encapsulated by a dampening means. For example, dampening means may include a muffler, such as a silicone casing, a foam and/or fabric layer or any other suitable material.

Tab portions may be connected to the nasal prong arrangement 1330 for removably attaching it to an adhesive facial pad. Tab portions may include integrally molded hooks to engage with loops provided on the adhesive facial pad. In an embodiment, attachment means may be provided as disclosed in pending U.S. application Ser. No. 12/478,537 filed Jun. 4, 2009, which is incorporated herein by reference in its entirety.

Muffling and/or filtering materials may be provided to the air inlet portions of the blowers 1350(1) and 1350(2). For example, foam pads may be attached or otherwise formed with blowers at their inlet portion.

Figures 1, 160:
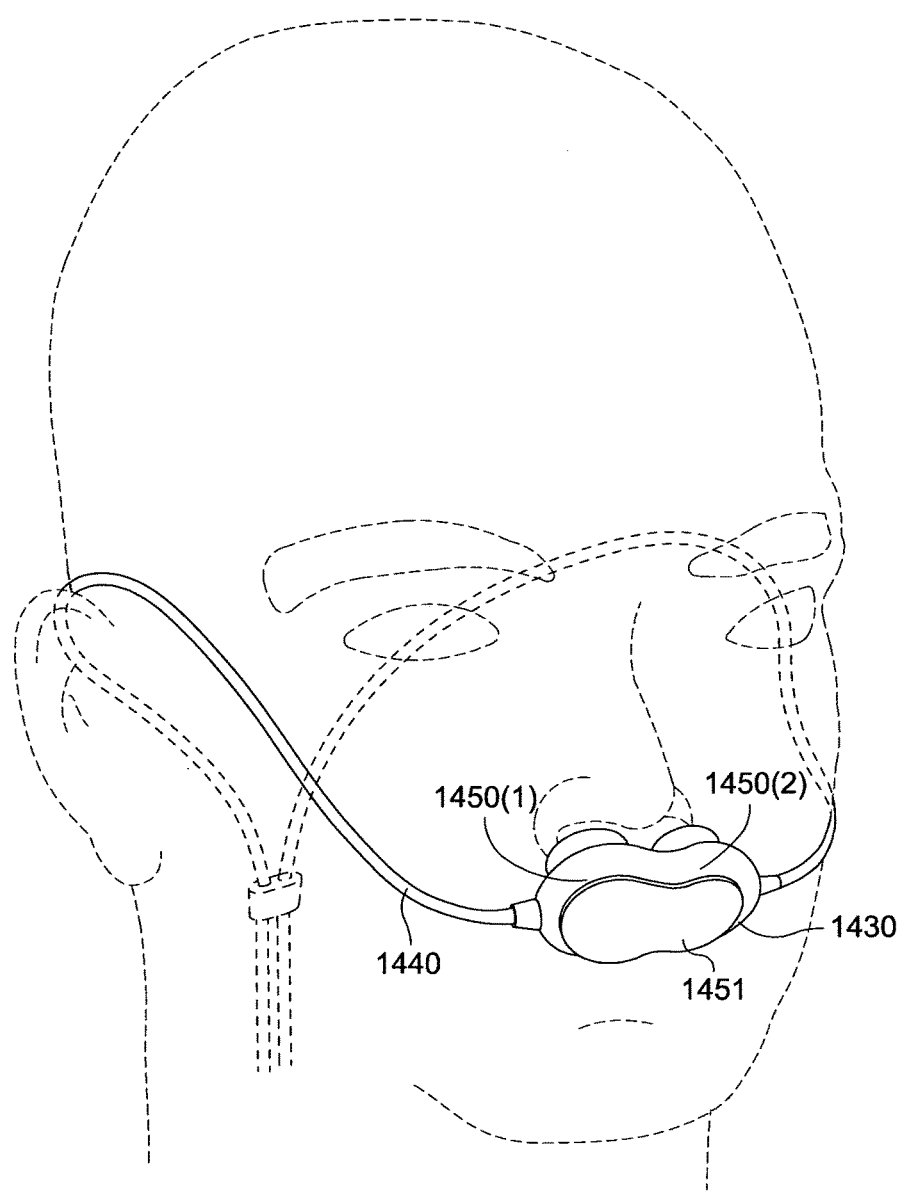
Figures 2, 160:
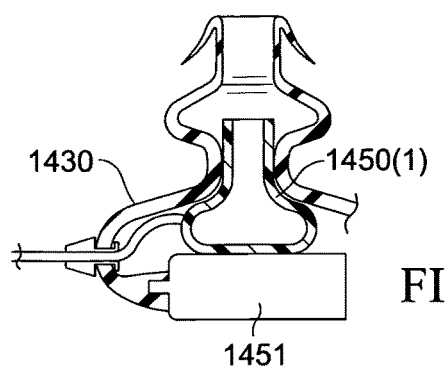

In FIGS. 160-1 and 160-2, the patient interface or mask includes a nasal prong or pillow arrangement 1430 adapted to form a seal with the patient's nares. First and second blowers 1450(1), 1450(2) are provided in-line with respective nasal prongs to provide pressurized air.

Nasal prongs may be provided with barbs or interference means to engage with an inner portion of a patient's naris.

The blower may be positioned such that the outlet directs airflow directly into a nasal prong, and the inlet receives air through an aperture in the cushion. The inlet may be adjacent or near a filter and/or muffler 1451 so as to reduce noise and provide the patient with clean air. The filter and/or muffler may comprise a filter material, foam, fabric, mesh or any other suitable material and any combination thereof.

Headgear straps 1440 may be connected to a cushion for securing the patient interface to the patient. The headgear straps may be connected at the rear of the patient's head by a slidably engaging portion. The headgear straps may connect to the blowers and comprise wiring to supply power to the blowers. Power is provided to the blower via a wire to a control unit that includes a power supply unit. The control unit may also comprise a user interface to allow the setting of parameters to control the blowers.

Figures 1, 161:
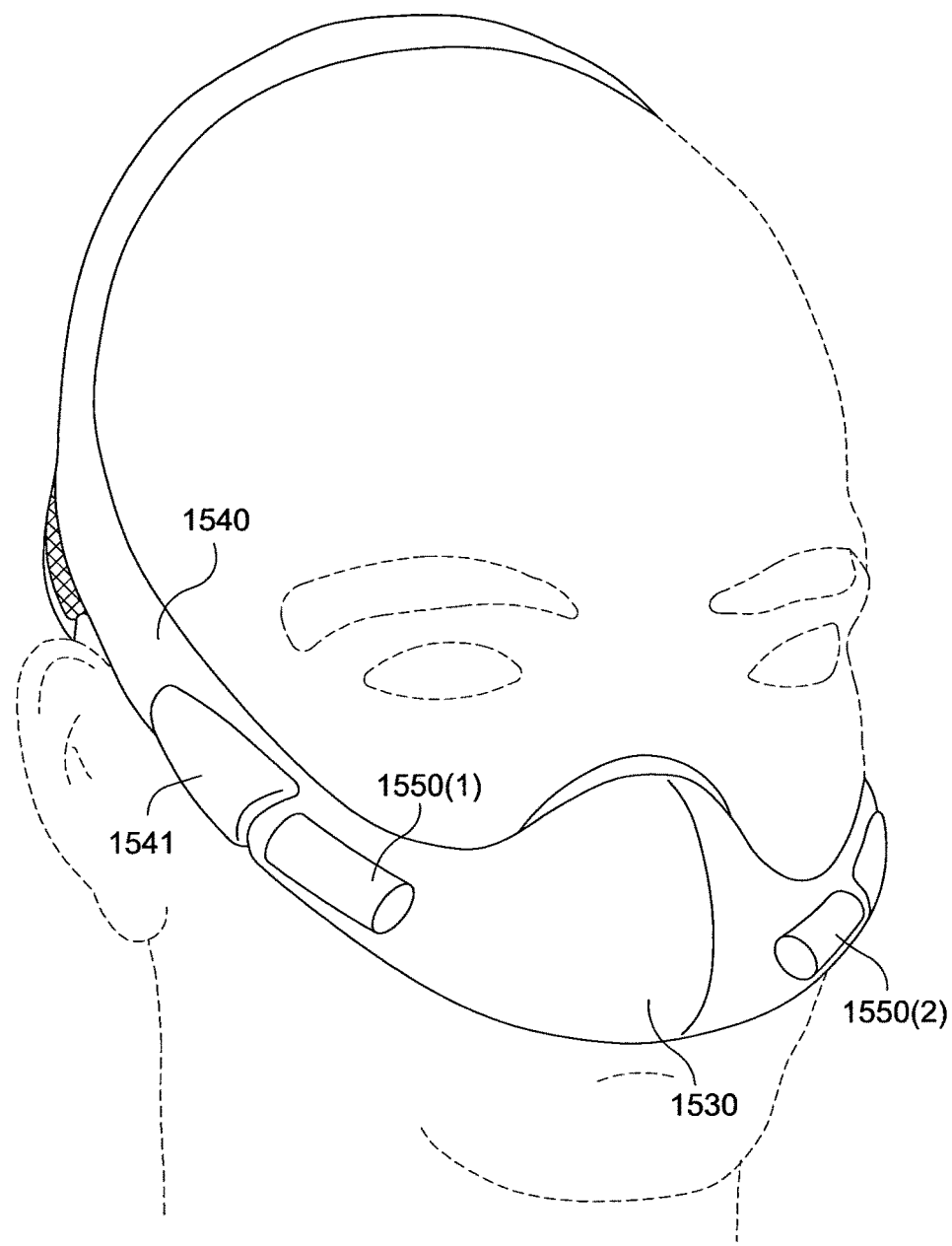
Figures 2, 161:
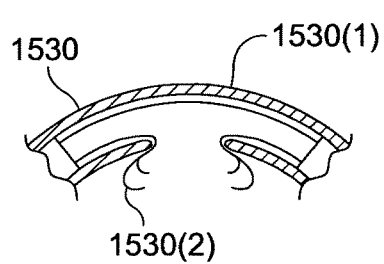

In FIGS. 161-1 and 161-2, the patient interface includes a nasal cushion 1530 and first and second blowers 1550(1), 1550(2) provided to respective ends of the nasal cushion to provide pressurized air to the nasal cushion. The silicone cushion provides ducting to communicate pressurized air from the blowers to the nasal cushion.

The cushion 1530 may be a thermoformed textile, e.g., see FIG. 161-2 including fabric portion 1530(1) and silicone sealing portion and ducts 1530(2). The textile could be woven or non-woven. The cushion may include a foam and/or fabric layer. The thermoformed textile may include a sealing surface, such that is non-air permeable or at least minimally permeable. This may be achieved by silicone spraying, molding or otherwise attaching a non-permeable or minimally permeable material to one or more portions of the fabric. Alternatively, the cushioning portion may be removably attached to the sealing surface. The sealing surface may include a patient contacting portion, a frame or support portion for maintaining the cushion away from the user's nose, and a ducted portion for attaching to air delivery tubes.

Headgear straps 1540 may be formed by ultrasonic welding and/or thermoforming. Headgear straps may be made from a fabric and foam composite. Headgear straps may alternatively be a fabric. Headgear straps may include reinforcing portions. Headgear straps may further include additional baffling or muffling portions 1541 to reduce noise from the blower and/or cushion. For example, muffling portions are shown in FIG. 161-1 positioned near or proximal to the patient's ears, to prevent excessive noise travelling to the patient's ears.

Figures 1, 2, 162:
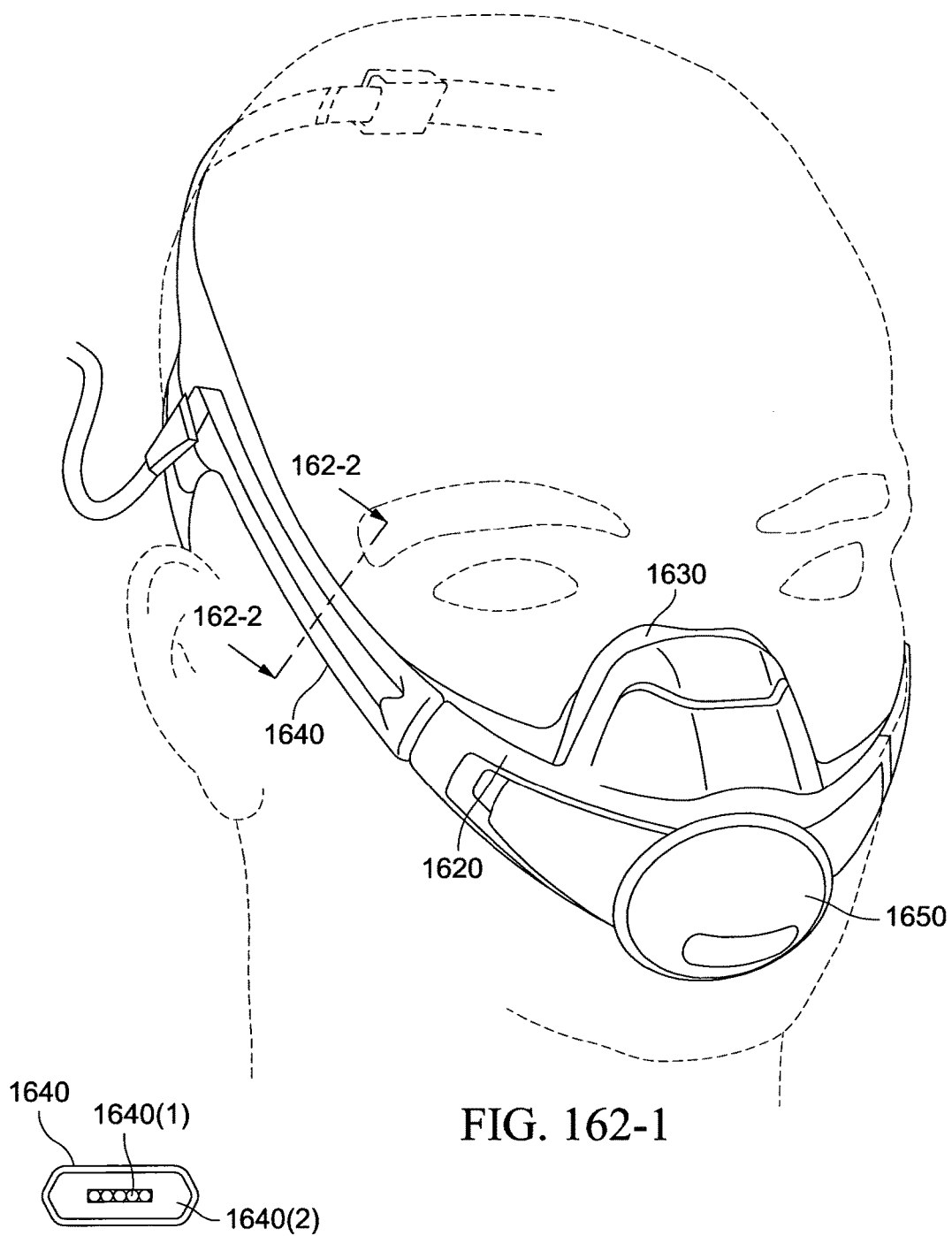

In FIGS. 162-1 and 162-2, the patient interface includes a frame 1620, a nasal cushion 1630 provided to the frame, and a blower 1650 provided to the front of the frame and communicated with the breathing chamber defined by the cushion. In an embodiment, the headgear and/or patient interface may include one or more aspects as described in WO 2009/052560 A1, U.S. Patent Application Publication 2009/0044808 A1, U.S. Pat. No. 7,318,437, or PCT Application No. PCT/AU2009/000241, filed Feb. 27, 2009, each of which is incorporated herein by reference in its entirety.

Headgear 1640 shown in FIGS. 162-1 and 162-2 may include a cable or wiring system that is molded into the headgear strap. For example, the wiring 1640(1) may be encapsulated within a foam and/or fabric strap 1640(2) as shown in FIG. 162-2, wherein the foam and/or fabric may be formed by thermoforming and/or ultrasonic welding. The foam may be used to support the wires in position, insulate the cables and maintain the wires in an unobtrusive manner. The wiring is shown in the form of a ribbon cable, although other forms of wiring may be utilized.

Figures 1, 2, 163:
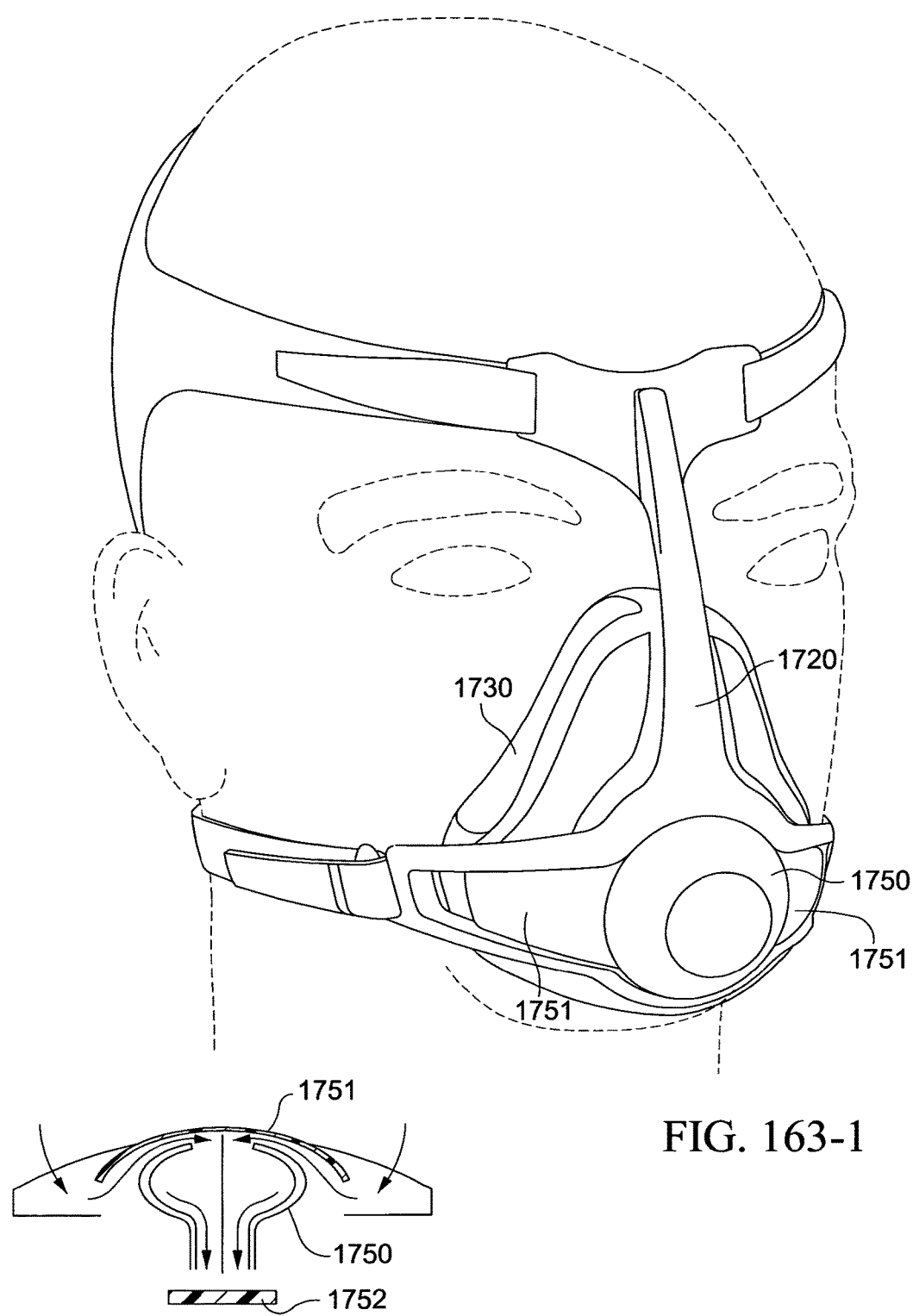

In FIGS. 163-1 and 163-2, the patient interface includes a frame 1720 (including a forehead support), a full-face cushion 1730 provided to the frame, and a blower 1750 provided to the front of the frame and communicated with the breathing chamber defined by the cushion. A mesh vent 1751 is mounted on either side of the blower. The mesh vent would allow air to flow into the blower as indicated by the arrows in FIG. 163-2. The mesh vent would act as a first filter to filter the incoming air.

The frame 1720 includes an aperture or ring for engaging with a blower 1750. The blower may clip or otherwise engage with the frame.

A second filter 1752, such as a HEPA filter, may be fitted to an inner portion of the mask near or proximal to the outlet of the blower to filter the air being delivered to or expired from the patient as indicated on FIG. 163-2. It may also assist in dampening the noise.

Figures 1, 164:
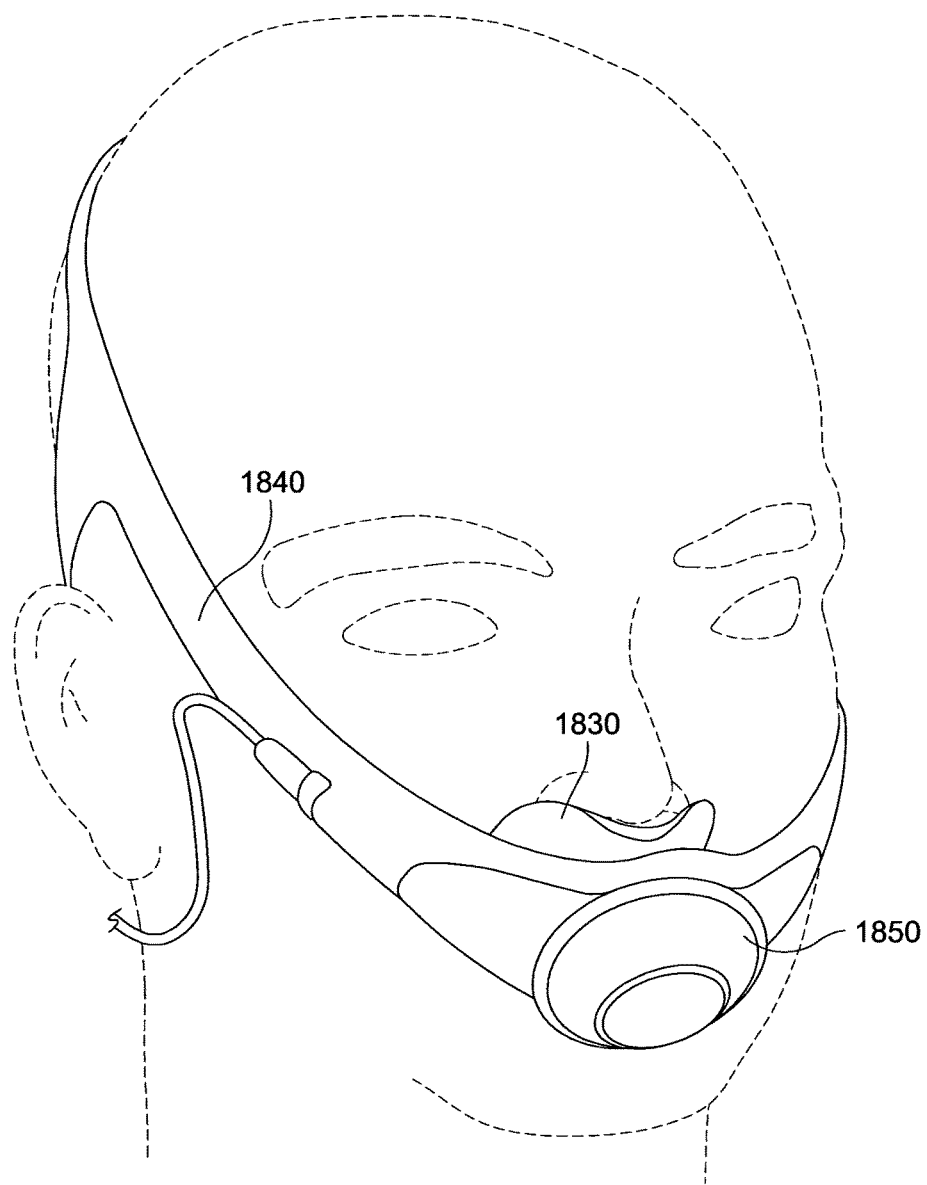
Figures 2, 164:
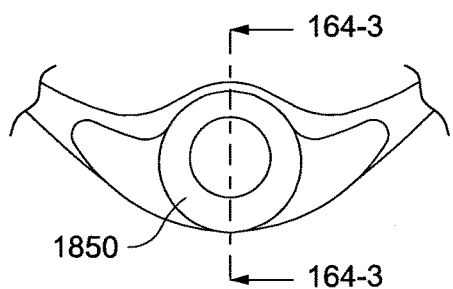
Figures 3, 164:
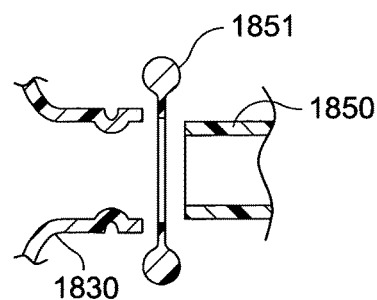
Figure 166:
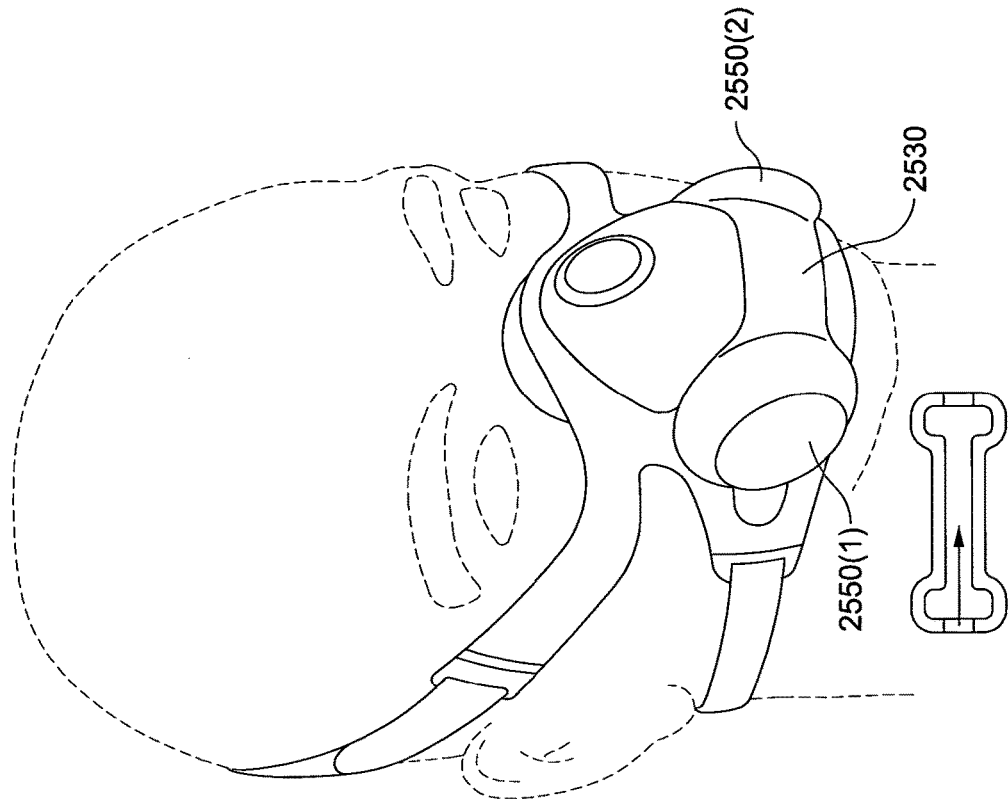

In FIGS. 164-1 to 164-3, the patient interface includes a nasal cushion 1830, headgear 1840 to support the cushion in position on the patient's head, and a blower 1850 supported by the headgear. The nasal cushion may be constructed of a compliant material such as silicone, gel, or foam. The blower may be overmolded or otherwise encapsulated in a housing, where the housing may be made from a plastic, metal, or other material that is able to maintain its shape. The housing may also function as a muffler to reduce noise. In an embodiment, the cushion may include one or more aspects as described in Australian Application 2009902524, filed Jun. 2, 2009, which is incorporated herein by reference in its entirety.

Headgear 1840 for supporting the mask 1830 may include a channel or other attachment means for a power supply cable to connect the motor to a power supply. The channel may be contained within the headgear. The channel may protect the wiring, prevent entanglement or strangulation of the patient and give the system a streamlined appearance. The headgear 1840 may be thermoformed or otherwise shaped.

A muffler or filter 1851 may also be fitted adjacent the mask 1830 and blower 1850, as a foam or fabric molded or attached to the headgear as shown in FIG. 164-3. Alternatively, the muffler or filter may be a non-woven material. The muffler or filter may filter exhaled gases and/or reduce the noise from the mask and blower. In a further alternative, the muffler or filter may be integrally formed or apart of the headgear.

Figures 1, 168:
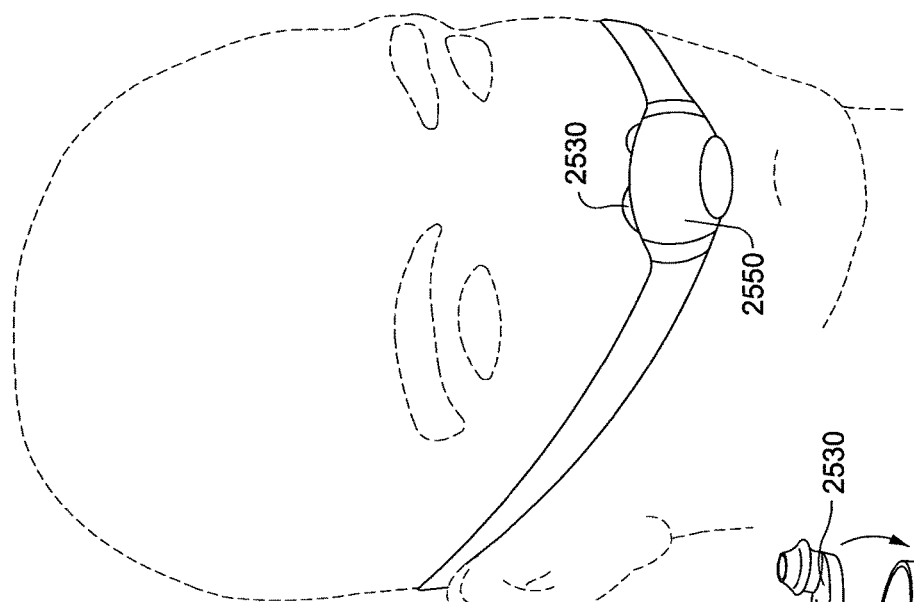
Figures 2, 168:
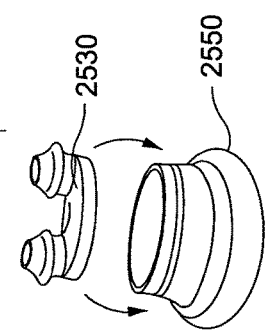
Figure 167:
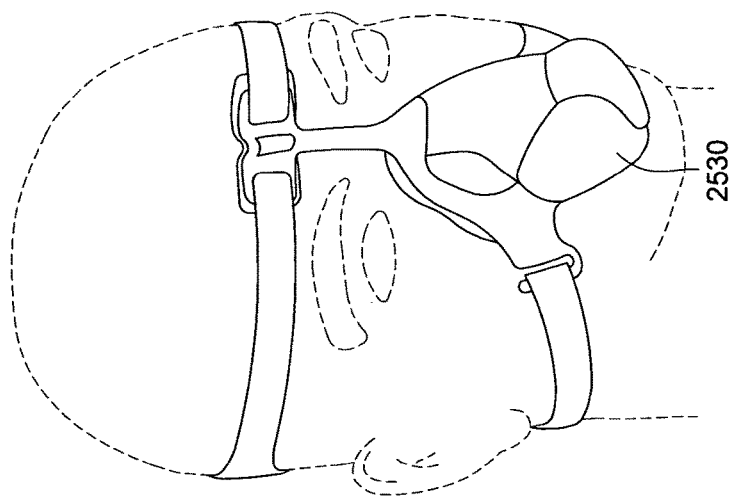
Figure 170:
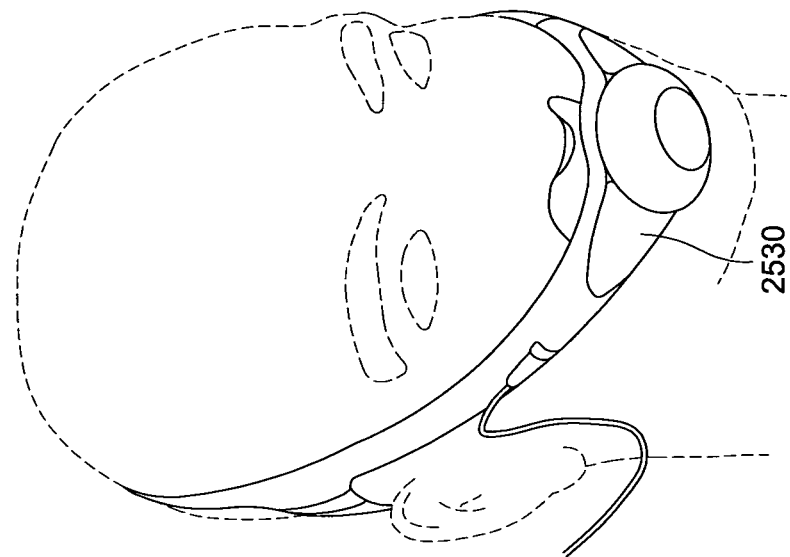
Figure 169:
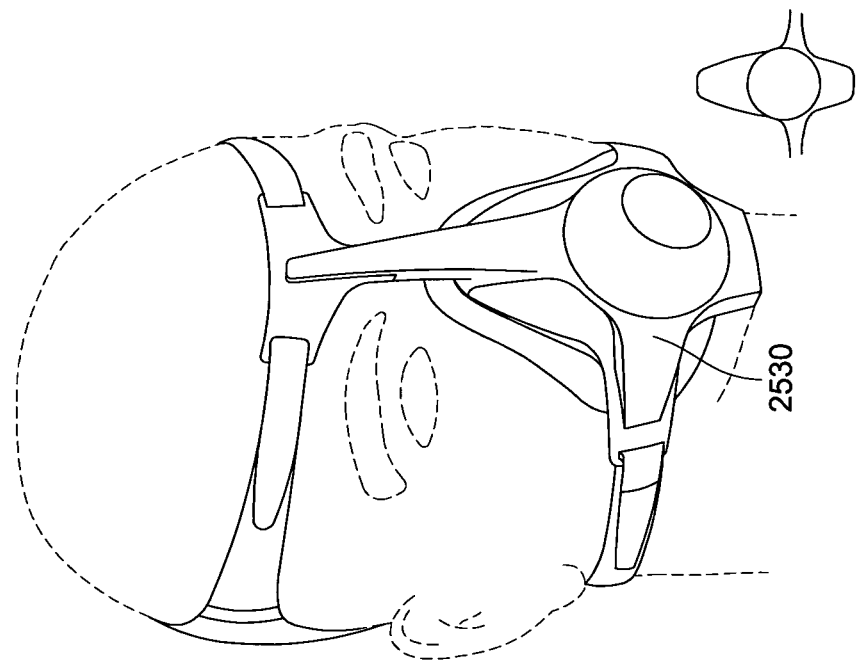
Figure 172:
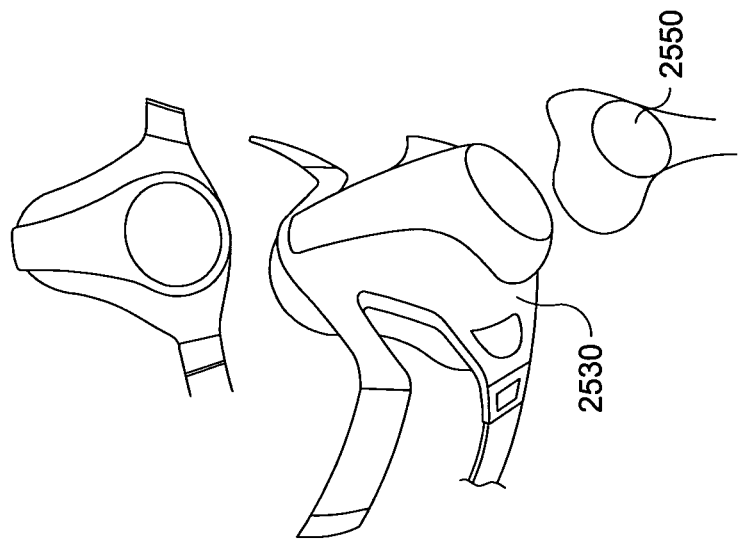
Figure 171:
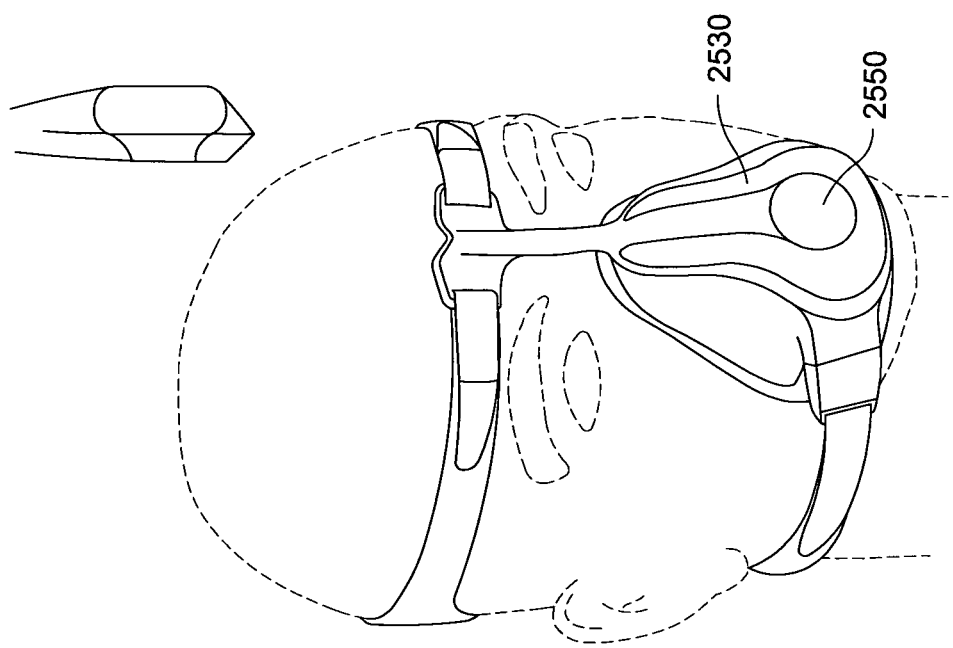
Figure 174:
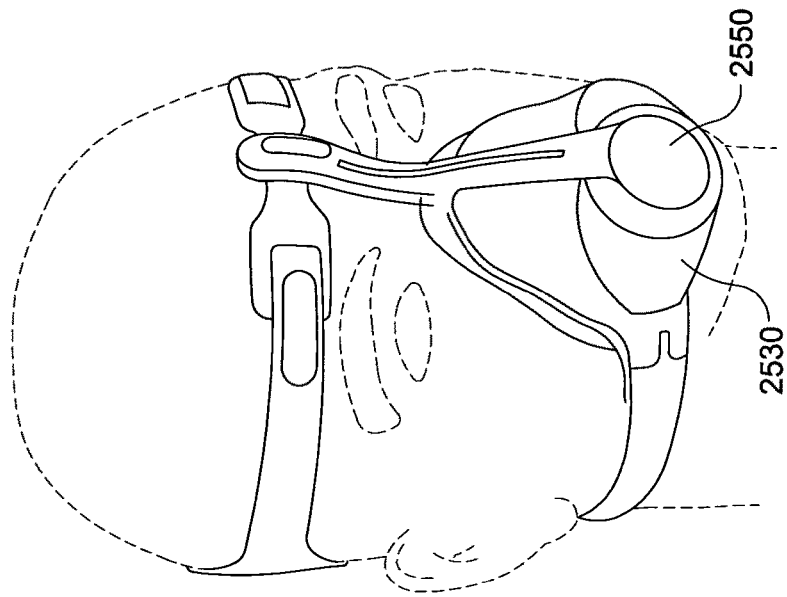
Figure 173:
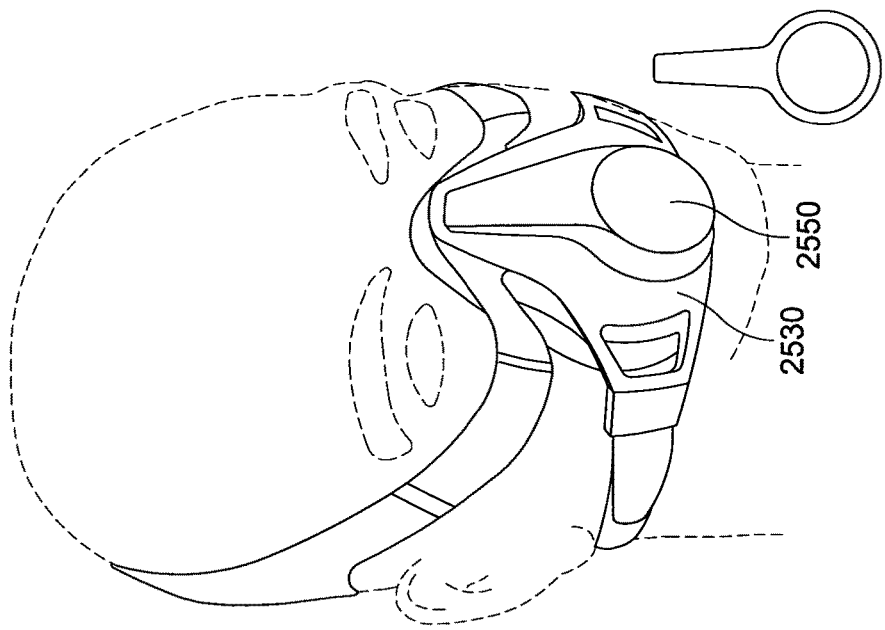

FIGS. 165-176 show alternative frame configurations for attaching headgear, alternative headgear arrangements, alternative cushion or sealing arrangements, and/or alternative ventilator configurations. For example, in FIGS. 165 and 166, the patient interface 2530 includes a dual blower (i.e., first and second blowers 2550(1), 2550(2)) supported by the mask frame. In FIG. 167 a mask 2530 wherein the blower is built into the mask is shown. In FIGS. 168-1 and 16802, snap-on pillows or nasal prongs 2530 may be provided to the blower 2550. In FIGS. 169 and 170, the patient interface 2530 may provide a foam intake. In FIGS. 171-176, the blower 2550 is provided to the front of the mask 2530 and the mask includes a streamline design.

Figure 165:
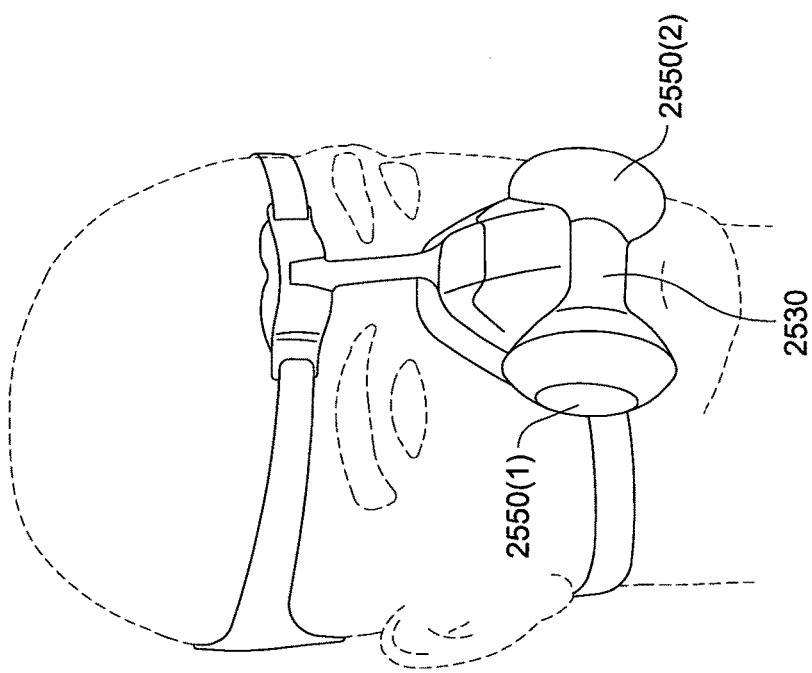

For example, FIG. 165 shows a pair of blowers or blower housings 2550(1), 2550(2) mounted on to the mask or patient interface. The inlets of the blowers are positioned horizontally outwards in the medial-lateral direction. A similar configuration is demonstrated in FIG. 166.

FIGS. 168-1 and 168-2 depict a blower outlet being connected directly to a patient interface 2530. The patient interface 2530 shown is a pillows or prong arrangement. Alternative patient interfaces may be used, for example nasal cradles, nasal, full face or oro-nasal masks.

Another aspect of the invention relates to a portable ventilator that may be attached to a bed, wheelchair, table, chair, etc. FIGS. 177-186 show portable ventilators according to alternative embodiments of the present invention.

As shown in FIG. 177, the portable ventilator 1950 may be adapted to be mounted by the patient's bedside or wall. The bedside embodiment may include a detachable blower mounted on a docking station 1970 or nightstand. The detachable ventilator may include batteries, such as lithium ion batteries, for powering the device when not connected to the main/AC power. The night stand may be fitted with an overhead tube 1960 (flexible tube, fixed shape tube, or combination thereof) adapted to connect to tubing associated with the mask. The overhead tube may be made from a metal such as stainless steel, or polymer such as thermoplastics or silicone, or combination thereof. The overhead tube may be able to rotate on the stand or bend in selected regions such as the top horizontal bar. The overhead tube includes a series of lights or LED's at the cuff or connection region with the mask tube which can be activated by touch or by a change in the system (such as detachment). Also the overhead tube can provide a soft light for the patient to see at night. The light may assist the patient when detaching or reattaching a flexible mask tube to the overhead tube. The color of the light may be associated with an activation reason. The cuff or connection region of the overhead tube may include a magnet that may attract a magnet or ferrous material at the end or connection region of the mask tube. This may aid attachment of the mask tube to the overhead tube.

In FIG. 178, the ventilator is adapted to be mounted to the wall or bedhead. An overhead tube 2060 may extend from the ventilator and adapted to connect to tubing associated with the patient interface. A muffler and/or filter may be attached to the blower to filter gases being delivered to the patient and/or reduce the noise of the system. Similar to the embodiment in FIG. 177, the overhead tube may be attached to the bed, bed head, wall or any other region proximal to the patient. The overhead tube may connect to a case 2050, where the case 2050 receives a power supply for the ventilator system. The power supply may be a battery or mains power supply. The case 2050 may be constructed of a polymer such as thermoplastic elastomer, thermoplastic urethane, or may be constructed from a metal such as aluminum. The case 2050 may have a wire or other means of carrying the power supply to the blower attached to the end of the overhead tube. The case may also include a microprocessor and user interface to allow the control and setting of parameters for the ventilator system.

In FIGS. 179 and 185, the portable ventilator 2650 may be attachable to a blower dock 2655 which may be structured to retain, charge, and/or download diagnostics from the blower.

In FIGS. 180-1 and 180-2, the blower 2650 is in the form of a ventilator pouch. The pouch may be deflatable when not in use for portability.

In FIGS. 181-1 to 181-4, the portable ventilator 2650 may be provided to a base 2656 adapted to charge the ventilator by induction charging.

FIG. 182 shows embodiments of an overhead tube 2657 which may include light-up tubing.

FIGS. 183, 184, and 186 show alternative casings 2658 for enclosing or protecting a portable ventilator. For example, FIG. 183 shows a fabric or foam/fabric type case 2658, FIG. 184 shows a silicone type case 2658, and FIG. 186 shows an aluminum alloy type case 2658.

A battery pack may be provided with the mask and ventilator system. The battery pack may be worn on the body of the patient. Alternatively, the battery may be provided with a cord such that it may be positioned away from the patient, for example on a bed side table. The battery may be flexible such that if it is worn on the body of the patient it may bend and conform to the general shape of the patient. The battery may have a wire or cable connecting it to the motor. The cable may have a quick release or force release portion, such that if a force is applied to the cable, the cable will disconnect the battery from the motor. This may be beneficial to avoid strangulation of the patient, or quick removal of the power from the motor.

Another aspect of the invention relates to a ventilator adapted to be wearable or carried by the patient and not mask or head mounted.

FIGS. 187-1 to 198-2 show wearable ventilator according to alternative embodiments of the present invention.

In FIGS. 187-1 and 187-2, the ventilator 2150 is supported by a shoulder-type harness 2180 which supports the ventilator adjacent the patient's chest.

In FIGS. 188-1 to 188-4, the ventilator 2150 is supported by a pendant-type arrangement. FIGS. 188-2 and 188-3 show alternative configurations for inlets and outlets of the ventilator.

In FIGS. 189-1 to 189-3, 190, 195, and 196, the ventilator 2150 is supported by an article of clothing, such as a shirt (e.g., T-shirt), pajamas, etc., wherein the clothing includes a blower support structure such as a pocket for example along the front of the shirt.

In FIGS. 191 and 197, the ventilator 2150 is supported by a shirt (e.g., T-shirt) including a blower support structure (e.g., pocket) along the shoulder of the shirt. In FIG. 196 the ventilator 2150 is shown used with a tracheotomy tube for providing invasive ventilation support.

FIGS. 192-1 to 194 show ventilator 2150 supported by a strap or band arrangement 2160. In FIGS. 192-1 and 192-2, the strap wraps around the patient's chest. In FIG. 193, the strap wraps around the patient's neck, e.g., collar style. In FIG. 194, the strap wraps around the patient's arm.

In FIGS. 198-1 and 198-2, the ventilator 2150 is supported by a soft casing adapted to wrap around the patient's neck. The casing may include pockets for supporting tubing 2166. In FIGS. 192-1 and 196, the ventilator is shown as an invasive system using a tracheotomy tube.

It should be appreciated that aspects of the ventilator system, e.g., blower, may include alternative arrangements. For example, U.S. provisional application Nos. 61/272,188, filed Aug. 28, 2009, and 61/272,919, filed Nov. 19, 2009 (each of which is incorporated herein by reference in its entirety) disclose alternative blower arrangements and CPAP systems including one or more aspects that may be incorporated into the ventilator system. That is, the blower arrangements and CPAP systems described in U.S. provisional application Nos. 61/272,188, filed Aug. 28, 2009, and 61/272,919, filed Nov. 19, 2009, may be adapted for use as a ventilator system.

4. CPAP Applications

In an embodiment, the blower may be useful in relation to applications for continuous positive air pressure (CPAP) flow generators.

In such CPAP applications, the blower may be reduced in size because the output flow rate and/or pressures needed are relatively lower, e.g., not as high as ventilators.

FIGS. 19-23 illustrate a CPAP version of a blower 310 according to an embodiment of the present invention. As illustrated, the blower includes a housing 320 with first and second housing parts 322, 324 defining a proximal opening 323 and distal opening 325, a stator component 330 including air directing grooves 335, a motor 340 supported by the stator component 330 and adapted to drive a rotatable shaft or rotor 350, and an impeller 360, as described above. The first and second parts 332, 334 of the stator component are coupled using an O-ring 376 as described above.

Figure 22:
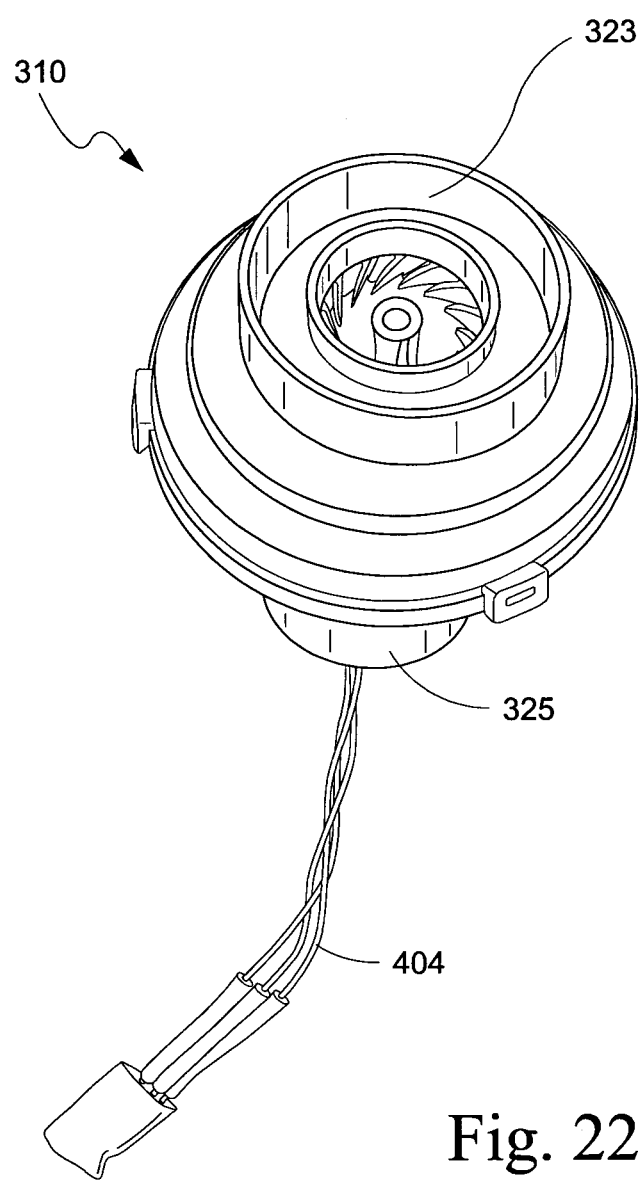
FIG. 22 is a perspective view of a CPAP version of a blower according to an embodiment of the present invention.
Figure 23:
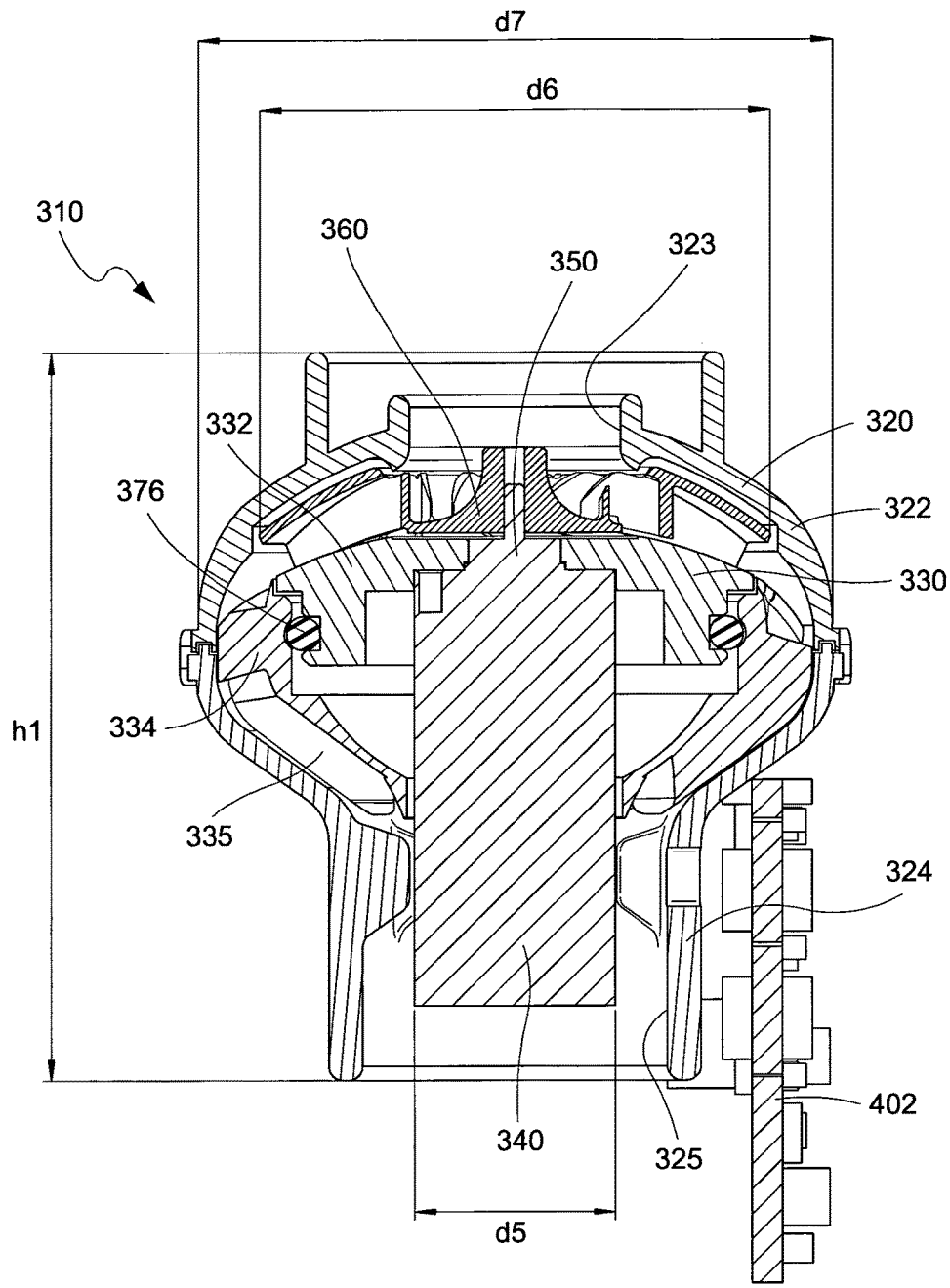
FIG. 23 is a cross-sectional view of the blower of FIG. 22.

The embodiment illustrated in FIG. 22 may also include wiring 404 for connecting power and/or control to the blower 310. The embodiment illustrated in FIG. 23 also includes PCBA 402, which may be used to control a flow sensor and pressure sensor, as explained above in conjunction with FIG. 12. PCBA 402 may be coupled to the housing 320 using screws, glue or plastic retaining snaps (not shown) molded into the housing 320, or by other coupling.

In an example, the motor may rotate at speeds of approximately up to 40,000 rpm and generate pressures up to 14 cmH2O. In an example, the impeller may have a diameter d6 between 20-40 mm (e.g., 30 mm) and the housing may have an outside maximum width d7 of 30-50 mm (e.g., 37 mm) and an outside maximum height h1 of 30-50 mm (e.g., 43 mm). In an example, the motor may have a diameter d5 of about 10-15 mm (e.g., 12 mm) and a length of about 20-30 mm (e.g., 26 mm). However, other suitable sizes are possible. The blower may weigh less than 500 gms, and more specifically may weigh between 50-200 gms.

Figure 24:
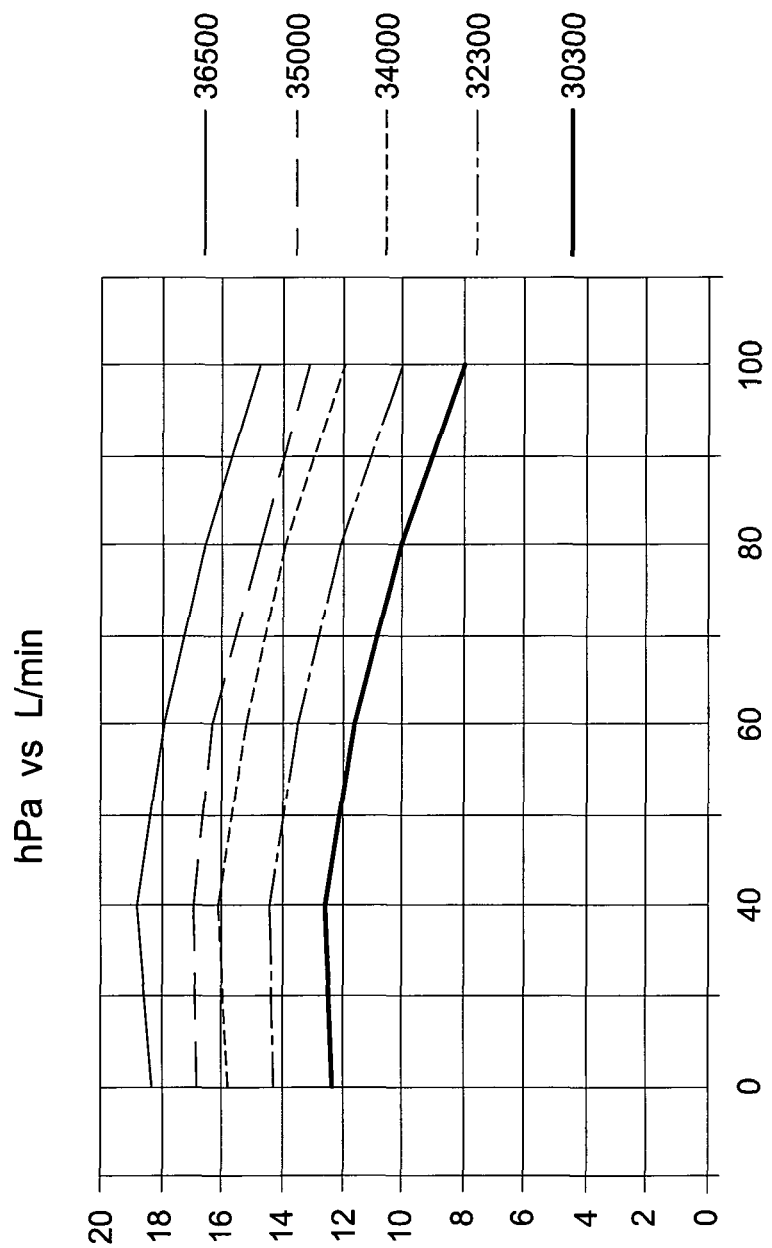
FIG. 24 is a diagram illustrating pressure versus flow for various RPM for a blower according to an embodiment of the present invention.

FIG. 24 illustrates pressure versus flow curves for various RPM illustrating characteristics of the blower according to embodiments of the invention. As illustrated, the pressure versus flow is relatively constant over a range of motor speeds, (e.g., 30,000 rpm to 40,000 rpm), which aids a patient being able to breathe back through the blower if there is no or a limited amount of tubing connected to the blower. This will limit or eliminate the need for a vent in a mask or patient interface attached to the tubing as part of a PAP device. Chart 1-1 below sets forth fan curve data for pressure versus flow rate at various RPM, as illustrated in FIG. 24.

CHART 1-1

|  | 0 L/min | 40 L/min | 60 L/min | 80 L/min |
|---|---|---|---|---|
| 30,300 RPM | 12.3 hPa | 12.6 hPa | 11.6 hPa | 10.2 hPa |
| 32,300 RPM | 14.3 hPa | 14.4 hPa | 13.5 hPa | 12.1 hPa |
| 34,000 RPM | 15.8 hPa | 16.1 hPa | 15.2 hPa | 13.9 hPa |
| 35,000 RPM | 16.8 hPa | 16.9 hPa | 16.3 hPa | 14.8 hPa |
| 36,500 RPM | 18.3 hPa | 18.7 hPa | 17.9 hPa | 16.6 hPa |

The embodiments described in this specification are preferably adapted to be used in travel applications and in situations where minimal size and bulk of the blower is preferred.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A blower, comprising:
   a housing including a proximal opening and a distal opening, the proximal opening and distal opening being co-axially aligned;
   a stator component provided to the housing;
   an impeller positioned between the proximal opening of the housing and the stator component, the impeller including a plurality of impeller blades; and
   a motor adapted to drive the impeller,
   wherein the stator component includes a plurality of air directing grooves along an exterior surface thereof configured and arranged to collect and divide air from the impeller, each of the air directing grooves including an inlet portion providing a leading edge extending tangentially outwards from outer tips of the impeller blades, the inlet portion of each of the air directing grooves configured to collect air exiting the impeller blades and direct the air from a generally tangential direction to a generally radial outward direction relative to the outer tips of the impeller blades, and each of the air directing grooves configured to subsequently direct the air from the inlet portion along a curved path to an outlet portion extending from the inlet portion of each of the air directing grooves, the outlet portion of each of the air directing grooves extending in a generally axial direction towards the distal opening, so that airflow becomes substantially laminar,
   wherein the outlet portion of each of the air directing grooves extends along a lower side of the stator component that is positioned out of a line of sight of the impeller, and
   wherein each of the air directing grooves includes a cross-sectional area that is substantially constant along an entire length of each of the air directing grooves from the inlet portion to the outlet portion.

2. The blower according to claim 1, wherein the stator component includes nine, eleven, or thirteen air directing grooves.

3. The blower according to claim 1, wherein the air directing grooves all converge at a base of the stator component.

4. The blower according to claim 1, wherein a depth of each of the air directing grooves increases or deepens as it extends from the inlet portion towards the outlet portion.

5. The blower according to claim 1, wherein a width of each of the air directing grooves decreases or narrows as it extends from the inlet portion towards the outlet portion.

6. The blower according to claim 1, wherein the stator component includes a hollow interior adapted to support the motor therewithin.

7. The blower according to claim 1, wherein the motor includes a stator assembly adapted to drive a rotor, and the impeller is coupled to an end portion of the rotor.

8. The blower according to claim 7, wherein the rotor is supported by a pair of bearings, the bearings supported by the housing.

9. The blower according to claim 1, wherein the impeller includes a number of impeller blades and the stator component includes a number of air directing grooves, and a ratio of the number of impeller blades to the number of air directing grooves includes no common divisible.

10. The blower according to claim 1, wherein the housing has a maximum diameter of about 30-50 mm.

11. The blower according to claim 1, wherein the blower is structured to provide pressurized air greater than 60 cmH$_2$O.

12. The blower according to claim 1, wherein the housing includes a housing piece configured and positioned to cover or shield power connection points to the motor.

13. The blower according to claim 1, further comprising a flow sensor and a pressure sensor downstream of the stator component.

14. The blower according to claim 13, wherein the housing includes flow straighteners downstream of the stator component and upstream of the flow sensor that are configured and positioned so as to straighten airflow entering the flow sensor.

15. The blower according to claim 13, wherein the pressure sensor includes a flexible membrane in fluid communication with an airflow path through the blower, and wherein displacement of the flexible membrane provides an indication of pressure of the air in the airflow path.

16. The blower according to claim 13, wherein the pressure sensor is positioned downstream of the flow sensor.

17. The blower according to claim 13, further comprising a printed circuit board assembly mounted to the housing to control the flow sensor and the pressure sensor.

18. The blower according to claim 1, further comprising a printed circuit board assembly mounted to the housing to control the motor.

19. The blower according to claim 1, wherein the stator component includes first and second parts that cooperate to define the plurality of air directing grooves.

20. The blower according to claim 1, wherein the stator component includes first and second parts that are coupled to one another by an o-ring.

21. The blower according to claim 1, further comprising a passive air valve assembly provided to the proximal opening of the housing.

22. The blower according to claim 21, wherein the valve assembly includes a first valve in communication with atmosphere and positioned and arranged to allow air to flow into the blower via the proximal opening during an inhalation phase of a patient's breathing cycle, and a second valve in communication with atmosphere and positioned and arranged to allow air to exit the blower via the proximal opening during an exhalation phase of the patient's breathing cycle.

23. The blower according to claim 1, wherein the housing has a maximum outside height of 30-50 mm.

24. The blower according to claim 1, wherein the blower has a weight of less than 500 gms.

25. The blower according to claim 24, wherein the blower has a weight of between 50-200 gms.

26. The blower according to claim 1, wherein the air directing grooves all converge or rejoin at a base of the stator component to form an axial exit.

27. The blower according to claim 1, wherein the air directing grooves are structured and arranged to direct air from a centrifugal flow to an axial flow.

28. The blower according to claim 1, wherein the stator component comprises a heat conductive material to dissipate heat from the motor.

29. The blower according to claim 1, wherein the airflow through the blower is arranged to flow over the motor to dissipate heat from the motor.

30. The blower according to claim 1, wherein the blower is adapted to provide relatively constant pressure at flow rates up to 80 L/min over a predetermined range of motor speeds.

31. The blower according to claim 30, wherein the range of motor speeds is from about 30,000 rpm to 40,000 rpm.

32. A ventilator device comprising a blower according to claim 30, further comprising tubing connected to the blower, and a patient interface connected to the tubing.

33. The ventilator device according to claim 32, wherein the patient interface does not include a vent due to the relatively constant pressure provided by the blower.

34. A ventilator device comprising the blower according to claim 1.

35. The ventilator device according to claim 34, wherein the ventilator device is a positive airway pressure (PAP) device.

36. A ventilator for a patient, comprising:
a blower according to claim 1 structured to provide a source of pressurized air; and
a valve assembly provided to the proximal opening of the blower and structured to allow air to flow through the blower along a flow path in both directions, the valve assembly structured to allow air to flow into the blower via the proximal opening during an inhalation phase of a patient's breathing cycle and allow air to exit the blower via the proximal opening during an exhalation phase of the patient's breathing cycle.

37. A ventilator according to claim 36, wherein the blower includes a flow element provided to the motor along the flow path structured to measure flow in both directions and conduct heat from the motor.

38. A ventilator according to claim 37, wherein the housing and the stator component cooperate to define a plenum chamber around the impeller.

39. A ventilator according to claim 38, further comprising a downstream chamber downstream from the plenum chamber to allow flow recirculation through the stator component without affecting the flow element.

40. A ventilator according to claim 37, further comprising a non-electrically conductive sleeve provided to a central segment of the motor along the flow path.

41. A ventilator according to claim 37, wherein the flow element and the stator component are constructed of heat conductive material to conduct heat from the motor.

42. A ventilator according to claim 41, wherein the flow element and the stator component are constructed of aluminum.

43. A ventilator according to claim 36, further comprising a mucous trap provided to the distal opening of the blower, the mucous trap providing a capture plate adapted to capture any particulate matter expired by the patient.

44. A ventilator according to claim 36, further comprising a heat moisture exchange filter provided to the distal opening of the blower, the heat moisture exchange filter including a filter and/or pad to condition air inhaled by the patient and/or protect the ventilator from particulate matter expired by the patient.

45. A ventilator according to claim 36, wherein a cross-sectional area of the flow path is maximized and balanced with minimal deadspace within the ventilator to provide low source impedance.

46. A ventilator according to claim 36, further comprising a battery powered control unit separate from the ventilator, the ventilator and control unit both including a microcontroller configured to record patient data and allow transfer of ventilator settings and patient details.

47. A ventilator according to claim 36, wherein the ventilator is adapted for use at a location proximal to the patient.

48. A ventilator according to claim 47, wherein the ventilator is incorporated into a headworn system.

49. A ventilator according to claim 47, wherein the ventilator is adapted to be mounted to a structure including a wall, bed, bed head, wheelchair, table or chair, and connected via tubing to a patient interface.

50. A ventilator according to claim 47, wherein the ventilator is adapted to fit into a support structure incorporated into clothing.

51. A ventilator according to claim 50, wherein the clothing is a shirt, T-shirt, or pajamas.

52. A ventilator according to claim 47, wherein the ventilator is built into a patient interface unit.

53. A ventilator according to claim 47, wherein the ventilator is supported by a shoulder-type harness.

54. A ventilator according to claim 47, wherein the ventilator is supported by a pendant-type arrangement.

55. A ventilator according to claim 47, wherein the ventilator is supported by a strap or band around a part of the patient's body.

56. A ventilator according to claim 55, wherein the strap or band is a chest band.

57. A ventilator according to claim 55, wherein the strap or band is an arm band.

58. A ventilator, comprising:
a blower according to claim 1 structured to provide a source of pressurized air; and a valve assembly provided to the blower and structured to allow air to flow through the blower along a flow path in both directions, the blower including a flow element along the flow path structured to measure flow in both directions and conduct heat from the motor of the blower.

59. A ventilator according to claim 58, wherein the flow element is constructed of a heat conductive material.

60. A ventilator according to claim 58, wherein the flow element is constructed of aluminum.

61. A ventilator according to claim 58, wherein the flow element includes an inner core and a plurality of vanes extending from the inner core.

62. A ventilator according to claim 61, wherein the flow element includes 40-60 vanes.

63. A ventilator according to claim 61, wherein the inner core of the flow element includes a split configuration structured to allow the flow element to be fit around the motor and to expand and contract with changes in heat from the motor.

64. A blower, comprising:
a housing including a proximal opening and a distal opening, the proximal opening and distal opening being co-axially aligned;
a stator component provided to the housing;
an impeller positioned between the proximal opening of the housing and the stator component, the impeller including a plurality of impeller blades; and
a motor adapted to drive the impeller, wherein the stator component includes a plurality of air directing grooves along an exterior surface thereof configured and arranged to collect and divide air from the impeller, each of the air directing grooves including an inlet portion providing a leading edge extending tangentially outwards from outer tips of the impeller blades, the inlet portion of each of the air directing grooves configured to collect air exiting the impeller blades and direct the air from a generally tangential direction to a generally radial outward direction relative to the outer tips of the impeller blades, and each of the air directing grooves configured to subsequently direct the air from the inlet portion along a curved path to an outlet portion extending from the inlet portion of each of the air directing grooves, the outlet portion of each of the air directing grooves extending in a generally axial direction towards the distal opening, so that airflow becomes substantially laminar, wherein each of the air directing grooves includes a cross-sectional area that is substantially constant along an entire length of each of the air directing grooves from the inlet portion to the outlet portion, wherein a depth of each of the air directing grooves increases or deepens as it extends along the entire length from the inlet portion towards the outlet portion, and wherein a width of each of the air directing grooves decreases or narrows as it extends along the entire length from the inlet portion towards the outlet portion.

* * * * *